(12) United States Patent
Dobbles et al.

(10) Patent No.: US 12,397,113 B2
(45) Date of Patent: Aug. 26, 2025

(54) INTEGRATED INSULIN DELIVERY SYSTEM WITH CONTINUOUS GLUCOSE SENSOR

(71) Applicant: DexCom, Inc., San Diego, CA (US)

(72) Inventors: John Michael Dobbles, San Clemente, CA (US); Apurv Ullas Kamath, San Diego, CA (US); Aarthi Mahalingam, San Diego, CA (US); James H. Brauker, Addison, MI (US)

(73) Assignee: Dexcom, Inc., San Diego, CA (US)

( * ) Notice: Subject to any disclaimer, the term of this patent is extended or adjusted under 35 U.S.C. 154(b) by 0 days.

(21) Appl. No.: 18/806,797

(22) Filed: Aug. 16, 2024

(65) Prior Publication Data

US 2024/0399060 A1 Dec. 5, 2024

Related U.S. Application Data

(63) Continuation of application No. 17/074,490, filed on Oct. 19, 2020, which is a continuation of application
(Continued)

(51) Int. Cl.
*A61M 5/172* (2006.01)
*A61B 5/145* (2006.01)
(Continued)

(52) U.S. Cl.
CPC ....... *A61M 5/1723* (2013.01); *A61B 5/14532* (2013.01); *A61B 5/14546* (2013.01); *A61M 5/14244* (2013.01); *A61M 5/14276* (2013.01); *A61M 5/20* (2013.01); *A61M 11/00* (2013.01); *A61M 15/0065* (2013.01); *A61M 15/0068* (2014.02); *A61M 15/008* (2014.02); *A61M 15/0083* (2014.02); *A61M 35/00* (2013.01); *G16H 20/17* (2018.01); *G16H 40/63* (2018.01); *A61B 5/0031* (2013.01); *A61M 5/003* (2013.01); *A61M 2005/14296* (2013.01); *A61M 5/178* (2013.01); *A61M 5/30* (2013.01);
(Continued)

(58) Field of Classification Search
None
See application file for complete search history.

(56) References Cited

U.S. PATENT DOCUMENTS 52,641 A 2/1866 Gates
62,334 A 2/1867 Holmes
(Continued)

FOREIGN PATENT DOCUMENTS

CA 2127172 C 7/1998
DE 10103803 A1 8/2001
(Continued)

OTHER PUBLICATIONS

US 7,530,950 B2, 05/2009, Brister et al. (withdrawn)
(Continued)

*Primary Examiner* — Manuel A Mendez
(74) *Attorney, Agent, or Firm* — Stuart H. Mayer; Kaplan Breyer Schwarz LLP

(57) ABSTRACT

Systems and methods for integrating a continuous glucose sensor 12, including a receiver 14, a medicament delivery device 16, a controller module, and optionally a single point glucose monitor 18 are provided. Integration may be manual, semi-automated and/or fully automated.

18 Claims, 16 Drawing Sheets

Related U.S. Application Data

No. 16/867,476, filed on May 5, 2020, now Pat. No. 10,835,672, which is a continuation of application No. 15/792,038, filed on Oct. 24, 2017, now Pat. No. 10,653,835, which is a continuation of application No. 15/362,571, filed on Nov. 28, 2016, now Pat. No. 9,827,372, which is a continuation of application No. 14/063,811, filed on Oct. 25, 2013, now Pat. No. 9,597,453, which is a continuation of application No. 13/885,604, filed as application No. PCT/US2007/080848 on Oct. 9, 2007, now Pat. No. 9,452,258.

(51) Int. Cl.

| | | |
|---|---|---|
| *A61M 5/142* | (2006.01) | |
| *A61M 5/20* | (2006.01) | |
| *A61M 11/00* | (2006.01) | |
| *A61M 15/00* | (2006.01) | |
| *A61M 35/00* | (2006.01) | |
| *G16H 20/17* | (2018.01) | |
| *G16H 40/63* | (2018.01) | |
| *A61B 5/00* | (2006.01) | |
| *A61M 5/00* | (2006.01) | |
| *A61M 5/178* | (2006.01) | |
| *A61M 5/30* | (2006.01) | |

(52) U.S. Cl.
CPC ..... *A61M 15/00* (2013.01); *A61M 2205/3569* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/587* (2013.01); *A61M 2205/8206* (2013.01); *A61M 2230/201* (2013.01)

(56) References Cited

U.S. PATENT DOCUMENTS

| | | |
|---|---|---|
| 65,604 A | 6/1867 | Reynolds |
| 1,954,643 A | 4/1934 | Neuhaus |
| 2,719,797 A | 10/1955 | Rosenblatt et al. |
| 3,210,578 A | 10/1965 | Sherer |
| 3,219,533 A | 11/1965 | Mullins |
| 3,381,371 A | 5/1968 | Russell |
| 3,506,032 A | 4/1970 | Eveleigh et al. |
| 3,556,950 A | 1/1971 | Dahms et al. |
| 3,610,226 A | 10/1971 | Albisser |
| 3,775,182 A | 11/1973 | Patton et al. |
| 3,780,727 A | 12/1973 | King |
| 3,826,244 A | 7/1974 | Salcman et al. |
| 3,837,339 A | 9/1974 | Aisenberg et al. |
| 3,838,682 A | 10/1974 | Clark et al. |
| 3,874,850 A | 4/1975 | Sorensen et al. |
| 3,898,984 A | 8/1975 | Mandel et al. |
| 3,910,256 A | 10/1975 | Clark et al. |
| 3,929,971 A | 12/1975 | Roy |
| 3,933,593 A | 1/1976 | Sternberg |
| 3,943,918 A | 3/1976 | Lewis |
| 3,957,613 A | 5/1976 | Macur |
| 3,964,974 A | 6/1976 | Banauch et al. |
| 3,979,274 A | 9/1976 | Newman |
| 4,008,717 A | 2/1977 | Kowarski |
| 4,016,866 A | 4/1977 | Lawton |
| 4,024,312 A | 5/1977 | Korpman |
| 4,040,908 A | 8/1977 | Clark, Jr. |
| 4,052,754 A | 10/1977 | Homsy |
| 4,055,175 A | 10/1977 | Clemens et al. |
| 4,073,713 A | 2/1978 | Newman |
| 4,076,656 A | 2/1978 | White et al. |
| 4,109,505 A | 8/1978 | Clark et al. |
| 4,119,406 A | 10/1978 | Clemens |
| 4,136,250 A | 1/1979 | Mueller et al. |
| 4,151,845 A | 5/1979 | Clemens |
| 4,172,770 A | 10/1979 | Semersky et al. |
| 4,176,659 A | 12/1979 | Rolfe |
| 4,197,840 A | 4/1980 | Beck et al. |
| 4,197,852 A | 4/1980 | Schindler et al. |
| 4,206,755 A | 6/1980 | Klein |
| 4,215,703 A | 8/1980 | Willson |
| 4,240,438 A | 12/1980 | Updike et al. |
| 4,240,889 A | 12/1980 | Yoda et al. |
| 4,245,634 A | 1/1981 | Albisser et al. |
| 4,253,469 A | 3/1981 | Aslan |
| 4,255,500 A | 3/1981 | Hooke |
| 4,259,540 A | 3/1981 | Sabia |
| 4,265,249 A | 5/1981 | Schindler et al. |
| 4,319,578 A | 3/1982 | Enger |
| 4,327,725 A | 5/1982 | Cortese et al. |
| 4,366,040 A | 12/1982 | Marsoner et al. |
| 4,369,785 A | 1/1983 | Rehkopf et al. |
| 4,374,013 A | 2/1983 | Enfors |
| 4,388,166 A | 6/1983 | Suzuki et al. |
| 4,403,984 A | 9/1983 | Ash et al. |
| 4,415,666 A | 11/1983 | D'Orazio et al. |
| 4,431,004 A | 2/1984 | Bessman et al. |
| 4,432,366 A | 2/1984 | Margules |
| 4,436,094 A | 3/1984 | Cerami |
| 4,442,841 A | 4/1984 | Uehara et al. |
| 4,454,295 A | 6/1984 | Wittmann et al. |
| 4,457,339 A | 7/1984 | Juan et al. |
| 4,477,314 A | 10/1984 | Richter et al. |
| 4,478,222 A | 10/1984 | Koning et al. |
| 4,486,290 A | 12/1984 | Cahalan et al. |
| 4,492,575 A | 1/1985 | Mabille |
| 4,494,950 A | 1/1985 | Fischell |
| 4,506,680 A | 3/1985 | Stokes |
| 4,519,973 A | 5/1985 | Cahalan et al. |
| RE31,916 E | 6/1985 | Oswin et al. |
| 4,526,569 A | 7/1985 | Bernardi |
| 4,534,825 A | 8/1985 | Koning et al. |
| 4,535,786 A | 8/1985 | Kater |
| 4,538,616 A | 9/1985 | Rogoff |
| 4,545,382 A | 10/1985 | Higgins et al. |
| 4,554,927 A | 11/1985 | Fussell |
| 4,565,665 A | 1/1986 | Fogt |
| 4,565,666 A | 1/1986 | Cahalan et al. |
| 4,568,444 A | 2/1986 | Nakamura et al. |
| 4,571,292 A | 2/1986 | Liu et al. |
| 4,573,968 A | 3/1986 | Parker |
| 4,577,642 A | 3/1986 | Stokes |
| 4,583,976 A | 4/1986 | Ferguson |
| 4,592,824 A | 6/1986 | Smith et al. |
| 4,600,495 A | 7/1986 | Fogt |
| 4,614,514 A | 9/1986 | Carr et al. |
| 4,619,793 A | 10/1986 | Lee |
| 4,625,730 A | 12/1986 | Fountain et al. |
| 4,626,104 A | 12/1986 | Pointon et al. |
| 4,632,968 A | 12/1986 | Yokota et al. |
| RE32,361 E | 2/1987 | Duggan |
| 4,655,880 A | 4/1987 | Liu |
| 4,663,824 A | 5/1987 | Kenmochi |
| 4,671,288 A | 6/1987 | Gough |
| 4,672,970 A | 6/1987 | Uchida et al. |
| 4,680,268 A | 7/1987 | Clark, Jr. |
| 4,685,463 A | 8/1987 | Williams |
| 4,685,903 A | 8/1987 | Cable et al. |
| 4,694,861 A | 9/1987 | Goodale et al. |
| 4,702,732 A | 10/1987 | Powers et al. |
| 4,703,756 A | 11/1987 | Gough et al. |
| 4,705,503 A | 11/1987 | Dorman et al. |
| 4,711,245 A | 12/1987 | Higgins et al. |
| 4,711,251 A | 12/1987 | Stokes |
| 4,721,677 A | 1/1988 | Clark, Jr. |
| 4,726,381 A | 2/1988 | Jones |
| 4,731,726 A | 3/1988 | Allen, III |
| 4,736,748 A | 4/1988 | Nakamura et al. |
| 4,747,822 A | 5/1988 | Peabody |
| 4,750,496 A | 6/1988 | Reinhart et al. |
| 4,753,652 A | 6/1988 | Langer et al. |
| 4,755,168 A | 7/1988 | Romanelli et al. |
| 4,757,022 A | 7/1988 | Shults et al. |

(56) References Cited

U.S. PATENT DOCUMENTS

| | | |
|---|---|---|
| 4,759,828 A | 7/1988 | Young et al. |
| 4,763,648 A | 8/1988 | Wyatt |
| 4,763,658 A | 8/1988 | Jones |
| 4,777,953 A | 10/1988 | Ash et al. |
| 4,781,798 A | 11/1988 | Gough |
| 4,784,157 A | 11/1988 | Halls et al. |
| 4,786,394 A | 11/1988 | Enzer et al. |
| 4,787,398 A | 11/1988 | Garcia et al. |
| 4,789,467 A | 12/1988 | Lindsay et al. |
| 4,791,932 A | 12/1988 | Margules |
| 4,803,243 A | 2/1989 | Fujimoto et al. |
| 4,805,624 A | 2/1989 | Yao et al. |
| 4,805,625 A | 2/1989 | Wyler |
| 4,807,632 A | 2/1989 | Liess et al. |
| 4,808,089 A | 2/1989 | Buchholtz et al. |
| 4,808,292 A | 2/1989 | Kessler et al. |
| 4,809,704 A | 3/1989 | Sogawa et al. |
| 4,810,243 A | 3/1989 | Howson |
| 4,810,470 A | 3/1989 | Burkhardt et al. |
| 4,815,471 A | 3/1989 | Stobie |
| 4,820,281 A | 4/1989 | Lawler, Jr. |
| 4,822,336 A | 4/1989 | DiTraglia |
| 4,823,808 A | 4/1989 | Clegg et al. |
| 4,828,544 A | 5/1989 | Lane et al. |
| 4,830,013 A | 5/1989 | Maxwell |
| 4,831,070 A | 5/1989 | McInally et al. |
| 4,832,005 A | 5/1989 | Takamiya et al. |
| 4,832,034 A | 5/1989 | Pizziconi et al. |
| 4,834,101 A | 5/1989 | Collison et al. |
| 4,838,281 A | 6/1989 | Rogers et al. |
| 4,841,974 A | 6/1989 | Gumbrecht et al. |
| 4,849,458 A | 7/1989 | Reed et al. |
| 4,852,573 A | 8/1989 | Kennedy |
| 4,854,322 A | 8/1989 | Ash et al. |
| 4,858,615 A | 8/1989 | Meinema |
| 4,867,741 A | 9/1989 | Portnoy |
| 4,871,440 A | 10/1989 | Nagata et al. |
| 4,874,363 A | 10/1989 | Abell |
| 4,883,057 A | 11/1989 | Broderick |
| 4,883,467 A | 11/1989 | Franetzki et al. |
| 4,889,528 A | 12/1989 | Nadai et al. |
| 4,889,744 A | 12/1989 | Quaid |
| 4,890,620 A | 1/1990 | Gough |
| 4,890,621 A | 1/1990 | Hakky |
| 4,900,305 A | 2/1990 | Smith et al. |
| 4,902,294 A | 2/1990 | Gosserez |
| 4,907,857 A | 3/1990 | Giuliani et al. |
| 4,908,208 A | 3/1990 | Lee et al. |
| 4,909,786 A | 3/1990 | Gijselhart et al. |
| 4,919,114 A | 4/1990 | Miyazaki |
| 4,919,141 A | 4/1990 | Zier et al. |
| 4,919,649 A | 4/1990 | Timothy et al. |
| 4,921,477 A | 5/1990 | Davis |
| 4,921,480 A | 5/1990 | Sealfon |
| 4,925,444 A | 5/1990 | Orkin et al. |
| 4,927,407 A | 5/1990 | Dorman |
| 4,927,516 A | 5/1990 | Yamaguchi et al. |
| 4,928,694 A | 5/1990 | Maxwell |
| 4,934,369 A | 6/1990 | Maxwell |
| 4,934,375 A | 6/1990 | Cole et al. |
| 4,944,299 A | 7/1990 | Silvian |
| 4,946,439 A | 8/1990 | Eggers |
| 4,950,246 A | 8/1990 | Muller |
| 4,951,657 A | 8/1990 | Pfister et al. |
| 4,951,669 A | 8/1990 | Maxwell et al. |
| 4,953,552 A | 9/1990 | DeMarzo |
| 4,957,483 A | 9/1990 | Gonser et al. |
| 4,963,595 A | 10/1990 | Ward et al. |
| 4,966,579 A | 10/1990 | Polaschegg |
| 4,967,940 A | 11/1990 | Blette et al. |
| 4,970,145 A | 11/1990 | Bennetto et al. |
| 4,973,320 A | 11/1990 | Brenner et al. |
| 4,974,592 A | 12/1990 | Branco |
| 4,974,929 A | 12/1990 | Curry |
| 4,975,636 A | 12/1990 | Desautels |
| 4,976,687 A | 12/1990 | Martin |
| 4,979,509 A | 12/1990 | Hakky |
| 4,984,929 A | 1/1991 | Rock et al. |
| 4,986,671 A | 1/1991 | Sun et al. |
| 4,988,341 A | 1/1991 | Columbus et al. |
| 4,989,607 A | 2/1991 | Keusch et al. |
| 4,992,794 A | 2/1991 | Brouwers |
| 4,994,026 A | 2/1991 | Fecondini |
| 4,994,167 A | 2/1991 | Shults et al. |
| 4,997,627 A | 3/1991 | Bergkuist et al. |
| 5,002,055 A | 3/1991 | Merki et al. |
| 5,002,572 A | 3/1991 | Picha |
| 5,006,050 A | 4/1991 | Cooke et al. |
| 5,006,111 A | 4/1991 | Inokuchi et al. |
| 5,007,929 A | 4/1991 | Quaid |
| 5,009,251 A | 4/1991 | Pike et al. |
| 5,019,974 A | 5/1991 | Beckers |
| 5,026,348 A | 6/1991 | Venegas |
| 5,030,199 A | 7/1991 | Barwick et al. |
| 5,030,333 A | 7/1991 | Clark, Jr. |
| 5,034,112 A | 7/1991 | Murase et al. |
| 5,035,711 A | 7/1991 | Aoki et al. |
| 5,041,092 A | 8/1991 | Barwick |
| 5,045,057 A | 9/1991 | Van Driessche et al. |
| 5,046,496 A | 9/1991 | Betts et al. |
| 5,048,525 A | 9/1991 | Maxwell |
| 5,050,612 A | 9/1991 | Matsumura |
| 5,055,171 A | 10/1991 | Peck |
| 5,055,198 A | 10/1991 | Shettigar |
| 5,059,654 A | 10/1991 | Hou et al. |
| 5,067,491 A | 11/1991 | Taylor, II et al. |
| 5,068,536 A | 11/1991 | Rosenthal |
| 5,070,169 A | 12/1991 | Robertson et al. |
| 5,077,476 A | 12/1991 | Rosenthal |
| 5,088,981 A | 2/1992 | Howson et al. |
| 5,089,421 A | 2/1992 | Dieffenbach |
| 5,096,669 A | 3/1992 | Lauks et al. |
| 5,097,834 A | 3/1992 | Skrabal |
| 5,098,377 A | 3/1992 | Borsanyi et al. |
| 5,101,814 A | 4/1992 | Palti |
| 5,108,819 A | 4/1992 | Heller et al. |
| 5,109,850 A | 5/1992 | Blanco et al. |
| 5,112,301 A | 5/1992 | Fenton, Jr. et al. |
| 5,116,313 A | 5/1992 | McGregor |
| 5,127,405 A | 7/1992 | Alcala et al. |
| 5,137,028 A | 8/1992 | Nishimura |
| 5,140,985 A | 8/1992 | Schroeder et al. |
| 5,145,565 A | 9/1992 | Kater et al. |
| 5,152,746 A | 10/1992 | Atkinson et al. |
| 5,153,827 A | 10/1992 | Coutre et al. |
| 5,160,418 A | 11/1992 | Mullen |
| 5,161,532 A | 11/1992 | Joseph |
| 5,165,406 A | 11/1992 | Wong |
| 5,165,407 A | 11/1992 | Wilson et al. |
| 5,174,291 A | 12/1992 | Schoonen et al. |
| 5,176,632 A | 1/1993 | Bernardi |
| 5,176,658 A | 1/1993 | Ranford |
| 5,178,142 A | 1/1993 | Harjunmaa et al. |
| 5,182,004 A | 1/1993 | Kohno |
| 5,188,591 A | 2/1993 | Dorsey, III |
| 5,190,041 A | 3/1993 | Palti |
| 5,195,963 A | 3/1993 | Yafuso et al. |
| 5,198,771 A | 3/1993 | Fidler et al. |
| 5,208,147 A | 5/1993 | Kagenow et al. |
| 5,208,313 A | 5/1993 | Krishnan |
| 5,220,917 A | 6/1993 | Cammilli et al. |
| 5,220,920 A | 6/1993 | Gharib |
| 5,224,929 A | 7/1993 | Remiszewski |
| 5,225,063 A | 7/1993 | Gumbrecht et al. |
| 5,232,434 A | 8/1993 | Inagaki et al. |
| 5,235,003 A | 8/1993 | Ward et al. |
| 5,243,982 A | 9/1993 | Mostl et al. |
| 5,243,983 A | 9/1993 | Tarr et al. |
| 5,249,576 A | 10/1993 | Goldberger et al. |
| 5,251,126 A | 10/1993 | Kahn et al. |
| 5,254,102 A | 10/1993 | Ogawa |
| 5,262,305 A | 11/1993 | Heller et al. |
| 5,265,594 A | 11/1993 | Olsson et al. |
| 5,266,179 A | 11/1993 | Nankai et al. |

(56) References Cited

U.S. PATENT DOCUMENTS

| | | |
|---|---|---|
| 5,269,891 A | 12/1993 | Colin |
| 5,271,736 A | 12/1993 | Picha |
| 5,271,815 A | 12/1993 | Wong |
| 5,279,294 A | 1/1994 | Anderson et al. |
| 5,281,319 A | 1/1994 | Kaneko et al. |
| 5,282,848 A | 2/1994 | Schmitt |
| 5,284,140 A | 2/1994 | Allen et al. |
| 5,284,570 A | 2/1994 | Savage et al. |
| 5,285,513 A | 2/1994 | Kaufman et al. |
| 5,287,753 A | 2/1994 | Routh et al. |
| 5,298,022 A | 3/1994 | Bernardi |
| 5,299,571 A | 4/1994 | Mastrototaro |
| 5,302,093 A | 4/1994 | Owens et al. |
| 5,304,468 A | 4/1994 | Phillips et al. |
| 5,307,263 A | 4/1994 | Brown |
| 5,310,469 A | 5/1994 | Cunningham et al. |
| 5,311,908 A | 5/1994 | Barone et al. |
| 5,312,361 A | 5/1994 | Zadini et al. |
| 5,314,471 A | 5/1994 | Brauker et al. |
| 5,316,008 A | 5/1994 | Suga et al. |
| 5,316,452 A | 5/1994 | Bogen et al. |
| 5,318,511 A | 6/1994 | Riquier et al. |
| 5,322,063 A | 6/1994 | Allen et al. |
| 5,324,322 A | 6/1994 | Grill, Jr. et al. |
| 5,326,356 A | 7/1994 | Della Valle et al. |
| 5,326,449 A | 7/1994 | Cunningham |
| 5,330,521 A | 7/1994 | Cohen |
| 5,330,634 A | 7/1994 | Wong et al. |
| 5,331,555 A | 7/1994 | Hashimoto et al. |
| 5,335,658 A | 8/1994 | Bedingham |
| 5,337,747 A | 8/1994 | Neftel |
| 5,342,409 A | 8/1994 | Mullett |
| 5,342,789 A | 8/1994 | Chick et al. |
| 5,343,869 A | 9/1994 | Pross et al. |
| 5,344,454 A | 9/1994 | Clarke et al. |
| 5,345,932 A | 9/1994 | Yafuso et al. |
| 5,348,788 A | 9/1994 | White |
| 5,352,348 A | 10/1994 | Young et al. |
| 5,352,351 A | 10/1994 | White et al. |
| 5,354,272 A | 10/1994 | Swendson et al. |
| 5,354,449 A | 10/1994 | Band et al. |
| 5,356,375 A | 10/1994 | Higley |
| 5,356,378 A | 10/1994 | Doan |
| 5,356,786 A | 10/1994 | Heller et al. |
| 5,368,028 A | 11/1994 | Palti |
| 5,368,224 A | 11/1994 | Richardson et al. |
| 5,368,562 A | 11/1994 | Blomquist et al. |
| 5,372,133 A | 12/1994 | Hogen Esch |
| 5,372,135 A | 12/1994 | Mendelson et al. |
| 5,372,709 A | 12/1994 | Hood |
| 5,376,070 A | 12/1994 | Purvis et al. |
| 5,378,229 A | 1/1995 | Layer et al. |
| 5,380,268 A | 1/1995 | Wheeler |
| 5,380,491 A | 1/1995 | Carver, Jr. et al. |
| 5,380,536 A | 1/1995 | Hubbell et al. |
| 5,380,665 A | 1/1995 | Cusack et al. |
| 5,384,028 A | 1/1995 | Ito |
| 5,390,671 A | 2/1995 | Lord et al. |
| 5,391,250 A | 2/1995 | Cheney, II et al. |
| 5,397,848 A | 3/1995 | Yang et al. |
| 5,405,510 A | 4/1995 | Betts et al. |
| 5,411,052 A | 5/1995 | Murray |
| 5,411,647 A | 5/1995 | Johnson et al. |
| 5,411,866 A | 5/1995 | Luong et al. |
| 5,417,206 A | 5/1995 | Kaneyoshi |
| 5,421,328 A | 6/1995 | Bedingham |
| 5,421,923 A | 6/1995 | Clarke et al. |
| 5,423,738 A | 6/1995 | Robinson et al. |
| 5,423,749 A | 6/1995 | Merte et al. |
| 5,428,123 A | 6/1995 | Ward et al. |
| 5,429,485 A | 7/1995 | Dodge |
| 5,429,602 A | 7/1995 | Hauser |
| 5,429,735 A | 7/1995 | Johnson et al. |
| 5,431,160 A | 7/1995 | Wilkins |
| 5,431,174 A | 7/1995 | Knute |
| 5,431,921 A | 7/1995 | Thombre |
| 5,434,412 A | 7/1995 | Sodickson et al. |
| 5,437,635 A | 8/1995 | Fields et al. |
| 5,438,984 A | 8/1995 | Schoendorfer |
| 5,443,508 A | 8/1995 | Giampapa |
| 5,445,610 A | 8/1995 | Evert |
| 5,448,992 A | 9/1995 | Kupershmidt |
| 5,451,260 A | 9/1995 | Versteeg et al. |
| 5,453,278 A | 9/1995 | Chan et al. |
| 5,458,631 A | 10/1995 | Xavier |
| 5,462,051 A | 10/1995 | Oka et al. |
| 5,462,064 A | 10/1995 | D'Angelo et al. |
| 5,466,356 A | 11/1995 | Schneider et al. |
| 5,469,846 A | 11/1995 | Khan |
| 5,474,552 A | 12/1995 | Palti |
| 5,476,776 A | 12/1995 | Wilkins |
| 5,482,008 A | 1/1996 | Stafford et al. |
| 5,482,446 A | 1/1996 | Williamson et al. |
| 5,482,473 A | 1/1996 | Lord et al. |
| 5,484,404 A | 1/1996 | Schulman et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,502,396 A | 3/1996 | Desarzens et al. |
| 5,505,828 A | 4/1996 | Wong et al. |
| 5,507,288 A | 4/1996 | Bocker et al. |
| 5,508,203 A | 4/1996 | Fuller et al. |
| 5,509,888 A | 4/1996 | Miller |
| 5,512,046 A | 4/1996 | Pusinelli et al. |
| 5,512,055 A | 4/1996 | Domb et al. |
| 5,512,248 A | 4/1996 | Van |
| 5,513,636 A | 5/1996 | Palti |
| 5,514,253 A | 5/1996 | Davis et al. |
| 5,515,851 A | 5/1996 | Goldstein |
| 5,518,601 A | 5/1996 | Foos et al. |
| 5,527,288 A | 6/1996 | Gross et al. |
| 5,531,679 A | 7/1996 | Schulman et al. |
| 5,531,878 A | 7/1996 | Vadgama et al. |
| 5,536,249 A | 7/1996 | Castellano et al. |
| 5,538,511 A | 7/1996 | Van Antwerp |
| 5,540,828 A | 7/1996 | Yacynych |
| 5,545,220 A | 8/1996 | Andrews et al. |
| 5,545,223 A | 8/1996 | Neuenfeldt et al. |
| 5,549,547 A | 8/1996 | Cohen et al. |
| 5,549,548 A | 8/1996 | Larsson |
| 5,549,569 A | 8/1996 | Lynn et al. |
| 5,549,651 A | 8/1996 | Lynn |
| 5,551,850 A | 9/1996 | Williamson et al. |
| 5,553,616 A | 9/1996 | Ham et al. |
| 5,554,339 A | 9/1996 | Cozzette et al. |
| 5,561,615 A | 10/1996 | Kuo et al. |
| 5,562,614 A | 10/1996 | O'Donnell |
| 5,562,615 A | 10/1996 | Nassif |
| 5,564,439 A | 10/1996 | Picha |
| 5,568,806 A | 10/1996 | Cheney, II et al. |
| 5,569,186 A | 10/1996 | Lord et al. |
| 5,569,188 A | 10/1996 | Mackool |
| 5,569,219 A | 10/1996 | Hakki et al. |
| 5,569,462 A | 10/1996 | Martinson et al. |
| 5,575,293 A | 11/1996 | Miller et al. |
| 5,575,930 A | 11/1996 | Tietje-Girault et al. |
| 5,577,499 A | 11/1996 | Teves |
| 5,582,184 A | 12/1996 | Erickson et al. |
| 5,582,593 A | 12/1996 | Hultman |
| 5,584,813 A | 12/1996 | Livingston et al. |
| 5,584,876 A | 12/1996 | Bruchman et al. |
| 5,586,553 A | 12/1996 | Halili et al. |
| 5,589,133 A | 12/1996 | Suzuki |
| 5,590,651 A | 1/1997 | Shaffer et al. |
| 5,593,440 A | 1/1997 | Brauker et al. |
| 5,609,572 A | 3/1997 | Lang |
| 5,611,900 A | 3/1997 | Worden et al. |
| 5,624,409 A | 4/1997 | Seale |
| 5,624,537 A | 4/1997 | Turner et al. |
| 5,626,563 A | 5/1997 | Dodge et al. |
| 5,628,619 A | 5/1997 | Wilson |
| 5,628,890 A | 5/1997 | Carter et al. |
| 5,637,083 A | 6/1997 | Bertrand et al. |

(56) References Cited

U.S. PATENT DOCUMENTS

| | | |
|---|---|---|
| 5,640,470 A | 6/1997 | Iyer et al. |
| 5,643,195 A | 7/1997 | Drevet et al. |
| 5,651,767 A | 7/1997 | Schulman et al. |
| 5,653,756 A | 8/1997 | Clarke et al. |
| 5,653,863 A | 8/1997 | Genshaw et al. |
| 5,658,250 A | 8/1997 | Blomquist et al. |
| 5,660,163 A | 8/1997 | Schulman et al. |
| 5,660,565 A | 8/1997 | Williams |
| 5,665,061 A | 9/1997 | Antwiler |
| 5,665,065 A | 9/1997 | Colman et al. |
| 5,667,504 A | 9/1997 | Baumann et al. |
| 5,673,694 A | 10/1997 | Rivers |
| 5,674,289 A | 10/1997 | Fournier et al. |
| 5,676,651 A | 10/1997 | Larson, Jr. et al. |
| 5,676,820 A | 10/1997 | Wang et al. |
| 5,681,572 A | 10/1997 | Seare, Jr. |
| 5,682,884 A | 11/1997 | Hill et al. |
| 5,683,562 A | 11/1997 | Schaffar et al. |
| 5,686,829 A | 11/1997 | Girault |
| 5,688,239 A | 11/1997 | Walker |
| 5,688,244 A | 11/1997 | Lang |
| 5,695,623 A | 12/1997 | Michel et al. |
| 5,696,314 A | 12/1997 | McCaffrey et al. |
| 5,697,366 A | 12/1997 | Kimball et al. |
| 5,697,899 A | 12/1997 | Hillman et al. |
| 5,704,354 A | 1/1998 | Preidel et al. |
| 5,706,807 A | 1/1998 | Picha |
| 5,711,861 A | 1/1998 | Ward et al. |
| 5,713,888 A | 2/1998 | Neuenfeldt et al. |
| 5,730,654 A | 3/1998 | Brown |
| 5,733,259 A | 3/1998 | Valcke et al. |
| 5,733,336 A | 3/1998 | Neuenfeldt et al. |
| 5,743,262 A | 4/1998 | Lepper, Jr. et al. |
| 5,749,832 A | 5/1998 | Vadgama et al. |
| 5,749,907 A | 5/1998 | Mann |
| 5,755,692 A | 5/1998 | Manicom |
| 5,756,632 A | 5/1998 | Ward et al. |
| 5,758,643 A | 6/1998 | Wong et al. |
| 5,763,760 A | 6/1998 | Gumbrecht et al. |
| 5,771,890 A | 6/1998 | Tamada |
| 5,773,286 A | 6/1998 | Dionne et al. |
| 5,776,324 A | 7/1998 | Usala |
| 5,779,665 A | 7/1998 | Mastrototaro et al. |
| 5,781,455 A | 7/1998 | Hyodo |
| 5,782,880 A | 7/1998 | Lahtinen et al. |
| 5,782,912 A | 7/1998 | Brauker et al. |
| 5,787,900 A | 8/1998 | Butler et al. |
| 5,791,344 A | 8/1998 | Schulman et al. |
| 5,791,880 A | 8/1998 | Wilson |
| 5,795,453 A | 8/1998 | Gilmartin |
| 5,795,774 A | 8/1998 | Matsumoto et al. |
| 5,798,065 A | 8/1998 | Picha |
| 5,800,383 A | 9/1998 | Chandler et al. |
| 5,800,420 A | 9/1998 | Gross et al. |
| 5,800,529 A | 9/1998 | Brauker et al. |
| 5,806,517 A | 9/1998 | Gerhardt et al. |
| 5,807,274 A | 9/1998 | Henning et al. |
| 5,807,312 A | 9/1998 | Dzwonkiewicz |
| 5,807,375 A | 9/1998 | Gross et al. |
| 5,807,406 A | 9/1998 | Brauker et al. |
| 5,810,770 A | 9/1998 | Chin et al. |
| 5,811,487 A | 9/1998 | Schulz, Jr. et al. |
| 5,814,599 A | 9/1998 | Mitragotri et al. |
| 5,820,589 A | 10/1998 | Torgerson et al. |
| 5,820,622 A | 10/1998 | Gross et al. |
| 5,822,715 A | 10/1998 | Worthington et al. |
| 5,836,887 A | 11/1998 | Oka et al. |
| 5,836,989 A | 11/1998 | Shelton |
| 5,837,454 A | 11/1998 | Cozzette et al. |
| 5,837,728 A | 11/1998 | Purcell |
| 5,840,026 A | 11/1998 | Uber, III et al. |
| 5,840,148 A | 11/1998 | Campbell et al. |
| 5,848,991 A | 12/1998 | Gross et al. |
| 5,851,197 A | 12/1998 | Marano et al. |
| 5,851,229 A | 12/1998 | Lentz et al. |
| 5,858,365 A | 1/1999 | Faller |
| 5,858,747 A | 1/1999 | Schinstine et al. |
| 5,861,019 A | 1/1999 | Sun et al. |
| 5,863,400 A | 1/1999 | Drummond et al. |
| 5,871,514 A | 2/1999 | Wiklund et al. |
| 5,873,862 A | 2/1999 | Lopez |
| 5,876,370 A | 3/1999 | Blomquist |
| 5,879,713 A | 3/1999 | Roth et al. |
| 5,882,494 A | 3/1999 | Van Antwerp |
| 5,895,235 A | 4/1999 | Droz |
| 5,897,525 A | 4/1999 | Dey et al. |
| 5,897,578 A | 4/1999 | Wiklund et al. |
| 5,899,855 A | 5/1999 | Brown |
| 5,904,666 A | 5/1999 | DeDecker et al. |
| 5,904,708 A | 5/1999 | Goedeke |
| 5,911,219 A | 6/1999 | Aylsworth et al. |
| 5,913,998 A | 6/1999 | Butler et al. |
| 5,914,026 A | 6/1999 | Blubaugh, Jr. et al. |
| 5,917,346 A | 6/1999 | Gord |
| 5,919,215 A | 7/1999 | Wiklund et al. |
| 5,919,216 A | 7/1999 | Houben et al. |
| 5,921,951 A | 7/1999 | Morris |
| 5,925,021 A | 7/1999 | Castellano et al. |
| 5,928,155 A | 7/1999 | Eggers et al. |
| 5,928,182 A | 7/1999 | Kraus et al. |
| 5,928,189 A | 7/1999 | Phillips et al. |
| 5,928,195 A | 7/1999 | Malamud et al. |
| 5,931,814 A | 8/1999 | Alex et al. |
| 5,932,175 A | 8/1999 | Knute et al. |
| 5,933,136 A | 8/1999 | Brown |
| 5,935,785 A | 8/1999 | Reber et al. |
| 5,938,636 A | 8/1999 | Kramer et al. |
| 5,944,661 A | 8/1999 | Swette et al. |
| 5,947,911 A | 9/1999 | Wong et al. |
| 5,954,643 A | 9/1999 | VanAntwerp et al. |
| 5,954,954 A | 9/1999 | Houck et al. |
| 5,957,854 A | 9/1999 | Besson et al. |
| 5,957,903 A | 9/1999 | Mirzaee et al. |
| 5,961,451 A | 10/1999 | Reber et al. |
| 5,963,132 A | 10/1999 | Yoakum |
| 5,964,745 A | 10/1999 | Lyles et al. |
| 5,964,993 A | 10/1999 | Blubaugh, Jr. et al. |
| 5,965,125 A | 10/1999 | Mineau-Hanschke |
| 5,965,380 A | 10/1999 | Heller et al. |
| 5,971,922 A | 10/1999 | Arita et al. |
| 5,972,369 A | 10/1999 | Roorda et al. |
| 5,976,085 A | 11/1999 | Kimball et al. |
| 5,987,352 A | 11/1999 | Klein et al. |
| 5,995,208 A | 11/1999 | Sarge et al. |
| 5,995,860 A | 11/1999 | Sun et al. |
| 5,997,501 A | 12/1999 | Gross et al. |
| 5,999,848 A | 12/1999 | Gord et al. |
| 6,001,067 A | 12/1999 | Shults et al. |
| 6,001,471 A | 12/1999 | Bries et al. |
| 6,002,954 A | 12/1999 | Van Antwerp et al. |
| 6,007,845 A | 12/1999 | Domb et al. |
| 6,011,984 A | 1/2000 | Van Antwerp et al. |
| 6,014,577 A | 1/2000 | Henning et al. |
| 6,016,448 A | 1/2000 | Busacker et al. |
| 6,017,435 A | 1/2000 | Hassard et al. |
| 6,023,629 A | 2/2000 | Tamada |
| 6,024,720 A | 2/2000 | Chandler et al. |
| 6,027,445 A | 2/2000 | Von Bahr |
| 6,027,479 A | 2/2000 | Alei et al. |
| 6,032,059 A | 2/2000 | Henning et al. |
| 6,032,667 A | 3/2000 | Heinonen |
| 6,036,924 A | 3/2000 | Simons et al. |
| 6,043,328 A | 3/2000 | Domschke et al. |
| 6,045,671 A | 4/2000 | Wu et al. |
| 6,048,691 A | 4/2000 | Maracas |
| 6,049,727 A | 4/2000 | Crothall |
| 6,059,946 A | 5/2000 | Yukawa et al. |
| 6,063,637 A | 5/2000 | Arnold et al. |
| 6,066,088 A | 5/2000 | Davis |
| 6,066,448 A | 5/2000 | Wohlstadter et al. |
| 6,071,391 A | 6/2000 | Gotoh et al. |
| 6,077,299 A | 6/2000 | Adelberg et al. |
| 6,080,583 A | 6/2000 | Von Bahr |
| 6,081,735 A | 6/2000 | Diab et al. |

(56) References Cited

U.S. PATENT DOCUMENTS

| | | |
|---|---|---|
| 6,081,736 A | 6/2000 | Colvin et al. |
| 6,083,523 A | 7/2000 | Dionne et al. |
| 6,083,710 A | 7/2000 | Heller et al. |
| 6,088,608 A | 7/2000 | Schulman et al. |
| 6,090,087 A | 7/2000 | Tsukada et al. |
| 6,091,975 A | 7/2000 | Daddona et al. |
| 6,093,172 A | 7/2000 | Funderburk et al. |
| 6,099,511 A | 8/2000 | Devos et al. |
| 6,103,033 A | 8/2000 | Say et al. |
| 6,103,533 A | 8/2000 | Hassard et al. |
| 6,107,083 A | 8/2000 | Collins et al. |
| 6,115,634 A | 9/2000 | Donders et al. |
| 6,117,290 A | 9/2000 | Say et al. |
| 6,120,676 A | 9/2000 | Heller et al. |
| 6,121,009 A | 9/2000 | Heller et al. |
| 6,122,536 A | 9/2000 | Sun et al. |
| 6,123,827 A | 9/2000 | Wong et al. |
| 6,127,154 A | 10/2000 | Mosbach et al. |
| 6,128,519 A | 10/2000 | Say |
| 6,129,891 A | 10/2000 | Rolander et al. |
| 6,134,461 A | 10/2000 | Say et al. |
| 6,135,978 A | 10/2000 | Houben et al. |
| 6,142,939 A | 11/2000 | Eppstein et al. |
| 6,144,869 A | 11/2000 | Berner et al. |
| 6,159,186 A | 12/2000 | Wickham et al. |
| 6,162,201 A | 12/2000 | Cohen et al. |
| 6,162,611 A | 12/2000 | Heller et al. |
| 6,163,720 A | 12/2000 | Gyory et al. |
| 6,164,921 A | 12/2000 | Moubayed et al. |
| 6,165,154 A | 12/2000 | Gray et al. |
| 6,167,614 B1 | 1/2001 | Tuttle et al. |
| 6,168,568 B1 | 1/2001 | Gavriely |
| 6,169,155 B1 | 1/2001 | Alvarez et al. |
| 6,171,276 B1 | 1/2001 | Lippe et al. |
| 6,175,752 B1 | 1/2001 | Say et al. |
| 6,180,416 B1 | 1/2001 | Kurnik et al. |
| 6,183,437 B1 | 2/2001 | Walker |
| 6,187,062 B1 | 2/2001 | Oweis et al. |
| 6,189,536 B1 | 2/2001 | Martinez et al. |
| 6,191,860 B1 | 2/2001 | Klinger et al. |
| 6,192,891 B1 | 2/2001 | Gravel et al. |
| 6,201,980 B1 | 3/2001 | Darrow et al. |
| 6,201,993 B1 | 3/2001 | Kruse et al. |
| 6,206,856 B1 | 3/2001 | Mahurkar |
| 6,208,894 B1 | 3/2001 | Schulman et al. |
| 6,212,416 B1 | 4/2001 | Ward et al. |
| 6,212,424 B1 | 4/2001 | Robinson |
| 6,213,739 B1 | 4/2001 | Phallen et al. |
| 6,214,185 B1 | 4/2001 | Offenbacher et al. |
| 6,219,574 B1 | 4/2001 | Cormier et al. |
| 6,223,080 B1 | 4/2001 | Thompson |
| 6,223,083 B1 | 4/2001 | Rosar |
| 6,230,059 B1 | 5/2001 | Duffin |
| 6,231,879 B1 | 5/2001 | Li et al. |
| 6,232,783 B1 | 5/2001 | Merrill |
| 6,233,080 B1 | 5/2001 | Brenner et al. |
| 6,234,964 B1 | 5/2001 | Iliff |
| 6,241,863 B1 | 6/2001 | Monbouquette |
| 6,248,067 B1 | 6/2001 | Causey, III et al. |
| 6,248,077 B1 | 6/2001 | Elson et al. |
| 6,248,093 B1 | 6/2001 | Moberg |
| 6,254,586 B1 | 7/2001 | Mann et al. |
| 6,256,522 B1 | 7/2001 | Schultz |
| 6,259,937 B1 | 7/2001 | Schulman et al. |
| 6,263,222 B1 | 7/2001 | Diab et al. |
| 6,264,825 B1 | 7/2001 | Blackburn et al. |
| 6,270,478 B1 | 8/2001 | Mernoee |
| 6,271,332 B1 | 8/2001 | Lohmann et al. |
| 6,272,364 B1 | 8/2001 | Kurnik |
| 6,272,382 B1 | 8/2001 | Faltys et al. |
| 6,272,480 B1 | 8/2001 | Tresp et al. |
| 6,274,285 B1 | 8/2001 | Gries et al. |
| 6,275,717 B1 | 8/2001 | Gross et al. |
| 6,280,408 B1 | 8/2001 | Sipin |
| 6,281,015 B1 | 8/2001 | Mooney et al. |
| 6,284,478 B1 | 9/2001 | Heller et al. |
| 6,293,925 B1 | 9/2001 | Safabash et al. |
| 6,298,254 B2 | 10/2001 | Tamada |
| 6,299,578 B1 | 10/2001 | Kurnik et al. |
| 6,299,583 B1 | 10/2001 | Eggers et al. |
| 6,300,002 B1 | 10/2001 | Webb et al. |
| 6,302,855 B1 | 10/2001 | Lav et al. |
| 6,309,351 B1 | 10/2001 | Kurnik et al. |
| 6,309,384 B1 | 10/2001 | Harrington et al. |
| 6,309,884 B1 | 10/2001 | Cooper et al. |
| 6,312,388 B1 | 11/2001 | Marcovecchio et al. |
| 6,315,738 B1 | 11/2001 | Nishikawa et al. |
| 6,325,978 B1 | 12/2001 | Labuda et al. |
| 6,326,160 B1 | 12/2001 | Dunn et al. |
| 6,329,161 B1 | 12/2001 | Heller et al. |
| 6,329,929 B1 | 12/2001 | Weijand et al. |
| 6,330,464 B1 | 12/2001 | Colvin, Jr. et al. |
| 6,343,225 B1 | 1/2002 | Clark, Jr. |
| 6,356,776 B1 | 3/2002 | Berner et al. |
| 6,358,225 B1 | 3/2002 | Butterfield |
| 6,365,670 B1 | 4/2002 | Fry |
| 6,366,794 B1 | 4/2002 | Moussy et al. |
| 6,368,274 B1 | 4/2002 | Van Antwerp et al. |
| 6,370,941 B2 | 4/2002 | Nakamura et al. |
| 6,372,244 B1 | 4/2002 | Antanavich et al. |
| 6,379,301 B1 | 4/2002 | Worthington et al. |
| 6,379,317 B1 | 4/2002 | Kintzig et al. |
| 6,383,478 B1 | 5/2002 | Prokop et al. |
| 6,387,709 B1 | 5/2002 | Mason et al. |
| 6,391,019 B1 | 5/2002 | Ito |
| 6,400,974 B1 | 6/2002 | Lesho |
| 6,402,703 B1 | 6/2002 | Kensey et al. |
| 6,403,944 B1 | 6/2002 | MacKenzie et al. |
| 6,406,066 B1 | 6/2002 | Uegane |
| 6,407,195 B2 | 6/2002 | Sherman et al. |
| 6,409,674 B1 | 6/2002 | Brockway et al. |
| 6,413,393 B1 | 7/2002 | Van Antwerp et al. |
| 6,416,651 B1 | 7/2002 | Millar |
| 6,424,847 B1 | 7/2002 | Mastrototaro et al. |
| 6,430,437 B1 | 8/2002 | Marro |
| 6,447,448 B1 | 9/2002 | Ishikawa et al. |
| 6,447,542 B1 | 9/2002 | Weadock |
| 6,459,917 B1 | 10/2002 | Gowda et al. |
| 6,461,331 B1 | 10/2002 | Van Antwerp |
| 6,461,496 B1 | 10/2002 | Feldman et al. |
| 6,464,849 B1 | 10/2002 | Say et al. |
| 6,466,810 B1 | 10/2002 | Ward et al. |
| 6,467,480 B1 | 10/2002 | Meier et al. |
| 6,471,689 B1 | 10/2002 | Joseph et al. |
| 6,474,360 B1 | 11/2002 | Ito |
| 6,475,750 B1 | 11/2002 | Han et al. |
| 6,477,392 B1 | 11/2002 | Honigs et al. |
| 6,477,395 B2 | 11/2002 | Schulman et al. |
| 6,481,440 B2 | 11/2002 | Gielen et al. |
| 6,484,045 B1 | 11/2002 | Holker et al. |
| 6,484,046 B1 | 11/2002 | Say et al. |
| 6,485,449 B2 | 11/2002 | Ito |
| 6,488,652 B1 | 12/2002 | Weijand et al. |
| 6,494,830 B1 | 12/2002 | Wessel |
| 6,494,879 B2 | 12/2002 | Lennox et al. |
| 6,497,729 B1 | 12/2002 | Moussy et al. |
| 6,498,043 B1 | 12/2002 | Schulman et al. |
| 6,498,941 B1 | 12/2002 | Jackson |
| 6,501,976 B1 | 12/2002 | Sohrab |
| 6,510,239 B1 | 1/2003 | Wieres et al. |
| 6,510,329 B2 | 1/2003 | Heckel |
| 6,512,939 B1 | 1/2003 | Colvin et al. |
| 6,514,718 B2 | 2/2003 | Heller et al. |
| 6,517,508 B1 | 2/2003 | Utterberg et al. |
| 6,520,326 B2 | 2/2003 | McIvor et al. |
| 6,520,477 B2 | 2/2003 | Trimmer |
| 6,520,937 B2 | 2/2003 | Hart et al. |
| 6,520,997 B1 | 2/2003 | Pekkarinen et al. |
| 6,526,298 B1 | 2/2003 | Khalil et al. |
| 6,527,729 B1 | 3/2003 | Turcott |
| 6,534,711 B1 | 3/2003 | Pollack |
| 6,536,433 B1 | 3/2003 | Cewers |
| 6,537,318 B1 | 3/2003 | Ita et al. |
| 6,541,266 B2 | 4/2003 | Modzelewski et al. |

(56) References Cited

U.S. PATENT DOCUMENTS

| | | |
|---|---|---|
| 6,542,765 B1 | 4/2003 | Guy et al. |
| 6,544,212 B2 * | 4/2003 | Galley ............... A61B 5/7275 604/504 |
| 6,545,085 B2 | 4/2003 | Kilgour et al. |
| 6,546,268 B1 | 4/2003 | Ishikawa et al. |
| 6,546,269 B1 | 4/2003 | Kurnik |
| 6,549,796 B2 | 4/2003 | Sohrab |
| 6,551,496 B1 | 4/2003 | Moles et al. |
| 6,553,241 B2 | 4/2003 | Mannheimer et al. |
| 6,553,244 B2 | 4/2003 | Lesho et al. |
| 6,554,805 B2 | 4/2003 | Hiejima |
| 6,554,822 B1 | 4/2003 | Holschneider et al. |
| 6,558,320 B1 | 5/2003 | Causey, III et al. |
| 6,558,321 B1 | 5/2003 | Burd et al. |
| 6,558,347 B1 | 5/2003 | Jhuboo et al. |
| 6,558,351 B1 | 5/2003 | Steil et al. |
| 6,558,955 B1 | 5/2003 | Kristal et al. |
| 6,561,978 B1 | 5/2003 | Conn et al. |
| 6,562,001 B2 | 5/2003 | Lebel et al. |
| 6,565,509 B1 | 5/2003 | Say et al. |
| 6,565,535 B2 | 5/2003 | Zaias et al. |
| 6,565,807 B1 | 5/2003 | Patterson et al. |
| 6,569,195 B2 | 5/2003 | Yang et al. |
| 6,569,521 B1 | 5/2003 | Sheridan et al. |
| 6,571,128 B2 | 5/2003 | Lebel et al. |
| 6,572,545 B2 | 6/2003 | Knobbe et al. |
| 6,572,579 B1 | 6/2003 | Raghavan et al. |
| 6,574,490 B2 | 6/2003 | Abbink et al. |
| 6,575,905 B2 | 6/2003 | Knobbe et al. |
| 6,577,899 B2 | 6/2003 | Lebel et al. |
| 6,579,257 B1 | 6/2003 | Elgas et al. |
| 6,579,498 B1 | 6/2003 | Eglise |
| 6,579,690 B1 | 6/2003 | Bonnecaze et al. |
| 6,585,644 B2 | 7/2003 | Lebel et al. |
| 6,585,675 B1 | 7/2003 | O'Mahony et al. |
| 6,585,763 B1 | 7/2003 | Keilman et al. |
| 6,587,705 B1 | 7/2003 | Kim et al. |
| 6,589,229 B1 | 7/2003 | Connelly et al. |
| 6,591,125 B1 | 7/2003 | Buse et al. |
| 6,594,514 B2 | 7/2003 | Berner et al. |
| 6,595,756 B2 | 7/2003 | Gray et al. |
| 6,595,919 B2 | 7/2003 | Berner et al. |
| 6,602,221 B1 | 8/2003 | Saravia et al. |
| 6,605,072 B2 | 8/2003 | Struys et al. |
| 6,607,509 B2 | 8/2003 | Bobroff et al. |
| 6,609,071 B2 | 8/2003 | Shapiro et al. |
| 6,612,984 B1 | 9/2003 | Kerr, II |
| 6,613,379 B2 | 9/2003 | Ward et al. |
| 6,615,061 B1 | 9/2003 | Khalil et al. |
| 6,615,078 B1 | 9/2003 | Burson et al. |
| 6,618,603 B2 | 9/2003 | Varalli et al. |
| 6,618,934 B1 | 9/2003 | Feldman et al. |
| 6,620,138 B1 | 9/2003 | Marrgi et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,642,015 B2 | 11/2003 | Vachon et al. |
| 6,645,181 B1 | 11/2003 | Lavi et al. |
| 6,648,821 B2 | 11/2003 | Lebel et al. |
| 6,653,091 B1 | 11/2003 | Dunn et al. |
| 6,654,625 B1 | 11/2003 | Say et al. |
| 6,656,114 B1 | 12/2003 | Poulsen et al. |
| 6,656,157 B1 | 12/2003 | Duchon et al. |
| 6,663,615 B1 | 12/2003 | Madou et al. |
| 6,673,022 B1 | 1/2004 | Bobo et al. |
| 6,673,596 B1 | 1/2004 | Sayler et al. |
| 6,679,865 B2 | 1/2004 | Shekalim |
| 6,679,872 B2 | 1/2004 | Turovskiy et al. |
| 6,683,535 B1 | 1/2004 | Utke |
| 6,684,904 B2 | 2/2004 | Ito |
| 6,685,668 B1 | 2/2004 | Cho et al. |
| 6,687,522 B2 | 2/2004 | Tamada |
| 6,689,089 B1 | 2/2004 | Tiedtke et al. |
| 6,689,265 B2 | 2/2004 | Heller et al. |
| 6,694,191 B2 | 2/2004 | Starkweather et al. |
| 6,695,860 B1 | 2/2004 | Ward et al. |
| 6,699,188 B2 | 3/2004 | Wessel |
| 6,699,218 B2 | 3/2004 | Flaherty et al. |
| 6,699,383 B2 | 3/2004 | Lemire et al. |
| 6,702,249 B2 | 3/2004 | Ito |
| 6,702,857 B2 | 3/2004 | Brauker et al. |
| 6,702,972 B1 | 3/2004 | Markle |
| 6,711,424 B1 | 3/2004 | Fine et al. |
| 6,712,796 B2 | 3/2004 | Fentis et al. |
| 6,721,587 B2 | 4/2004 | Gough |
| 6,723,086 B2 | 4/2004 | Bassuk et al. |
| 6,731,976 B2 | 5/2004 | Penn et al. |
| 6,736,783 B2 | 5/2004 | Blake et al. |
| 6,740,072 B2 | 5/2004 | Starkweather et al. |
| 6,740,075 B2 | 5/2004 | Lebel et al. |
| 6,741,877 B1 | 5/2004 | Shults et al. |
| 6,742,635 B2 | 6/2004 | Hirshberg |
| 6,743,635 B2 | 6/2004 | Neel et al. |
| 6,749,587 B2 | 6/2004 | Flaherty |
| 6,750,055 B1 | 6/2004 | Connelly et al. |
| 6,770,030 B1 | 8/2004 | Schaupp et al. |
| 6,770,067 B2 | 8/2004 | Lorenzen et al. |
| 6,773,565 B2 | 8/2004 | Kunimoto et al. |
| 6,780,297 B2 | 8/2004 | Matsumoto et al. |
| 6,793,632 B2 | 9/2004 | Sohrab |
| 6,801,041 B2 | 10/2004 | Karinka et al. |
| 6,802,957 B2 | 10/2004 | Jung et al. |
| 6,804,002 B2 | 10/2004 | Fine et al. |
| 6,805,693 B2 | 10/2004 | Gray et al. |
| 6,809,653 B1 | 10/2004 | Mann et al. |
| 6,810,290 B2 | 10/2004 | Lebel et al. |
| 6,811,548 B2 | 11/2004 | Jeffrey |
| 6,813,519 B2 | 11/2004 | Lebel et al. |
| 6,832,200 B2 | 12/2004 | Greeven et al. |
| 6,850,790 B2 | 2/2005 | Berner et al. |
| 6,858,020 B2 | 2/2005 | Rusnak |
| 6,862,465 B2 | 3/2005 | Shults et al. |
| 6,869,413 B2 | 3/2005 | Langley et al. |
| 6,875,195 B2 | 4/2005 | Choi |
| 6,887,228 B2 | 5/2005 | Mckay |
| 6,892,085 B2 | 5/2005 | McIvor et al. |
| 6,893,552 B1 | 5/2005 | Wang et al. |
| 6,895,263 B2 | 5/2005 | Shin et al. |
| 6,895,265 B2 | 5/2005 | Silver |
| 6,902,544 B2 | 6/2005 | Ludin et al. |
| 6,925,393 B1 | 8/2005 | Kalatz et al. |
| 6,926,691 B2 | 8/2005 | Miethke |
| 6,931,327 B2 | 8/2005 | Goode, Jr. et al. |
| 6,932,584 B2 | 8/2005 | Gray et al. |
| 6,936,006 B2 | 8/2005 | Sabra |
| 6,936,029 B2 | 8/2005 | Mann et al. |
| 6,945,965 B2 | 9/2005 | Whiting |
| 6,948,492 B2 | 9/2005 | Wermeling et al. |
| 6,952,604 B2 | 10/2005 | Denuzzio et al. |
| 6,954,662 B2 | 10/2005 | Freger et al. |
| 6,960,192 B1 | 11/2005 | Flaherty et al. |
| 6,965,791 B1 | 11/2005 | Hitchcock et al. |
| 6,966,325 B2 | 11/2005 | Erickson |
| 6,975,893 B2 | 12/2005 | Say et al. |
| 6,979,315 B2 | 12/2005 | Rogers et al. |
| 6,989,891 B2 | 1/2006 | Braig et al. |
| 6,997,921 B2 | 2/2006 | Gray et al. |
| 6,998,247 B2 | 2/2006 | Monfre et al. |
| 7,008,979 B2 | 3/2006 | Schottman et al. |
| 7,011,630 B2 | 3/2006 | Desai et al. |
| 7,016,713 B2 | 3/2006 | Gardner et al. |
| 7,022,072 B2 | 4/2006 | Fox et al. |
| 7,022,219 B2 | 4/2006 | Mansouri et al. |
| 7,025,727 B2 | 4/2006 | Brockway et al. |
| 7,025,743 B2 | 4/2006 | Mann et al. |
| 7,027,848 B2 | 4/2006 | Robinson et al. |
| 7,029,444 B2 | 4/2006 | Shin et al. |
| 7,033,322 B2 | 4/2006 | Silver |
| 7,044,911 B2 | 5/2006 | Drinan et al. |
| 7,048,727 B1 | 5/2006 | Moss |
| 7,058,437 B2 | 6/2006 | Buse et al. |
| 7,060,059 B2 | 6/2006 | Keith et al. |
| 7,061,593 B2 | 6/2006 | Braig et al. |
| 7,063,086 B2 | 6/2006 | Shahbazpour et al. |

(56) References Cited

U.S. PATENT DOCUMENTS

| | | |
|---|---|---|
| 7,066,884 B2 | 6/2006 | Custer et al. |
| 7,070,577 B1 | 7/2006 | Haller et al. |
| 7,074,307 B2 | 7/2006 | Simpson et al. |
| 7,081,195 B2 | 7/2006 | Simpson et al. |
| 7,097,775 B2 | 8/2006 | Greenberg et al. |
| 7,098,803 B2 | 8/2006 | Mann et al. |
| 7,100,628 B1 | 9/2006 | Izenson et al. |
| 7,108,778 B2 | 9/2006 | Simpson et al. |
| 7,120,483 B2 | 10/2006 | Russell et al. |
| 7,131,967 B2 | 11/2006 | Gray et al. |
| 7,134,999 B2 | 11/2006 | Brauker et al. |
| 7,136,689 B2 | 11/2006 | Shults et al. |
| 7,146,202 B2 | 12/2006 | Ward et al. |
| 7,150,741 B2 | 12/2006 | Erickson et al. |
| 7,162,290 B1 | 1/2007 | Levin |
| 7,166,074 B2 | 1/2007 | Reghabi et al. |
| 7,168,597 B1 | 1/2007 | Jones et al. |
| 7,169,289 B2 | 1/2007 | Schuelein et al. |
| 7,183,102 B2 | 2/2007 | Monfre et al. |
| 7,184,810 B2 | 2/2007 | Caduff et al. |
| 7,207,968 B1 | 4/2007 | Harcinske |
| 7,211,074 B2 | 5/2007 | Sansoucy |
| 7,221,970 B2 | 5/2007 | Parker |
| 7,223,253 B2 | 5/2007 | Hogendijk |
| 7,225,535 B2 | 6/2007 | Feldman et al. |
| 7,228,162 B2 | 6/2007 | Ward et al. |
| 7,229,288 B2 | 6/2007 | Stuart et al. |
| 7,238,165 B2 | 7/2007 | Mncent et al. |
| 7,247,138 B2 | 7/2007 | Reghabi et al. |
| 7,254,450 B2 | 8/2007 | Christopherson et al. |
| 7,255,690 B2 | 8/2007 | Gray et al. |
| 7,258,681 B2 | 8/2007 | Houde |
| 7,261,690 B2 | 8/2007 | Teller et al. |
| 7,266,400 B2 | 9/2007 | Fine et al. |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,279,174 B2 | 10/2007 | Pacetti et al. |
| 7,282,029 B1 | 10/2007 | Poulsen et al. |
| 7,288,085 B2 | 10/2007 | Olsen |
| 7,291,114 B2 | 11/2007 | Mault |
| 7,295,867 B2 | 11/2007 | Berner et al. |
| 7,299,082 B2 | 11/2007 | Feldman et al. |
| 7,311,690 B2 | 12/2007 | Burnett |
| 7,313,425 B2 | 12/2007 | Finarov et al. |
| 7,314,452 B2 | 1/2008 | Madonia |
| 7,315,767 B2 | 1/2008 | Caduff et al. |
| 7,316,662 B2 | 1/2008 | Delnevo et al. |
| 7,317,939 B2 | 1/2008 | Fine et al. |
| 7,318,814 B2 | 1/2008 | Levine et al. |
| 7,327,273 B2 | 2/2008 | Hung et al. |
| 7,329,234 B2 | 2/2008 | Sansoucy |
| 7,334,594 B2 | 2/2008 | Ludin |
| 7,335,179 B2 | 2/2008 | Burnett |
| 7,335,195 B2 | 2/2008 | Mehier |
| 7,338,464 B2 | 3/2008 | Blischak et al. |
| 7,344,500 B2 | 3/2008 | Talbot et al. |
| 7,354,420 B2 | 4/2008 | Steil et al. |
| 7,357,793 B2 | 4/2008 | Pacetti |
| 7,359,723 B2 | 4/2008 | Jones |
| 7,361,155 B2 | 4/2008 | Sage, Jr. et al. |
| 7,364,562 B2 | 4/2008 | Braig et al. |
| 7,367,942 B2 | 5/2008 | Grage et al. |
| 7,396,353 B2 | 7/2008 | Lorenzen et al. |
| 7,399,277 B2 | 7/2008 | Saidara et al. |
| 7,402,153 B2 | 7/2008 | Steil et al. |
| 7,417,164 B2 | 8/2008 | Suri |
| 7,426,408 B2 | 9/2008 | DeNuzzio et al. |
| 7,433,727 B2 | 10/2008 | Ward et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,534,230 B2 | 5/2009 | Follman et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,604,593 B2 | 10/2009 | Parris et al. |
| 7,615,007 B2 | 11/2009 | Shults et al. |
| 7,618,368 B2 | 11/2009 | Brown |
| 7,618,369 B2 | 11/2009 | Hayter et al. |
| 7,624,028 B1 | 11/2009 | Brown |
| 7,640,032 B2 | 12/2009 | Jones |
| 7,640,048 B2 | 12/2009 | Dobbles et al. |
| 7,647,237 B2 | 1/2010 | Malave et al. |
| 7,654,955 B2 | 2/2010 | Polidori et al. |
| 7,657,297 B2 | 2/2010 | Simpson et al. |
| 7,670,288 B2 | 3/2010 | Sher |
| 7,695,434 B2 | 4/2010 | Malecha |
| 7,727,147 B1 | 6/2010 | Osorio et al. |
| 7,731,659 B2 | 6/2010 | Malecha |
| 7,761,126 B2 | 7/2010 | Gardner et al. |
| 7,766,830 B2 | 8/2010 | Fox et al. |
| 7,857,760 B2 | 12/2010 | Brister et al. |
| 7,901,394 B2 | 3/2011 | Ireland et al. |
| 7,905,833 B2 | 3/2011 | Brister et al. |
| 7,927,274 B2 | 4/2011 | Rasdal et al. |
| 7,946,985 B2 | 5/2011 | Mastrototaro et al. |
| 7,976,492 B2 | 7/2011 | Brauker et al. |
| 8,000,901 B2 | 8/2011 | Brauker et al. |
| 8,005,524 B2 | 8/2011 | Brauker et al. |
| 8,005,525 B2 | 8/2011 | Goode, Jr. et al. |
| 8,010,174 B2 | 8/2011 | Goode, Jr. et al. |
| 8,460,231 B2 | 6/2013 | Brauker et al. |
| 8,512,276 B2 | 8/2013 | Talbot et al. |
| 8,721,585 B2 | 5/2014 | Brauker et al. |
| 8,808,228 B2 | 8/2014 | Brister et al. |
| 8,882,741 B2 | 11/2014 | Brauker et al. |
| 8,920,401 B2 | 12/2014 | Brauker et al. |
| 8,926,585 B2 | 1/2015 | Brauker et al. |
| 9,050,413 B2 | 6/2015 | Brauker et al. |
| 9,155,843 B2 | 10/2015 | Brauker et al. |
| 9,451,908 B2 | 9/2016 | Kamath et al. |
| 9,452,258 B2 | 9/2016 | Dobbles et al. |
| 9,452,259 B2 | 9/2016 | Dobbles et al. |
| 9,457,146 B2 | 10/2016 | Dobbles et al. |
| 9,463,277 B2 | 10/2016 | Dobbles et al. |
| 9,498,155 B2 | 11/2016 | Brauker et al. |
| 9,572,935 B2 | 2/2017 | Dobbles et al. |
| 9,572,936 B2 | 2/2017 | Dobbles et al. |
| 9,586,004 B2 | 3/2017 | Dobbles et al. |
| 9,597,453 B2 | 3/2017 | Dobbles et al. |
| 9,750,441 B2 | 9/2017 | Brauker et al. |
| 9,827,372 B2 | 11/2017 | Dobbles et al. |
| 9,937,293 B2 | 4/2018 | Brauker et al. |
| 10,278,580 B2 | 5/2019 | Brister et al. |
| 10,653,835 B2 | 5/2020 | Dobbles et al. |
| 10,966,609 B2 | 4/2021 | Brister et al. |
| 11,373,347 B2 | 6/2022 | Kamath et al. |
| 11,744,943 B2 | 9/2023 | Dobbles et al. |
| 2001/0007950 A1 | 7/2001 | North et al. |
| 2001/0016682 A1 | 8/2001 | Berner et al. |
| 2001/0021817 A1 | 9/2001 | Brugger et al. |
| 2001/0039053 A1 | 11/2001 | Liseo et al. |
| 2001/0041830 A1 | 11/2001 | Varalli et al. |
| 2001/0044588 A1 | 11/2001 | Mault |
| 2001/0051768 A1 | 12/2001 | Schulman et al. |
| 2002/0009810 A1 | 1/2002 | O'Connor et al. |
| 2002/0016535 A1 | 2/2002 | Martin et al. |
| 2002/0016719 A1 | 2/2002 | Nemeth et al. |
| 2002/0018843 A1 | 2/2002 | Van Antwerp et al. |
| 2002/0019022 A1 | 2/2002 | Dunn et al. |
| 2002/0019330 A1 | 2/2002 | Murray et al. |
| 2002/0022883 A1 | 2/2002 | Burg |
| 2002/0023852 A1 | 2/2002 | McIvor et al. |
| 2002/0026110 A1 | 2/2002 | Parris et al. |
| 2002/0026111 A1 | 2/2002 | Ackerman |
| 2002/0042090 A1 | 4/2002 | Heller et al. |
| 2002/0042561 A1 | 4/2002 | Schulman et al. |
| 2002/0043471 A1 | 4/2002 | Ikeda et al. |
| 2002/0045808 A1 | 4/2002 | Ford et al. |
| 2002/0060692 A1 | 5/2002 | Broemmelsiek |
| 2002/0065453 A1 | 5/2002 | Lesho et al. |
| 2002/0068860 A1 | 6/2002 | Clark |

(56) References Cited

U.S. PATENT DOCUMENTS

| | | |
|---|---|---|
| 2002/0071776 A1 | 6/2002 | Bandis et al. |
| 2002/0084196 A1 | 7/2002 | Liamos et al. |
| 2002/0099282 A1 | 7/2002 | Knobbe et al. |
| 2002/0099997 A1 | 7/2002 | Piret |
| 2002/0111547 A1 | 8/2002 | Knobbe et al. |
| 2002/0119711 A1 | 8/2002 | Vanantwerp et al. |
| 2002/0123048 A1 | 9/2002 | Gau |
| 2002/0133224 A1 | 9/2002 | Bajgar et al. |
| 2002/0151796 A1 | 10/2002 | Koulik |
| 2002/0155615 A1 | 10/2002 | Novikov et al. |
| 2002/0161288 A1 | 10/2002 | Shin et al. |
| 2002/0182241 A1 | 12/2002 | Borenstein et al. |
| 2002/0188185 A1 | 12/2002 | Sohrab |
| 2002/0193679 A1 | 12/2002 | Malave et al. |
| 2002/0193885 A1 | 12/2002 | Legeay et al. |
| 2002/0198513 A1 | 12/2002 | Lebel et al. |
| 2003/0004432 A1 | 1/2003 | Assenheimer |
| 2003/0006669 A1 | 1/2003 | Pei et al. |
| 2003/0021729 A1 | 1/2003 | Moller et al. |
| 2003/0023171 A1 | 1/2003 | Sato et al. |
| 2003/0023317 A1 | 1/2003 | Brauker et al. |
| 2003/0028089 A1 | 2/2003 | Galley et al. |
| 2003/0031699 A1 | 2/2003 | Van Antwerp |
| 2003/0032874 A1 | 2/2003 | Rhodes et al. |
| 2003/0050546 A1 | 3/2003 | Desai et al. |
| 2003/0054428 A1 | 3/2003 | Monfre et al. |
| 2003/0060692 A1 | 3/2003 | L. Ruchti et al. |
| 2003/0060753 A1 | 3/2003 | Starkweather et al. |
| 2003/0060765 A1 | 3/2003 | Campbell et al. |
| 2003/0070548 A1 | 4/2003 | Clausen |
| 2003/0072741 A1 | 4/2003 | Berglund et al. |
| 2003/0076082 A1 | 4/2003 | Morgan et al. |
| 2003/0078481 A1 | 4/2003 | McIvor et al. |
| 2003/0078560 A1 | 4/2003 | Miller et al. |
| 2003/0088238 A1 | 5/2003 | Poulsen et al. |
| 2003/0091433 A1 | 5/2003 | Tam et al. |
| 2003/0097082 A1 | 5/2003 | Purdy et al. |
| 2003/0099682 A1 | 5/2003 | Moussy et al. |
| 2003/0100040 A1 | 5/2003 | Bonnecaze et al. |
| 2003/0100821 A1 | 5/2003 | Heller et al. |
| 2003/0114836 A1 | 6/2003 | Estes et al. |
| 2003/0117296 A1 | 6/2003 | Seely |
| 2003/0119208 A1 | 6/2003 | Yoon et al. |
| 2003/0120152 A1 | 6/2003 | Omiya |
| 2003/0125612 A1 | 7/2003 | Fox et al. |
| 2003/0125613 A1 | 7/2003 | Enegren et al. |
| 2003/0130616 A1 | 7/2003 | Steil et al. |
| 2003/0132227 A1 | 7/2003 | Geisler et al. |
| 2003/0134347 A1 | 7/2003 | Heller et al. |
| 2003/0143746 A1 | 7/2003 | Sage |
| 2003/0153821 A1 | 8/2003 | Berner et al. |
| 2003/0176183 A1 | 9/2003 | Drucker et al. |
| 2003/0187338 A1 | 10/2003 | Say et al. |
| 2003/0188427 A1 | 10/2003 | Say et al. |
| 2003/0199744 A1 | 10/2003 | Buse et al. |
| 2003/0199745 A1 | 10/2003 | Burson et al. |
| 2003/0208113 A1 | 11/2003 | Mault et al. |
| 2003/0211050 A1 | 11/2003 | Majeti et al. |
| 2003/0211625 A1 | 11/2003 | Cohan et al. |
| 2003/0212317 A1 | 11/2003 | Kovatchev et al. |
| 2003/0212346 A1 | 11/2003 | Yuzhakov et al. |
| 2003/0212347 A1 | 11/2003 | Sohrab |
| 2003/0212379 A1 | 11/2003 | Bylund et al. |
| 2003/0225324 A1 | 12/2003 | Anderson et al. |
| 2003/0225437 A1 | 12/2003 | Ferguson |
| 2003/0231550 A1 | 12/2003 | MacFarlane |
| 2003/0235817 A1 | 12/2003 | Bartkowiak et al. |
| 2004/0006263 A1 | 1/2004 | Anderson et al. |
| 2004/0010207 A1 | 1/2004 | Flaherty et al. |
| 2004/0011671 A1 | 1/2004 | Shults et al. |
| 2004/0015063 A1 | 1/2004 | DeNuzzio et al. |
| 2004/0015134 A1 | 1/2004 | Lavi et al. |
| 2004/0023253 A1 | 2/2004 | Kunwar et al. |
| 2004/0023317 A1 | 2/2004 | Motamedi et al. |
| 2004/0024327 A1 | 2/2004 | Brodnick |
| 2004/0030285 A1 | 2/2004 | Lavi et al. |
| 2004/0030294 A1 | 2/2004 | Mahurkar |
| 2004/0039298 A1 | 2/2004 | Abreu |
| 2004/0039406 A1 | 2/2004 | Jessen |
| 2004/0040840 A1 | 3/2004 | Mao et al. |
| 2004/0044272 A1 | 3/2004 | Moerman et al. |
| 2004/0045879 A1 | 3/2004 | Shults et al. |
| 2004/0052689 A1 | 3/2004 | Yao |
| 2004/0054352 A1 | 3/2004 | Adams et al. |
| 2004/0068230 A1 | 4/2004 | Estes et al. |
| 2004/0074785 A1 | 4/2004 | Holker et al. |
| 2004/0078219 A1 | 4/2004 | Kaylor et al. |
| 2004/0106857 A1 | 6/2004 | Gough |
| 2004/0122297 A1 | 6/2004 | Stahmann et al. |
| 2004/0122353 A1 | 6/2004 | Shahmirian et al. |
| 2004/0138543 A1 | 7/2004 | Russell et al. |
| 2004/0143173 A1 | 7/2004 | Reghabi et al. |
| 2004/0146909 A1 | 7/2004 | Duong et al. |
| 2004/0152187 A1 | 8/2004 | Haight et al. |
| 2004/0152622 A1 | 8/2004 | Keith et al. |
| 2004/0162678 A1 | 8/2004 | Hetzel et al. |
| 2004/0167801 A1 | 8/2004 | Say et al. |
| 2004/0173472 A1 | 9/2004 | Jung et al. |
| 2004/0176672 A1 | 9/2004 | Silver et al. |
| 2004/0180391 A1 | 9/2004 | Gratzl et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0199059 A1 | 10/2004 | Brauker et al. |
| 2004/0204687 A1 | 10/2004 | Mogensen et al. |
| 2004/0219664 A1 | 11/2004 | Heller et al. |
| 2004/0220517 A1 | 11/2004 | Starkweather et al. |
| 2004/0224001 A1 | 11/2004 | Pacetti et al. |
| 2004/0248282 A1 | 12/2004 | Sobha M. et al. |
| 2004/0253365 A1 | 12/2004 | Warren et al. |
| 2004/0254433 A1 | 12/2004 | Bandis et al. |
| 2005/0003399 A1 | 1/2005 | Blackburn et al. |
| 2005/0010265 A1 | 1/2005 | Baru et al. |
| 2005/0026689 A1 | 2/2005 | Marks |
| 2005/0027180 A1 | 2/2005 | Goode et al. |
| 2005/0027181 A1 | 2/2005 | Goode, Jr. et al. |
| 2005/0027182 A1 | 2/2005 | Siddiqui et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0043598 A1 | 2/2005 | Goode et al. |
| 2005/0049472 A1 | 3/2005 | Manda et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056552 A1 | 3/2005 | Simpson et al. |
| 2005/0065464 A1 | 3/2005 | Talbot et al. |
| 2005/0077584 A1 | 4/2005 | Uhland et al. |
| 2005/0090607 A1 | 4/2005 | Tapsak et al. |
| 2005/0096519 A1 | 5/2005 | DeNuzzio et al. |
| 2005/0101847 A1 | 5/2005 | Routt et al. |
| 2005/0107677 A1 | 5/2005 | Ward et al. |
| 2005/0112169 A1 | 5/2005 | Brauker et al. |
| 2005/0113653 A1 | 5/2005 | Fox et al. |
| 2005/0113744 A1 | 5/2005 | Donoghue et al. |
| 2005/0115832 A1 | 6/2005 | Simpson et al. |
| 2005/0118344 A1 | 6/2005 | Pacetti |
| 2005/0119720 A1 | 6/2005 | Gale et al. |
| 2005/0121322 A1 | 6/2005 | Say et al. |
| 2005/0124873 A1 | 6/2005 | Shults et al. |
| 2005/0131305 A1 | 6/2005 | Danielson et al. |
| 2005/0139489 A1 | 6/2005 | Davies et al. |
| 2005/0143635 A1 | 6/2005 | Kamath et al. |
| 2005/0143675 A1 | 6/2005 | Neel et al. |
| 2005/0154271 A1 | 7/2005 | Rasdal et al. |
| 2005/0176136 A1 | 8/2005 | Burd et al. |
| 2005/0177036 A1 | 8/2005 | Shults et al. |
| 2005/0177398 A1 | 8/2005 | Watanabe et al. |
| 2005/0181012 A1 | 8/2005 | Saint et al. |
| 2005/0182451 A1 | 8/2005 | Griffin et al. |
| 2005/0183954 A1 | 8/2005 | Hitchcock et al. |
| 2005/0187720 A1 | 8/2005 | Goode, Jr. et al. |

(56) References Cited

U.S. PATENT DOCUMENTS

| | | |
|---|---|---|
| 2005/0192557 A1 | 9/2005 | Brauker et al. |
| 2005/0197553 A1 | 9/2005 | Cooper |
| 2005/0197554 A1 | 9/2005 | Polcha |
| 2005/0203360 A1 | 9/2005 | Brauker et al. |
| 2005/0211571 A1 | 9/2005 | Schulein et al. |
| 2005/0215871 A1 | 9/2005 | Feldman et al. |
| 2005/0215872 A1 | 9/2005 | Berner et al. |
| 2005/0239154 A1 | 10/2005 | Feldman et al. |
| 2005/0242479 A1 | 11/2005 | Petisce et al. |
| 2005/0245795 A1 | 11/2005 | Goode, Jr. et al. |
| 2005/0245799 A1 | 11/2005 | Brauker et al. |
| 2005/0245904 A1 | 11/2005 | Estes et al. |
| 2005/0251083 A1 | 11/2005 | Carr-Brendel et al. |
| 2005/0261563 A1 | 11/2005 | Zhou et al. |
| 2005/0288596 A1 | 12/2005 | Eigler et al. |
| 2006/0001550 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0047095 A1 | 3/2006 | Pacetti |
| 2006/0052745 A1 | 3/2006 | Van Antwerp et al. |
| 2006/0067908 A1 | 3/2006 | Ding |
| 2006/0078908 A1 | 4/2006 | Pitner et al. |
| 2006/0079740 A1 | 4/2006 | Silver et al. |
| 2006/0079809 A1 | 4/2006 | Goldberger et al. |
| 2006/0094946 A1 | 5/2006 | Kellogg et al. |
| 2006/0100588 A1 | 5/2006 | Brunnberg et al. |
| 2006/0134165 A1 | 6/2006 | Pacetti |
| 2006/0171980 A1 | 8/2006 | Helmus et al. |
| 2006/0173406 A1 | 8/2006 | Hayes et al. |
| 2006/0177379 A1 | 8/2006 | Asgari |
| 2006/0183871 A1 | 8/2006 | Ward et al. |
| 2006/0183984 A1 | 8/2006 | Dobbles et al. |
| 2006/0183985 A1 | 8/2006 | Brister et al. |
| 2006/0189863 A1 | 8/2006 | Peyser et al. |
| 2006/0195029 A1 | 8/2006 | Shults et al. |
| 2006/0222566 A1 | 10/2006 | Brauker et al. |
| 2006/0224141 A1 | 10/2006 | Rush et al. |
| 2006/0253085 A1 | 11/2006 | Geismar et al. |
| 2006/0258929 A1 | 11/2006 | Goode et al. |
| 2006/0263839 A1 | 11/2006 | Ward et al. |
| 2006/0269586 A1 | 11/2006 | Pacetti |
| 2006/0275857 A1 | 12/2006 | Naer et al. |
| 2006/0281985 A1 | 12/2006 | Ward et al. |
| 2007/0007133 A1 | 1/2007 | Mang et al. |
| 2007/0016381 A1 | 1/2007 | Kamath et al. |
| 2007/0027385 A1 | 2/2007 | Brister et al. |
| 2007/0032706 A1 | 2/2007 | Kamath et al. |
| 2007/0038044 A1 | 2/2007 | Dobbles et al. |
| 2007/0049873 A1 | 3/2007 | Hansen et al. |
| 2007/0066873 A1 | 3/2007 | Kamath et al. |
| 2007/0066956 A1 | 3/2007 | Finkel |
| 2007/0085995 A1 | 4/2007 | Pesach et al. |
| 2007/0100222 A1 | 5/2007 | Mastrototaro et al. |
| 2007/0106135 A1 | 5/2007 | Sloan et al. |
| 2007/0112298 A1 | 5/2007 | Mueller, Jr. et al. |
| 2007/0116600 A1 | 5/2007 | Kochar et al. |
| 2007/0129619 A1 | 6/2007 | Ward et al. |
| 2007/0129621 A1 | 6/2007 | Kellogg et al. |
| 2007/0135698 A1 | 6/2007 | Shah et al. |
| 2007/0135699 A1 | 6/2007 | Ward et al. |
| 2007/0151869 A1 | 7/2007 | Heller et al. |
| 2007/0173706 A1 | 7/2007 | Neinast et al. |
| 2007/0173710 A1 | 7/2007 | Petisce et al. |
| 2007/0173761 A1 | 7/2007 | Kanderian, Jr. et al. |
| 2007/0179434 A1 | 8/2007 | Weinert et al. |
| 2007/0197889 A1 | 8/2007 | Brister et al. |
| 2007/0200254 A1 | 8/2007 | Curry |
| 2007/0200267 A1 | 8/2007 | Tsai |
| 2007/0203407 A1 | 8/2007 | Hoss et al. |
| 2007/0203410 A1 | 8/2007 | Say et al. |
| 2007/0203966 A1 | 8/2007 | Brauker et al. |
| 2007/0206193 A1 | 9/2007 | Pesach |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213610 A1 | 9/2007 | Say et al. |
| 2007/0218097 A1 | 9/2007 | Heller et al. |
| 2007/0219441 A1 | 9/2007 | Carlin et al. |
| 2007/0225579 A1 | 9/2007 | Lucassen et al. |
| 2007/0225675 A1 | 9/2007 | Robinson et al. |
| 2007/0227907 A1 | 10/2007 | Shah et al. |
| 2007/0233013 A1 | 10/2007 | Schoenberg |
| 2007/0233051 A1 | 10/2007 | Hohl et al. |
| 2007/0235331 A1 | 10/2007 | Simpson et al. |
| 2007/0240497 A1 | 10/2007 | Robinson et al. |
| 2007/0244381 A1 | 10/2007 | Robinson et al. |
| 2007/0244382 A1 | 10/2007 | Robinson et al. |
| 2007/0249916 A1 | 10/2007 | Pesach et al. |
| 2007/0255126 A1 | 11/2007 | Moberg et al. |
| 2007/0275193 A1 | 11/2007 | DeSimone et al. |
| 2007/0293742 A1 | 12/2007 | Simonsen et al. |
| 2007/0299409 A1 | 12/2007 | Whitbourne et al. |
| 2008/0021666 A1 | 1/2008 | Goode et al. |
| 2008/0021668 A1 | 1/2008 | Son |
| 2008/0027301 A1 | 1/2008 | Ward et al. |
| 2008/0029390 A1 | 2/2008 | Roche et al. |
| 2008/0029391 A1 | 2/2008 | Mao et al. |
| 2008/0033254 A1 | 2/2008 | Kamath et al. |
| 2008/0034972 A1 | 2/2008 | Gough et al. |
| 2008/0045824 A1 | 2/2008 | Tapsak et al. |
| 2008/0071157 A1 | 3/2008 | McGarraugh et al. |
| 2008/0071158 A1 | 3/2008 | McGarraugh et al. |
| 2008/0072663 A1 | 3/2008 | Keenan et al. |
| 2008/0086040 A1 | 4/2008 | Heller et al. |
| 2008/0086041 A1 | 4/2008 | Heller et al. |
| 2008/0086042 A1 | 4/2008 | Brister et al. |
| 2008/0086043 A1 | 4/2008 | Heller et al. |
| 2008/0086044 A1 | 4/2008 | Brister et al. |
| 2008/0086273 A1 | 4/2008 | Shults et al. |
| 2008/0091094 A1 | 4/2008 | Heller et al. |
| 2008/0091095 A1 | 4/2008 | Heller et al. |
| 2008/0097289 A1 | 4/2008 | Steil et al. |
| 2008/0108942 A1 | 5/2008 | Brister et al. |
| 2008/0119703 A1 | 5/2008 | Brister et al. |
| 2008/0119704 A1 | 5/2008 | Brister et al. |
| 2008/0119706 A1 | 5/2008 | Brister et al. |
| 2008/0125751 A1 | 5/2008 | Fjield et al. |
| 2008/0139910 A1 | 6/2008 | Mastrototaro et al. |
| 2008/0154101 A1 | 6/2008 | Jain et al. |
| 2008/0183061 A1 | 7/2008 | Goode et al. |
| 2008/0183399 A1 | 7/2008 | Goode et al. |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0188731 A1 | 8/2008 | Brister et al. |
| 2008/0189051 A1 | 8/2008 | Goode et al. |
| 2008/0193936 A1 | 8/2008 | Squirrell |
| 2008/0194837 A1 | 8/2008 | Kim et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |

(56) References Cited

U.S. PATENT DOCUMENTS

| | | |
|---|---|---|
| 2008/0210557 A1 | 9/2008 | Heller et al. |
| 2008/0214915 A1 | 9/2008 | Brister et al. |
| 2008/0262469 A1 | 10/2008 | Brister et al. |
| 2008/0269723 A1 | 10/2008 | Mastrototaro et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0300572 A1 | 12/2008 | Rankers et al. |
| 2008/0305009 A1 | 12/2008 | Gamsey et al. |
| 2008/0305506 A1 | 12/2008 | Suri |
| 2008/0306368 A1 | 12/2008 | Goode, Jr. et al. |
| 2008/0306433 A1 | 12/2008 | Cesaroni |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0005666 A1 | 1/2009 | Shin et al. |
| 2009/0012379 A1 | 1/2009 | Goode, Jr. et al. |
| 2009/0018418 A1 | 1/2009 | Markle et al. |
| 2009/0018424 A1 | 1/2009 | Kamath et al. |
| 2009/0018426 A1 | 1/2009 | Markle et al. |
| 2009/0036758 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0061528 A1 | 3/2009 | Suri |
| 2009/0062635 A1 | 3/2009 | Brauker et al. |
| 2009/0062645 A1 | 3/2009 | Fehre et al. |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0081803 A1 | 3/2009 | Gamsey et al. |
| 2009/0099434 A1 | 4/2009 | Liu et al. |
| 2009/0124877 A1 | 5/2009 | Goode, Jr. et al. |
| 2009/0124878 A1 | 5/2009 | Goode, Jr. et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0156924 A1 | 6/2009 | Shariati et al. |
| 2009/0177143 A1 | 7/2009 | Markle et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0264719 A1 | 10/2009 | Markle et al. |
| 2009/0264856 A1 | 10/2009 | Lebel et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0022855 A1 | 1/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036224 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0161269 A1 | 6/2010 | Kamath et al. |
| 2010/0179401 A1 | 7/2010 | Rasdal et al. |
| 2010/0179407 A1 | 7/2010 | Goode, Jr. et al. |
| 2010/0179408 A1 | 7/2010 | Kamath et al. |
| 2010/0179409 A1 | 7/2010 | Kamath et al. |
| 2010/0234707 A1 | 9/2010 | Goode, Jr. et al. |
| 2010/0235106 A1 | 9/2010 | Kamath et al. |
| 2010/0240975 A1 | 9/2010 | Goode, Jr. et al. |
| 2010/0240976 A1 | 9/2010 | Goode, Jr. et al. |
| 2010/0331656 A1 | 12/2010 | Mensinger et al. |
| 2010/0331657 A1 | 12/2010 | Mensinger et al. |
| 2011/0009727 A1 | 1/2011 | Mensinger et al. |
| 2011/0118579 A1 | 5/2011 | Goode, Jr. et al. |
| 2011/0124997 A1 | 5/2011 | Goode, Jr. et al. |
| 2011/0130970 A1 | 6/2011 | Goode, Jr. et al. |
| 2011/0137601 A1 | 6/2011 | Goode, Jr. et al. |
| 2011/0201910 A1 | 8/2011 | Rasdal et al. |
| 2011/0218414 A1 | 9/2011 | Kamath et al. |
| 2011/0231107 A1 | 9/2011 | Brauker et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0257895 A1 | 10/2011 | Brauker et al. |
| 2011/0270158 A1 | 11/2011 | Brauker et al. |
| 2012/0059673 A1 | 3/2012 | Cohen et al. |
| 2012/0097289 A1 | 4/2012 | Chun et al. |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0227737 A1 | 9/2012 | Mastrototaro et al. |
| 2012/0238852 A1 | 9/2012 | Brauker et al. |
| 2012/0259278 A1 | 10/2012 | Hayes et al. |
| 2012/0296311 A1 | 11/2012 | Brauker et al. |
| 2018/0043096 A1 | 2/2018 | Dobbles et al. |
| 2018/0185587 A1 | 7/2018 | Brauker et al. |
| 2019/0070360 A1 | 3/2019 | Sloan et al. |
| 2019/0209009 A1 | 7/2019 | Brister et al. |

FOREIGN PATENT DOCUMENTS

| | | |
|---|---|---|
| EP | 0098592 A2 | 1/1984 |
| EP | 0107634 A2 | 5/1984 |
| EP | 0127958 A2 | 12/1984 |
| EP | 0286118 A2 | 10/1988 |
| EP | 0288793 A2 | 11/1988 |
| EP | 0320109 A1 | 6/1989 |
| EP | 0352610 A2 | 1/1990 |
| EP | 0352631 A2 | 1/1990 |
| EP | 0353328 A1 | 2/1990 |
| EP | 0390390 A1 | 10/1990 |
| EP | 0396788 A1 | 11/1990 |
| EP | 0406473 A1 | 1/1991 |
| EP | 0440044 A1 | 8/1991 |
| EP | 0441252 A2 | 8/1991 |
| EP | 0441394 A2 | 8/1991 |
| EP | 0467078 A2 | 1/1992 |
| EP | 0534074 A1 | 3/1993 |
| EP | 0535898 A1 | 4/1993 |
| EP | 0539751 A1 | 5/1993 |
| EP | 0563795 A1 | 10/1993 |
| EP | 0323605 B1 | 1/1994 |
| EP | 0647849 A2 | 4/1995 |

(56) References Cited

FOREIGN PATENT DOCUMENTS

| | | |
|---|---|---|
| EP | 0424633 B1 | 1/1996 |
| EP | 0729366 A1 | 9/1996 |
| EP | 0747069 A2 | 12/1996 |
| EP | 0776628 A2 | 6/1997 |
| EP | 0817809 A1 | 1/1998 |
| EP | 0838230 A2 | 4/1998 |
| EP | 0880936 A2 | 12/1998 |
| EP | 0885932 A2 | 12/1998 |
| EP | 0967788 A2 | 12/1999 |
| EP | 0995805 A1 | 4/2000 |
| EP | 1077634 A1 | 2/2001 |
| EP | 1078258 A1 | 2/2001 |
| EP | 1102194 A2 | 5/2001 |
| EP | 0789540 B1 | 9/2001 |
| EP | 1144028 A1 | 10/2001 |
| EP | 1153571 A1 | 11/2001 |
| EP | 0817809 B1 | 7/2002 |
| EP | 1266607 A2 | 12/2002 |
| EP | 1338295 A1 | 8/2003 |
| EP | 1067862 B1 | 5/2004 |
| EP | 1144028 B1 | 6/2004 |
| EP | 1498067 A1 | 1/2005 |
| EP | 1571582 A2 | 9/2005 |
| EP | 2223710 A1 | 9/2010 |
| EP | 2226086 A1 | 9/2010 |
| EP | 2228642 A1 | 9/2010 |
| FR | 2656423 A1 | 6/1991 |
| FR | 2760962 A1 | 9/1998 |
| GB | 1442303 A | 7/1976 |
| GB | 2149918 A | 6/1985 |
| JP | S6283649 A | 4/1987 |
| JP | S6283849 A | 4/1987 |
| JP | H0783871 A | 3/1995 |
| JP | 2000060826 A | 2/2000 |
| JP | 2002515302 A | 5/2002 |
| JP | 2002189015 A | 7/2002 |
| JP | 2003079723 A | 3/2003 |
| JP | 2003108679 A | 4/2003 |
| JP | 2004000555 A | 1/2004 |
| WO | 8902720 A1 | 4/1989 |
| WO | 9000738 A1 | 1/1990 |
| WO | 9010861 A1 | 9/1990 |
| WO | 9013021 A1 | 11/1990 |
| WO | 9116416 A1 | 10/1991 |
| WO | 9213271 A1 | 8/1992 |
| WO | 9314693 A1 | 8/1993 |
| WO | 9323744 A1 | 11/1993 |
| WO | 9422367 A1 | 10/1994 |
| WO | 9507109 A1 | 3/1995 |
| WO | 9513838 A1 | 5/1995 |
| WO | 9601611 A1 | 1/1996 |
| WO | 9603117 A1 | 2/1996 |
| WO | 9614026 A1 | 5/1996 |
| WO | 9625089 A1 | 8/1996 |
| WO | 9630431 A1 | 10/1996 |
| WO | 9632076 A1 | 10/1996 |
| WO | 9637246 A1 | 11/1996 |
| WO | 9701986 A1 | 1/1997 |
| WO | 9706727 A1 | 2/1997 |
| WO | 9719188 A1 | 5/1997 |
| WO | 9728737 A1 | 8/1997 |
| WO | 9743633 A1 | 11/1997 |
| WO | 9824358 A2 | 6/1998 |
| WO | 9838906 A1 | 9/1998 |
| WO | 9948419 A1 | 9/1999 |
| WO | 9956613 A1 | 11/1999 |
| WO | 9958051 A1 | 11/1999 |
| WO | 9958973 A1 | 11/1999 |
| WO | 9959657 A1 | 11/1999 |
| WO | 0012720 A2 | 3/2000 |
| WO | 0013002 A2 | 3/2000 |
| WO | 0013003 A1 | 3/2000 |
| WO | 0019887 A1 | 4/2000 |
| WO | 0032098 A1 | 6/2000 |
| WO | 0033065 A1 | 6/2000 |
| WO | 0049941 A1 | 8/2000 |
| WO | 0059373 A1 | 10/2000 |
| WO | 0074753 A1 | 12/2000 |
| WO | 0078210 A1 | 12/2000 |
| WO | 0112158 A1 | 2/2001 |
| WO | 0116579 A1 | 3/2001 |
| WO | 0120019 A2 | 3/2001 |
| WO | 0120334 A1 | 3/2001 |
| WO | 0134243 A1 | 5/2001 |
| WO | 0143660 A2 | 6/2001 |
| WO | 0152727 A1 | 7/2001 |
| WO | 0158348 A2 | 8/2001 |
| WO | 0168901 A2 | 9/2001 |
| WO | 0169222 A2 | 9/2001 |
| WO | 0188524 A1 | 11/2001 |
| WO | 0188534 A2 | 11/2001 |
| WO | 0205702 A2 | 1/2002 |
| WO | 0224065 A1 | 3/2002 |
| WO | 0078210 A9 | 5/2002 |
| WO | 02082989 A1 | 10/2002 |
| WO | 02089666 A2 | 11/2002 |
| WO | 02100266 A1 | 12/2002 |
| WO | 03000127 A2 | 1/2003 |
| WO | 03022125 A2 | 3/2003 |
| WO | 03022327 A2 | 3/2003 |
| WO | 03047426 A1 | 6/2003 |
| WO | 03063700 A1 | 8/2003 |
| WO | 03072269 A1 | 9/2003 |
| WO | 03101862 A1 | 12/2003 |
| WO | 2004009161 A1 | 1/2004 |
| WO | 2004110256 A2 | 12/2004 |
| WO | 2005011489 A1 | 2/2005 |
| WO | 2005012873 A2 | 2/2005 |
| WO | 2005026689 A2 | 3/2005 |
| WO | 2005032400 A2 | 4/2005 |
| WO | 2005057168 A2 | 6/2005 |
| WO | 2005057175 A2 | 6/2005 |
| WO | 2005078424 A1 | 8/2005 |
| WO | 2005026689 A9 | 10/2005 |
| WO | 2005093629 A2 | 10/2005 |
| WO | 2005106446 A1 | 11/2005 |
| WO | 2006017358 A1 | 2/2006 |
| WO | 2006021430 A2 | 3/2006 |
| WO | 2006050405 A1 | 5/2006 |
| WO | 2006105146 A2 | 10/2006 |
| WO | 2006118713 A1 | 11/2006 |
| WO | 2006131288 A1 | 12/2006 |
| WO | 2007002209 A2 | 1/2007 |
| WO | 2007002579 A2 | 1/2007 |
| WO | 2007065285 A2 | 6/2007 |
| WO | 2007097754 A1 | 8/2007 |
| WO | 2007114943 A2 | 10/2007 |
| WO | 2007127606 A1 | 11/2007 |
| WO | 2007137286 A2 | 11/2007 |
| WO | 2007143225 A2 | 12/2007 |
| WO | 2008001091 A1 | 1/2008 |
| WO | 2008076868 A2 | 6/2008 |

OTHER PUBLICATIONS

Klonoff D., et al., "Performance Metrics for Continuous Interstitial Glucose Monitoring; Approved Guideline," Clinical and Laboratory Standards Institute, POCT05-A, vol. 28 (33), 2008, 72 pages.

Klonoff D.C., "Editorial: Current, Emerging, and Future Trends in Metabolic Monitoring," Diabetes Technology Therapeutics, vol. 4 (5), 2002, pp. 583-588.

Klueh U., et al., "Inflammation and Glucose Sensors: Use of Dexamethasone to Extend Glucose Sensor Function and Life Span in Vivo," Journal of Diabetes Science and Technology, vol. 1 (4), Jul. 2007, pp. 496-504.

Klueh U., et al., "Use of Vascular Endothelial Cell Growth Factor Gene Transfer to Enhance Implantable Sensor Function in Vivo," Biosensor Function and VEGF-Gene Transfer, vol. 67 (4), 2003, pp. 1072-1086.

Kondo T., et al., "A Miniature Glucose Sensor, Implantable in the Blood Stream," Diabetes Care, vol. 5 (3), May-Jun. 1982, 218-221.

(56) References Cited

OTHER PUBLICATIONS

Koschinsky T., et al., "Sensors for Glucose Monitoring: Technical And Clinical Aspects," Diabetes Metabolism Research and Reviews, vol. 17, No. 2, Jan. 1, 2001, pp. 113-123.

Koschinsky T., et al., "New Approach to Technical and Clinical Evaluation of Devices for Self-Monitoring of Blood Glucose," Diabetes Care, vol. 11 (8), Sep. 1988, pp. 619-629.

Koschinsky T., et al., "Review: Glucose Sensors and the Alternate Site Testing-like Phenomenon: Relationship Between Rapid Blood Glucose Changes and Glucose Sensor Signals," Diabetes Technology & Therapeutics, vol. 5 (5), 2003, pp. 829-842.

Kost J., et al., "Glucose-Sensitive Membranes Containing Glucose Oxidase: Activity, Swelling, and Permeability Studies," Journal of Biomedical Materials Research, vol. 19, 1985, pp. 1117-1133.

Koudelka M., et al., "In Vivo Response of Microfabricated Glucose Sensors to Glycemia Changes in Normal Rats," Biomed. Biochim. Acta, vol. 48 (11/12), Nov.-Dec. 1989, pp. 953-956.

Koudelka M., et al., "In-Vivo Behaviour of Hypodermically Implanted Microfabricated Glucose Sensors," Biosensors and Bioelectronics, vol. 6, 1991, pp. 31-36.

Kovatchev B.P., et al., "Evaluating the Accuracy of Continuous Glucose-Monitoring Sensors: Continuous Glucose-Error Grid Analysis Illustrated by TheraSense Freestyle Navigator Data," Diabetes Care, vol. 27 (8), Aug. 2004, pp. 1922-1928.

Kraver., et al., "A Mixed-Signal Sensor Interface Microinstrument," Sensors and Actuators A, Physical 2001, vol. 91, pp. 266-277.

Krouwer U.S., "Setting Performance Goals and Evaluating Total Analytical Error for Diagnostic Assays," Clinical Chemistry, vol. 48 (6), 2002, pp. 919-927.

Kruger D., et al., "Psychological Motivation and Patient Education: A Role for Continuous Glucose Monitoring," Diabetes Technology and Therapeutics, vol. 2 (1), 2000, pp. S93-S97.

Kulys J., et al., "Carbon-Paste Biosensors Array for Long-Term Glucose Measurement," Biosensors & Bioelectronics, vol. 9, 1994, pp. 491-500.

Kunjan K., et al., "Automated Blood Sampling and Glucose Sensing in Critical Care Settings," Journal of Diabetes Science and Technology, vol. 2 (2), Mar. 2008, pp. 194-200.

Kunzler J., et al.,"Hydrogels based on Hydrophilic Side Chain Siloxanes," Poly Mat Sci and Eng, 1993, vol. 69, pp. 226-227.

Kunzler J F., et al., "Contact Lens Materials," Chemistry & Industry, Aug. 21, 1995, pp. 651-655.

Kurnik R.T., et al., "Application of the Mixtures of Experts Algorithm for Signal Processing in a Noninvasive Glucose Monitoring System," Sensors and Actuators B, vol. 60, 1999, pp. 19-26.

Kurtz T.W., et al., "Recommendations for Blood Pressure Measurement in Humans and Experimental Animals, Part 2: Blood Pressure Measurement In Experimental Animals: A Statement for Professionals From the Subcommittee of Professional and Public Education of the American Heart Association Council on High Blood Pressure Research," Hypertension, Feb. 2005, vol. 45, pp. 299-310.

Lacourse W.R., et al., "Optimization of Waveforms for Pulsed Amperometric Detection of Carbohydrates Based on Pulsed Voltammetry," Analytical Chemistry, vol. 65, 1993, pp. 50-52.

Ladd M.F.C., et al., "Structure Determination by X-Ray Crystallography," 3rd Edition, Plenum Press, 1994, Ch. 1, pp. xxi-xxiv and 1-58.

Lee E., et al., "Effects of Pore Size, Void Volume and Pore Connectivity on Tissue Responses to Porous Silicone Implants," Society for Biomaterials, 25th Annual Meeting, 1999, p. 171.

Lee S.W., et al., "Combined Insulin Pump Therapy with Real-Time Continuous Glucose Monitoring Significantly Improves Glycemic Control Compared to Multiple Daily Injection Therapy in Pump Nave Patients with Type 1 Diabetes; Single Center Pilot Study Experience," Journal of Diabetes Science and Technology, vol. 1 (3), May 2007, pp. 400-404.

Lehmann E.D., et al., Retrospective Validation of a Physiological Model of Glucose-Insulin Interaction in Type 1 Diabetes Mellitus. Medical Engineering & Physics, vol. 16, May 1994, pp. 193-202.

Lerner., et al., "An Implantable Electrochemical Glucose Sensor," Ann. N. Y. Acad. Sci., vol. 428, May 1984, pp. 263-278.

Lewandowski J.J., et al., "Evaluation of a Miniature Blood Glucose Sensor," Transactions—American Society for Artificial Internal Organs, vol. 34, 1988, pp. 255-258.

Leypoldt J.K., et al., "Model of a Two-Substrate Enzyme Electrode for Glucose," Analytical Chemistry, vol. 56, 1984, pp. 2896-2904.

Linke B., et al., "Amperometric Biosensor for In Vivo Glucose Sensing Based on Glucose Oxidase Immobilized in a Redox Hydrogel," Biosensors and Bioelectronics, vol. 9, 1994, pp. 151-158.

Loffler P., et al., "Separation and Determination of Traces of Ammonia in Air by Means of Chromatomembrane Cells," Fresenius Journal of Analytical Chemistry, 1995, vol. 352, pp. 613-614.

Lohn A., et al., "A Knowledge-Based System for Real-Time Validation of Calibrations and Measurements," Chemometrics and Intelligent Laboratory Systems, vol. 46, 1999, pp. 57-66.

Lowe C.R., "Biosensors," Trends in Biotechnology, vol. 2 (3), 1984, pp. 59-65.

Luong J.H.T., et al., "Solubilization of Multiwall Carbon Nanotubes by 3-Aminopropyltriethoxysilane towards the Fabrication of Electrochemical Biosensors with Promoted Electron Transfer," Electroanalysis, vol. 16 (1-2), 2004, pp. 132-139.

Lyandres O., et al. "Progress toward an In Vivo Surface-Enhanced Raman Spectroscopy Glucose Sensor," Diabetes Technology and Therapeutics, vol. 10 (4), 2008, pp. 257-265.

Lyman D J., "Polyurethanes. I. The Solution Polymerization of Diisocyanates with Ethylene Glycol," Journal of Polymer Science, 1960, vol. XLV, pp. 49-59.

Lynch S.M., et al., "Estimation-Based Model Predictive Control of Blood Glucose in Type I Diabetics: A Simulation Study," Proceedings of the IEEE 27th Annual Northeast Bioengineering Conference, 2001, pp. 79-80.

Lynn P.A., "Recursive Digital Filters for Biological Signals," Med. Biol. Engineering, vol. 9, 1971, pp. 37-43.

Madaras M B., et al., "Microfabricated Amperometric Creatine and Creatinine Biosensors," Analytica Chimica Acta, 1996, vol. 319, pp. 335-345.

Maidan R., et al., "Elimination of Electrooxidizable Interferent-Produced Currents in Amperometric Biosensors," Analytical Chemistry, vol. 64, 1992, pp. 2889-2896.

Makale M.T., et al., "Tissue Window Chamber System for Validation of Implanted Oxygen Sensors," American Journal of Physiology—Heart and Circulatory Physiology, vol. 284, Feb. 21, 2003, pp. 1-27.

Malin S.F., et al., "Noninvasive Prediction of Glucose by Near-Infrared Diffuse Reflectance Spectroscopy," Clinical Chemistry, vol. 45 (9), 1999, pp. 1651-1658.

Mancy K.H., et al., "A Galvanic Cell Oxygen Analyzer," Journal of Electroanalytical Chemistry, vol. 4, 1962, pp. 65-92.

Maran A., et al., "Continuous Subcutaneous Glucose Monitoring in Diabetic Patients," A Multicenter Analysis, Diabetes Care, vol. 25 (2), Feb. 2002, pp. 347-352.

March W.F., "Dealing with the Delay," Diabetes Technology & Therapeutics, vol. 4 (1), 2002, pp. 49-50.

Marena S., et al., "The Artificial Endocrine Pancreas in Clinical Practice and Research," Panminerva Medica, vol. 35 (2), 1993, pp. 67-74.

Martin R.F., "General Deming Regression for Estimating Systematic Bias and its Confidence Interval in Method-Comparison Studies," Clinical Chemistry, vol. 46 (1), 2000, pp. 100-104.

Mascini M., et al., "Glucose Electrochemical Probe with Extended Linearity for Whole Blood," Journal Pharmaceutical and Biomedical Analysis, vol. 7 (12), 1989, pp. 1507-1512.

Mastrototaro J., et al., "An Electroenzymatic Glucose Sensor Fabricated on a Flexible Substrate," Sensors and Actuators B, vol. 5, 1991, pp. 139-144.

Mastrototaro J.J., et al., "Reproducibility of the Continuous Glucose Monitoring System Matches Previous Reports and the Intended Use of the Product," Diabetes Care, vol. 26 (1), Jan. 2003, pp. 256-257.

Ernst H., et al., "Reliable Glucose Monitoring Through the Use of Microsystem Technology," Analytical Bioanalytical Chemistry, vol. 373, 2002, pp. 758-761.

(56) References Cited

OTHER PUBLICATIONS

Fabietti P.G., et al., "Clinical Validation of a New Control-Oriented Model of Insulin and Glucose Dynamics in Subjects with Type 1 Diabetes," Diabetes Technology & Therapeutics, vol. 9 (4), 2007, pp. 327-338.

Fahy B.G., et al., "An Analysis: Hyperglycemic Intensive Care Patients Need Continuous Glucose Monitoring—Easier Said Than Done," Journal of Diabetes Science and Technology, Diabetes Technology Society, vol. 2 (2), Mar. 2008, pp. 201-204.

Fare T.L., et al., "Functional Characterization of a Conducting Polymer-Based Immunoassay System," Biosensors & Bioelectronics, vol. 13 (3-4), 1998, pp. 459-470.

Feldman B., et al., "A Continuous Glucose Sensor Based on Wired EnzymeTM Technology—Results from a 3-Day Trial in Patients with Type 1 Diabetes," Diabetes Technology & Therapeutics, vol. 5 (5), 2003, pp. 769-779.

Fischer U., et al., "Assessment of Subcutaneous Glucose Concentration: Validation of the Wick Technique as a Reference for Implanted Electrochemical Sensors in Normal and Diabetic Dogs," Diabetologia, vol. 30, 1987, pp. 940-945.

Fischer U., et al., "Hypoglycaemia—Warning by Means of Subcutaneous Electrochemical Glucose Sensors: An Animal Study," Horm. Metab. Res, vol. 27, 1995, p. 53. (Abstract Only).

Fischer U., et al., "Oxygen Tension at the Subcutaneous Implantation Site of Glucose Sensors," Biomed. Biochim. Acta, vol. 48 (11/12), 1989, pp. 965-971.

Freedman D., et al., "Statistics," Second Edition, W.W. Norton & Company, New York & London, 1991, p. 74 (3 pages).

Freiberger P., "Video Game Takes on Diabetes Superhero 'Captain Novolin' Offers Treatment Tips," Fourth Edition, Jun. 26, 1992, Business Section, 2 pages.

Frohnauer M.K., et al., "Graphical Human Insulin Time-Activity Profiles Using Standardized Definitions," Diabetes Technology & Therapeutics, vol. 3 (3), 2001, pp. 419-429.

Frost M.C., et al., "Implantable Chemical Sensors for Real-Time Clinical Monitoring: Progress and Challenges," Current Opinion in Chemical Biology, Analytical Techniques, vol. 6, 2002, pp. 633-641.

Gabby R.A., et al., "Optical Coherence Tomography-Based Continuous Noninvasive Glucose Monitoring in Patients with Diabetes," Diabetes Technology & Therapeutics, vol. 10, Nov. 3, 2008, pp. 188-193.

Ganesan N., et al., "Gold Layer-Based Dual Crosslinking Procedure of Glucose Oxidase with Ferrocene Monocarboxylic Acid Provides a Stable Biosensor," Analytical Biochemistry, Notes & Tips, vol. 343, 2005, pp. 188-191.

Ganesh A., et al., "Evaluation of the VIA Blood Chemistry Monitor for Glucose in Healthy and Diabetic Volunteers," Journal of Diabetes Science and Technology, vol. 2 (2), Mar. 2008, pp. 182-193.

Garg S.K., et al., "Correlation of Fingerstick Blood Glucose Measurements With GlucoWatch Biographer Glucose Results in Young Subjects With Type 1 Diabetes," Emerging Treatments and Technologies, Diabetes Care, vol. 22 (10), Oct. 1999, pp. 1708-1714.

Garg S.K., et al., "Improved Glucose Excursions Using an Implantable Real-Time Continuous Glucose Sensor in Adults With Type 1 Diabetes," Emerging Treatments and Technologies, Diabetes Care, vol. 27 (3), 2004, pp. 734-738.

Garg S.K., "New Insulin Analogues," Diabetes Technology & Therapeutics, vol. 7 (5), 2005, pp. 813-817.

Geller R.I., et al., "Use of an Immunoisolation Device for Cell Transplantation and Tumor Immunotherapy," Annals of the New York Academy of Science, 1997, vol. 831, pp. 438-451.

Gerritsen M., et al., "Influence of Inflammatory Cells and Serum on the Performance of Implantable Glucose Sensors," Journal of Biomedical Material Research, 2001, vol. 54, pp. 69-75.

Gerritsen M., et al., "Performance of Subcutaneously Implanted Glucose Sensors for Continuous Monitoring," The Netherlands Journal of Medicine, vol. 54, 1999, pp. 167-179.

Gerritsen M., et al., "Problems Associated with Subcutaneously Implanted Glucose Sensors," Diabetes Care, vol. 23 (2), Feb. 2000, pp. 143-145.

Gilligan B.J., et al., "Evaluation of a Subcutaneous Glucose Sensor Out to 3 Months in a Dog Model" Diabetes Care, vol. 17 (8), Aug. 1994, pp. 882-887.

Gilligan B.J., et al., "Feasibility of Continuous Long-Term Glucose Monitoring from a Subcutaneous Glucose Sensor in Humans," Diabetes Technology & Therapeutics, vol. 6 (3), 2004, pp. 378-386.

Godsland I.F., et al., "Maximizing the Success Rate of Minimal Model Insulin Sensitivity Measurement in Humans: The Importance of Basal Glucose Levels," The Biochemical Society and the Medical Research Society, Clinical Science, vol. 101, 2001, pp. 1-9.

Gouda M.D., et al., "Thermal Inactivation of Glucose Oxidase," The Journal of Biological Chemistry, vol. 278 (27), Issue of Jul. 4, 2003, pp. 24324-24333.

Gough D.A., et al., "Frequency Characterization of Blood Glucose Dynamics," Annals of Biomedical Engineering, vol. 31, 2003, pp. 91-97.

Gough D.A., et al., "Immobilized Glucose Oxidase in Implantable Glucose Sensor Technology," Diabetes Technology & Therapeutics, vol. 2 (3), 2000, pp. 377-380.

Gough D.A., "The implantable Glucose Sensor: An Example of Bioengineering Design," Introduction to Bioengineering, 2001, Chapter 3, pp. 57-66.

Gregg B A., et al., "Cross-Linked Redox Gels Containing Glucose Oxidase for Amperometric Biosensor Applications," Anal Chem, 1990, vol. 62, pp. 258-263.

Gross, et al., "Diabetes Technology & Therapeutics," Letters to the Editor, Diabetes Technology & Therapeutics, vol. 3 (1), 2001, pp. 129-131.

Gross T.M., et al., "Efficacy and Reliability of the Continuous Glucose Monitoring System," Diabetes Technology & Therapeutics, vol. 2, Supplement 1, 2000, pp. S19-S26.

Gross T.M., et al., "Performance Evaluation of the Minimed® Continuous Glucose Monitoring System During Patient Home Use," Diabetes Technology & Therapeutics, vol. 2(1), 2000, pp. 49-56.

Guerci B., et al., "Clinical Performance of CGMS in Type 1 Diabetic Patients Treated by Continuous Subcutaneous Insulin Infusion Using Insulin Analogs," Diabetes Care, vol. 26, 2003, pp. 582-589.

Hagvik J., "Glucose Measurement: Time for a Gold Standard," Journal of Diabetes Science and Technology, vol. 1 (2), Mar. 2007, pp. 169-172.

Hall S.B., et al., "Electrochemical Oxidation of Hydrogen Peroxide at Platinum Electrodes. Part 1. An Adsorption-controlled Mechanism," Electrochimica Acta, vol. 43, Nos. 5/6, 1998, pp. 579-588.

Hall S.B., et al., "Electrochemical Oxidation of Hydrogen Peroxide at Platinum Electrodes. Part II: Effect of potential," Electrochimica Acta, vol. 43 (14-15), 1998, pp. 2015-2024.

Hall S.B., et al., "Electrochemical Oxidation of Hydrogen Peroxide at Platinum Electrodes. Part III: Effect of Temperature," Electrochimica Acta, vol. 44, 1999, pp. 2455-2462.

Hall S.B., et al., "Electrochemical Oxidation of Hydrogen Peroxide at Platinum Electrodes. Part IV: Phosphate Buffer Dependence," Electrochimica Acta, vol. 44, 1999, pp. 4573-4582.

Hall S.B., et al., "Electrochemical Oxidation of Hydrogen Peroxide at Platinum Electrodes. Part V: Inhibition by Chloride," Electrochimica Acta, vol. 45, 2000, pp. 3573-3579.

Hamilton, "Complete Guide to Selecting the Right Hamilton Gastight, Microliter, and Specialty Syringe for your Application," Syringe Selection, www.hamiltoncompany.com 2006, 20 pages.

Harrison, et al., "Characterization of Perfluorosulfonic Acid Polymer Coated Enzyme Electrodes and a Miniaturized Integrated Potentiostat for Glucose Analysis in Whole Blood," Analytical Chemistry, 1988, vol. 60, pp. 2002-2007.

Hashiguchi Y., et al., "Development of a Miniaturized Glucose Monitoring System by Combining a Needle-Type Glucose Sensor with Microdialysis Sampling Method: Long-term subcutaneous tissue glucose monitoring in ambulatory diabetic patients," Diabetes Care, vol. 17, No. 5, May 1994, pp. 387-396.

(56) References Cited

OTHER PUBLICATIONS

Heinemann L., et al., "Review: Measurement of Insulin Absorption and Insulin Action," Diabetes Technology & Therapeutics, vol. 6 (5), 2004, pp. 698-718.
Heinemann L., "Measurement Quality of Blood Glucose Meters: Is There a Need for an Institution with an Unbiased View?," Journal of Diabetes Science and Technology, vol. 1 (2), Mar. 2007, pp. 178-180.
Heinemann L., "Review: Variability of Insulin Absorption and Insulin Action," Diabetes Technology & Therapeutics, vol. 4 (5), 2002, pp. 673-682.
Heise T., et al., "Hypoglycemia warning signal and glucose sensors: Requirements and concepts," Diabetes Technology & Therapeutics, vol. 5, No. 4, 2003, pp. 563-571.
Heller A., "Electrical Connection of Enzyme Redox Centers to Electrodes," J. Phys. Chem., vol. 96, 1992, pp. 3579-3587.
Heller A., "Electrical Wiring of Redox Enzymes," Ace. Chem. Res., vol. 23, 1990, pp. 128-134.
Heller A., "Implanted Electrochemical Glucose Sensors forthe Management of Diabetes," Annu. Rev., Biomed Eng., vol. 1, 1999, pp. 153-175.
Machine Translation of DE10103803A1, 2001, 1 page.
Machine Translation of JP2003079723A, 2003, 16 pages.
Patel H., et al., "Amperometric Glucose Sensors Based on Ferrocene Containing Polymeric Electron Transfer Systems—A Preliminary Report," Biosensors & Bioelectronics, vol. 18, 2003, pp. 1073-1076.
Peacock W.F., et al., "Cardiac Troponin and Outcome in Acute Heart Failure," N. Engl. J. Med., vol. 358, 2008, pp. 2117-2126.
Peguin S., et al., "Pyruvate Oxidase and Oxaloacetate Decarboxylase Enzyme Electrodes—Simultaneous Determination of Transaminases with a Two-electrode-based Analyzer," Analytica Chimica Acta, vol. 222, 1989, pp. 83-93.
Pfeiffer E.F., et al., "On Line Continuous Monitoring of Subcutaneous Tissue Glucose is Feasible by Combining Portable Glucosensor with Microdialysis," Horm. Metab. Res., vol. 25, 1993, pp. 121-124.
Pfeiffer E.F., "The Glucose Sensor: The Missing Link in Diabetes Therapy," Horm Metab Res Suppl., vol. 24, 1990, pp. 154-164.
Phillips R.E., et al., "Biomedical Applications of Polyurethanes: Implications of Failure Mechanisms," Journal of Biomedical application, vol. 3, Oct. 1988, pp. 206-227.
Phillips R.P., "A High Capacity Transcutaneous Energy Transmission System," ASIAO Journal, vol. 41, 1995, pp. M259-M262.
Pichert J.W., et al., "Issues for the Coming Age of Continuous Glucose Monitoring," Diabetes Educator, vol. 26 (6), Nov.-Dec. 2000, pp. 969-980.
Pickup J.C., et al., "Developing Glucose Sensors for In Vivo Use," Elsevier Science Publishers Ltd (UK), TIBTECH, vol. 11, 1993, pp. 285-291.
Pickup J.C., et al., "Implantable Glucose Sensors: Choosing the Appropriate Sensor Strategy," Biosensors, vol. 3, (1987/1988), pp. 335-346.
Pickup J.C., et al., "In Vivo Molecular Sensing in Diabetes Mellitus: An Implantable Glucose Sensor with Direct Electron Transfer," Diabetologia, vol. 32, 1989, pp. 213-217.
Pickup J.C., et al., "Potentially-Implantable, Amperometric Glucose Sensors with Mediated Electron Transfer: Improving the Operating Stability," Biosensors, vol. 4, 1989, pp. 109-119.
Pickup J.C., et al., "Progress Towards in Vivo Glucose Sensing with a Ferrocene-Mediated Amperometric Enzyme Electrode," Horm Metab Res Suppl, vol. 20, 1988, pp. 34-36.
Pickup J.C., et al., "Responses and Calibration of Amperometric Glucose Sensors Implanted in the Subcutaneous Tissue of Man," ACTA Diabetol, vol. 30, 1993, pp. 143-148.
Pineda L.M., et al., "Bone Regeneration with Resorbable Polymeric Membranes. III. Effect of Poly(L-lactide) Membrane Pore Size on the Bone Healing Process in Large Defects," Journal of Biomedical Materials Research, vol. 31, 1996, pp. 385-394.
Pinner S.H., et al., "Cross-Linking of Cellulose Acetate by Ionizing Radiation," Nature, vol. 184, Oct. 24, 1959, pp. 1303-1304.
Pishko M.V., et al., "Amperometric Glucose Microelectrodes Prepared Through Immobilization of Glucose Oxidase in Redox Hydrogels," Analytical Chemistry, vol. 63 (20), 1991, pp. 2268-2272.
Pitzer K.R., et al., "Detection of Hypoglycemia with the Glucowatch Biographer," Diabetes Care, vol. 24 (5), 2001, pp. 881-885.
Poirier J.Y., et al., "Clinical and Statistical Evaluation of Self-Monitoring Blood Glucose Meters," Diabetes Care, vol. 21 (11), Nov. 1998, pp. 1919-1924.
Poitout V., et al., "A Glucose Monitoring System for on Line Estimation in Man of Blood Glucose Concentration Using a Miniaturized Glucose Sensor Implanted in the Subcutaneous Tissue and a Wearable Control Unit," Diabetologia, vol. 36, 1993, pp. 658-663.
Poitout V., et al., "Development of a Glucose Sensor for Glucose Monitoring in Man: The Disposable Implant Concept," Clinical Materials, vol. 15, 1994, pp. 241-246.
Poitout V., et al., "In Vitro and In Vivo Evaluation in Dogs of a Miniaturized Glucose Sensor," ASAIO Transactions, vol. 37, 1991, pp. M298-M300.
Postlethwaite T.A., et al., "Interdigitated Array Electrode as an Alternative to the Rotated Ring-Disk Electrode for Determination of the Reaction Products of Dioxygen Reduction," Analytical Chemistry, vol. 68 (17), Sep. 1996, pp. 2951-2958.
Prabhu V.G., et al., "Electrochemical Studies of Hydrogen Peroxide at a Platinum Disc Electrode," Electrochimica Acta, vol. 26 (6), 1981, pp. 725-729.
Quinn C.A.P., et al., "Biocompatible, Glucose-Permeable Hydrogel for In situ Coating of Implantable Biosensors," Biomaterials, vol. 18 (24), 1997, pp. 1665-1670.
Quinn C.P., et al., "Kinetics of Glucose Delivery to Subcutaneous Tissue in Rats Measured with 0.3-mm Amperometric Microsensors," The American Physiological Society, vol. 269, 1995, pp. E155-E161.
Rabah M.A., et al., "Electrochemical Wear of Graphite Anodes During Electrolysis of Brine," Carbon, vol. 29 (2), 1991, pp. 165-171.
Rafael E., "Cell Transplantation and Immunoisolation: Studies on a Macroencapsulation Device," Departments of Transplantation Surgery and Pathology, Karolinska Institutet, Huddinge Hospital, Stockholm, Sweden, 1999, pp. 1-83.
Ratner B.D., "Reducing Capsular Thickness and Enhancing Angiogenesis around Implant Drug Release Systems," Journal of Controlled Release, vol. 78, 2002, pp. 211-218.
Raya Systems Pioneers, "Raya Systems Pioneers Healthy Video Games," PlayRight, Nov. 1993, pp. 14-15.
Reach G., "A Method for Evaluating in vivo the Functional Characteristics of Glucose Sensors," Biosensors, vol. 2, 1986, pp. 211-220.
Reach G., et al., "Can Continuous Glucose Monitoring Be Used for the Treatment of Diabetes?," Analytical Chemistry, vol. 64 (6), Mar. 15, 1992, pp. 381A-386A.
Reach G., "Which Threshold to Detect Hypoglycemia? Value of Receiver-Operator Curve Analysis to Find a Compromise Between Sensitivity and Specificity," Diabetes Care, vol. 24 (5), May 2001, pp. 803-804.
Rebrin K., et al., "Automated Feedback Control of Subcutaneous Glucose Concentration in Diabetic Dogs," Diabetologia, vol. 32, 1989, pp. 573-576.
Rebrin K., et al., "Subcutaneous Glucose Monitoring by Means of Electrochemical Sensors: Fiction or Reality?," Journal of Biomedical Engineering, vol. 14, Jan. 1992, pp. 33-40.
Rebrin K., et al., "Subcutaneous Glucose Predicts Plasma Glucose Independent of Insulin: Implications for Continuous Monitoring," The American Physiological Society, vol. 277, 1999, pp. E561-E571.
Renard E., "Implantable Closed-Loop Glucose Sensing and Insulin Delivery: The Future for Insulin Pump Therapy," Current Opinion in Pharmacology, vol. 2 (6), 2002, pp. 708-716.
Reush, "Organometallic Compounds," Chemical Reactivity, Virtual Textbook of Organic Chemistry, Retrieved from http://www.cem.msu.edu/-reuschlVirtualText/orgmetal.htm 2004, pp. 1-16.

(56) References Cited

OTHER PUBLICATIONS

Rhodes R.K., et al., "Prediction of Pocket-Portable and Implantable Glucose Enzyme Electrode Performance from Combined Species Permeability and Digital Simulation Analysis," Analytical Chemistry, vol. 66 (9), May 1, 1994, pp. 1520-1529.

Rigla M., et al., "Real-Time Continuous Glucose Monitoring Together with Telemedical Assistance Improves Glycemic Control and Glucose Stability in Pump-Treated Patients," Diabetes Technology & Therapeutics, vol. 10 (3), 2008, pp. 194-199.

Rinken T., et al., "Calibration of Glucose Biosensors by Using Pre-Steady State Kinetic Data," Biosensors & Bioelectronics, vol. 13, 1998, pp. 801-807.

Ristic S., et al., "Review: Effects of Rapid-Acting Insulin Analogs on Overall Glycemic Control in Type 1 and Type 2 Diabetes Mellitus," Diabetes Technology & Therapeutics, vol. 5 (1), 2003, pp. 57-66.

Rivers E.P., et al., "Central Venous Oxygen Saturation Monitoring in the Critically Ill Patient," Current Opinion in Critical Care, 2001, vol. 7, pp. 204-211.

Sachlos E., et al., "Making Tissue Engineering Scaffolds Work Review on the Application of Solid Freeform Fabrication Technology to the Production of Tissue Engineering Scaffolds," European Cells and Materials, vol. 5, 2003, pp. 29-40.

Sakakida M., et al., "Development of Ferrocene-Mediated Needle-Type Glucose Sensor as a Measure of True Subcutaneous Tissue Glucose Concentrations," Artif. Organs Today, vol. 2 (2), 1992, pp. 145-158.

Sakakida M., et al., "Ferrocene-Mediated Needle Type Glucose Sensor Covered with Newly Designed Biocompatible Membrane," Sensors and Actuators B, vol. 13-14, 1993, pp. 319-322.

Salardi S., et al., "The Glucose Area Under the Profiles Obtained with Continuous Glucose Monitoring System Relationships with HbA1C in Pediatric Type 1 Diabetic Patients," Diabetes Care, vol. 25 (10), Oct. 2002, pp. 1840-1844.

Samuels M.P., "The Effects of Flight and Altitude," Arch Dis Child, vol. 89, 2004, pp. 448-455.

San Diego Plastics Inc, "Polyethylene," Datasheet, Retrieved from http://www.sdplastics.com/polyeth.html on Aug. 19, 2009, 7 pages.

Sanders E., et al., "Fibrous Encapsulation of Single Polymer Microfibers Depends on their Vertical Dimension in Subcutaneous Tissue Polymer Microfibers," Journal of Biomedical Material Research, vol. 67A, 2003, pp. 1181-1187.

Mastrototaro J.J., "The MiniMed Continuous Glucose Monitoring System," Diabetes Technology & Therapeutics, vol. 2, Supplement 1, 2000, pp. S13-S18.

Matsuki H., "Energy Transfer System Utilizing Amorphous Wires For Implantable Medical Devices," IEEE Transactions on Magnetics, vol. 31 (2), 1994, pp. 1276-1282.

Matsumoto T., et al., "A long-Term Lifetime Amperometric Glucose Sensor with a Perfluorocarbon Polymer Coating," Biosensors & Bioelectronics, vol. 16, 2001, pp. 271-276.

Matsumoto T., et al., "A Micro-Planar Amperometric Glucose Sensor Unsusceptible to Interference Species," Sensors and Actuators B, 49, 1998, pp. 68-72.

Matthews D.R., et al., "An Amperometric Needle-Type Glucose Sensor Testing in Rats and Man," Diabetic Medicine, vol. 5, 1988, pp. 248-252.

Mazze R.S., et al., "Characterizing Glucose Exposure for Individuals with Normal Glucose Tolerance Using Continuous Glucose Monitoring and Ambulatory Glucose Profile Analysis," Diabetes Technology & Therapeutics, vol. 10 (3), 2008, pp. 149-159.

Mazzola F., et al., "Video Diabetes: A Teaching Tool for Children with Insulin-Dependent Diabetes," IEEE, Proceedings 7th Annual Symposium on Computer Applications in Medical Care, Oct. 1983, 1 page Abstract.

McCartney L.J., et al., "Near-Infrared Fluorescence Lifetime Assay for Serum Glucose Based on Allophycocyanin-Labeled Concanavalin A," Analytical Biochemistry, vol. 292, 2001, pp. 216-221.

McGrath M.J., et al., "The Use of Differential Measurements with a Glucose Biosensor for Interference Compensation During Glucose Determinations by Flow Injection Analysis," Biosens Bioelectron, vol. 10, 1995, pp. 937-943.

McKean B.D., et al., "A Telemetry Instrumentation System for Chronically Implanted Glucose and Oxygen Sensors," IEEE Transactions on Biomedical Engineering, vol. 35 (7), Jul. 1988, pp. 526-532.

Memoli A., et al., "A Comparison between Different Immobilised Glucoseoxidase-Based Electrodes," Journal of Pharmaceutical and Biomedical Analysis, vol. 29, 2002, pp. 1045-1052.

Merriam Webster Online Dictionary, Definition for "Aberrant," retrieved from https://www.merriam-webster.com/dictionary/aberrant Aug. 19, 2008, 1 page.

Merriam-Webster Online Dictionary, Definition of "Acceleration" retrieved from http://www.merriam-webster.com/dictionary/Acceleration Jan. 11, 2010, 1 page.

Merriam-Webster Online Dictionary, Definition of "Nominal" retrieved from http://www.merriam-webster.com/dictionary/nominal Apr. 23, 2007, 1 page.

Merriam-Webster Online Dictionary, Definition of "System". http://www.merriamwebster.com/dictionary/System Jan. 11, 2010, 2 pages.

Metzger M., et al., "Reproducibility of Glucose Measurements using the Glucose Sensor," Diabetes Care, vol. 25 (6), Jul. 2002, pp. 1185-1191.

Meyerhoff C., et al., "On Line Continuous Monitoring of Subcutaneous Tissue Glucose in Men by Combining Portable Glucosensor With Microdialysis," Diabetologia, vol. 35 (11), 1992, pp. 1087-1092.

Miller J.A., et al., "Development of an Autotuned Transcutaneous Energy Transfer System," ASAIO Journal, vol. 39, 1993, pp. M706-M710.

Miller K.M., et al., "Generation of IL-1 like Activity in Response to Biomedical Polymer Implants: a Comparison of in Vitro and in Vivo Models," Journal of Biomedical Materials Research, vol. 23(9), 1989, pp. 1007-1026.

Miller K.M., et al., "Human monocyte/macrophage activation and interleukin 1 generation by biomedical polymers," Journal of Biomedical Materials Research, vol. 22 (8), 1988, pp. 713-731.

Miller K.M., et al., "In Vitro Stimulation of Fibroblast Activity by Factors Generated from Human Monocytes Activated by Biomedical Polymers," Journal of Biomedical Materials Research, vol. 23(8), 1989, pp. 911-930.

Moatti-Sirat D., et al., "Evaluating In Vitro and In Vivo the Interference of Ascorbate and Acetaminophen on Glucose Detection by a Needle-Type Glucose Sensor," Biosensors and Bioelectronics, vol. 7, 1992, pp. 345-352.

Moatti-Sirat D., et al., "Reduction of Acetaminophen Interference in Glucose Sensors by a Composite Nafion Membrane: Demonstration in Rats and Man," Diabetologia, vol. 37 (6), Jun. 1994, pp. 610-616.

Moatti-Sirat., et al., "Towards Continuous Glucose Monitoring: In Vivo Evaluation of a Miniaturized Glucose Sensor Implanted for Several Days in Rat Subcutaneous Tissue," Diabetologia, vol. 35, 1992, pp. 224-230.

Monsod T.P., et al., "Do Sensor Glucose Levels Accurately Predict Plasma Glucose Concentrations During Hypoglycemia and Hyperinsulinemia?," Diabetes Care, vol. 25 (5), 2002, pp. 889-893.

Morff R.J., et al., "Microfabrication of Reproducible, Economical, Electroenzymatic Glucose Sensors," Annual International Conference of the IEEE Engineering in Medicine and Biology Society, vol. 12 (2), 1990, pp. 0483-0484.

Mosbach K., et al., "Determination of Heat Changes in the Proximity of Immobilized Enzymes with an Enzyme Thermistor and its Use for the Assay of Metabolites," Biochimica Biophysica Acta, vol. 403, 1975, pp. 256-265.

Motonaka J., et al., "Determination of Cholesterol and Cholesterol Ester with Novel enzyme Microsensors," Anal. Chem., vol. 65, 1993, pp. 3258-3261.

Moussy F., et al., "A Miniaturized Nafion-Based Glucose Sensor: In Vitro and In Vivo Evaluation in Dogs," International Journals of Artificial Organs, vol. 17 (2), 1994, pp. 88-94.

(56) References Cited

OTHER PUBLICATIONS

Moussy F., et al., "Biomaterials community examines biosensor biocompatibility," Diabetes Technology & Therapeutics, vol. 2(3), 2000, pp. 473-477.
Moussy F., et al., "Performance of Subcutaneously Implanted Needle-Type Glucose Sensors Employing a Novel Trilayer Coating," Analytical Chemistry, vol. 65, Aug. 1, 1993, pp. 2072-2077.
Moussy F., "Implantable Glucose Sensor: Progress and Problems," IEEE, Nov. 2002, pp. 270-273.
Mowery K.A., et al., "Preparation and Characterization by Hydrophobic Polymeric Films that are Thromboresistant via Nitric Oxide Release," Biomaterials, vol. 21, 2000, pp. 9-21.
Murphy S.M., et al., "Polymer Membranes in Clinical Sensor Applications, II. The Design and Fabrication of Permselective Hydrogels for Electrochemical Devices," Biomaterials, 1992, vol. 13 (14), pp. 979-990.
Muslu, "Trickling Filter Performance," Applied Biochemistry and Biotechnology, vol. 37, 1992, pp. 211-224.
Myler S., et al., "Ultra-Thin-Polysiloxane-Film-Composite Membranes for the Optimisation of Amperometric Oxidase Enzyme Electrodes," Biosensors & Bioelectronics, vol. 17, 2002, pp. 35-43.
Nakayama Y., et al., "Surface Fixation of Hydrogels: Heparin and Glucose Oxidase Hydrogelated Surfaces" ASAIO Journal, 1992, pp. M421-M424.
Nam Y.S., et al., "A Novel Fabrication Method of Macroporous Biodegradable Polymer Scaffolds Using Gas Foaming Salt as a Porogen Additive," J Biomed Mater Res, 2000, vol. 53, pp. 1-7.
Neuburger G.G., et al., "Pulsed Amperometric Detection of Carbohydrates at Gold Electrodes with a Two-Step Potential Waveform," Anal. Chem., vol. 59, 1987, pp. 150-154.
Newsrx, "Glucose Monitoring: FDA OKs New Device to Manage Diabetes," Medical Letter on the CDC & FDA via NewsRx.com, Aug. 3, 2003, 1 page.
Nintendo Healthcare, Wired, Dec. 1993, 1 page.
Novo Nordisk Pharmaceuticals Inc., "Diabetes Educational Video Game Recognized by Software Publishers Association," Press Release, Mar. 14, 1994, 4 pages.
Ohara T.J., et al., "Glucose Electrodes Based on Cross-Linked [Os(bpy)2Cl](+/2+) Complexed Poly(1-Vinylimidazole) Films," Analytical Chemistry, vol. 65, Dec. 1993, pp. 3512-3517.
Ohara T.J., et al., ""Wired" Enzyme Electrodes for Amperometric Determination of Glucose or Lactate in the Presence of Interfering Substances," Anal Chem, vol. 66, 1994, pp. 2451-2457.
Okuda, et al., "Mutarotase Effect on Micro Determinations of D-Glucose and its Anomers with β D-Glucose Oxidase," Anal Biochem, vol. 43 (1), 1971, pp. 312-315.
Oxford English Dictionary Online, Definition of "Impending," http://www.askoxford.com/results/?view=devdict&field-12668446_Impending&branch Jan. 11, 2010, 1 page.
Palmisano F., et al., "Simultaneous Monitoring of Glucose and Lactate by an Interference and Cross-Talk Free Dual Electrode Amperometric Biosensor Based on Electropolymerized Thin Films," Biosensors & Bioelectronics, vol. 15, 2000, pp. 531-539.
Panetti T.S., "Differential Effects of Sphingosine 1-Phosphate and Lysophosphatidic Acid on Endothelial Cells," Biochimica et Biophysica Acta, vol. 1582, 2002, pp. 190-196.
Panteleon A.E., et al., "The Role of the Independent Variable to Glucose Sensor Calibration," Diabetes Technology & Therapeutics, vol. 5 (3), 2003, pp. 401-410.
Parker R.S., et al., "A Model-Based Algorithm for Blood Glucose Control In Type I Diabetic Patients," IEEE Trans Biomed Engg (BME), vol. 46(2), 1999, pp. 148-157.
Heller A., "Plugging Metal Connectors into Enzymes," Nature Biotechnology, vol. 21, No. 6, Jun. 2003, pp. 631-632.
Hicks J.M., "In Situ Monitoring," Clinical Chemistry, vol. 31 (12), 1985, pp. 1931-1935.
Hitchman M.L., "Measurement of Dissolved Oxygen," Edited by Elving P.J et al., Chemical Analysis, New York, John Wiley & Sons, vol. 49, Chapter 3, 1978, pp. 34-49 and 59-123.

Hoel P.G., "Elementary Statistics," Fourth Edition, John Wiley & Sons, Inc., 1976, pp. 113-114.
Houghton Mifflin Company, "American Heritage Dictionary," 4th Edition, 2000, pp. 82.
Houghton Mifflin Company, "Xenogenic, the American Heritage Stedman's Medical Dictionary," 2002, Answers.Com, retrieved from http://www.answers.com/topic/xenogenic, on Nov. 7, 2006, 2 Pages.
Hovorka R., et al., "Closing the Loop: The Adicol Experience," Diabetes Technology & Therapeutics, vol. 6 (3), 2004, pp. 307-318.
Hrapovic S., et al., "Picoamperometric Detection of Glucose at Ultrasmall Platinum-Based Biosensors Preparation and Characterization," Anal. Chem, vol. 75, 2003, pp. 3308-3315.
Hu Y., et al., "A Needle-Type Enzyme-Based Lactate Sensor for In Vivo Monitoring," Analytica Chimica Acta, vol. 281, 1993, pp. 503-511.
Huang C., et al., "Electrochemical Generation of Oxygen. 1: The Effects of Anions and Cations on Hydrogen Chemisorption and Anodic Oxide Film Formation on Platinum Electrode. 2: The Effects of Anions and Cations on Oxygen Generation on Platinum Electrode," U.S. Department of Commence/NTIS, 1975, 126 pages.
Huang Q., et al., "A 0.5mW Passive Telemetry IC for Biomedical Applications," Proceedings of the 23rd European Solid-State Circuits Conference (ESSCIRC '97), Southampton, UK, Sep. 16-18, 1997, pp. 172-175.
Hunsley B., et al.. "Whole Blood Glucose Standard Is Key to Accurate Insulin Dosages," Journal of Diabetes Science and Technology, vol. 1 (2), Mar. 2007, pp. 173-177.
Hunter I., et al., "Minimally Invasive Glucose Sensor and Insulin Delivery System," MIT Home Automation and Healthcare Consortium, Mar. 31, 2000, Progress Report No. 25, 17 pages.
International Preliminary Report on Patentability for Application No. PCT/US2005/006301, mailed Aug. 30, 2006, 4 pages.
International Preliminary Report on Patentability for Application No. PCT/US2007/080848 mailed Apr. 13, 2010, 6 pages.
International Preliminary Report on Patentability for Application No. PCT/US2008/058158, mailed Sep. 29, 2009, 9 pages.
International Preliminary Report on Patentability for Application No. PCT/US2008/065978 mailed Jun. 19, 2008, 14 pages.
International Search Report and Written Opinion for Application No. PCT/US2005/006301, mailed Jun. 22, 2005, 4 pages.
International Search Report and Written Opinion for Application No. PCT/US2007/080848 mailed Aug. 28, 2008, 6 pages.
International Search Report and Written Opinion for Application No. PCT/US2008/058158 mailed Aug. 8, 2008, 10 pages.
International Search Report and Written opinion for Application No. PCT/US2008/065978 mailed Oct. 2, 2008, 14 pages.
Ishikawa M., et al., "Initial Evaluation of a 290-Mm Diameter Subcutaneous Glucose Sensor: Glucose Monitoring With a Biocompatible, Flexible-Wire, Enzyme-Based Amperometric Microsensor in Diabetic and Nondiabetic Humans," Journal of Diabetes and Its Complications, vol. 12, 1998, pp. 295-301.
Jablecki M., et al., "Simulations of the Frequency Response of Implantable Glucose Sensors," Analytical Chemistry, vol. 72, 2000, 1853-1859.
Jaffari S.A., et al., "Recent Advances in Amperometric Glucose Biosensors for In Vivo Monitoring," Physiological Measurement, 1995, vol. 16, pp. 1-15.
Jaremko J., et al., "Advances Toward the Implantable Artificial Pancreas for Treatment of Diabetes," Diabetes Care, vol. 21 (3), Mar. 1998, pp. 444-450.
Jensen M.B., et al., "Fast Wave Forms for Pulsed Electrochemical Detection of Glucose by Incorporation of Reductive Desorption of Oxidation Products, "Analytical Chemistry, vol. 69 (9), May 1997, pp. 1776-1781.
Jeong R.A., et al., "In Vivo Calibration of the Subcutaneous Amperometric Glucose Sensors Using a Non-Enzyme Electrode," Biosensors and Bioelectronics, Elsevier, vol. 19, 2003, pp. 313-319.
Jeutter D.C., "A Transcutaneous Implanted Battery Recharging and Biotelemeter Power Switching System," IEEE Transactions on Biomedical Engineering, vol. BME-29 (5), May 1982, pp. 314-321.

(56) References Cited

OTHER PUBLICATIONS

Jeutter D.C., et al., "Design of a Radio-Linked Implantable Cochlear Prosthesis Using Surface Acoustic Wave Devices," IEEE Transactions on Ultrasonics, Ferroelectrics and Frequency Control, vol. 40 (5), Sep. 1993, pp. 469-477.
Jobst G., et al., "Thin-Film Microbiosensors for Glucose-Lactate Monitoring," Anal Chem, Sep. 15, 1996, vol. 68(18), pp. 3173-3179.
Johnson K.W., et al., "In Vivo Evaluation of an Electroenzymatic Glucose Sensor Implanted in Subcutaneous Tissue," Biosensors and Bioelectronics, 1992, vol. 7, pp. 709-714.
Johnson K.W., "Reproducible Electrodeposition of Biomolecules for the Fabrication of Miniature Electroenzymatic Biosensors," Sensors and Actuators B, vol. 5, 1991, pp. 85-89.
Jones S.M., et al., "Optimal Insulin Pump Dosing and Postprandial Glycemia Following a Pizza Meal Using the Continuous Glucose Monitoring System," Diabetes Technology & Therapeutics, vol. 7 (2), Apr. 2005, pp. 233-240.
Joung G.B., et al., "An Energy Transmission System for an Artificial Heart Using Leakage Inductance Compensation of Transcutaneous Transformer," IEEE Transactions on Power Electronics, vol. 13 (6), Nov. 1998, pp. 1013-1022.
Jovanovic L.M.D., "The Role of Continuous Glucose Monitoring in Gestational Diabetes Mellitus," Diabetes Technology and Therapeutics, vol. 2 (1), 2000, pp. S67-S71.
Kacaniklic V., et al., "Amperometric Biosensors for Detection of L- and D-Amino Acids Based on Coimmoblized Peroxidase and L- and D-Amino Acid Oxidases in Carbon Paste Electrodes," Electroanalysis, vol. 6, May-Jun. 1994, pp. 381-390.
Kamath A., et al., "Calibration of a Continuous Glucose Monitor: Effect of Glucose Rate of Change," Eighth Annual Diabetes Technology Meeting, Nov. 13-15, 2008, pp. A88 (2 pages).
Kang S.K., et al., "In Vitro and Short-Term in Vivo Characteristics of a Kel-F Thin Film Modified Glucose Sensor," Analytical Sciences, vol. 19, Nov. 2003, pp. 1481-1486.
Kaplan S.M., "Wiley Electrical and Electronics Engineering Dictionary," IEEE Press, John Wiley & Sons, Inc., 2004, pp. 141, 142, 548 549.
Kargol M., et al., "Studies on the Structural Properties of Porous Membranes: Measurement of Linear Dimensions of Solutes," Biophysical Chemistry, 2001, vol. 91, pp. 263-271.
Karube I., et al., "Microbiosensors for Acetylcholine and Glucose," Biosensors & Bioelectronics, 1993, vol. 8, pp. 219-228.
Kaufman F.R., et al., "A Pilot Study of the Continuous Glucose Monitoring System," Diabetes Care, vol. 24 (12), Dec. 2001, pp. 2030-2034.
Kaufman F.R., "Role of the Continuous Glucose Monitoring System in Pediatric Patients," Diabetes Technology and Therapeutics, vol. 2 (1), 2000, S49-S52.
Kawagoe J.L., et al., "Enzyme-Modified Organic Conducting Salt Microelectrode," Analytical Chemistry, vol. 63, 1991, pp. 2961-2965.
Keedy F.H., et al., "Determination of Urate in Undiluted Whole Blood by Enzyme Electrode," Biosensors and Bioelectronics, vol. 6, 1991, pp. 491-499.
Kerner, et al., "A Potentially Implantable Enzyme Electrode for Amperometric Measurement of Glucose," Hormone and Metabolic Research Supplement, vol. 20, 1988, pp. 8-13.
Kerner W., et al., "The Function of a Hydrogen Peroxide-Detecting Electroenzymatic Glucose Electrode is Markedly Impaired in Human Sub-Cutaneous Tissue and Plasma," Biosensors and Bioelectronics, vol. 8, 1993, pp. 473-482.
Kerner W., "Implantable Glucose Sensors: Present Status and Future Developments," Experimental and Clinical Endocrinol Diabetes, vol. 109 (2), 2001, pp. S341-S346.
Kiechle F.L., "The Impact of Continuous Glucose Monitoring on Hospital Point-of-Care Testing Programs," Diabetes Technology and Therapeutics, vol. 3 (4), 2001, pp. 647-649.
Kizilel S., et al., "Review: The Bioartificial Pancreas: Progress and Challenges," Diabetes Technology & Therapeutics, vol. 7 (6), 2005, pp. 968-985.
Tang, et al., "Mast Cells Mediate Acute Inflammatory Responses to Implanted Biomaterials," Proceedings of the National Academy of Sciences of the USA, 1998, vol. 95, pp. 8841-8846.
Tang, et al., "Molecular Determinants of Acute Inflammatory Responses to Biomaterials," J Clin Invest, 1996, vol. 97, pp. 1329-1334.
Tatsuma T., et al., "Oxidase/Peroxidase Bilayer-Modified Electrodes as Sensors for Lactate, Pyruvate, Cholesterol and Uric Acid," Analytica Chimica Acta, vol. 242, 1991, pp. 85-89.
Thennadil S.N., et al., "Comparison of Glucose Concentration in Interstitial Fluid, and Capillary and Venous Blood During Rapid Changes in Blood Glucose Levels," Diabetes Technology & Therapeutics, vol. 3 (3), 2001, pp. 357-365.
Thijssen, et al., "A Kalman Filter for Calibration, Evaluation of Unknown Samples and Quality Control in Drifting Systems," Part 1,Theory and Simulations, Analytica chimica Acta, 1984, vol. 156, pp. 87-101.
Thijssen, et al., "A Kalman Filter for Calibration, Evaluation of Unknown Samples and Quality Control in Drifting Systems," Part 3, Variance Reduction ,Analytica chimica Acta, 1985, vol. 173, pp. 265-272.
Thijssen, et al., "A Kalman Filter for Calibration, Evaluation of Unknown Samples and Quality Control in Drifting Systems," Part 4,Flow Injection Analysis, Analytica chimica Acta, 1985, vol. 174, pp. 27-40.
Thijssen P.C.,"A Kalman Filter for Calibration, Evaluation of Unknown Samples and Quality Control in Drifting Systems," Part 2,Optimal Designs, Analytica chimica Acta, vol. 162, 1984, pp. 253-262.
Thome V., et al., "(Abstract) Can the Decrease in Subcutaneous Glucose Concentration Precede the Decrease in Blood Glucose Level? Proposition for a Push-Pull Kinetics Hypothesis," Horm. metab. Res., vol. 27, 1995, p. 53.
Thome-Duret V., et al., "Continuous Glucose Monitoring in the Free-Moving Rat," Metabolism, vol. 47 (7), Jul. 1998, pp. 799-803.
Thome-Duret V., et al., "Modification of the Sensitivity of Glucose Sensor Implanted into Subcutaneous Tissue," Diabetes Metabolism, vol. 22, 1996, pp. 174-178.
Thome-Duret V., et al., "Use of a Subcutaneous Glucose Sensor to Detect Decreases in Glucose Concentration Prior to Observation in Blood," Analytical Chemistry, vol. 68 (21), Nov. 1, 1996, pp. 3822-3826.
Thompson M., et al., "In Vivo Probes: Problems and Perspectives," Clinical Biochemistry, vol. 19 (5), Oct. 1986, pp. 255-261.
Tibell, et al., "Survival of Macroencapsulated Allogeneic Parathyroid Tissue One Year after Transplantation in Nonimmunosuppressed Humans," Cell Transplantation, 2001, vol. 10, pp. 591-599.
Tierney M.J., et al., "Effect of Acetaminophen on the Accuracy of Glucose Measurements Obtained with the GlucoWatch Biographer," Diabetes Technology & Therapeutics, vol. 2 (2), 2000, pp. 199-207.
Tierney M.J., et al., "The Gluco Watch® Biographer: A Frequent, Automatic and Noninvasive Glucose Monitor," Annals of Medicine, vol. 32, 2000, pp. 632-641.
Tilbury J.B., et al., "Receiver Operating Characteristic Analysis for Intelligent Medical Systems—A New Approach for Finding Confidence Intervals," IEEE Transactions on Biomedical Engineering, vol. 47 (7), Jul. 2000, pp. 952-963.
Torjman M.C., et al., "Glucose Monitoring in Acute Care: Technologies on the Horizon," Journal of Diabetes Science and Technology, vol. 2 (2), Mar. 2008, pp. 178-181.
Trajanoski Z., et al., "Neural Predictive Controller For Insulin Delivery Using The Subcutaneous Route," IEEE Transactions on Biomedical Engineering, vol. 45(9), 1998, pp. 1122-1134.
Trecroci D., "A Glimpse into the Future-Continuous Monitoring of Glucose with a Microfiber," Diabetes Interview, Jul. 2002, pp. 42-43.
Tse P.S.H., et al., "Time-Dependent Inactivation of Immobilized Glucose Oxidase and Catalase," Biotechnology & Bioengineering, vol. 29, 1987, pp. 705-713.

(56) References Cited

OTHER PUBLICATIONS

Turner A.P.F., "Amperometric Biosensor based on Mediator-Modified Electrodes," Methods in Enzymology, 1988, vol. 137, pp. 90-103.
Turner A.P.F., et al., "Carbon Monoxide: Acceptor Oxidoreductase from Pseudomonas Thermocarboxydovorans Strain C2 and its Use in a Carbon Monoxide Sensor," Analytica Chimica Acta, vol. 163, 1984, pp. 161-174.
Turner A.P.F., et al., "Diabetes Mellitus: Biosensors for Research and Management," Biosensors, vol. 1, 1985, pp. 85-115.
Unger J., et al., "Glucose Control in the Hospitalized Patient," Emergency Medicine, vol. 36 (9), 2004, pp. 12-18.
Updike S.J., et al., "A Subcutaneous Glucose Sensor with Improved Longevity, Dynamic Range, and Stability of Calibration," Diabetes Care, vol. 23 (2), Feb. 2000, pp. 208-214.
Updike S.J., et al., "Continuous Glucose Monitor Based on an Immobilized Enzyme Electrode Detector," Journal of Laboratory and Clinical Medicine, vol. 93(4), 1979, pp. 518-527.
Updike S.J., et al., "Enzymatic Glucose Sensor: Improved Long-Term Performance in Vitro and In Vivo," ASAIO Journal, vol. 40 (2), Apr.-Jun. 1994, pp. 157-163.
Updike S.J., et al., "Implanting the Glucose Enzyme Electrode: Problems, Progress, and Alternative Solutions," Diabetes Care, vol. 5 (3), May-Jun. 1982, pp. 207-212.
Updike S.J., et al., "Laboratory Evaluation of New Reusable Blood Glucose Sensor," Diabetes Care, vol. 11 (10), Nov.-Dec. 1988, pp. 801-807.
Updike S.J., et al., "Principles of Long-Term Fully Implanted Sensors with Emphasis on Radiotelemetric Monitoring of Blood Glucose Form Inside a Subcutaneous Foreign Body Capsule (FBC)," Edited by Fraser D M, Biosensors in the Body: Continuous in vivo Monitoring, John Wiley & Sons Ltd., New York, 1997, Chapter 4, pp. 117-137.
Updike S.J., et al., "The Enzyme Electrode," Nature, vol. 214, Jun. 3, 1967, pp. 986-988.
Utah Medical Products Inc., "Deltran—Disposable Blood Pressure Transducers," Product Specifications, 2003-2006, 6 pages.
Vadgama P., "Diffusion Limited Enzyme Electrodes," NATO ASI Series: Series C, Math and Phys. Sci, vol. 226, 1988, pp. 359-377.
Vadgama P., "Enzyme Electrodes as Practical Biosensors," Journal of Medical Engineering Technology, vol. 5 (6), Nov. 1981, pp. 293-298.
Valdes T.I., et al., "In Vitro and In Vivo Degradation of Glucose Oxidase Enzyme used for an Implantable Glucose Biosensor," Diabetes Technology & Therapeutics, vol. 2 (3), 2000, pp. 367-376.
Van Den Berghe, "Tight Blood Glucose Control with Insulin in "Real-Life" Intensive Care," Mayo Clinic Proceedings, vol. 79 (8), Aug. 2004, pp. 977-978.
Velho G., et al., "In Vitro and In Vivo Stability of Electrode Potentials in Needle-Type Glucose Sensors," Influence of Needle Material, Diabetes, vol. 38, Feb. 1989, pp. 164-171.
Velho G., et al., "Strategies for Calibrating a Subcutaneous Glucose Sensor," Biomed Biochim Acta, vol. 48 (11/12), 1989, pp. 957-964.
Vesper H.W., et al., "Assessment of Trueness of a Glucose Monitor Using Interstitial Fluid and Whole Blood as Specimen Matrix," Diabetes Technology & Therapeutics, vol. 8 (1), 2006, pp. 76-80.
Von Woedtke T., et al., "In Situ Calibration of Implanted Electrochemical Glucose Sensors," Biomed. Biochim. Acta 48 vol. 11/12, 1989, pp. 943-952.
Wade L.G., "Reactions of Aromatic Compounds," Organic Chemistry, Chapter 17, 5th edition, 2003, pp. 762-763.
Wagner, et al., "Continuous Amperometric Monitoring of Glucose in a Brittle Diabetic Chimpanzee with a Miniature Subcutaneous Electrode," Proc. Natl. Acad. Sci. USA, vol. 95, May 1998, pp. 6379-6382.
Wang J., et al., "Highly Selective Membrane-Free Mediator-Free Glucose Biosensor," Analytical Chemistry, vol. 66 (21), Nov. 1, 1994, pp. 3600-3603.
Wang X., et al., "Improved Ruggedness for Membrane-Based Amperometric Sensors using a Pulsed Amperometric Method," Analytical Chemistry, vol. 69 (21), Nov. 1, 1997, pp. 4482-4489.
Ward W.K., et al., "A New Amperometric Glucose Microsensor: In Vitro and Short-Term In Vivo Evaluation," Biosensors & Bioelectronics, vol. 17, 2002, pp. 181-189.
Ward W.K., et al., "Assessment of Chronically Subcutaneous Glucose Sensors in Dogs: The Effect of Surrounding Fluid Masses," ASAIO Journal, 1999, vol. 45 (6), pp. 555-561.
Ward W.K., et al., "Rise in Background Current Over Time in a Subcutaneous Glucose Sensor in the Rabbit," Relevance to Calibration and Accuracy, Biosensors & Bioelectronics, vol. 15, 2000, pp. 53-61.
Ward W.K., et al., "Understanding Spontaneous Output Fluctuations of an Amperometric Glucose Sensor: Effect of Inhalation Anesthesia and Use of a Nonenzyme Containing Electrode," ASAIO Journal, 2000, pp. 540-546.
Wentholt I.M.E., et al., "Relationship between Interstitial and Blood Glucose in Type 1 Diabetes Patients: Delay and the Push-pull Phenomenon Revisited," Diabetes Technology & Therapeutics, vol. 9 (2), 2007, pp. 169-175.
Aalders, et al., "Development of a Wearable Glucose Sensor; Studies in Healthy Volunteers and in Diabetic Patients," The International Journal of Artificial Organs, 1991, vol. 14, No. 2, pp. 102-108.
Abe, et al., "Characterization of Glucose Microsensors for Intracellular Measurements," Analytical Chemistry, 1992, vol. 64, No. 18, pp. 2160-2163.
Abel, et al., "Biosensors for in Vivo Glucose Measurements: Can We Cross the Experimental Stage," Biosensors & Bioelectronics, 2002, vol. 17, pp. 1059-1070.
Abel, et al., "Experience With an Implantable Glucose Sensor as a Prerequisite of an Artificial Beta Cell," Biomed. Biochim. Actan, 1984, vol. 43, No. 5, pp. 577-584.
Adilman, et al., "Videogames: Knowing The Score, Creative Computing," Dec. 1983, Dialog: File 148; IAC Trade & Industry Database, vol. 9, p. 224(5) (9 pages).
Alcock S.J., et al., "Continuous Analyte Monitoring to Aid Clinical Practice," IEEE Engineering in Medicine Biology, 1994, vol. 13, pp. 319-325.
Amer M.M.B., "An Accurate Amperometric Glucose Sensor Based Glucometer with Eliminated Cross-Sensitivity," Journal of Medical Engineering & Technology, vol. 26 (5), Sep./Oct. 2002, pp. 208-213.
American Diabetes Association., "Position Statement: Diagnosis and Classification of Diabetes Mellitus," Diabetes Care, vol. 30, Supplement 01, Jan. 2007, pp. S42-S47.
American Diabetes Association., "Position Statement: Standards of Medical Care in Diabetes," Diabetes Care, vol. 30, Supplement 01, Jan. 2007, pp. S4-S41.
American Diabetes Association., "Summary of Revisions for the 2007 Clinical Practice Recommendations," Diabetes Care, vol. 30, Supplement 01, Jan. 2007, pp. S3.
Amin R., et al., "Hypoglycemia Prevalence in Prepubertal Children With Type 1 Diabetes on Standard Insulin Regimen: Use of Continuous Glucose Monitoring System," Diabetes Care, 2003, vol. 26, No. 3, pp. 662-667.
Armour J.C., et al., "Application of Chronic Intravascular Blood Glucose Sensor in Dogs," Diabetes, Dec. 1990, vol. 39, pp. 1519-1526.
Asberg P., et al., "Hydrogels of a Conducting Conjugated Polymer as 3-D Enzyme Electrode," Biosensors Bioelectronics, 2003, vol. 19, pp. 199-207.
Assolant-Vinet C.H., et al., "New Immobilized Enzyme Membranes for Tailor-Made Biosensors," Analytical Letters, 1986, vol. 19(78), pp. 875-885.
Atanasov P., et al., "Biosensor for Continuous Glucose Monitoring," Biotechnology and Bioengineering, John Wiley & sons Inc, 1994, vol. 43, pp. 262-266.
Atanasov P., et al., "Implantation of a Refillable Glucose Monitoring-Telemetry Device," Biosensors and Bioelectronics, vol. 12 (7), 1997, pp. 669-680.

(56) References Cited

OTHER PUBLICATIONS

Aussedat B., et al., "A User-Friendly Method For Calibrating a Subcutaneous Glucose Sensor-Based Hypoglycaemic Alarm," Elsevier Science Limited, Biosensors & Bioelectronic, 1997, vol. 12, No. 11, pp. 1061-1071.
Aussedat B., et al., "Interstitial Glucose Concentration and Glycemia: Implications for Continuous Subcutaneous Glucose Monitoring," American Journal of Physiology—Endocrinology and Metabolism, vol. 278 (4), Apr. 1, 2000, pp. E716-E728.
Bailey T.S., et al., "Reduction in Hemoglobin A1C with Real-Time Continuous Glucose Monitoring: Results from a 12-Week Observational Study," Diabetes Technology Therapeutics, vol. 9 (3), 2007, pp. 203-210.
Baker D.A., et al., "Dynamic Concentration Challenges for Biosensor Characterization," Biosensors & Bioelectronics, vol. 8, 1993, pp. 433-441.
Baker D.A., et al., "Dynamic Delay and Maximal Dynamic Error in Continuous Biosensors," Analytical Chemistry, vol. 68 (8), Apr. 15, 1996, pp. 1292-1297.
Bard A.J., et al., "Electrochemical Methods," Fundamentals and Applications, John Wiley & Sons, New York, 1980, pp. 173-175.
Bardeletti G., et al., "A Reliable L-Lactate Electrode with a New Membrane for Enzyme Immobilization for Amperometric Assay of Lactate," Analytica Chemica Acta, vol. 187, 1986, pp. 47-54.
Beach R.D., et al., "Subminiature Implantable Potentiostat and Modified Commercial Telemetry Device for Remote Glucose Monitoring," IEEE Transactions on Instrumentation and Measurement, vol. 48 (6), Dec. 1999, pp. 1239-1245.
Bellucci F., et al., "Electrochemical Behaviour of Graphite-Epoxy Composite Materials (GECM) in Aqueous Salt Solutions," Journal of Applied Electrochemistry, vol. 16 (1), Jan. 1986, pp. 15-22.
Berger M., et al., "Computer Programs to Assist the Physician in the Analysis of Self-Monitored Blood Glucose Data," Proceedings of the Annual Symposium on Computer Applications in Medical Care, 1988, pp. 52-57.
Bertrand C., et al., "Multipurpose Electrode with Different Enzyme Systems Bound to Collagen Films," Analytica Chemica Acta, 1981, vol. 126, pp. 23-34.
Bessman S.P., et al., "Progress toward a Glucose Sensor for the Artificial Pancreas," Proceedings of a Workshop on Ion-Selective Microelectrodes, Jun. 4-5, 1973, Boston University, 1973, pp. 189-197.
Biermann E., et al., "How Would Patients Behave if they were Continually Informed of their Blood Glucose Levels? A Simulation Study Using a "Virtual" Patient," Diabetes Technology & Therapeutics, vol. 10 (3), 2008, pp. 178-187.
Bindra D.S., et al., "Design and in Vitro Studies of a Needle-Type Glucose Sensor for Subcutaneous Monitoring," Analytical Chemistry, vol. 63, Sep. 1, 1991, pp. 1692-1696.
Bindra D.S., et al., "Pulsed Amperometric Detection of Glucose in Biological Fluids at a Surface-Modified Gold Electrode," Analytical Chemistry, vol. 61 (22), Nov. 15, 1989, pp. 2566-2570.
Bisenberger M., et al., "A Triple-Step Potential Waveform at Enzyme Multisensors with Thick-Film Gold Electrodes for Detection of Glucose and Sucrose," Sensors and Actuators B, vol. 28, 1995, pp. 181-189.
Bland J.M., et al., "A Note on the Use of the Intraclass Correlation Coefficient in the Evaluation of Agreement between Two Methods of Measurement," Computers in Biology and Medicine, vol. 20 (5), 1990, pp. 337-340.
Bland J.M., et al., "Statistical Methods for Assessing Agreement Between Two Methods of Clinical Measurement," The Lancet, Feb. 8, 1986, pp. 307-310.
Bobbioni-Harsch E., et al., "Lifespan of Subcutaneous Glucose Sensors and their Performances during Dynamic Glycaemia Changes in Rats," J. Biomed. Eng., vol. 15, 1993, pp. 457-463.
Bode B.W., "Clinical Utility of the Continuous Glucose Monitoring System," Diabetes Technology & Therapeutics, vol. 2, Supplement 1, 2000, pp. S35-S41.
Bode B.W., et al., "Continuous Glucose Monitoring Used to Adjust Diabetes Therapy Improves Glycosylated Hemoglobin: A Pilot Study," Diabetes Research and Clinical Practice, vol. 46, 1999, pp. 183-190.
Bode B.W., et al., "Using the Continuous Glucose Monitoring System to Improve the Management of Type 1 Diabetes," Diabetes Technology & Therapeutics, vol. 2, Supplement 1, 2000, pp. S43-S48.
Boedeker Plastics Inc, "Polyethylene Specifications," Polyethylene Data Sheet, Retrieved from http://www.boedeker.com/polye.sub.--p.htm on Aug. 19, 2009, 4 pages.
Boland E., et al., "Limitations of Conventional Methods of Self-Monitoring of Blood Glucose," Diabetes Care, vol. 24 (11), Nov. 2001, pp. 1858-1862.
Bolinder J., et al., "Self-Monitoring of Blood Glucose in Type I Diabetic Patients: Comparison with Continuous Microdialysis Measurements of Glucose in Subcutaneous Adipose Tissue during Ordinary Life Conditions," Diabetes Care, vol. 20 (1), Jan. 1997, pp. 64-70.
Bolinder J., et al., "Microdialysis Measurement of the Absolute Glucose Concentration in Subcutaneous Adipose Tissue Allowing Glucose Monitoring in Diabetic Patients," Rapid Communication, Diabetologia, vol. 35, 1992, pp. 1177-1180.
Bott A.W., "A Comparison of Cyclic Voltammetry and Cyclic Staircase Voltammetry," Current Separations, vol. 16 (1), 1997, pp. 23-26.
Bott A.W., "Electrochemical Methods for the Determination of Glucose," Current Separations, vol. 17 (1), 1998, pp. 25-31.
Bowman L., et al., "The Packaging of Implantable Integrated Sensors," IEEE Transactions in Biomedical Engineering, vol. BME-33 (2), Feb. 1986, pp. 248-255.
Brauker, et al., "Sustained Expression of High Levels of Human Factor IX from Human Cells Implanted within an Immunoisolation Device into Athymic Rodents," Human Gene Therapy, Apr. 10, 1998, vol. 9, pp. 879-888.
Brauker J., et al., "Local Inflammatory Response Around Diffusion Chambers Containing Xenografts," Transplantation, vol. 61 (12), Jun. 27, 1996, pp. 1671-1677.
Brauker J H., et al., "Neovascularization of Synthetic Membranes Directed by Membrane Microarchitecture," Journal of Biomedical Material Research, 1995, vol. 29, pp. 1517-1524.
Brauker J., "Unraveling Mysteries at the Biointerface: Molecular Mediator of Inhibition of Blood Vessel Formation in the Foreign Body Capsule Revealed," SurFACTS in Biomaterials, vol. 6 (3), 2001, pp. 1,5.
Braunwald E., "Biomarkers in Heart Failure," Medical Progress, The New England Journal of Medicine, vol. 358, May 15, 2008, pp. 2148-2159.
Bremer T., et al., "Is Blood Glucose Predictable from Previous Values? A Solicitation for Data," Perspectives in Diabetes, vol. 48, Mar. 1999, pp. 445-451.
Bremer T.M., et al., "Benchmark Data from the Literature for Evaluation of New Glucose Sensing Technologies," Diabetes Technology Therapeutics, vol. 3 (3), 2001, pp. 409-418.
Brooks S.L., et al., "Development of an On-line Glucose Sensor for Fermentation Monitoring," Biosensors, vol. 3, 1987/1988, pp. 45-56.
Bruckel J., et al., "In Vivo Measurement of Subcutaneous Glucose Concentrations with an Enzymatic Glucose Sensor and a Wick Method," Klin Wochenschr, vol. 67, 1989, pp. 491-495.
Brunner G.A., et al., "Validation of Home Blood Glucose Meters with Respect to Clinical and Analytical Approaches," Diabetes Care, vol. 21, No. 4, Apr. 1998, pp. 585-590.
Brunstein E., et al., "Preparation and Validation of Implantable Electrodes for the Measurement of Oxygen and Glucose," Biomed Biochim. Acta, vol. 48 (11/12), 1989, pp. 911-917.
Cai Q., et al., "A Wireless, Remote Query Glucose Biosensor Based on a pH-Sensitive Polymer," Analytical Chemistry, vol. 76 (14), Jul. 15, 2004, pp. 4038-4043.
Cameron T., et al., "Micromodular Implants to Provide Electrical Stimulation of Paralyzed Muscles and Limbs," IEEE Transactions on Biomedical Engineering, vol. 44 (9), Sep. 1997, pp. 781-790.

(56) References Cited

OTHER PUBLICATIONS

Campanella L., et al., "Biosensor for Direct Determination of Glucose and Lactate in Undiluted Biological Fluids," Biosensors & Bioelectronics, vol. 8, 1993, pp. 307-314.

Candas B., et al., "An Adaptive Plasma Glucose Controller Based on a Nonlinear Insulin/Glucose Model," IEEE Transactions on Biomedical Engineering, vol. 41 (2), Feb. 1994, pp. 116-124.

Cass A.E.G., et al., "Ferrocene-Mediated Enzyme Electrodes for Amperometric Determination of Glucose," Analytical Chemistry, vol. 56 (4), Apr. 1984, pp. 667-671.

Cassidy J.F., et al., "Novel Electrochemical Device for the Detection of Cholesterol or Glucose," Analyst, vol. 118, Apr. 1993, pp. 415-418.

Chase H.P., et al., "Continuous Subcutaneous Glucose Monitoring in Children with Type 1 Diabetes," Pediatrics, vol. 107 (2), Feb. 2001, pp. 222-226.

Chase J.G., et al., "Targeted Glycemic Reduction in Critical Care Using Closed-Loop Control," Diabetes Technology & Therapeutics, vol. 7 (2), 2005, pp. 274-282.

Chen C., et al., "A Noninterference Polypyrrole Glucose Biosensor," Biosensors and Bioelectronics, vol. 22, 2006, pp. 639-643.

Chen T., et al., "Defining the Period of Recovery of the Glucose Concentration after its Local Perturbation by the Implantation of a Miniature Sensor," Clinical Chemistry and Laboratory Medicine, vol. 40 (8), 2002, pp. 786-789.

Chia C.W., et al., "Glucose Sensors: Toward Closed Loop Insulin Delivery," Endocrinology and Metabolism Clinics of North America, vol. 33, 2004, pp. 175-195.

Choleau C., et al., "Calibration of a Subcutaneous Amperometric Glucose Sensor Implanted for 7 Days in Diabetic Patients Part 2. Superiority of the One-point Calibration Method," Biosensors and Bioelectronics, vol. 17 (8), 2002, pp. 647-654.

Choleau C., et al., "Calibration of a Subcutaneous Amperometric Glucose Sensor Part 1. Effect of Measurement Uncertainties on the Determination of Sensor Sensitivity and Background Current," Biosensors and Bioelectronics, vol. 17, 2002, pp. 641-646.

Ciba Specialty Chemicals, "Ciba® IRGACURE® 2959," Coating Effects Segment, Photoinitiator Product Description, Basel Switzerland, Apr. 2, 1998, 3 pages.

Claremont D.J., et al., "Potentially-Implantable, Ferrocene-Mediated Glucose Sensor," Journal of Biomedical Engineering, vol. 8, Jul. 1986, pp. 272-274.

Claremont D.J., et al., "Subcutaneous Implantation of a Ferrocene-Mediated Glucose Sensor in Pigs," Diabetologia, vol. 29, 1986, pp. 817-821.

Clark L.C., et al., "Configurational Cyclic Voltammetry: Increasing the Specificity and Reliability of Implanted Electrodes," IEEE/Ninth Annual Conference of the Engineering in Medicine and Biology Society, 1987, pp. 0782-0783.

Clark L.C., et al., "Long-Term Stability of Electroenzymatic Glucose Sensors Implanted in Mice," vol. XXXIV, Transactions—American Society for Artificial Internal Organs, 1988, vol. 34, pp. 259-265.

Clark L.C., et al., "One-Minute Electrochemical Enzymic Assay for Cholesterol in Biological Materials," Clinical Chemistry, vol. 27 (12), 1981, pp. 1978-1982.

Clarke W.L., et al., "Evaluating Clinical Accuracy of Systems for Self Monitoring of Blood Glucose," Technical Articles, Diabetes Care, vol. 10 (5), Sep.-Oct. 1987, pp. 622-628.

Colangelo V.J., et al., "Corrosion Rate Measurements in Vivo," Journal of Biomedical Materials Research, vol. 1, 1967, pp. 405-414.

Colowick S.P., et al., "Methods in Enzymology," vol. XLIV, Immobilized Enzymes, Edited by Mosbach K, New York Academic Press, 1976, 11 pages.

Coulet P.R., et al., "Enzymes Immobilized on Collagen Membranes: A Tool for Fundamental Research and Enzyme Engineering," Journal of Chromatography, vol. 215, 1981, pp. 65-72.

Coulet P.R., "Polymeric Membranes and Coupled Enzymes in the Design of Biosensors," Journal of Membrane Science, 1992, vol. 68, pp. 217-228.

Cox D.J., et al., "Accuracy of Perceiving Blood Glucose in IDDM," Diabetes Care, vol. 8 (6), Nov.-Dec. 1985, pp. 529-536.

Csoregi E., et al., "Amperometric Microbiosensors for Detection of Hydrogen Peroxide and Glucose Based on Peroxidase-Modified Carbon Fibers," Electroanalysis, vol. 6, 1994, pp. 925-933.

Csoregi E., et al., "Design, Characterization and One-Point in Vivo Calibration of a Subcutaneously Implanted Glucose Electrode," American Chemical Society, Analytical Chemistry, vol. 66 (19), Oct. 1, 1994, pp. 3131-3138.

Currie J.F., et al., "Novel Non-Intrusive Trans-Dermal Remote Wireless Micro-Fluidic Monitoring System Applied to Continuous Glucose and Lactate Assays for Casualty Care and Combat Readiness Assessment," RTO HFM Symposium, RTO-MP-HFM-109, Aug. 16-18, 2004, pp. 24-1-24-18.

Dai W.S., et al., "Hydrogel Membranes with Mesh Size Asymmetry based on the Gradient Crosslinking of Poly(Vinyl Alcohol)," Journal of Membrane Science, 1999, vol. 156, pp. 67-79.

Danielsson B., et al., "Enzyme Thermistors," Methods in Enzymology, vol. 137, 1988, pp. 181-197.

D'Arrigo G., et al., "Porous-Si Based Bio Reactors for Glucose Monitoring and Drugs Production," Proceedings of SPIE, 2003, vol. 4982, pp. 178-184.

Dassau E., et al., "In Silico Evaluation Platform for Artificial Pancreatic β-Cell Development—A Dynamic Simulator for Closed-Loop Control with Hardware-in-the-loop," Diabetes Technology & Therapeutics, vol. 11 (3), 2009, pp. 1-8.

Davies M.L., et al., "Polymer Membranes in Clinical Sensor Applications," An overview of membrane function, Biomaterials, vol. 13 (14), 1992, pp. 971-978.

Davis G., et al., "Bioelectrochemical Fuel Cell and Sensor Based on a Quinoprotein, Alcohol Dehydrogenase," Enzyme and Microbial Technology, vol. 5 (5), Sep. 1983, pp. 383-388.

De Vos P., et al., "Considerations for Successful Transplantation of Encapsulated Pancreatic Islets," Diabetologia, vol. 45, 2002, pp. 159-173.

Deutsch T., et al., "Time Series Analysis and Control of Blood Glucose Levels in Diabetic Patients," Computer Methods and Programs in Biomedicine, Elsevier Scientific Publishers, vol. 41, 1994, pp. 167-182.

Dixon B.M., et al., "Characterization in Vitro and in Vivo of the Oxygen Dependence of an Enzyme/Polymer Biosensor for Monitoring Brain Glucose," Journal of Neuroscience Methods, vol. 119, 2002, pp. 135-142.

DuPont, "Dimension® AR Clinical Chemistry System," The Chemistry Analyzer that Makes the most of your Time, Money and Effort, Dade International, Chemistry Systems, Newark, 1998, 18 pages.

Durliat H., et al., "Spectrophotometric and Electrochemical Determinations of L(+)-Lactate in Blood by Use of Lactate Dehydrogenase from Yeast," Clinical Chemistry, vol. 22 (11), 1976, pp. 1802-1805.

Edwards Lifesciences, "Accuracy for You and Your Patients," Marketing materials, 2002, 4 pages.

El Degheidy M.M., et al., "Optimization of an Implantable Coated Wire Glucose Sensor," Journal of Biomedical Engineering, vol. 8, Apr. 1986, pp. 121-129.

ELCO Diagnostics Company, "Direct 30/30® Blood Glucose Sensor," Markwell Medical Catalog, 1990, 1 page.

El-Khatib F.H., et al., "Adaptive Closed-Loop Control Provides Blood-Glucose Regulation Using Dual Subcutaneous Insulin and Glucagon Infusion in Diabetic Swine," Journal of Diabetes Science and Technology, Diabetes Technology Society, vol. 1 (2), 2007, pp. 181-192.

El-Sa'ad L., et al., "Moisture Absorption by Epoxy Resins: The Reverse Thermal Effect," Journal of Materials Science, vol. 25, 1990, pp. 3577-3582.

Sansen W., et al., "A Smart Sensor for the Voltammetric Measurement of Oxygen or Glucose Concentrations," Sensors and Actuators B1, 1990, pp. 298-302.

Sansen W., et al., "Glucose Sensor with Telemetry System," In Implantable Sensors for Closed Loop Prosthetic Systems edited by Ko W.H, Chapter 12, 1985, pp. 167-175.

(56) References Cited

OTHER PUBLICATIONS

Schaffar B.P.H., "Thick Film Biosensors for Metabolites in Undiluted Whole Blood and Plasma Samples," Analytical Bioanalytical Chemistry, Dec. 2001, vol. 372, pp. 254-260.

Schmidt F.J., et al., "Calibration of a Wearable Glucose Sensor," The International Journal of Artificial Organs, Wichtig Publishing,IT, vol. 15 (1), Jan. 1, 1992, pp. 55-61.

Schmidt F.J., et al., "Glucose Concentration in Subcutaneous Extracellular Space," Diabetes Care, vol. 16 (5), May 1993, pp. 695-700.

Schmidtke D.W., et al., "Accuracy of the One-Point in Vivo Calibration of "Wired" Glucose Oxidase Electrodes Implanted in Jugular Veins of Rats in Periods of Rapid Rise and Decline of the Glucose Concentration," Analytical Chemistry, vol. 70 (10), May 15, 1998, pp. 2149-2155.

Schmidtke D.W., et al., "Measurement and Modeling of the Transient Difference Between Blood and Subcutaneous Glucose Concentrations in the Rat After Injection of Insulin," Proceedings of the National Academy of Sciences, vol. 95, Jan. 1998, pp. 294-299.

Schoemaker M., et al., "The SCGMI System: Subcutaneous Continuous Glucose Monitoring Based on Microdialysis Technique," Diabetes Technology & Therapeutics, vol. 5 (4), 2003, pp. 599-608.

Schoonen A.J.M., et al., "Development of a Potentially Wearable Glucose Sensor for Patients with Diabetes Mellitus: Design and In-vitro Evaluation," Biosensors & Bioelectronics, vol. 5, 1990, pp. 37-46.

Schuler, et al., "Modified Gas-Permeable Silicone Rubber Membranes for Covalent Immobilisation of Enzymes and their Use in Biosensor Development," Analyst, 1999, vol. 124, pp. 1181-1184.

Selam J.L., "Management of Diabetes with Glucose Sensors and Implantable Insulin Pumps," From the Dream of the 60s to the Realities of the 90s, ASAIO Journal 1997, vol. 43, pp. 137-142.

Service F.J., et al., "Mean Amplitude of Glycemic Excursions, A Measure of Diabetic Instability," Diabetes, vol. 19 (9), Sep. 1970, pp. 644-655.

Service F.J., et al., "Measurements of Glucose Control," Diabetes Care, vol. 10 (2), Mar.-Apr. 1987, pp. 225-237.

Service R.F., "Can Sensors Make a Home in the Body?," Science, Materials Science: Soft Surface, vol. 297, Aug. 9, 2002, pp. 962-963.

Sharkawy A.A., et al., "Engineering the Tissue Which Encapsulates Subcutaneous Implants. I. Diffusion Properties," Journal of Biomedical Materials Research, vol. 37, 1996, pp. 401-412.

Shaw G.W., et al., "In Vitro Testing of a Simply Constructed, Highly Stable Glucose Sensor Suitable for Implantation in Diabetic Patients," Biosensors & Bioelectronics, vol. 6, 1991, pp. 401-406.

Shichiri M., et al., "Glycaemic Control in Pancreatectomized Dogs with a Wearable Artificial Endocrine Pancreas," Diabetologia, vol. 24, 1983, pp. 179-184.

Shichiri M., et al., "Membrane Design for Extending the Long-Life of an Implantable Glucose Sensor," Diabetes Nutrition & Metabolism, vol. 2 (4), 1989, pp. 309-313.

Shichiri M., et al., "Needle Type Glucose Sensor for Wearable Artificial Endocrine Pancreas," In Implantable Sensors for Closed-Loop Prosthetic Systems edited by Ko W.H, Chapter 15, 1985, pp. 197-210.

Shichiri M., et al., "Telemetry Glucose Monitoring Device with Needle-Type Glucose Sensor: A Useful Tool for Blood Glucose Monitoring in Diabetic Individuals," Diabetes Care, vol. 9 (3), May-Jun. 1986, pp. 298-301.

Shichiri M., et al., "Wearable Artificial Endocrine Pancreas with Needle-Type Glucose Sensor," Preliminary Communication, Lancet, vol. 2, Nov. 20, 1982, pp. 1129-1131.

Shults M.C., et al., "A Telemetry-Instrumentation System for Monitoring Multiple Subcutaneously Implanted Glucose Sensors," IEEE Transactions on Biomedical Engineering, vol. 41 (10), Oct. 1994, pp. 937-942.

Sieminski, et al., "Biomaterial-Microvasculature Interactions," Biomaterials, 2000, vol. 21, pp. 2233-2241.

Sigma-Aldrich Corp., "Cellulose Acetate," Product Description, Product No. 419028, St. Louis, MO, 2005, 1 page.

Sigma-Aldrich Corp. "Nafion® 117 Solution Product Description, Product No. 70160," retrieved from https//:www.sigmaaldrich.com/cgi-bin/hsrun/Suite7/Suite/HAHTpage/Suite.HsExternalProd on Apr. 7, 2005, 1 page.

Skyler J.S., "The Economic Burden of Diabetes and the Benefits of Improved Glycemic Control: The Potential Role of a Continuous Glucose Monitoring System," Diabetes Technology & Therapeutics, vol. 2, Supplement 1, 2000, pp. S7-S12.

Slater-Maclean L., et al., "Accuracy of Glycemic Measurements in the Critically Ill," Diabetes Technology and Therapeutics, vol. 10 (3), 2008, pp. 169-177.

Smith B., et al., "An Externally Powered, Multichannel, Implantable Stimulator-Telemeter for Control of Paralyzed Muscle," IEEE Transactions on Biomedical Engineering, vol. 45 (4), Apr. 1998, pp. 463-475.

Smith, et al.," A Comparison of Islet Transplantation and Subcutaneous Insulin Injections for the Treatment of Diabetes Mellitus," Computers in Biology and Medicine, 1991, vol. 21 (6), pp. 417-427.

Sokol L., et al., "Immobilized-Enzyme Rate-Determination Method for Glucose Analysis," Clinical Chemistry, vol. 26 (1), 1980, pp. 89-92.

Sokolov S., et al., "Metrological Opportunities of the Dynamic Mode of Operating an Enzyme Amperometric Biosensor," Medical Engineering & Physics, vol. 17 (6), 1995, pp. 471-476.

Sparacino G., et al., "Continuous Glucose Monitoring Time Series and Hypo-Hyperglycemia Prevention: Requirements, Methods, Open Problems," Current Diabetes Reviews, vol. 4 (3), 2008, pp. 181-192.

Sproule B.A., et al., "Fuzzy Pharmacology: Theory and Applications," Trends in Pharmacological Sciences, vol. 23 (9), Sep. 2002, pp. 412-417.

Sriyudthsak M., et al., "Enzyme-Epoxy Membrane Based Glucose Analyzing System and Medical Applications," Biosensors & Bioelectronics, vol. 11 (8), 1996, pp. 735-742.

Steil G.M., et al., "Determination of Plasma Glucose During Rapid Glucose Excursions with a Subcutaneous Glucose Sensor," Diabetes Technology & Therapeutics, vol. 5 (1), 2003, pp. 27-31.

Stern M., et al., "Electrochemical Polarization: I. A Theoretical Analysis of the Shape of Polarization Curves," Journal of the Electrochemical Society, vol. 104 (1), Jan. 1957, pp. 56-63.

Sternberg, et al., "Covalent Enzyme Coupling on Cellulose Acetate Membranes for Glucose Sensor Development," Anal Chem, Dec. 1988, vol. 60(24), pp. 2781-2786.

Sternberg F., et al., "Does Fall in Tissue Glucose Precede Fall in Blood Glucose?," Diabetologia, vol. 39, 1996, pp. 609-612.

Sternberg R., et al., "Study and Development of Multilayer Needle-type Enzyme Based Glucose Microsensors," Biosensors, Mar. 20, 1988, vol. 4 (1), pp. 27-40.

Stokes, "Polyether Polyurethanes: Biostable or Not," Journal of Biomaterials Applications, Oct. 1988, vol. 3, pp. 228-259.

Street, et al., "Islet Graft Assessment in the Edmonton Protocol: Implications for Predicting Long-Term Clinical Outcome," Diabetes, 2004, vol. 53, pp. 3107-3114.

Street J.O., et al., "A Note on Computing Robust Regression Estimates via Iteratively Reweighted Least Squares," The American Statistician, vol. 42 (2), May 1988, pp. 152-154.

Suh, et al., "Behavior of Fibroblasts on a Porous Hyaluronic Acid Incorporated Collagen Matrix," Yonsei Medical Journal, 2002, vol. 43 (2), pp. 193-202.

Sumino T., et al., "Preliminary Study of Continuous Glucose Monitoring with a Microdialysis Technique," Proceedings of the 20th Annual International Conference of the IEEE Engineering in Medicine and Biology Society, vol. 20 (4), 1998, pp. 1775-1778.

Takatsu I., et al., "Solid State Biosensors Using Thin-Film Electrodes," Sensors and Actuators, 1987, vol. 11, pp. 309-317.

Takegami S., et al., "Pervaporation of Ethanol/Water Mixtures Using Novel Hydrophobic Membranes Containing Polydimethylsiloxane," Journal of Membrane Science, vol. 75, 1992, pp. 93-105.

(56) References Cited

OTHER PUBLICATIONS

Tamura T., et al., "Preliminary Study of Continuous Glucose Monitoring with a Microdialysis Technique and a Null Method—A Numerical Analysis," Frontiers of Medical Biological Engineering, vol. 10 (2), 2000, pp. 147-156.
Tanenberg R.J., et al., "Continuous Glucose Monitoring System: A New Approach to the Diagnosis of Diabetic Gastroparesis," Diabetes Technology Therapeutics, vol. 2, Supplement 1, 2000, pp. S73-S80.
Tang, et al., "Fibrin(ogen) Mediates Acute Inflammatory Responses to Biomaterials," J.Exp.Med, 1993, vol. 178, pp. 2147-2156.
Tang, et al., "Inflammatory Responses to Biomaterials," Am J Clin Pathol, 1995, vol. 103, pp. 466-471.
Wientjes K.J.C., "Development of a Glucose Sensor for Diabetic Patients," (Ph.D. Thesis), 2000,212 pages.
Wikipedia., "Intravenous Therapy," http://en.wikipedia.org/wiki/Intravenous_therapy, Aug. 15, 2006, 6 pages.
Wilkins E., et al., "Glucose Monitoring: State of the Art and Future Possibilities," Med. Eng. Phys., vol. 18 (4), 1996, pp. 273-288.
Wilkins E., et al., "Integrated Implantable Device for Long-Term Glucose Monitoring," Biosensors & Bioelectronics, vol. 10, 1995, pp. 485-494.
Wilkins E.S., et al., "The Coated Wire Electrode Glucose Sensor," Horm Metab Res Suppl., vol. 20, 1988, pp. 50-55.
Wilson G.S., et al., "Enzyme-Based Biosensors for In Vivo Measurements," Chem. Rev., vol. 100, 2000, pp. 2693-2704.
Wilson G.S., et al., "Progress Toward the Development of an Implantable Sensor for Glucose," Clinical Chemistry, vol. 38 (9), 1992, pp. 1613-1617.
Wolpert H., "Establishing a Continuous Glucose Monitoring Program," Journal of Diabetes Science and Technology, Mar. 2008, vol. 2 (2), pp. 307-310.
Wolpert H.A., "Commentary: A Clinician's Perspective on Some of the Challenges in Closed Loop," Diabetes Technology & Therapeutics, vol. 5 (5), 2003, pp. 843-846.
Wood W D., et al., "Hermetic Sealing with Epoxy," Pave Technology—Mechanical Engineering, Mar. 1990, 3 pages.
Woodward S.C., "How Fibroblasts and Giant Cells Encapsulate Implants: Considerations in Design of Glucose Sensors," Diabetes Care, vol. 5 (3) May-Jun. 1982, pp. 278-281.
Worsley G.J et al., "Measurement of Glucose in Blood with a Phenylboronic Acid Optical Sensor," Journal of Diabetes Science and Technology, vol. 2 (2), Mar. 2008, pp. 213-220.
Wright M., et al., "Bioelectrochemical Dehalogenations via Direct Electrochemistry of Poly(ethylene oxide)-Modified Myoglobin," Electrochemistry Communications, vol. 1, 1999, pp. 609-613.
Wu H., et al., "In Situ Electrochemical Oxygen Generation with an Immunoisolation Device," Annals New York Academy of Sciences, vol. 875, 1999, pp. 105-125.
Yamasaki Y., et al., "Direct Measurement of Whole Blood Glucose by a Needle-Type Sensor," Clinica Chimica Acta. 93, 1989, pp. 93-98.
Yamasaki Y., "The Development of a Needle-Type Glucose Sensor for Wearable Artificial Endocrine Pancreas," Medical Journal of Osaka University, vol. 35 (1-2), Sep. 1984, pp. 25-34.
Yang C., et al., "A Comparison of Physical Properties and Fuel Cell Performance of Nafion and Zirconium Phosphate/Nation Composite Membranes," Journal of Membrane Science, vol. 237, 2004, pp. 145-161.
Yang Q., et al., "Development of Needle-Type Glucose Sensor with High Selectivity," Science and Actuators B, vol. 46, 1998, pp. 249-256.
Yang S., et al., "A Glucose Biosensor Based on an Oxygen Electrode: In-Vitro Performances in a Model Buffer Solution and in Blood Plasma," Biomedical Instrumentation & Technology, vol. 30 (1), 1996, pp. 55-61.
Yang S., et al., "Glucose Biosensors with Enzyme Entrapped in Polymer Coating," Biomedical Instrument and Technology, Mar./Apr. 1995, vol. 29 (2), pp. 125-133.
Ye L., et al., "High Current Density Wired Quinoprotein Glucose Dehydrogenase Electrode," Analytical Chemistry, vol. 65, 1993, pp. 238-241.
Zamzow K.L., et al., "Development and Evaluation of a Wearable Blood Glucose Monitor," ASAIO Transactions, vol. 36 (3), 1990, pp. M588-M591.
Zavalkoff S.R., et al., "Evaluation of Conventional Blood Glucose Monitoring as an Indicator of Integrated Glucose Values Using a Continuous Subcutaneous Sensor," Diabetes Care, vol. 25(9), 2002, pp. 1603-1606.
Zethelius B., et al., "Use of Multiple Biomarkers to Improve the Prediction of Death From Cardiovascular Causes," N. Engl. J. Med., vol. 358, May 2008, pp. 2107-2116.
Zhang, et al., "Elimination of the Acetaminophen Interference in an Implantable Glucose Sensor," Analytical Chemistry, 1994, vol. 66 (7), pp. 1183-1188.
Zhang Y., et al., "Electrochemical Oxidation of H2O2 on Pt and Pt + Ir Electrodes in Physiological Buffer and its Applicability to H2O2-Based Biosensors," J. Electro Analytical Chemistry, vol. 345, 1993, pp. 253-271.
Zhang Y., et al., "In Vitro and In Vivo Evaluation of Oxygen Effects on a Glucose Oxidase Based Implantable Glucose Sensor," Analytica Chimica Acta, vol. 281, 1993, pp. 513-520.
Zhu, et al., "Fabrication and Characterization of Glucose Sensors Based on a Microarray H2O2 Electrode," Biosensors & Bioelectronics, 1994, vol. 9, pp. 295-300.
Zhu, et al., "Planar Amperometric Glucose Sensor Based on Glucose Oxidase Immobilized by Chitosan Film on Prussian blue Layer," Sensors, 2002, vol. 2, pp. 127-136.
Ziaie, et al., "A Single-Channel Implantable Microstimulator for Functional Neuromuscular Stimulation," IEEE Transactions on Biomedical Engineering, 1997, vol. 44(10), pp. 909-920.
Machine Translation of EP1144028B1, 2004, 32 Pages.

\* cited by examiner

INTEGRATED INSULIN DELIVERY SYSTEM WITH CONTINUOUS GLUCOSE SENSOR

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 17/074,490, filed Oct. 19, 2020, which is a continuation of U.S. application Ser. No. 16/867,476, filed May 5, 2020, which is a continuation of U.S. application Ser. No. 15/792,038, filed Oct. 24, 2017, now U.S. Pat. No. 10,653,835, which is a continuation of U.S. application Ser. No. 15/362,571, filed Nov. 28, 2016, now U.S. Pat. No. 9,827,372, which is a continuation of U.S. application Ser. No. 14/063,811, filed Oct. 25, 2013, now U.S. Pat. No. 9,597,453, which is a continuation of U.S. application Ser. No. 13/885,604, filed on Sep. 11, 2013, now U.S. Pat. No. 9,452,258, which is the national phase under 35 U.S.C. § 371 of prior PCT International Application No. PCT/US2007/080848 filed on Oct. 9, 2007. Each of the aforementioned applications is incorporated by reference herein in its entirety, and each is hereby expressly made a part of this specification.

FIELD OF THE INVENTION

The present invention relates generally to systems and methods monitoring glucose in a host. More particularly, the present invention relates to an integrated medicament delivery device and continuous glucose sensor.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high glucose, which may cause an array of physiological derangements (for example, kidney failure, skin ulcers, or bleeding into the vitreous of the eye) associated with the deterioration of small blood vessels. A hypoglycemic reaction (low glucose) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically comprises uncomfortable finger pricking methods. Due to the lack of comfort and convenience, a diabetic generally measures his glucose level only two to four times per day. Unfortunately, these time intervals are spread so far apart that the diabetic will likely find out too late that he has entered a hyper- or hypo-glycemic condition, sometimes incurring dangerous side effects. In fact, it is not only unlikely that a diabetic will take a timely SMBG value, but he will not know if his blood glucose is going up (higher) or down (lower), which inhibits his ability to make educated insulin therapy decisions.

Home diabetes therapy requires personal discipline of the user, appropriate education from a doctor, proactive behavior under sometimes-adverse situations, patient calculations to determine appropriate therapy decisions, including types and amounts of administration of insulin and glucose into his or her system, and is subject to human error. Technologies are needed that ease the burdens faced by diabetic patients, simplify the processes involved in treating the disease, and minimize user error which may cause unnecessarily dangerous situations in some circumstances.

SUMMARY OF THE INVENTION

In a first aspect, an integrated system for monitoring a glucose concentration in a host and for delivering insulin to a host is provided, the system comprising a continuous glucose sensor, wherein the continuous glucose sensor is configured to substantially continuously measure a glucose concentration in a host, and to provide sensor data associated with the glucose concentration in the host; an electronics module comprising an on/off controller module configured to iteratively determine an insulin therapy instruction in response to an evaluation of a relationship of internally derived data and a glucose boundary, wherein the insulin therapy instruction comprises an instruction selected from the group consisting of on and off; and an insulin delivery device configured to deliver insulin to the host, wherein the insulin delivery device is at least one of physically connected to a receiver and operably connected to a receiver, wherein the insulin delivery device is configured to receive the insulin therapy instruction from the controller.

In an embodiment of the first aspect, the insulin therapy instruction is determined solely on internally derived data and the glucose boundary.

In an embodiment of the first aspect, the glucose boundary is programmable by at least one of the host, a caretaker of the host, the on/off controller module, and a manufacturer of the integrated system.

In an embodiment of the first aspect, the glucose boundary is a glucose concentration of from about 70 mg/dl to about 160 mg/dl.

In an embodiment of the first aspect, an on insulin therapy instruction is determined when the glucose concentration exceeds the glucose boundary.

In an embodiment of the first aspect, the insulin delivery device is configured to deliver insulin automatically in response to selection of the on insulin therapy instruction.

In an embodiment of the first aspect, the insulin is flash insulin.

In an embodiment of the first aspect, the insulin delivery device is further configured to deliver insulin at a programmable delivery rate, wherein the delivery rate is programmable by at least one of the host, a caretaker of the host, the on/off controller module, and a manufacturer of the system.

In an embodiment of the first aspect, the insulin delivery device is further configured to deliver insulin at a programmed delivery rate and wherein the on/off controller module is configured to iteratively determine the insulin therapy instruction in response to internally derived data and the glucose boundary, wherein the on/off controller module comprises programming configured to adjust an insulin delivery rate in response to internally derived data and the glucose boundary.

In an embodiment of the first aspect, the on/off controller module is further configured to iteratively determine the insulin therapy instruction in response to a host's metabolic response to an insulin therapy, wherein the on/off controller module comprises programming configured to adjust an insulin delivery rate in response to the host's metabolic response.

In an embodiment of the first aspect, the off insulin therapy instruction is selected when the glucose concentration falls below the glucose boundary.

In an embodiment of the first aspect, the insulin delivery device is configured to automatically terminate insulin delivery in response to selection of the off insulin therapy instruction.

In an embodiment of the first aspect, the insulin delivery device is configured to provide delivery device data associated with insulin delivery.

In an embodiment of the first aspect, the internally derived data comprises at least one of sensor data, processed sensor data, delivery device data, and processed delivery device data.

The integrated system of Claim 14, wherein the internally derived data further comprises at least one of a glucose concentration, a glucose concentration range, a change in glucose concentration, a glucose concentration rate of change, an acceleration of a glucose concentration rate of change, a host insulin sensitivity, a change in host insulin sensitivity, a host metabolic response to insulin therapy, an amount of insulin delivered, a time of insulin delivery, an insulin on board, and a time.

In an embodiment of the first aspect, the integrated system further comprises an auxiliary sensor configured to provide auxiliary sensor data associated with at least one measurement made by the auxiliary sensor in the host, wherein the internally derived data further comprises auxiliary sensor data.

In an embodiment of the first aspect, the auxiliary sensor comprises at least one of an accelerometer, a pressure sensor, a pH sensor, a temperature sensor, an oxygen sensor, an auxiliary glucose sensor, an analyte sensor configured to measure an analyte other than glucose, a proximity sensor, and an orientation sensor.

In a second aspect, an integrated system for monitoring a glucose concentration in a host and for delivering insulin to a host is provided, the system comprising a continuous glucose sensor, wherein the continuous glucose sensor is configured to substantially continuously measure a glucose concentration in a host, and to provide sensor data associated with a glucose concentration of the host; an electronics module comprising a basal controller module configured to iteratively determine an insulin therapy instruction in response to an evaluation of a relationship of internally derived data and a basal profile, wherein the basal profile comprises at least one time block associated with a maximum insulin delivery rate; and an insulin delivery device configured to deliver insulin to the host, wherein the insulin delivery device is at least one of physically connected to a receiver and operably connected to a receiver, wherein the insulin delivery device is configured to receive the insulin therapy instruction from the controller module, wherein the insulin therapy instruction is constrained by a maximum insulin delivery rate associated with a current time block.

In an embodiment of the second aspect, the insulin therapy instruction is determined solely on internally derived data and the basal profile.

In an embodiment of the second aspect, the maximum insulin delivery rate is an insulin delivery rate of from about 0.01 U/hour to about 6.0 U/hour.

In an embodiment of the second aspect, the insulin delivery device is configured to deliver insulin automatically in response to receiving the insulin therapy instruction.

In an embodiment of the second aspect, the insulin therapy instruction instructs delivery of insulin at less than the maximum insulin delivery rate associated with the current time block.

In an embodiment of the second aspect, the basal profile is programmable by at least one of the host and a caretaker of the host.

In an embodiment of the second aspect, the basal profile is programmable by at least one of the basal controller module and a manufacturer of the integrated system.

In an embodiment of the second aspect, the basal controller module is configured to iteratively determine the insulin therapy instruction in response to internally derived data and the basal profile, wherein the basal controller module comprises programming to adjust the basal profile in response to internally derived data.

In an embodiment of the second aspect, the basal controller module is further configured to iteratively determine the insulin therapy instruction in response to a host's metabolic response to an insulin therapy, wherein the basal controller module comprises programming to adjust the basal profile in response to the host's metabolic response.

In an embodiment of the second aspect, the insulin delivery device is configured to provide delivery device data associated with insulin delivery.

In an embodiment of the second aspect, the internally derived data comprises at least one of sensor data, processed sensor data, delivery device data, and processed delivery device data.

In an embodiment of the second aspect, the internally derived data further comprises at least one of a glucose concentration, a glucose concentration range, a change in glucose concentration, a glucose concentration rate of change, an acceleration of the glucose concentration rate of change, a host insulin sensitivity, a change in host insulin sensitivity, a host metabolic response to insulin therapy, an amount of insulin delivered, a time of insulin delivery, an insulin on board, and a time.

In an embodiment of the second aspect, the integrated system further comprises an auxiliary sensor configured to provide auxiliary sensor data associated with at least one measurement made by the auxiliary sensor in the host, wherein the internally derived data further comprises auxiliary sensor data.

In an embodiment of the second aspect, the auxiliary sensor comprises at least one of an accelerometer, a pressure sensor, a pH sensor, a temperature sensor, an oxygen sensor, an auxiliary glucose sensor, an analyte sensor configured to measure an analyte other than glucose, a proximity sensor, and an orientation sensor.

In a third embodiment, an integrated system for monitoring a glucose concentration in a host and for delivering insulin to a host is provided, the system comprising a continuous glucose sensor, wherein the continuous glucose sensor is configured to substantially continuously measure a glucose concentration in a host, and to provide sensor data associated with the glucose concentration of the host; an electronics module comprising a bolus controller module configured to iteratively determine an insulin therapy instruction in response to an evaluation of a relationship of internally derived data and an engageable bolus constraint, wherein a relationship of internally derived data to the bolus constraint is evaluated in response to engagement of the bolus constraint, and wherein the bolus constraint comprises a maximum total insulin dose that can be delivered within a predefined time period in response to engagement of the bolus constraint; and an insulin delivery device configured to deliver insulin to the host, wherein the insulin delivery device is at least one of physically connected to a receiver and operably connected to a receiver, wherein the insulin delivery device is configured to receive the insulin therapy from the controller module.

In an embodiment of the third aspect, the insulin therapy instruction is determined solely on internally derived data and the bolus constraint.

In an embodiment of the third aspect, the system further comprises at least one of a selectable button configured to allow a user to engage the engageable bolus constraint, a scroll wheel configured to allow a user to engage the engageable bolus constraint, and a menu selection configured to allow a user to engage the engageable bolus constraint.

In an embodiment of the third aspect, the insulin therapy instruction comprises an instruction to deliver a portion of the maximum total insulin dose.

In an embodiment of the third aspect, the insulin delivery device is configured to deliver insulin automatically in response to receiving the insulin therapy instruction.

In an embodiment of the third aspect, the bolus constraint is programmable by as least one of the host and a caretaker of the host.

In an embodiment of the third aspect, the bolus constraint is programmable by as least one of the bolus controller module and a manufacturer of the integrated system.

In an embodiment of the third aspect, the bolus controller module is configured to iteratively determine an insulin therapy instruction in response to internally derived data and an engaged bolus constraint, wherein the bolus controller module comprises programming to adjust the bolus constraint in response to internally derived data.

In an embodiment of the third aspect, the bolus controller module is further configured to calculate insulin therapy in response to a host's metabolic response to an insulin therapy, wherein the controller module comprises programming to adjust the bolus constraint in response to the host's metabolic response.

In an embodiment of the third aspect, the insulin delivery device is configured to provide delivery device data associated with insulin delivery.

In an embodiment of the third aspect, the internally derived data comprises at least one of sensor data, processed sensor data, delivery device data and processed delivery device data.

In an embodiment of the third aspect, the internally derived data further comprises at least one of a glucose concentration, a glucose concentration range, a change in glucose concentration, a glucose concentration rate of change, an acceleration of the glucose concentration rate of change, a host insulin sensitivity, a change in host insulin sensitivity, a host metabolic response to insulin therapy, an amount of insulin delivered, a time of insulin delivery, an insulin on board, and a time.

In an embodiment of the third aspect, the integrated system further comprises an auxiliary sensor configured to provide auxiliary sensor data associated with at least one measurement taken by the auxiliary sensor in the host, wherein the internally derived data further comprises auxiliary sensor data.

In an embodiment of the third aspect, the auxiliary sensor comprises at least one of an accelerometer, a pressure sensor, a pH sensor, a temperature sensor, an oxygen sensor, an auxiliary glucose sensor, an analyte sensor configured to measure an analyte other than glucose, a proximity sensor, and an orientation sensor.

DETAILED DESCRIPTION OF THE PREFERRED EMBODIMENT

Figure 1:
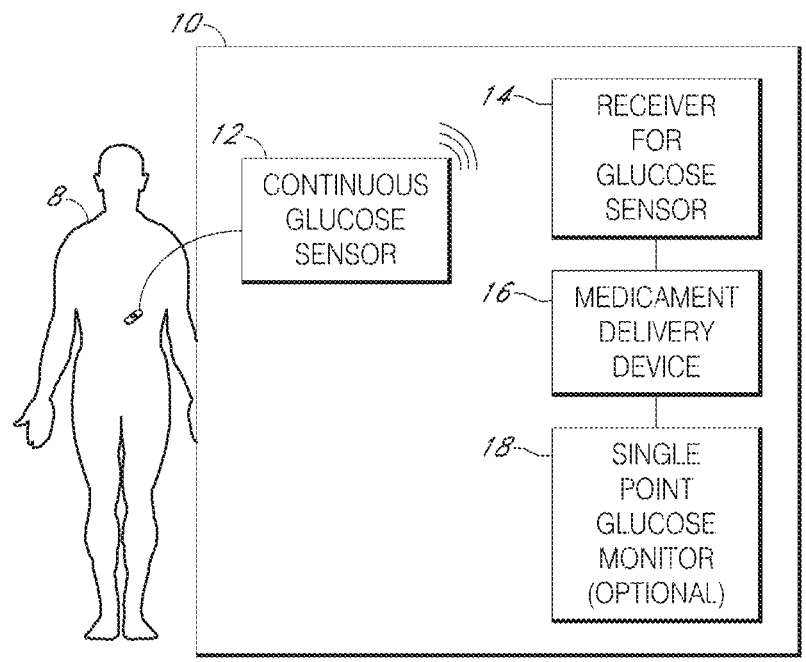
FIG. 1 is a block diagram of an integrated system of the preferred embodiments, including a continuous glucose sensor, a receiver for processing and displaying sensor data, a medicament delivery device, and an optional single point glucose-monitoring device.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the disclosed invention, a number of terms are defined below.

The term "continuous glucose sensor," as used herein is a broad term, and is to be given its ordinary and customary meaning to a person of ordinary skill in the art (and is not to be limited to a special or customized meaning), and refers without limitation to a device that continuously or continually measures the glucose concentration of a bodily fluid (e.g., blood, plasma, interstitial fluid and the like), for example, at time intervals ranging from fractions of a second up to, for example, 1, 2, or 5 minutes, or longer. It should be understood that continual or continuous glucose sensors can continually measure glucose concentration without requiring user initiation and/or interaction for each measurement, such as described with reference to U.S. Pat. No. 6,001,067, for example.

The phrase "continuous glucose sensing," as used herein is a broad term, and is to be given its ordinary and customary meaning to a person of ordinary skill in the art (and is not to be limited to a special or customized meaning), and refers without limitation to the period in which monitoring of the glucose concentration of a host's bodily fluid (e.g., blood, serum, plasma, extracellular fluid, etc.) is continuously or continually performed, for example, at time intervals ranging from fractions of a second up to, for example, 1, 2, or 5 minutes, or longer. In one exemplary embodiment, the glucose concentration of a host's extracellular fluid is measured every 1, 2, 5, 10, 20, 30, 40, 50 or 60-seconds.

The term "biological sample," as used herein is a broad term, and is to be given its ordinary and customary meaning to a person of ordinary skill in the art (and is not to be limited to a special or customized meaning), and refers without limitation to sample of a host body, for example, blood, interstitial fluid, spinal fluid, saliva, urine, tears, sweat, or the like.

The term "host," as used herein as used herein is a broad term, and is to be given its ordinary and customary meaning to a person of ordinary skill in the art (and is not to be limited to a special or customized meaning), and refers without limitation to mammals such as humans.

The term "biointerface membrane," as used herein is a broad term, and is to be given its ordinary and customary meaning to a person of ordinary skill in the art (and is not to be limited to a special or customized meaning), and refers without limitation to a permeable or semi-permeable membrane that can include two or more domains and is typically constructed of materials of a few microns thickness or more, which can be placed over the sensing region to keep host cells (for example, macrophages) from gaining proximity to, and thereby damaging the sensing membrane or forming a barrier cell layer and interfering with the transport of glucose across the tissue-device interface.

The term "sensing membrane," as used herein is a broad term, and is to be given its ordinary and customary meaning to a person of ordinary skill in the art (and is not to be limited to a special or customized meaning), and refers without limitation to a permeable or semi-permeable membrane that can be comprised of two or more domains and is typically constructed of materials of a few microns thickness or more, which are permeable to oxygen and are optionally permeable to glucose. In one example, the sensing membrane comprises an immobilized glucose oxidase enzyme, which enables an electrochemical reaction to occur to measure a concentration of glucose.

The term "domain," as used herein is a broad term, and is to be given its ordinary and customary meaning to a person of ordinary skill in the art (and is not to be limited to a special or customized meaning), and refers without limitation to regions of a membrane that can be layers, uniform or non-uniform gradients (for example, anisotropic), functional aspects of a material, or provided as portions of the membrane.

As used herein, the term "copolymer," as used herein is a broad term, and is to be given its ordinary and customary meaning to a person of ordinary skill in the art (and is not to be limited to a special or customized meaning), and refers without limitation to polymers having two or more different repeat units and includes copolymers, terpolymers, tetrapolymers, etc.

The term "sensing region," as used herein is a broad term, and is to be given its ordinary and customary meaning to a person of ordinary skill in the art (and is not to be limited to a special or customized meaning), and refers without limitation to the region of a monitoring device (e.g., an analyte sensor) responsible for the detection of a particular analyte, such as but not limited to glucose. In one embodiment, the sensing region generally comprises a non-conductive body, a working electrode (anode), a reference electrode and a counter electrode (cathode) passing through and secured within the body forming an electrochemically reactive surface at one location on the body and an electronic connection at another location on the body, and a sensing membrane affixed to the body and covering the electrochemically reactive surface. The counter electrode typically has a greater electrochemically reactive surface area than the working electrode. During general operation of the sensor a biological sample (for example, blood or interstitial fluid) or a portion thereof contacts (for example, directly or after passage through one or more domains of the sensing membrane) an enzyme (for example, glucose oxidase, GOx); the reaction of the biological sample (or portion thereof) results in the formation of reaction products that allow a determination of the glucose level in the biological sample. In one exemplary embodiment, the sensing region includes at least one working electrode and a second electrode, which can function as a reference and/or counter electrode. In another exemplary embodiment, the sensing region includes a plurality of working electrodes, a counter electrode and a reference electrode.

The term "electrochemically reactive surface," as used herein is a broad term, and is to be given its ordinary and customary meaning to a person of ordinary skill in the art (and is not to be limited to a special or customized meaning), and refers without limitation to the surface of an electrode where an electrochemical reaction takes place. In the case of the working electrode, the hydrogen peroxide produced by the enzyme catalyzed reaction of the glucose being detected reacts creating a measurable electronic current (for example, detection of glucose utilizing glucose oxidase produces $H_2O_2$ as a by product, $H_2O_2$ reacts with the surface of the working electrode producing two protons ($2H^+$), two electrons (2e⁻) and one molecule of oxygen ($O_2$) which produces the electronic current being detected). In the case of the counter electrode, a reducible species (for example, $O_2$) is reduced at the electrode surface in order to balance the current being generated by the working electrode.

The term "electrochemical cell," as used herein is a broad term, and is to be given its ordinary and customary meaning to a person of ordinary skill in the art (and is not to be limited to a special or customized meaning), and refers without limitation to a device in which chemical energy is converted to electrical energy. Such a cell typically consists of two or more electrodes held apart from each other and in contact with an electrolyte solution. Connection of the electrodes to a source of direct electric current renders one of them negatively charged and the other positively charged. Positive ions in the electrolyte migrate to the negative electrode (cathode) and there combine with one or more electrons, losing part or all of their charge and becoming new ions having lower charge or neutral atoms or molecules; at the same time, negative ions migrate to the positive electrode (anode) and transfer one or more electrons to it, also becoming new ions or neutral particles. The overall effect of the two processes is the transfer of electrons from the negative ions to the positive ions, a chemical reaction.

The term "proximal" as used herein is a broad term, and is to be given its ordinary and customary meaning to a person of ordinary skill in the art (and is not to be limited to a special or customized meaning), and refers without limitation to near to a point of reference such as an origin or a point of attachment. For example, in some embodiments of a sensing membrane that covers an electrochemically reactive surface, the electrolyte domain is located more proximal to the electrochemically reactive surface than the interference domain.

The term "distal" as used herein is a broad term, and is to be given its ordinary and customary meaning to a person of ordinary skill in the art (and is not to be limited to a special or customized meaning), and refers without limitation to spaced relatively far from a point of reference, such as an origin or a point of attachment. For example, in some embodiments of a sensing membrane that covers an electrochemically reactive surface, a resistance domain is located more distal to the electrochemically reactive surfaces than the enzyme domain.

The term "substantially" as used herein is a broad term, and is to be given its ordinary and customary meaning to a person of ordinary skill in the art (and is not to be limited to a special or customized meaning), and refers without limitation to being largely but not necessarily wholly that which is specified, which may include an amount greater than 50 percent, an amount greater than 60 percent, an amount greater than 70 percent, an amount greater than 80 percent, an amount greater than 90 percent or more.

The terms "processor" and "processor module," as used herein are a broad terms, and are to be given their ordinary and customary meaning to a person of ordinary skill in the art (and are not to be limited to a special or customized meaning), and refer without limitation to a computer system, state machine, processor, or the like designed to perform arithmetic or logic operations using logic circuitry that responds to and processes the basic instructions that drive a computer. In some embodiments, the terms can include ROM and/or RAM associated therewith.

The term "ROM," as used herein is a broad term, and is to be given its ordinary and customary meaning to a person of ordinary skill in the art (and is not to be limited to a special or customized meaning), and refers without limitation to read-only memory, which is a type of data storage device manufactured with fixed contents. ROM is broad enough to include EEPROM, for example, which is electrically erasable programmable read-only memory (ROM).

The term "RAM," as used herein is a broad term, and is to be given its ordinary and customary meaning to a person of ordinary skill in the art (and is not to be limited to a special or customized meaning), and refers without limitation to a data storage device for which the order of access to different locations does not affect the speed of access. RAM is broad enough to include SRAM, for example, which is static random access memory that retains data bits in its memory as long as power is being supplied.

The term "A/D Converter," as used herein is a broad term, and is to be given its ordinary and customary meaning to a person of ordinary skill in the art (and is not to be limited to a special or customized meaning), and refers without limitation to hardware and/or software that converts analog electrical signals into corresponding digital signals.

The term "RF module," as used herein is a broad term, and is to be given its ordinary and customary meaning to a person of ordinary skill in the art (and is not to be limited to a special or customized meaning), and refers without limitation to a radio frequency transmitter and/or receiver for transmitting and/or receiving signals.

The terms "raw data stream" and "data stream," as used herein are broad terms, and are to be given their ordinary and customary meaning to a person of ordinary skill in the art (and are not to be limited to a special or customized meaning), and refer without limitation to an analog or digital signal directly related to the analyte concentration measured by the analyte sensor. In one example, the raw data stream is digital data in "counts" converted by an A/D converter from an analog signal (for example, voltage or amps) representative of an analyte concentration. The terms broadly encompass a plurality of time spaced data points from a substantially continuous analyte sensor, which comprises individual measurements taken at time intervals ranging from fractions of a second up to, for example, 1, 2, or 5 minutes or longer.

The term "counts," as used herein is a broad term, and is to be given its ordinary and customary meaning to a person of ordinary skill in the art (and is not to be limited to a special or customized meaning), and refers without limitation to a unit of measurement of a digital signal. In one example, a raw data stream measured in counts is directly related to a voltage (for example, converted by an A/D converter), which is directly related to current from a working electrode.

The term "electronic circuitry," as used herein is a broad term, and is to be given its ordinary and customary meaning to a person of ordinary skill in the art (and is not to be limited to a special or customized meaning), and refers without limitation to the components (for example, hardware and/or software) of a device configured to process data. In the case of an analyte sensor, the data includes biological information obtained by a sensor regarding the concentration of the analyte in a biological fluid. U.S. Pat. Nos. 4,757,022, 5,497,772 and 4,787,398, which are hereby incorporated by reference in their entirety, describe suitable electronic circuits that can be utilized with devices of certain embodiments.

The term "potentiostat," as used herein is a broad term, and is to be given its ordinary and customary meaning to a person of ordinary skill in the art (and is not to be limited to a special or customized meaning), and refers without limitation to an electrical system that controls the potential between the working and reference electrodes of a three-electrode cell at a preset value. The potentiostat forces whatever current is necessary to flow between the working and counter electrodes to keep the desired potential, as long as the needed cell voltage and current do not exceed the compliance limits of the potentiostat.

The terms "operably connected" and "operably linked," as used herein are broad terms, and are to be given their ordinary and customary meaning to a person of ordinary skill in the art (and are not to be limited to a special or customized meaning), and refer without limitation to one or more components being linked to another component(s) in a manner that allows transmission of signals between the components. For example, one or more electrodes can be used to detect the amount of glucose in a sample and convert that information into a signal; the signal can then be transmitted to an electronic circuit. In this case, the electrode is "operably linked" to the electronic circuit. These terms are broad enough to include wired and wireless connectivity.

The term "algorithmically smoothed," as used herein is a broad term, and is to be given its ordinary and customary meaning to a person of ordinary skill in the art (and is not to be limited to a special or customized meaning), and refers without limitation to modification of a set of data to make it smoother and more continuous and remove or diminish outlying points, for example, by performing a moving average of the raw data stream.

The term "algorithm," as used herein is a broad term, and is to be given its ordinary and customary meaning to a person of ordinary skill in the art (and is not to be limited to a special or customized meaning), and refers without limitation to the computational processes (for example, programs) involved in transforming information from one state to another, for example using computer processing.

The term "regression," as used herein is a broad term, and is to be given its ordinary and customary meaning to a person of ordinary skill in the art (and is not to be limited to a special or customized meaning), and refers without limitation to finding a line in which a set of data has a minimal measurement (for example, deviation) from that line. Regression can be linear, non-linear, first order, second order, and so forth. One example of regression is least squares regression.

The terms "recursive filter" and "auto-regressive algorithm," as used herein are broad terms, and are to be given their ordinary and customary meaning to a person of ordinary skill in the art (and are not to be limited to a special or customized meaning), and refer without limitation to an equation in which previous averages are part of the next filtered output. More particularly, the generation of a series of observations whereby the value of each observation is partly dependent on the values of those that have immediately preceded it. One example is a regression structure in which lagged response values assume the role of the independent variables.

The terms "velocity" and "rate of change," as used herein are broad terms, and are to be given their ordinary and customary meaning to a person of ordinary skill in the art (and are not to be limited to a special or customized meaning), and refer without limitation to time rate of change; the amount of change divided by the time required for the change. In one embodiment, these terms refer to the rate of increase or decrease in an analyte for a certain time period.

The term "acceleration" as used herein is a broad term, and is to be given its ordinary and customary meaning to a person of ordinary skill in the art (and is not to be limited to a special or customized meaning), and refers without limitation to the rate of change of velocity with respect to time. This term is broad enough to include deceleration.

The term "clinical risk," as used herein is a broad term, and is to be given its ordinary and customary meaning to a person of ordinary skill in the art (and is not to be limited to a special or customized meaning), and refers without limitation to an identified danger or potential risk to the health of a host based on a measured or estimated analyte concentration, its rate of change, and/or its acceleration.

The term "clinically acceptable," as used herein is a broad term, and is to be given its ordinary and customary meaning to a person of ordinary skill in the art (and is not to be limited to a special or customized meaning), and refers without limitation to an analyte concentration, rate of change, and/or acceleration associated with that measured analyte that is considered to be safe for a host.

The term "time period," as used herein is a broad term, and is to be given its ordinary and customary meaning to a person of ordinary skill in the art (and is not to be limited to a special or customized meaning), and refers without limitation to an amount of time including a single point in time and a path (for example, range of time) that extends from a first point in time to a second point in time.

The term "measured analyte values," as used herein is a broad term, and is to be given its ordinary and customary meaning to a person of ordinary skill in the art (and is not to be limited to a special or customized meaning), and refers without limitation to an analyte value or set of analyte values for a time period for which analyte data has been measured by an analyte sensor. The term is broad enough to include data from the analyte sensor before or after data processing in the sensor and/or receiver (for example, data smoothing, calibration, or the like).

The term "alarm," as used herein is a broad term, and is to be given its ordinary and customary meaning to a person of ordinary skill in the art (and is not to be limited to a special or customized meaning), and refers without limitation to audible, visual, or tactile signal that are triggered in response to detection of clinical risk to a host. In one embodiment, hyperglycemic and hypoglycemic alarms are triggered when present or future clinical danger is assessed based on continuous analyte data.

The term "computer," as used herein is a broad term, and is to be given its ordinary and customary meaning to a person of ordinary skill in the art (and is not to be limited to a special or customized meaning), and refers without limitation to a machine that can be programmed to manipulate data.

The term "modem," as used herein is a broad term, and is to be given its ordinary and customary meaning to a person of ordinary skill in the art (and is not to be limited to a special or customized meaning), and refers without limitation to an electronic device for converting between serial data from a computer and an audio signal suitable for transmission over a telecommunications connection to another modem.

The term "intelligent," as used herein is a broad term, and is to be given its ordinary and customary meaning to a person of ordinary skill in the art (and is not to be limited to a special or customized meaning), and refers without limitation to systems and methods programmed to be able to adjust to changes in the current conditions and make deductions from information being processed.

The term "adaptive," as used herein is a broad term, and is to be given its ordinary and customary meaning to a person of ordinary skill in the art (and is not to be limited to a special or customized meaning), and refers without limitation to an ability (e.g., systems and methods able to) to be adjusted for use in different conditions; to change something to suit different conditions. In some embodiments, an adaptive controller module can be configured to adjust the medicament delivery rate, the medicament volume, the time of delivery, and the like, based on evaluation of internally derived data and the host metabolic response to therapy.

The term "condition," as used herein is a broad term, and is to be given its ordinary and customary meaning to a person of ordinary skill in the art (and is not to be limited to a special or customized meaning), and refers without limitation to a mode or state of being; the physical status of the body as a whole or of one of its parts. For example, a host's condition can refer to his state of health, his metabolic state and the like.

The term "glucose boundary," as used herein is a broad term, and is to be given its ordinary and customary meaning to a person of ordinary skill in the art (and is not to be limited to a special or customized meaning), and refers without limitation to a glucose concentration or range of glucose concentrations. In some embodiments, the system is configured to compare and/or evaluate internally derived data with a glucose boundary. In some embodiments, a glucose boundary can include a maximum glucose concentration.

The term "on/off controller module," as used herein is a broad term, and is to be given its ordinary and customary meaning to a person of ordinary skill in the art (and is not to be limited to a special or customized meaning), and refers without limitation to a mechanism configured to select between two instructions, namely either "on" or "off." An on/off controller module can include a device, such as a switch, programming or a combination thereof, that can actuate and/or de-actuate an insulin delivery device, such that the device is either delivering insulin or not delivering insulin. In some embodiments, the on instruction is sent to the insulin delivery device, which is configured to deliver the insulin, such as to automatically deliver the insulin; similarly, the off instruction can be sent to the insulin delivery device, which terminates insulin delivery upon receipt of the off instruction.

The term "basal," as used herein is a broad term, and is to be given its ordinary and customary meaning to a person of ordinary skill in the art (and is not to be limited to a special or customized meaning), and refers without limitation to the minimum required rate or other value for something to function. For example, in the case of insulin therapy, the term "basal rate" can refer to a regular (e.g., in accordance with fixed order or procedure, such as regularly scheduled for/at a fixed time), periodic or continuous delivery of low levels of insulin, such as but not limited to throughout a 24-hour period.

The term "basal profile," as used herein is a broad term, and is to be given its ordinary and customary meaning to a person of ordinary skill in the art (and is not to be limited to a special or customized meaning), and refers without limitation to an insulin delivery schedule that includes one or more blocks of time (e.g., time blocks), wherein each block is associated with a maximum insulin delivery rate.

The term "dynamic basal controller module," as used herein is a broad term, and is to be given its ordinary and customary meaning to a person of ordinary skill in the art (and is not to be limited to a special or customized meaning), and refers without limitation to a controller module configured to intelligently and adaptively evaluate internally derived data relative to a basal profile and to determine a basal insulin therapy (e.g., an insulin delivery rate) based thereon, wherein the insulin therapy can include a delivery rate of up to the maximum delivery rate associated with a time block of the basal profile.

The term "bolus," as used herein is a broad term, and is to be given its ordinary and customary meaning to a person of ordinary skill in the art (and is not to be limited to a special or customized meaning), and refers without limitation to a single dose of insulin, usually given over a short, defined period of time, that has been calculated and/or estimated to be sufficient to cover an expected rise in blood glucose, such as the rise that generally occurs during/after a meal.

The term "bolus constraint," as used herein is a broad term, and is to be given its ordinary and customary meaning to a person of ordinary skill in the art (and is not to be limited to a special or customized meaning), and refers without limitation to an engageable (e.g., selectable) maximum total insulin therapy (e.g., maximum total dose) that can be delivered during a defined period of time. In some embodiments, the bolus constraint has been calculated/estimated to be sufficient to cover an expected rise in glucose, such as an average glucose increase associate with consumption of a meal. In some embodiments, the host, a caretaker of the host, and/or the manufacturer can program a bolus constraint. In some circumstances, a bolus constraint can be programmed by an intelligent/adaptive controller module.

The term "dynamic bolus controller module," as used herein is a broad term, and is to be given its ordinary and customary meaning to a person of ordinary skill in the art (and is not to be limited to a special or customized meaning), and refers without limitation to a controller module configured to intelligently and adaptively evaluate internally derived data against (e.g., relative to) an engaged bolus constraint and to calculate an therapy based thereon, wherein the calculations are constrained by the engaged bolus constraint. A dynamic bolus controller module can include one or more instructions for calculation and/or delivery of a dynamic basal insulin therapy, such as but not limited to instructions to the insulin delivery device to delivery the bolus therapy automatically.

The term "range," as used herein is a broad term, and is to be given its ordinary and customary meaning to a person of ordinary skill in the art (and is not to be limited to a special or customized meaning), and refers without limitation to a sequence, series, or scale between limits (e.g., maximum and minimum values). For example, a range of glucose concentrations can include glucose concentrations from 60 mg/dl to 200 mg/dl. In another example, a range of insulin delivery rates can include rates from about 0.01 U/hr to about 40 U/hr. In some embodiments, a range is a single value.

The terms "programmed" and "programmable," as used herein are broad terms, and are to be given their ordinary and customary meaning to a person of ordinary skill in the art (and are not to be limited to a special or customized meaning), and refer without limitation to being or able to be arranged, as in a series of steps and/or instructions to be carried out, such as by a computer. As used herein, the terms programmed and programmable includes "pre-programmed," "pre-programmable," "re-programmed" and "re-programmable." In one example, a constraint can be programmed prior to use and/or reprogrammed at a later time.

The term "internally derived data," as used herein is a broad term, and is to be given its ordinary and customary meaning to a person of ordinary skill in the art (and is not to be limited to a special or customized meaning), and refers without limitation to data measured and/or processed by the integrated system, or a component thereof. Internally derived data can include data from a system component, such as but not limited to an analyte sensor (e.g., continuous glucose sensor), an auxiliary sensor, and/or an insulin delivery device. Internally derived data can include data derived (e.g., by processing and/or algorithmic evaluation) from the data received from a system component, such as but not limited to processed data, evaluated raw and/or processed data, host insulin sensitivity, host metabolic response, relationship of insulin sensitivity and/or metabolic response to each other, time, activity level, tracking of internally derived data to establish trends, insulin delivered and/or on-board, and the like. In some circumstances, internally derived data can include older and/or new data, such as but not limited to data received in the past (e.g., minutes, hours, days, weeks or months) and/or recently received data (e.g., currently received, instant, such as but not limited to within the previous 1-15 minutes). In some embodiments, a controller module can evaluate the internally derived data as it is received.

The term "insulin therapy," as used herein is a broad term, and is to be given its ordinary and customary meaning to a person of ordinary skill in the art (and is not to be limited to a special or customized meaning), and refers without limitation to an amount and/or schedule of the insulin to be delivered to the host. An insulin therapy can include one or more doses of insulin, up to the maximum (e.g., dose, therapy) associated with a constraint, such as but not limited to a basal profile and/or a bolus constraint. In some circumstances, the insulin therapy calculated and/or delivered can include a one or more partial doses that sum to an amount less than or equal to the maximum (e.g., dose, therapy) associated with a constraint. In some circumstances, the user can override the insulin therapy calculated by a controller module and/or associated with a constraint, such as, for example, to command the integrated system to deliver a manually entered insulin therapy.

The term "target range," as used herein is a broad term, and is to be given its ordinary and customary meaning to a person of ordinary skill in the art (and is not to be limited to a special or customized meaning), and refers without limitation to a range of glucose concentrations within which a host is to try to maintain his blood sugar. In general, a target range is a range of glucose concentrations considered to be euglycemic. Euglycemic glucose concentrations are discussed in detail in the section entitled "Programming and Processing."

The term "meal," as used herein is a broad term, and is to be given its ordinary and customary meaning to a person of ordinary skill in the art (and is not to be limited to a special or customized meaning), and refers without limitation to an amount of food or beverage consumed by the host. In some circumstances, a meal is associated with a time of day, during which that meal is generally consumed, such as but not limited to breakfast, lunch, dinner, supper, snack, and the like. In some circumstances, a meal is associated with a particular type of food or beverage, such as one that a host consumes only occasionally, such as but not limited to a high fat meal (e.g., pizza) or a high carbohydrate meal (e.g., cake, cookies, candy, ice cream, and the like).

The term "auxiliary sensor," as used herein is a broad term, and is to be given its ordinary and customary meaning to a person of ordinary skill in the art (and is not to be limited to a special or customized meaning), and refers without limitation to a sensor other than the continuous glucose sensor, which is configured to sense glucose or an analyte other than glucose, or to sense a condition, such as but not limited to temperature, pH, host activity level, orientation, pressure, proximity and the like.

Overview

FIG. 1 is a block diagram of an integrated system 10 of the preferred embodiments, including a continuous glucose sensor 12, a receiver 14 for processing and displaying sensor data, a medicament delivery device 16, and optionally a single point glucose-monitoring device 18. The integrated diabetes management system 10 of the preferred embodiments provides improved convenience and accuracy thus affording a diabetic host 8 with improved convenience, functionality, and safety in the care of their disease.

FIG. 1 shows a continuous glucose sensor 12 that measures a concentration of glucose or a substance indicative of the concentration or presence of the glucose. In some embodiments, the glucose sensor 12 is an invasive, minimally invasive, or non-invasive device, for example a subcutaneous, transdermal, intravascular or extracorporeal device. In some embodiments, the sensor 12 can analyze a plurality of intermittent biological samples. The glucose sensor can use any method of glucose-measurement, including enzymatic, chemical, physical, electrochemical, spectrophotometric, polarimetric, calorimetric, radiometric, or the like. In alternative embodiments, the sensor 12 can be any sensor capable of determining the level of an analyte in the body, for example oxygen, lactase, insulin, hormones, cholesterol, medicaments, viruses, or the like. The glucose sensor 12 uses any known method to provide an output signal indicative of the concentration of the glucose. The output signal is typically a raw data stream that is used to provide a useful value of the measured glucose concentration to a host or doctor, for example.

Accordingly, a receiver 14 is provided that receives and processes the raw data stream, including calibrating, validating, and displaying meaningful glucose values to a host, such as described in more detail below. A medicament delivery device 16 is further provided as a part of the integrated system 10. In some embodiments, the medicament delivery device 16 is a manual delivery device, for example a syringe, inhaler, or transdermal patch, which is manually integrated with the receiver 14. In some embodiments, the medicament delivery device 16 is a semi-automated delivery device, for example a pen or jet-type injector, an inhaler, a spray, or pump, which provides a semi-automated integration with the receiver 14. In some embodiments, the medicament delivery device 16 is an automated delivery device, for example a transcutaneous or implantable pump system, which provides an automated integration with the receiver 14. In some embodiments, an optional single point glucose monitor 18 is further provided as a part of the integrated system 10, for example a self-monitoring blood glucose meter (SMBG), non-invasive glucose meter, or the like.

Conventionally, each of these devices separately provides valuable information and or services to diabetic hosts. Thus, a typical diabetic host has numerous individual devices, which they track and consider separately. In some cases, the amount of information provided by these individual devices may require complex understanding of the nuances and implications of each device, for example types and amounts of insulin to deliver. Typically, each individual device is a silo of information that functions as well as the data provided therein, therefore when the devices are able to communicate with each other, enhanced functionality and safety can be realized. For example, when a continuous glucose monitor functions alone (for example, without data other than that which was gathered by the device), sudden changes in glucose level are tracked, but may not be fully understood, predicted, preempted, or otherwise considered in the processing of the sensor data; however, if the continuous glucose sensor were provided with information about time, amount, and type of insulin injections, calories consumed, time or day, meal time, or like, more meaningful, accurate and useful glucose estimation, prediction, and other such processing can be provided, such as described in more detail herein. By integrating these devices, the information from each component can be leveraged to increase the intelligence, benefit provided, convenience, safety, and functionality of the continuous glucose sensor and other integrated components. Therefore, it would be advantageous to provide a device that aids the diabetic host in integrating these individual devices in the treatment of his/her disease.

In the non-diabetic host, pancreatic β-cells generally respond quickly to spikes in blood glucose by releasing stored insulin (e.g., within about 10-minutes). In preferred embodiments, the integrated system 10 is configured to mimic pancreatic β-cells, and thereby to provide substantially physiological detection of glucose levels and/or insulin response. Accordingly, the system 10 includes a continuous analyte sensor, a medicament delivery device (e.g., an infusion pump, a pen, a syringe, an inhaler, a medicament patch, and the like), and associated electronics, as described elsewhere herein. In various embodiments, the electronics include one or more of an on/off controller module, a dynamic basal controller module and/or a dynamic bolus controller module, as described elsewhere herein. In some embodiments, the electronics include two or more controller modules configured to work in concert. The system 10 is configured for use with regular, rapid-acting, fast-acting and/or flash-acting insulins, which are described elsewhere herein. In one exemplary embodiment, the system 10 is configured to determine a medicament dose (e.g., an insulin dose) using solely internally derived data.

Glucose Sensor

Figure 2A:
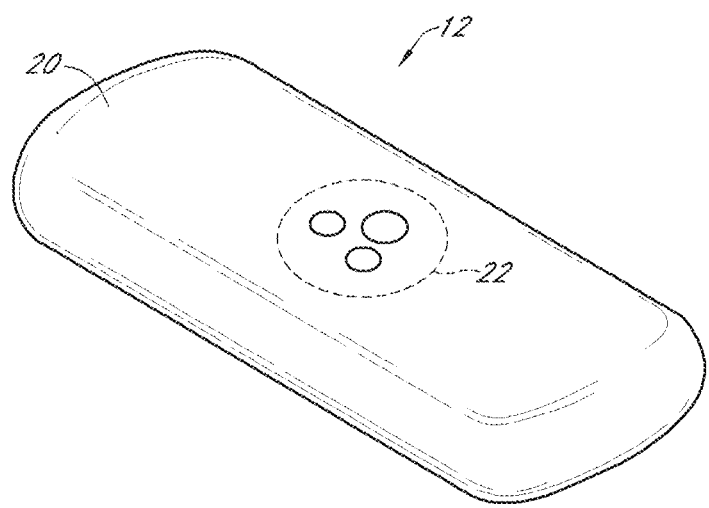
FIG. 2A is a perspective view of a continuous glucose sensor in one embodiment.
Figure 3:
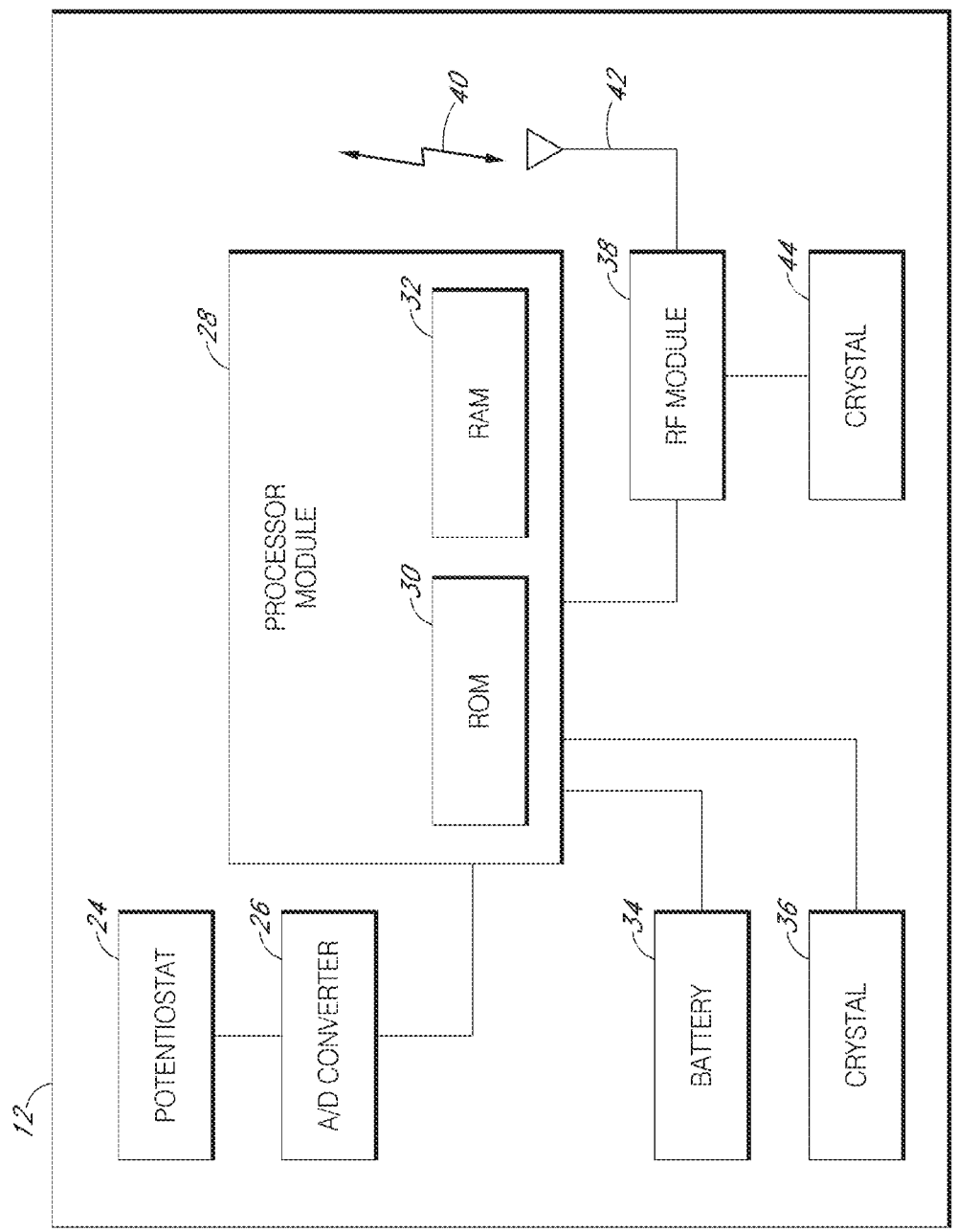
FIG. 3 is a block diagram of the electronics associated with a continuous glucose sensor in one embodiment.

FIG. 2A is a perspective view of one embodiment of a wholly implantable continuous glucose sensor 12 (e.g., the primary analyte sensor). In this embodiment, a body 20 and a sensing region 22 house the electrodes and sensor electronics (FIG. 3). The three electrodes within the sensing region are operably connected to the sensor electronics (FIG. 3) and are covered by a sensing membrane and a biointerface membrane (not shown), which are described in more detail below.

The body 20 is preferably formed from epoxy molded around the sensor electronics, however the body can be formed from a variety of materials, including metals, ceramics, plastics, or composites thereof. U.S. Pat. No. 7,134,999 discloses suitable configurations suitable for the body 20, and is incorporated by reference in its entirety.

In one embodiment, the sensing region 22 comprises three electrodes including a platinum working electrode, a platinum counter electrode, and a silver/silver chloride reference electrode, for example. However a variety of electrode materials and configurations can be used with the implantable glucose sensor of the preferred embodiments. The top ends of the electrodes are in contact with an electrolyte phase (not shown), which is a free-flowing fluid phase disposed between the sensing membrane and the electrodes. In one embodiment, the counter electrode is provided to balance the current generated by the species being measured at the working electrode. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction:

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons ($2H^+$), two electrons ($2e^-$), and one oxygen molecule ($O_2$).

In one embodiment, a potentiostat (FIG. 3) is employed to monitor the electrochemical reaction at the electroactive surface(s). The potentiostat applies a constant potential to the working and reference electrodes to determine a current value. The current that is produced at the working electrode (and flows through the circuitry to the counter electrode) is substantially proportional to the amount of $H_2O_2$ that diffuses to the working electrode. Accordingly, a raw signal can be produced that is representative of the concentration of glucose in the user's body, and therefore can be utilized to estimate a meaningful glucose value.

In some embodiments, the sensing membrane includes an enzyme, for example, glucose oxidase, and covers the electrolyte phase. In one embodiment, the sensing membrane generally includes a resistance domain most distal from the electrochemically reactive surfaces, an enzyme domain less distal from the electrochemically reactive surfaces than the resistance domain, and an electrolyte domain adjacent to the electrochemically reactive surfaces. However, it is understood that a sensing membrane modified for other devices, for example, by including fewer or additional domains, is within the scope of the preferred embodiments. U.S. Patent Publication No. US-2003-0032874-A1 describes membranes that can be used in some embodiments of the sensing membrane. It is noted that in some embodiments, the sensing membrane can additionally include an interference domain that blocks some interfering species; such as described in the above-cited co-pending patent application. U.S. Patent Publication No. US-2005-0090607-A1 also describes membranes that can be used for the sensing membrane of the preferred embodiments, and is incorporated herein by reference in its entirety.

Preferably, the biointerface membrane supports tissue ingrowth, serves to interfere with the formation of a barrier cell layer, and protects the sensitive regions of the device from host inflammatory response. In one embodiment, the biointerface membrane generally includes a cell disruptive domain most distal from the electrochemically reactive surfaces and a cell impermeable domain less distal from the electrochemically reactive surfaces than the cell disruptive domain. The cell disruptive domain is preferably designed to support tissue ingrowth, disrupt contractile forces typically found in a foreign body response, encourage vascularity within the membrane, and disrupt the formation of a barrier cell layer. The cell impermeable domain is preferably resistant to cellular attachment, impermeable to cells, and composed of a biostable material. U.S. Pat. Nos. 6,702,857, 7,192,450, and U.S. Patent Publication No. US-2005-0251083-A1 describe biointerface membranes that can be used in conjunction with the preferred embodiments, and are incorporated herein by reference in their entireties. It is noted that the preferred embodiments can be used with a short term (for example, 1 to 7 day sensor), in which case a biointerface membrane may not be required. It is noted that the biointerface membranes described herein provide a continuous glucose sensor that has a useable life of greater than about one week, greater than about one month, greater than about three months, or greater than about one year, herein after referred to as "long-term."

In some embodiments, the domains of the biointerface and sensing membranes are formed from materials such as silicone, polytetrafluoroethylene, polyethylene-co-tetrafluoroethylene, polyolefin, polyester, polycarbonate, biostable polytetrafluoroethylene, homopolymers, copolymers and/or terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones and block copolymers thereof including, for example, di-block, tri-block, alternating, random and graft copolymers.

Figure 2C:
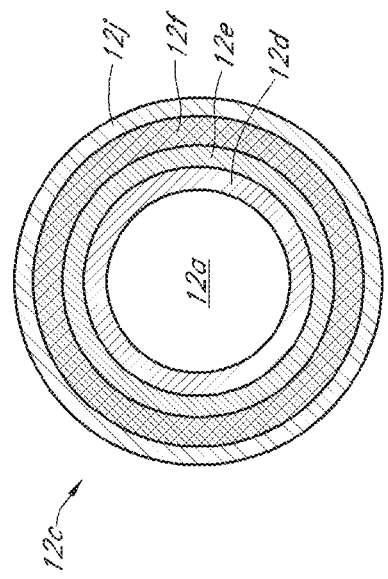
FIG. 2C is a cross-section of the portion of a transcutaneous continuous glucose sensor, of FIG. 2B, taken along line 2C-2C, in one embodiment.
Figure 2B:
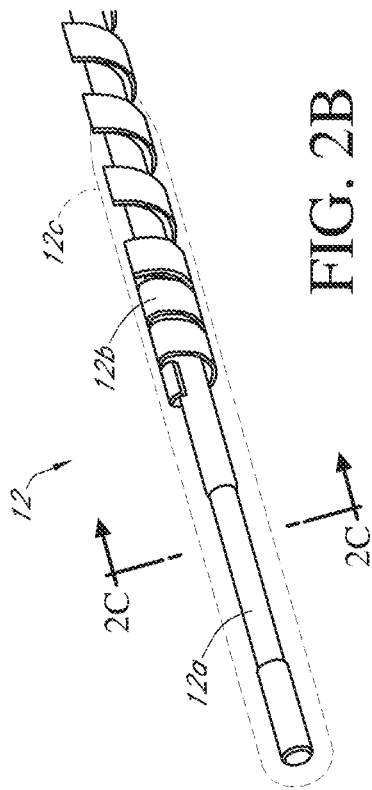
FIG. 2B is a perspective view of an in vivo portion of a transcutaneous continuous glucose sensor in one embodiment.

FIG. 2B is a perspective view of an in vivo portion of a transcutaneous continuous glucose sensor 12, in one embodiment. In this embodiment, the in vivo portion of the sensor includes at least one working electrode 12a and a reference electrode 12b and a sensing membrane 12c.

FIG. 2C is a cross-section of the sensor shown in FIG. 2B, taken on line 2C-2C. In preferred embodiments, the sensing membrane 12c (e.g., a biointerface and/or sensing membrane) includes at least an enzyme domain 12f having an enzyme configured to detect the analyte, such as but not limited to glucose oxidase, as described elsewhere herein. In some preferred embodiments, the sensing membrane 12c can include one or more additional domains, such as but not limited to an electrode domain 12d, an interference domain 12e, a resistance domain 12j, a cell disruptive domain and a cell impermeable domain, for example. Additional sensor and sensing membrane configurations can be found in U.S. Patent Publication No. US-2006-0020187-A1, U.S. Patent Publication No. US-2005-0031689-A1, U.S. Patent Publication No. 2007-0027370-A1, U.S. Patent Publication No. 2006-0229512-A1, U.S. Patent Publication No. 2006-0253012-A1, U.S. Patent Publication No. US-2007-0197890-A1, U.S. application Ser. No. 11/404,417 filed on Apr. 14, 2006 and entitled "SILICONE BASED MEMBRANES FOR USE IN IMPLANTABLE GLUCOSE SENSORS," and U.S. application Ser. No. 11/750,907 filed on May 18, 2007 and entitled "ANALYTE SENSORS HAVING AN OPTIMIZED SIGNAL-TO-NOISE RATIO," each of which is incorporated herein by reference in its entirety.

In preferred embodiments, the analyte sensor 12 is configured to provide response to changes in host glucose concentration, such as but not limited to a sensor response time of about 20-minutes or less. The term "sensor response time" as used herein is a broad term, and is to be given its ordinary and customary meaning to a person of ordinary skill in the art (and is not to be limited to a special or customized meaning), and refers without limitation to the time required for the sensor to measure a stable signal value associated with a change in glucose concentration, from a first concentration to a second concentration. The sensor response time can be measured by in vitro experimentation. For example, sensor response time can be measured by first placing a continuous glucose sensor in a first glucose solution (e.g., 100 mg/dl glucose); then moving the sensor to a second glucose solution (e.g., 200 mg/dl glucose) and allowing the sensor to equilibrate. In some embodiments, the sensor response time is less than about 10-minutes. In preferred embodiments, the sensor response time is less than 1, 2, 3, 4, or 5-minutes. In more preferred embodiments, the sensor response time is less than about 30-seconds. In some alternative embodiments, sensor response time includes an additional period of time required to process the measured glucose concentration change and provide a numerical output to the user (e.g., via a receiver).

FIG. 3 is a block diagram that illustrates the electronics associated with a continuous glucose sensor 12 in one embodiment. In this embodiment, a potentiostat 24 is shown, operably connected to an electrode system (such as described above) and provides a voltage to the electrodes (FIG. 2), which biases the sensor to enable measurement of a current signal indicative of the analyte concentration in the host (also referred to as the analog portion). In some embodiments, the potentiostat includes a resistor (not shown) that translates the current into voltage. In some alternative embodiments, a current to frequency converter is provided that is configured to continuously integrate the measured current, for example, using a charge counting device. An A/D converter 26 digitizes the analog signal into a digital signal, also referred to as "counts" in some embodiments for processing. Accordingly, the resulting raw data stream in counts, also referred to as raw sensor data, is directly related to the current measured by the potentiostat 24.

A processor module 28 includes the central control unit (houses ROM 30 and RAM 32) that controls the processing of the sensor electronics. In some embodiments, the processor module includes a microprocessor, however a computer system other than a microprocessor can be used to process data as described herein, for example an ASIC can be used for some or all of the sensor's central processing. The processor typically provides semi-permanent storage of data, for example, storing data such as sensor identifier (ID) and programming to process data streams (for example, programming for data smoothing and/or replacement of signal artifacts such as is described in U.S. Publication No. US-2005-0043598-A1). The processor additionally can be used for the system's cache memory, for example for temporarily storing recent sensor data. In some embodiments, the processor module comprises memory storage components such as ROM 30, RAM 32, dynamic-RAM, static-RAM, non-static RAM, EEPROM, rewritable ROMs, flash memory, or the like.

In some embodiments, the processor module comprises a digital filter, for example, an infinite impulse response (IIR) or finite impulse response (FIR) filter, configured to smooth the raw data stream from the A/D converter. Generally, digital filters are programmed to filter data sampled at a predetermined time interval (also referred to as a sample rate). In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter as described above, the processor module can be programmed to request a digital value from the A/D converter at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter. In preferred embodiments, the processor module is configured with a programmable acquisition time, namely, the predetermined time interval for requesting the digital value from the A/D converter is programmable by a user within the digital circuitry of the processor module. An acquisition time of from about 2 seconds to about 512 seconds is preferred; however any acquisition time can be programmed into the processor module. A programmable acquisition time is advantageous in optimizing noise filtration, time lag, and processing/battery power.

Preferably, the processor module 28 is configured to build the data packet for transmission to an outside source, for example, a Radio Frequency (RF) transmission (e.g., via RF module 38) to a receiver as described in more detail below. Generally, the data packet comprises a plurality of bits that can include a preamble, a unique identifier identifying the electronics unit, the receiver, or both, (e.g., sensor ID code), data (e.g., raw data, filtered data, and/or an integrated value) and/or error detection or correction. Preferably, the data (transmission) packet has a length of from about 8 bits to about 128 bits, preferably about 48 bits; however, larger or smaller packets can be desirable in certain embodiments. The processor module 28 can be configured to transmit any combination of raw and/or filtered data. In one exemplary embodiment, the transmission packet contains a fixed preamble, a unique ID of the electronics unit, a single five-minute average (e.g., integrated) sensor data value, and a cyclic redundancy code (CRC).

In some embodiments, the processor module 28 further comprises a transmitter portion that determines the transmission interval of the sensor data to a receiver, or the like. In some embodiments, the transmitter portion, which determines the interval of transmission, is configured to be programmable. In one such embodiment, a coefficient can be chosen (e.g., a number of from about 1 to about 100, or more), wherein the coefficient is multiplied by the acquisition time (or sampling rate), such as described above, to define the transmission interval of the data packet. Thus, in some embodiments, the transmission interval is programmable from about 2 seconds to about 850 minutes, more preferably from about 30 second to about 5 minutes; however, any transmission interval can be programmable or programmed into the processor module. However, a variety of alternative systems and methods for providing a programmable transmission interval can also be employed. By providing a programmable transmission interval, data transmission can be customized to meet a variety of design criteria (e.g., reduced battery consumption, timeliness of reporting sensor values, etc.).

Conventional glucose sensors measure current in the nanoAmp range. In contrast to conventional glucose sensors, the preferred embodiments are configured to measure the current flow in the picoAmp range, and in some embodiments, femtoAmps. Namely, for every unit (mg/dL) of glucose measured, at least one picoAmp of current is measured. Preferably, the analog portion of the A/D converter 26 is configured to continuously measure the current flowing at the working electrode and to convert the current measurement to digital values representative of the current. In one embodiment, the current flow is measured by a charge counting device (e.g., a capacitor). Preferably, a charge counting device provides a value (e.g., digital value) representative of the current flow integrated over time (e.g., integrated value). In some embodiments, the value is integrated over a few seconds, a few minutes, or longer. In one exemplary embodiment, the value is integrated over 5 minutes; however, other integration periods can be chosen. Thus, a signal is provided, whereby a high sensitivity maximizes the signal received by a minimal amount of measured hydrogen peroxide (e.g., minimal glucose requirements without sacrificing accuracy even in low glucose ranges), reducing the sensitivity to oxygen limitations in vivo (e.g., in oxygen-dependent glucose sensors).

In some embodiments, the electronics unit is programmed with a specific ID, which is programmed (automatically or by the user) into a receiver to establish a secure wireless communication link between the electronics unit and the receiver. Preferably, the transmission packet is Manchester encoded; however, a variety of known encoding techniques can also be employed.

A battery 34 is operably connected to the sensor electronics and provides the power for the sensor 12. In one embodiment, the battery is a lithium manganese dioxide battery; however, any appropriately sized and powered battery can be used (for example, AAA, nickel-cadmium, zinc-carbon, alkaline, lithium, nickel-metal hydride, lithium-ion, zinc-air, zinc-mercury oxide, silver-zinc, and/or hermetically-sealed). In some embodiments, the battery is rechargeable, and/or a plurality of batteries can be used to power the system. The sensor can be transcutaneously powered via an inductive coupling, for example. In some embodiments, a quartz crystal 36 is operably connected to the processor 28 and maintains system time for the computer system as a whole, for example for the programmable acquisition time within the processor module.

An RF module 38 is operably connected to the processor 28 and transmits the sensor data from the sensor 12 to a receiver within a wireless transmission 40 via antenna 42. In some embodiments, a second quartz crystal 44 provides the time base for the RF carrier frequency used for data transmissions from the RF module 38. In some alternative embodiments, however, other mechanisms, such as optical, infrared radiation (IR), ultrasonic, or the like, can be used to transmit and/or receive data.

In the RF telemetry module of the preferred embodiments, the hardware and software are designed for low power requirements to increase the longevity of the device (for example, to enable a life of from about 3 to about 24 months, or more) with maximum RF transmittance from the in vivo environment to the ex vivo environment for wholly implantable sensors (for example, a distance of from about one to ten meters or more). Preferably, a high frequency carrier signal of from about 402 MHz to about 433 MHz is employed in order to maintain lower power requirements. In some embodiments, the RF module employs a one-way RF communication link to provide a simplified ultra low power data transmission and receiving scheme. The RF transmission can be OOK or FSK modulated, preferably with a radiated transmission power (EIRP) fixed at a single power level of typically less than about 100 microwatts, preferably less than about 75 microwatts, more preferably less than about 50 microwatts, and most preferably less than about 25 microwatts.

In one alternative embodiment, the continuous glucose sensor comprises a transcutaneous sensor such as described in U.S. Pat. No. 6,565,509 to Say et al. In another alternative embodiment, the continuous glucose sensor comprises a subcutaneous sensor such as described with reference to U.S. Pat. No. 6,579,690 to Bonnecaze et al. and U.S. Pat. No. 6,484,046 to Say et al. In another alternative embodiment, the continuous glucose sensor comprises a refillable subcutaneous sensor such as described with reference to U.S. Pat. No. 6,512,939 to Colvin et al. In another alternative embodiment, the continuous glucose sensor comprises an intravascular sensor such as described with reference to U.S. Pat. No. 6,477,395 to Schulman et al. In another alternative embodiment, the continuous glucose sensor comprises an intravascular sensor such as described with reference to U.S. Pat. No. 6,424,847 to Mastrototaro et al. All of the above patents are incorporated in their entirety herein by reference. In general, it should be understood that the disclosed embodiments are applicable to a variety of continuous glucose sensor configurations.

Receiver

Figure 9:
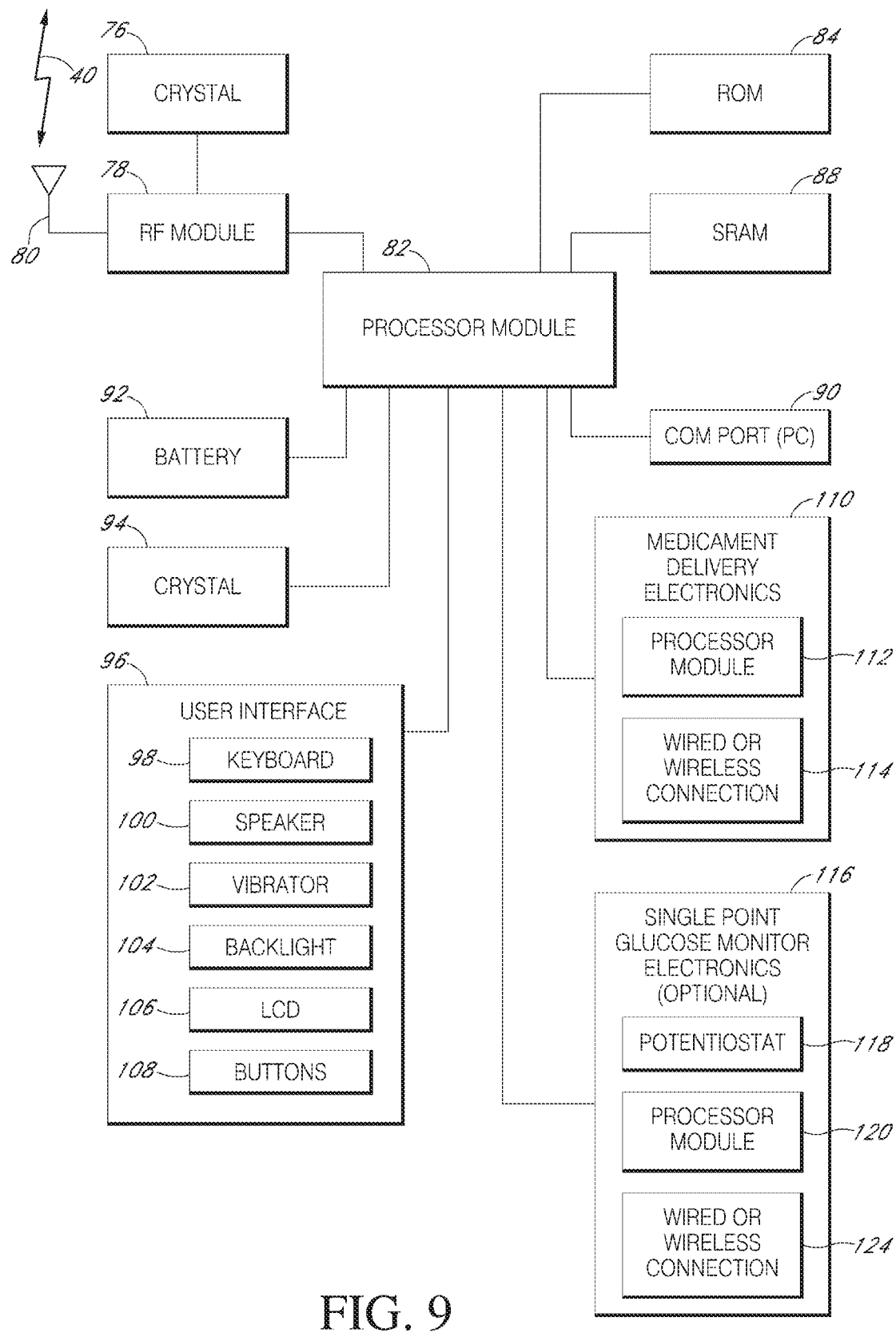
FIG. 9 is a block diagram that illustrates integrated system electronics in one embodiment.
Figure 10:
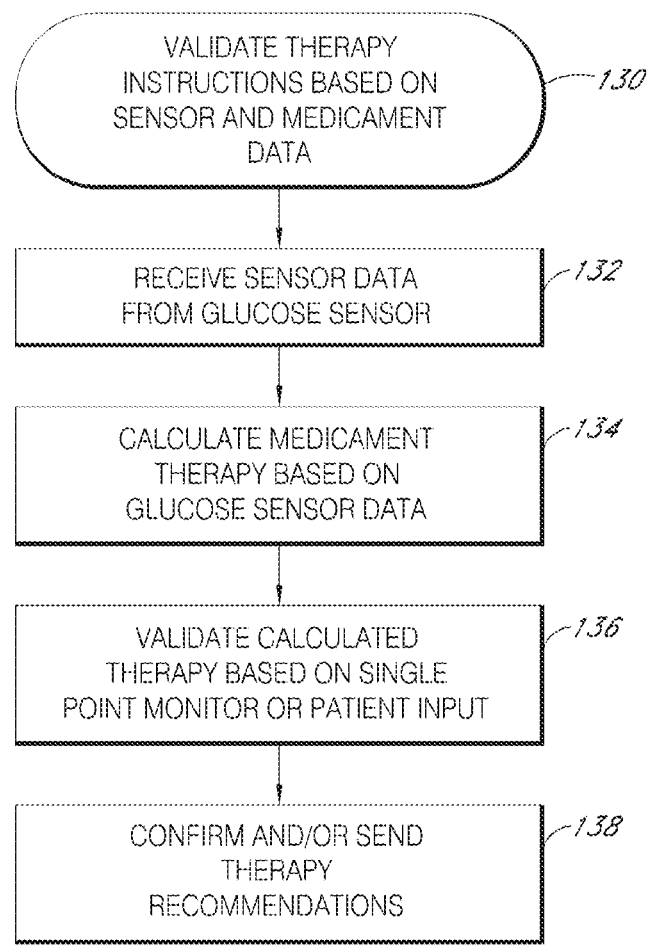
FIG. 10 is a flow chart that illustrates the process of validating therapy instructions prior to medicament delivery in one embodiment.
Figure 11:
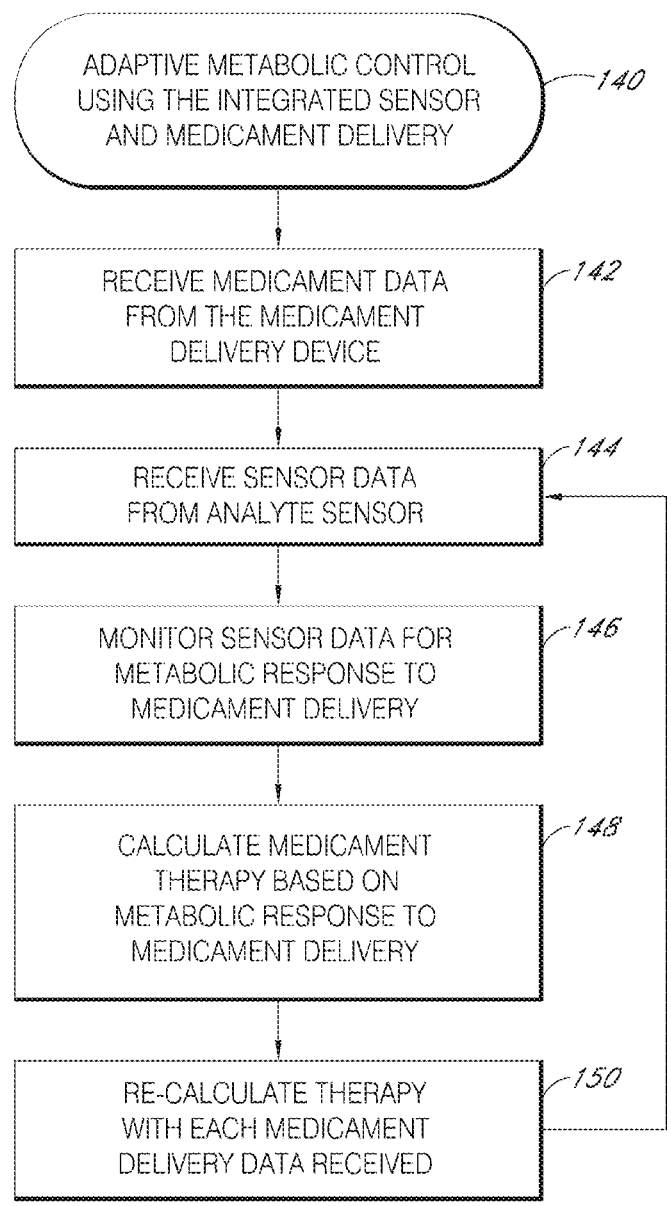
FIG. 11 is a flow chart that illustrates the process of providing adaptive metabolic control using an integrated sensor and medicament delivery device in one embodiment.

The preferred embodiments provide an integrated system, which includes a receiver 14 that receives and processes the raw data stream from the continuous glucose sensor 12. The receiver can perform all or some of the following operations: a calibration, converting sensor data, updating the calibration, evaluating received reference and sensor data, evaluating the calibration for the analyte sensor, validating received reference and sensor data, displaying a meaningful glucose value to a user, calculating therapy recommendations, validating recommended therapy, adaptive programming for learning individual metabolic patterns, and prediction of glucose values, for example. Some complementary systems and methods associated with the receiver are described in more detail with reference to U.S. Patent Publication No. US-2005-0027463-A1 which is incorporated herein by reference in its entirety. FIGS. 9 to 11 describe some processes that can be programmed into the receiver. Additionally, the receiver 14 of the preferred embodiments works together with the other components of the system (for example, the medicament delivery device 16 and the single point glucose monitor 18) to provide enhanced functionality, convenience, and safety, such as described in more detail herein. FIGS. 4 to 7 are illustrates of a few exemplary integrated systems of the preferred embodiments, each of which include the receiver, such as described in more detail herein.

In some embodiments, the receiver 14 is a PDA- or pager-sized housing 46, for example, and comprises a user interface 48 that has a plurality of buttons 50 and a liquid crystal display (LCD) screen, which can include a backlight. In some embodiments, the receiver can take other forms, for example a computer, server, or other such device capable of receiving and processing the data such as described herein. In some embodiments the user interface can also include a keyboard, a speaker, and a vibrator such as described with reference to FIG. 8. The receiver 46 comprises systems (for example, electronics) necessary to receive, process, and display sensor data from the glucose sensor 12, such as described in more detail with reference to FIG. 8. The receiver 14 processes data from the continuous glucose sensor 12 and additionally processes data associated with at least one of the medicament delivery device 16, single point glucose meter 16, and user 8.

In some embodiments, the receiver 14 is integrally formed with at least one of the medicament delivery device 16, and single point glucose monitor 18. In some embodiments, the receiver 14, medicament delivery device 16 and/or single point glucose monitor 18 are detachably connected, so that one or more of the components can be individually detached and attached at the user's convenience. In some embodiments, the receiver 14, medicament delivery device 16, and/or single point glucose monitor 18 are separate from, detachably connectable to, or integral with each other; and one or more of the components are operably connected through a wired or wireless connection, allowing data transfer and thus integration between the components. In some embodiments, one or more of the components are operably linked as described above, while another one or more components (for example, the syringe or patch) are provided as a physical part of the system for convenience to the user and as a reminder to enter data for manual integration of the component with the system. Some exemplary embodiments are described with reference to FIGS. 4 to 7, however suffice it to say that each of the components of the integrated system can be manually, semi-automatically, or automatically integrated with each other, and each component can be in physical and/or data communication with another component, which can include wireless connection, wired connection (for example, via cables or electrical contacts), or the like. In some embodiments, the receiver is configured to process data from the glucose sensor, an auxiliary sensor and/or the medicament delivery device, and can include a controller module.

Medicament Delivery Device

The preferred embodiments provide an integrated system 10, which includes a medicament delivery device 16 for administering a medicament to the host 8. The integrated medicament delivery device can be designed for bolus injection/infusion, basal injection/infusion, continuous injection/infusion, inhalation, transdermal absorption, other method for administering medicament, or any combinations thereof. In one exemplary embodiment, the medicament delivery device is an infusion pump configured for transcutaneous (e.g., injection/infusion and absorption into the subcutaneous tissue), intraperitoneal or intravenous infusion. In some embodiments, the infusion device is wholly implantable. In other embodiments, the infusion device is worn outside of the body, with infusion via a catheter. In some embodiments, the infusion device is configured for one or more maintenance functions, such as but not limited to checking for catheter clogs or monitoring the rate of insulin leaving the infusion device or the remaining volume of insulin within the pump. In some embodiments, the medicament delivery device is an insulin pump configured to deliver insulin to the host. In some embodiments, the insulin pump is further configured to receive and process instructions for delivery of an insulin therapy from a controller module.

In some embodiments, the medicament delivery device is an injection pen configured to inject insulin transcutaneously. In some embodiments, the medicament delivery device is an inhaler that delivers an inhalable insulin formulation. In other embodiments, the medicament delivery device is an oral medicament, such as an insulin preparation formulated for buccal absorption. In still other embodiments, the medicament delivery device is configured for transdermal delivery, such as a transdermal patch. In some embodiments, the at least two insulin delivery devices are used in conjunction with each other. For example, delivery of insulin by an infusion device (e.g., a pump) can be supplemented with delivery of another medicament (e.g., either the same or different types of insulin, or another medicament such as glucagon) with a second medicament delivery device, such as but not limited to a pen, a transdermal patch or an inhaler. For example, in some circumstances, a host can use an infusion pump to deliver rapid acting insulin and a patch to constantly deliver a slow-acting insulin. In another exemplary circumstance, a transcutaneous insulin pump can provide the insulin therapy, which can be supplemented by instructions to provide a therapeutic dose of glucagon via an inhaler or an oral preparation. The term medicament includes any substance used in therapy for a host using the system 10, for example, insulin, glucagon, or derivatives thereof. PCT International Publication No. WO02/43566-A1 describes glucose, glucagon, and vitamins A, C, or D that can be used with the preferred embodiments. U.S. Pat. Nos. 6,051,551 and 6,024,090 describe types of insulin suitable for inhalation that can be used with the preferred embodiments. U.S. Pat. No. 5,234,906, 6,319,893, and European Patent No. EP-760677-B1 describe various derivatives of glucagon that can be used with the preferred embodiments. U.S. Pat. No. 6,653,332 describes a combination therapy that can be used with the preferred embodiments. U.S. Pat. No. 6,471,689 and PCT International Publication No. WO81/01794-A1 describe insulin useful for delivery pumps that can be used with the preferred embodiments. U.S. Pat. No. 5,226,895 describes a method of providing more than one type of insulin that can be used with the preferred embodiments. Each of the above references is incorporated herein by reference in its entirety and the medicaments and methods disclosed can be useful in the preferred embodiments.

As described elsewhere herein, in preferred embodiments, the system is configured to substantially mimic the body's metabolic response to changes in glucose (e.g., the host's blood sugar concentration), similar to the response of a pancreatic 3-cell to changes in glucose concentration. As is understood by one skilled in the art, insulin activity can be influenced by a variety of factors, such as but not limited to method/location of delivery (e.g., injected transcutaneously, infused IV or intraperitoneally, inhaled, etc.), the host's insulin sensitivity, method of insulin preparation, and the like. However, it is possible to compare different insulins by comparing their time-activity profiles (TAP), as defined by methods of Frohnauer, et al. 2001, in "Graphical Human Insulin Time-Activity Profiles Using Standardized Definitions," *Diab. Tech. & Therap.* 3(3):419-429. Table 1 presents the TAPs of some purified human insulins (e.g., wild type and/or analogs) and one exemplary flash insulin (described elsewhere herein).

Figure 4:
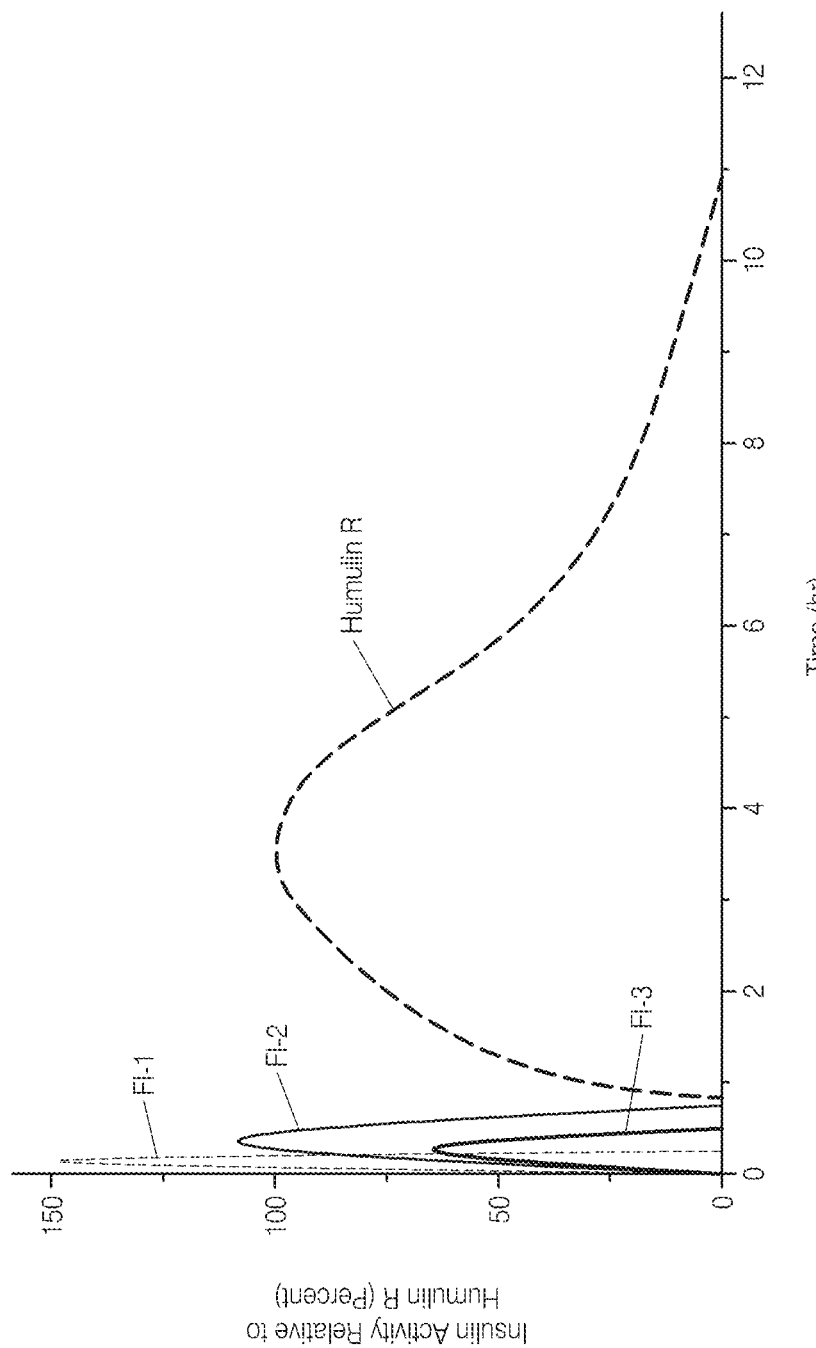
FIG. 4 is a graph comparing the time-activity profiles of some exemplary flash insulins (FI-1, FI2, FI3) to the time-activity profile of Humulin R, as taken from Frohnauer, et al. 2001, in "Graphical Human Insulin Time-Activity Profiles Using Standardized Definitions," *Diab. Tech. & Therap.* 3(3):419-429.

FIG. 4 illustrates the TAP of Humulin R (according to Frohnauer, et al. 2001, in "Graphical Human Insulin Time-Activity Profiles Using Standardized Definitions," *Diab. Tech. & Therap.* 3(3):419-429) and three possible TAPs for a "Flash Insulin," which is described below. As is known to those skilled in the art, the times of onset, peak and duration of an insulin's activity can be determined by conducting glucose clamp studies (e.g., on human volunteers) and examining the pharmacokinetics of the insulin (e.g., by examining the plasma insulin level or the glucose infusion rate during glucose clamp studies). According to the methods of Frohnauer, et al., "onset" of an insulin's activity can be determined by graphing the insulin's activity over an extended period of time (e.g., about 24- to 38-hours). On a graph of an insulin's activity (see FIG. 4), onset occurs at a time point between last baseline measurement and the first measurement above the baseline. In some circumstances, onset of an insulin's activity can be very abrupt or sharp, occurring within a few minutes. In other circumstances, onset can be prolonged, taking up to several hours. The peak of insulin activity occurs at a time point between the first maximum activity measurement and the last maximum activity measurement. In some circumstances, the peak of activity is very brief, such as a single time point. In other circumstances, the peak is prolonged (e.g., lasts a period of minutes or hours) and falls within a range of consecutive time points. The duration of an insulin's activity is the length of time during which the insulin has been active (e.g., functioning, working in the body), up to the termination of activity. At termination, the insulin's activity generally declines, tapers off and/or plateau's out (e.g., flattens out). On a graph of the insulin's activity, activity termination occurs between the last point above horizontal and the first

TABLE 1

| Insulin Formulation | Onset (hrs) | $T_{i50}$ (hrs) | Peak (hrs) | $T_{d50}$ (hrs) | Duration (hrs) |
|---|---|---|---|---|---|
| Humulin R | | | | | |
| Plasma Insulin Level | 0.08-1.0 | | 0.5-3.25 | | 4.0-12.0 |
| Glucose Infusion Rate | 0.25-1.0 | 0.6-1.25 | 1.5-4.0 | 4.0-7.0 | 9.5-12.0 |
| NPH | | | | | |
| Plasma Insulin Level | 0.08-1.5 | | 1.0-8.0 | | 6.0-28.0 |
| Glucose Infusion Rate | 0.25-2.0 | 1.25-3.25 | 3.5-10.0 | 8.5-18.0 | 14.0-27.0 |
| Lente | | | | | |
| Plasma Insulin Level | 0.5-2.25 | | 4.0-6.5 | | 21.0-24.0 |
| Glucose Infusion Rate | 0.75-2.0 | 3.0-4.5 | 9.4-12.0 | 19.25-23.5 | 21.0-24.0 |
| Ultralente | | | | | |
| Plasma Insulin Level | 0.5-3.0 | | 4.0-16.0 | | 9.0-28.0 |
| Glucose Infusion Rate | 0.75-3.0 | 3.5-8.0 | 5.0-14.5 | 17.0-22.0 | 22.5-36.6 |
| Insulin lispro | | | | | |
| Plasma Insulin Level | 0.08-0.25 | | 0.6-1.0 | | 3.0-8.0 |
| Glucose Infusion Rate | 0.16-0.5 | 0.6-0.75 | 1.25-2.0 | 2.5-4.25 | 5.0-7.0 |
| Flash Insulin | | | | | |
| Plasma Insulin Level | ≤0.08-≤0.25 | | ≤0.6-≤1.0 | | ≤3.0-≤8.0 |
| Glucose Infusion Rate | ≤0.25-≤0.5 | ≤0.6-≤0.75 | ≤1.25-≤2.0 | ≤2.5-≤4.25 | ≤5.0-≤7.0 |

Humulin R = a purified wild type human insulin;
NPH = a purified human insulin analog (Humulin N)
Lente = another purified human insulin analog (Humulin L)
Ultralente = yet another purified human insulin analog (Humulin U)
$T_{i50}$ = the time point at which insulin activity is half of the maximal activity, as the level increases.
$T_{d50}$ = the time point at which the insulin activity is half of the maximal activity, as the level decreases.

point on the horizontal. In some circumstances, an insulin's termination can be abrupt, such as at a single point. In other circumstances, an insulin's termination can be extended over a period of several minutes or a few hours.

In some embodiments, the insulin used in conjunction with the integrated system 10 is configured such that the system mimics the function of a pancreatic β-cell, with a substantially immediate onset of activity, a very rapid peak and a very brief duration (as determined by plasma insulin concentration according to the methods of Frohnauer et al). In some embodiments, the insulin is configured to have an onset time of about 5-minutes to about 10-minutes or less and a peak of activity of about 5-minutes to about 1.25-hours. Additionally, the insulin is configured to have a substantially short (e.g., brief) duration of about 3-hours or less.

In some embodiments, a very rapid-acting insulin is preferred, such that the insulin can be delivered by a system having an on/off controller, as described elsewhere herein. Such an insulin is referred to herein as a "Flash Insulin." In FIG. 4, three possible TAPs, of an exemplary flash insulin, are denoted by the curves labeled FI-1, FI-2 and FI-3. Depending upon the flash insulin developed, other TAPs are possible. In preferred embodiments, a flash insulin is configured to have a substantially "instant on" onset, such that the flash insulin reaches its peak of activity within a short time after delivery. For example, in some embodiments, a flash insulin's onset can occur within about 10-minutes or less (e.g., after delivery), preferably within about 6-minutes or less. In another example, in some embodiments, the flash insulin's peak of activity can occur within about 2-minutes to about 30-minutes, preferably within about 5-minutes to about 15-minutes. In another example, in some embodiments, the flash insulin's duration is substantially short, such as less than about 3, 2 or 1-hours. In some preferred embodiments, the flash insulin's activity peaks within about 4, 5, 8, 10, 15 or 20-minutes of the insulin's onset of activity and/or infusion of the insulin into the host. In some more preferred embodiments, the flash insulin's duration is sufficiently brief that "dose stacking" (e.g., from sequential doses) has substantially no effect on the host's glucose concentration. For example, in some embodiments, the flash insulin's duration is about 10, 20, 30 or 40-minutes, preferably less than about 20-minutes. In some embodiments, the flash insulin is configured for use with an on/off controller (discussed elsewhere herein), such that when the on instruction is selected, the flash insulin is delivered at substantially constant rate.

Manual Integration

In some embodiments, the medicament delivery device 16 is a manual delivery device, for example a syringe, inhaler, transdermal patch, cell transplantation device, and/or manual pump for manual integration with the receiver. Manual integration includes medicament delivery devices wherein a user (for example, host or doctor) manually selects the amount, type, and/or time of delivery. In some embodiments, the medicament delivery device 16 is any syringe suitable for injecting a medicament, as is appreciated by one skilled in the art. One example of a syringe suitable for the medicament delivery device of the preferred embodiments is described in U.S. Pat. No. 5,137,511, which is incorporated herein by reference in its entirety.

Figure 5A:
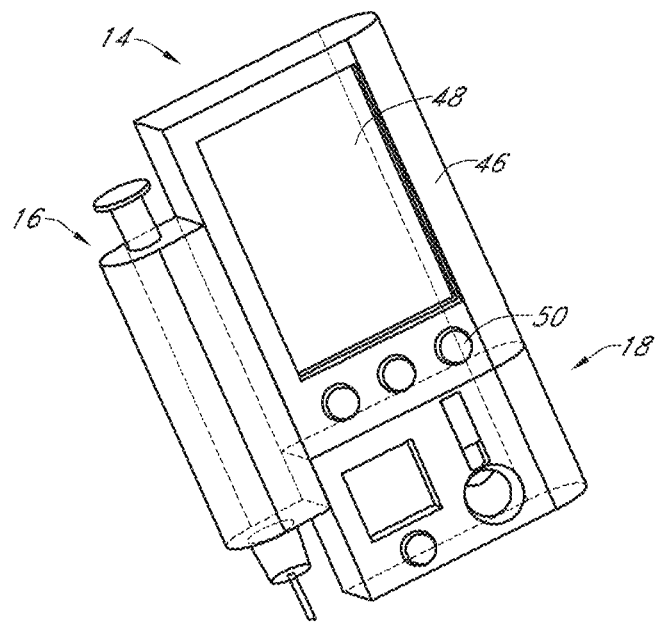
FIGS. 5A and 5B are perspective views of an integrated system 10 in one embodiment, wherein a receiver is integrated with a medicament delivery device in the form of a manual syringe, and optionally includes a single point glucose monitor.
Figure 5B:
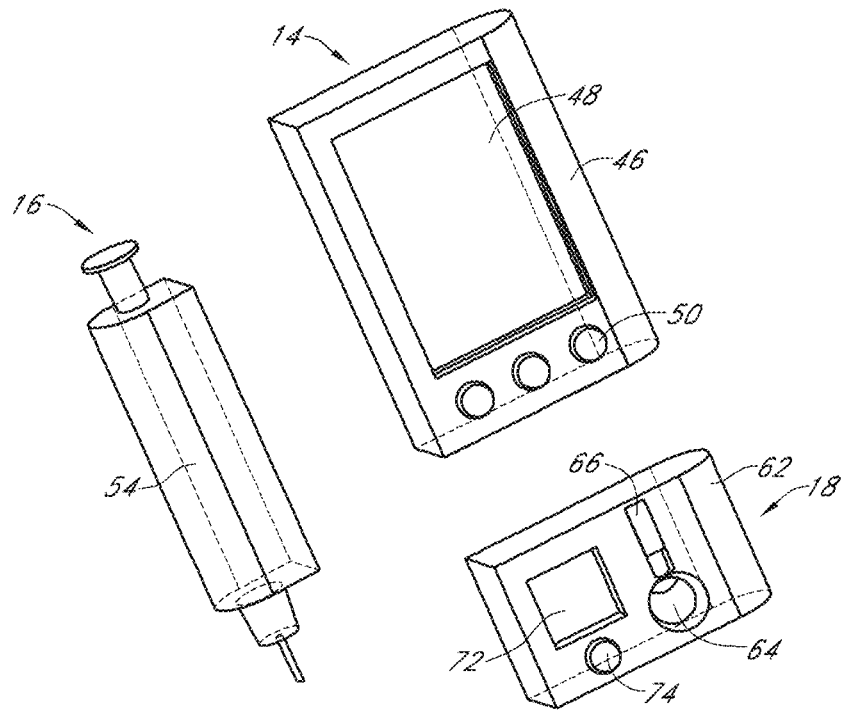

FIGS. 5A and 5B are perspective views of an integrated system 10 in one embodiment, wherein a receiver 14 is integrated with a medicament delivery device 16 in the form of a manual syringe 54, and optionally includes a single point glucose monitor 18, which will be described in more detail elsewhere herein. The receiver 14 receives, processes, and displays data from the continuous glucose monitor 12, such as described in more detail above, and can also receive, process, and display data manually entered by the user. In some embodiments, the receiver includes algorithms that use parameters provided by the continuous glucose sensor, such as glucose concentration, rate-of-change of the glucose concentration, and acceleration of the glucose concentration to more particularly determine the type, amount, and time of medicament administration. The medicament delivery device 16 is in the form of a syringe 54, which can comprise any known syringe configuration, such as described in more detail above. In some embodiments, the syringe 54 includes a housing, which is designed to hold a syringe as well as a plurality of types and amounts of medicament, for example fast-acting insulin, slow-acting insulin, and glucagon. In some embodiments, the syringe is detachably connectable to the receiver 14, and the receiver 14 provides and receives information to and from the host associated with the time, type, and amount of medicament administered. In some embodiments, the syringe is stored in a holder that is integral with or detachably connected to the receiver 14. In some embodiments, the syringe 54 can be detachable connected directly to the receiver, provided in a kit with the receiver, or other configuration, which provides easy association between the syringe and the receiver.

Referring now to the integration between the syringe and the receiver, it is noted that the receiver can be programmed with information about the time, amount, and types of medicament that can be administered with the syringe, for example. In some embodiments during set-up of the system, the host and/or doctor manually enters information about the amounts and types of medicament available via the syringe of the integrated system. In some alternative embodiments, manufacturer-provided data can be downloaded to the receiver so that the host and/or doctor can select appropriate information from menus on the screen, for example, to provide easy and accurate data entry. Thus, by knowing the available medicaments, the receiver can be programmed to customize the host's therapy recommendations considering available types and amounts of medicaments in combination with concentration, rate-of-change, and/or acceleration of the host's glucose. While not wishing to be bound by theory, it is believed that by storing available medicament therapies, the receiver is able to customize medicament calculations and recommend appropriate therapy based glucose on trend information and the preferred types and the amounts of medicament available to the host.

Subsequently in some embodiments, once the host has administered a medicament (including via the syringe and or by other means), the amount, type, and/or time of medicament administration are input into the receiver by the host. Similarly, the receiver can be programmed with standard medicaments and dosages for easy selection by the host (for example, menus on the user interface). This information can be used by the receiver to increase the intelligence of the algorithms used in determining the glucose trends and patterns that can be useful in predicting and analyzing present, past, and future glucose trends, and in providing therapy recommendations, which will be described in more detail below. Additionally, by continuously monitoring the glucose concentration over time, the receiver provides valuable information about how a host responds to a particular medicament, which information can be used by a doctor, host, or by the algorithms within the receiver, to determine patterns and provide more personalized therapy recommendations. In other words, in some embodiments, the receiver includes programming that learns the patterns (for example, an individual's metabolic response to certain medicament deliveries and host behavior) and to determine an optimum time, amount, and type of medicament to delivery in a variety of conditions (e.g., glucose concentration, rate-of-change, and acceleration). While not wishing to be bound by theory, it is believed that by continuously monitoring an individual's response to various medicaments, the host's glucose levels can be more proactively treated, keeping the diabetic host within safe glucose ranges substantially all the time.

In some embodiments, the receiver includes programming to predict glucose trends, such as described in U.S. Patent Publication No. US-2005-0203360-A1, which is incorporated herein by reference in its entirety. In some embodiments, the predictive algorithms consider the amount, type, and time of medicament delivery in predicting glucose values. For example, a predictive algorithm that predicts a glucose value or trend for the upcoming 15 to 20 minutes uses a mathematical algorithm (for example, regression, smoothing, or the like) such as described in the above-cited U.S. Patent Publication No. US-2005-0203360-A1 to project a glucose value. However outside influences, including medicament delivery can cause this projection to be inaccurate. Therefore, some embodiments provide programming in the receiver that uses the medicament delivery information received from the delivery device 14, in addition to other mathematical equations, to more accurately predict glucose values in the future.

In some alternative embodiments, the medicament delivery device 16 includes one or more transdermal patches 58 suitable for administering medicaments as is appreciated by one skilled in the art. PCT International Publication No. WO02/43566 describes one such transdermal patch, which can be used in the preferred embodiments. Although the above-cited reference and description associated with the FIGS. 6A to 6C describe a medicament (for example, glucagon) useful for treating hypoglycemia, it is understood that transdermal patches that release a medicament (for example, insulin) useful for treating hyperglycemia are also contemplated within the scope of the preferred embodiments.

Figure 6A:
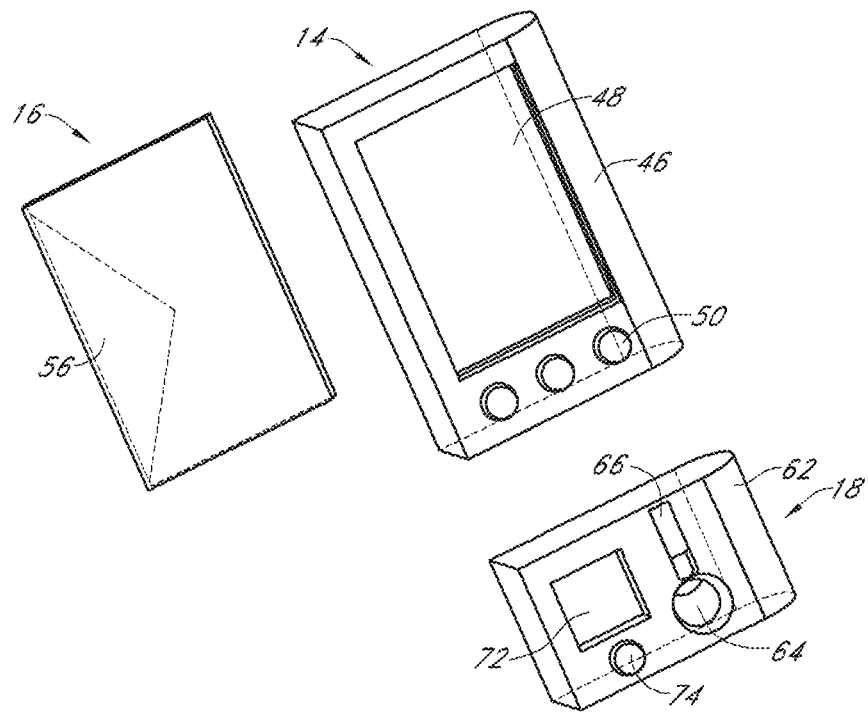
FIGS. 6A to 6C are perspective views of an integrated system in one embodiment, wherein a receiver is integrated with a medicament delivery device in the form of one or more transdermal patches housed within a holder, and optionally includes a single point glucose monitor.
Figure 6B:
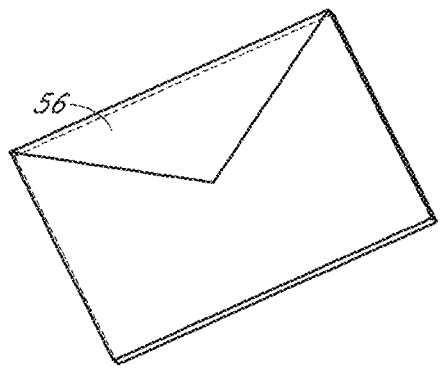
Figure 6C:
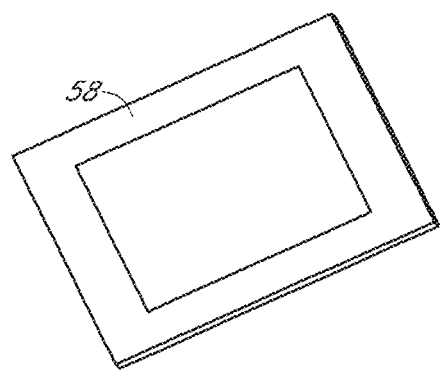

FIGS. 6A to 6C are perspective views of an integrated system 10 in one embodiment, wherein a receiver 14 is integrated with a medicament delivery device 16 in the form of one or more transdermal patches 58 housed within a holder 56, and optionally includes a single point glucose monitor 18, which will be described in more detail elsewhere herein. The receiver 14 receives, processes, and displays data from the continuous glucose monitor 12, such as described in more detail above. The medicament delivery device 16 is in the form of one or more transdermal patches 58 held in a holder 56, which can comprise any known patch configuration.

The integration of the patches 58 with the receiver 14 includes similar functionality and provides similar advantages as described with reference to other manual integrations including manual medicament delivery devices (for example, syringe and inhaler). However, a unique advantage can be seen in the integration of a continuous glucose sensor with a glucagon-type patch. Namely, a continuous glucose sensor, such as described in the preferred embodiments, provides more than single point glucose readings. In fact, because the continuous glucose sensor 12 knows the concentration, rate-of-change, acceleration, the amount of insulin administered (in some embodiments), and/or individual patterns associated with a host's glucose trends (learned over time as described in more detail elsewhere herein), the use of the glucagon patch can be iteratively optimized (inputting its usage into the receiver and monitoring the individual's metabolic response) to proactively preempt hypoglycemic events and maintain a more controlled range of glucose values. This can be particularly advantageous for nighttime hypoglycemia by enabling the diabetic host (and his/her caretakers) to improve overall nighttime diabetic health. While not wishing to be bound by theory, the integration of the continuous glucose sensor and transdermal glucagon-type patch can provide diabetic hosts with a long-term solution to reduce or avoid hypoglycemic events.

In some embodiments, the holder 58 is detachably connectable to the receiver 14 (for example on the side opposite the LCD), which enables convenient availability of the patch to the host when the receiver indicates that a medicament (for example, glucose or glucagon) is recommended. It is further noted that although this holder is shown without another medicament delivery device 16 in the illustrations of FIGS. 6A to 6C, other medicaments (for example, insulin pen, insulin pump, such as described with reference to FIGS. 7 and 8) can be integrated into the system in combination with the medicament patch illustrated herein. While not wishing to be bound by theory, it is believed that by combining medicaments that aid the diabetic host in different ways (for example, medicaments for treating hyper- and hypo-glycemic events, or, fast-acting and slow-acting medicaments), a simplified comprehensive solution for treating diabetes can be provided.

Manual integration of delivery devices with the continuous glucose sensor 12 of the preferred embodiments can additionally be advantageous because the continuous device of the preferred embodiments is able to track glucose levels long-term (for example weeks to months) and adaptively improve therapy decisions based on the host's response over time.

In some alternative embodiments, the medicament delivery device 16 includes an inhaler or spray device suitable for administering a medicament into the circulatory system, as is appreciated by one skilled in the art. Some examples of inhalers suitable for use with the preferred embodiments include U.S. Pat. Nos. 6,167,880, 6,051,551, and 6,024,090, which are incorporated herein by reference in their entirety. In some embodiments, the inhaler or spray device is considered a manual medicament delivery device, such as described with reference to FIGS. 5 and 6, wherein the inhaler or spray is manually administered by a host, and wherein the host manually enters data into the continuous receiver about the time, amount, and types of therapy. However, it is also possible that the inhaler or spray device used for administering the medicament can also comprise a processor module and operable connection to the receiver (for example, RF), such that data is sent and received between the receiver and inhaler or spray device, making it a semi-automated integration, which is described in more detail with reference to the integrated insulin pen below, for example.

In some embodiments, the inhaler or spray device is integrally housed within, detachably connected to, or otherwise physically associated with (for example, in a kit) to the receiver. The functionality and advantages of the integrated inhaler or spray device are similar to those described with reference to the syringe and/or patch integration, above. It is noted that the inhaler or spray device can be provided in combination with any other of the medicament delivery devices of the preferred embodiments, for example, a fast-acting insulin inhaler and a slow acting insulin pump can be advantageously integrated into the system of the preferred embodiments and utilized at the appropriate time as is appreciated by one skilled in the art. In some embodiments, wherein the inhaler or spray device includes a semi-automated integration with the receiver, the inhaler or spray device can by physically integrated with receiver such as described above and also operably connected to the receiver, for example via a wired (for example, via electrical contacts) or wireless (for example, via RF) connection.

In one alternative embodiment, a manual medicament delivery pump is implanted such as described in U.S. Pat. No. 6,283,944, which is incorporated herein by reference in its entirety. In this alternative embodiment, the host-controlled implantable pump allows the host to press on the device (through the skin) to administer a bolus injection of a medicament when needed. It is believed that providing glucagon or other medicament for treating hypoglycemia within this device will provide the ease and convenience that can be easily released by the host and/or his or her caretaker when the continuous glucose sensor indicates severe hypoglycemia, for example. In some alternative embodiments, the manual implantable pump is filled with insulin, or other medicament for treating hyperglycemia. In either case, the manual pump and continuous glucose sensor will benefit from manual integrations described in more detail above.

In another alternative embodiment, a cell transplantation device, such as described in U.S. Pat. Nos. 6,015,572, 5,964,745, and 6,083,523, which are incorporated herein by reference in their entirety, is manually integrated with the continuous sensor of the preferred embodiments. In this alternative embodiment, a host would be implanted with beta islet cells, which provide insulin secretion responsive to glucose levels in the body. The receiver associated with the implantable glucose sensor can be programmed with information about the cell transplantation (for example, time, amount, type, etc). In this way, the long-term continuous glucose sensor can be used to monitor the body's response to the beta islet cells. This can be particularly advantageous when a host has been using the continuous glucose sensor for some amount of time prior to the cell transplantation, and the change in the individual's metabolic patterns associated with the transplantation of the cells can be monitored and quantified. Because of the long-term continuous nature of the glucose sensor of the preferred embodiments, the long-term continuous effects of the cell transplantation can be consistently and reliably monitored. This integration can be advantageous to monitor any person's response to cell transplantation before and/or after the implantation of the cells, which can be helpful in providing data to justify the implantation of islet cells in the treatment of diabetes.

It is noted that any of the manual medicament delivery devices can be provided with an RF ID tag or other communication-type device, which allows semi-automated integration with that manual delivery device, such as described in more detail below.

Semi-Automated Integration

Semi-automated integration of medicament delivery devices 16 in the preferred embodiments includes any integration wherein an operable connection between the integrated components aids the user (for example, host or doctor) in selecting, inputting, or calculating the amount, type, or time of medicament delivery of glucose values, for example, by transmitting data to another component and thereby reducing the amount of user input required. In the preferred embodiments, semi-automated can also refer to a fully automated device (for example, one that does not require user interaction), wherein the fully automated device requires a validation or other user interaction, for example to validate or confirm medicament delivery amounts. In some embodiments, the semi-automated medicament delivery device is an inhaler or spray device, a pen or jet-type injector, or a transdermal or implantable pump.

Figure 7A:
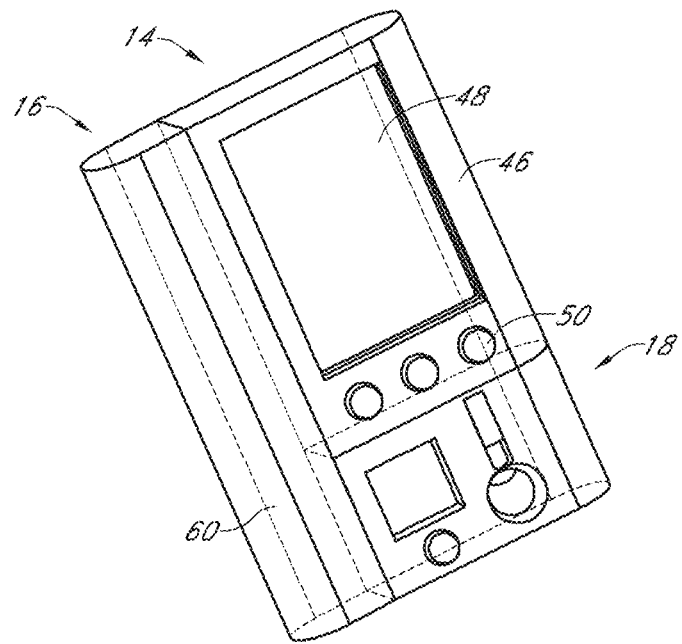
FIGS. 7A and 7B are perspective views of an integrated system in one embodiment, wherein a receiver is integrated with a medicament delivery device in the form of a pen or jet-type injector, and optionally includes a single point glucose monitor.
Figure 7B:
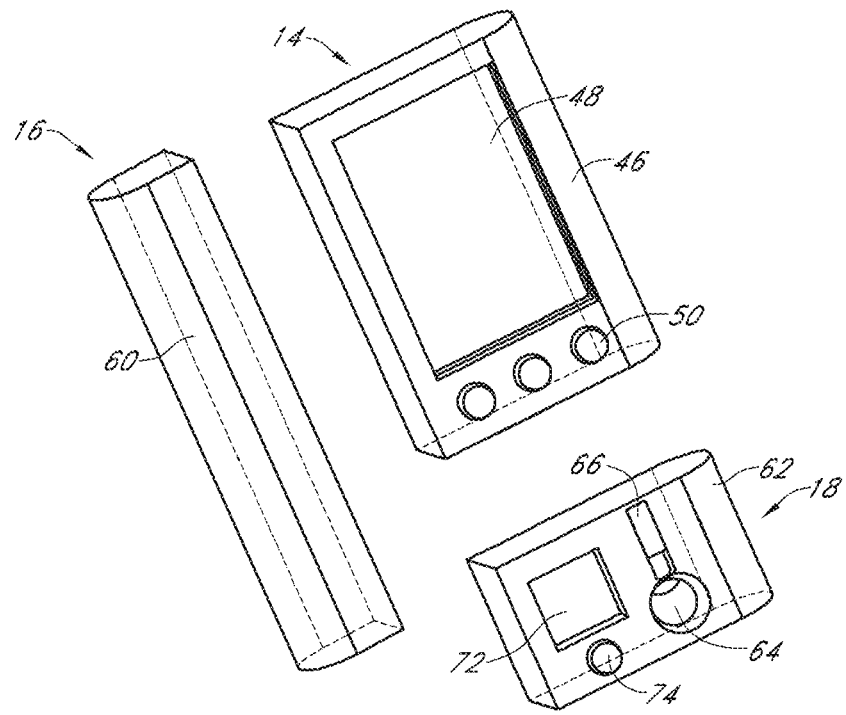

FIGS. 7A and 7B are perspective views of an integrated system 10 in one embodiment, wherein a receiver 14 is integrated with a medicament delivery device 16 in the form of a pen or jet-type injector, hereinafter referred to as a pen 60, and optionally includes a single point glucose monitor 18, which will be described in more detail elsewhere herein. The receiver 14 receives, processes, and displays data from the continuous glucose monitor 12, such as described in more detail above. The medicament delivery pen 60 of the preferred embodiments includes any pen-type injector, such as is appreciated by one skilled in the art. A few examples of medicament pens that can be used with the preferred embodiments, include U.S. Pat. Nos. 5,226,895, 4,865,591, 6,192,891, and 5,536,249, each of which are incorporated herein by reference in its entirety.

FIG. 7A is a perspective view of an integrated system 10 in embodiment. The integrated system 10 is shown in an attached state, wherein the various elements are held by a mechanical means, as is appreciated by one skilled in the art. The components 14, 16, and 18 (optional) are also in operable connection with each other, which can include a wired or wireless connection. In some embodiments, the components include electrical contacts that operably connect the components together when in the attached state. In some embodiments, the components are operably connected via wireless connection (for example, RF), and wherein the components may or may not be detachably connectable to each other. FIG. 7B shows the components in an unattached state, which can be useful when the host would like to carry minimal components and/or when the components are integrated via a wireless connection, for example.

Medicament delivery pen 60 includes at least a processor module and a wired or wireless connection to the receiver 14, which are described in more detail with reference to FIG. 9. In some embodiments, the pen 60 includes programming that receives instructions sent from the receiver 14 regarding type and amount of medicament to administer. In some embodiments, wherein the pen includes more than one type of medicament, the receiver provides the necessary instructions to determine which type or types of medicament to administer, and can provide instructions necessary for mixing the one or more medicaments. In some embodiments, the receiver provides the glucose trend information (for example, concentration, rate-of-change, acceleration, or other user input information) and pen 60 includes programming necessary to determine appropriate medicament delivery.

Subsequently, the pen 60 includes programming to send information regarding the amount, type, and time of medicament delivery to the receiver 14 for processing. The receiver 14 can use this information received from the pen 60, in combination with the continuous glucose data obtained from the sensor, to monitor and determine the host's glucose patterns to measure their response to each medicament delivery. Knowing the host's individual response to each type and amount of medicament delivery can be useful in adjusting or optimizing the host's therapy. It is noted that individual metabolic profiles (for example, insulin sensitivity) are variable from host to host. While not wishing to be bound by theory, it is believed that once the receiver has learned (for example, monitored and determined) the individual's metabolic patterns, including glucose trends and associated medicament deliveries, the receiver can be programmed to adjust and optimize the therapy recommendations for the host's individual physiology to maintain their glucose levels within a desired target range. In alternative embodiments, the pen 60 can be manually integrated with the receiver.

In some embodiments, the receiver includes algorithms that use parameters (e.g., data) provided by the continuous glucose sensor, such as glucose concentration, rate-of-change of the glucose concentration, and acceleration of the glucose concentration to more particularly determine the type, amount, and time of medicament administration. In fact, all of the functionality of the above-described manual and semi-automated integrated systems, including therapy recommendations, adaptive programming for learning individual metabolic patterns, and prediction of glucose values, can be applied to the semi-automated integrated system 10, such as described herein. However, the semi-automated integrated sensing and delivery system additionally provides convenience by automation (for example, data transfer through operable connection) and reduced opportunity for human error than can be experienced with the manual integration.

In some alternative embodiments, the semi-automated integration provides programming that requires at least one of the receiver 14, single point glucose monitor 18, and medicament delivery device 16 to be validated or confirmed by another of the components to provide a fail safe accuracy check; in these embodiments, the validation includes algorithms programmed into any one or more of the components. In some alternative embodiments, the semi-automated integration provides programming that requires at least one of the receiver 14 and medicament delivery device 16 to be validated or confirmed by an a human (for example, confirm the amount and/or type of medicament). In these embodiments, validation provides a means by which the receiver can be used adjunctively, when the host or doctor would like to have more control over the host's therapy decisions, for example. See FIGS. 10 to 12 for processes that can be implemented herein.

Although the above description of semi-automated medicament delivery is mostly directed to an integrated delivery pen, the same or similar integration can be accomplished between a semi-automated inhaler or spray device, and/or a semi-automated transdermal or implantable pump device. Additionally, any combination of the above semi-automated medicament delivery devices can be combined with other manual and/or automated medicament delivery device within the scope of the preferred embodiments as is appreciated by one skilled in the art.

In some embodiments, the semi-automated integrated system 10 includes a dynamic bolus controller module that is configured to intelligently evaluate an engaged (e.g., selectable) bolus constraint (e.g., pre-set and/or programmable) and internally derived data, and to calculate an insulin therapy (e.g., dose) less than or equal to the maximum total insulin dose associated with the engaged bolus constraint, in response to the host engaging the bolus constraint, such as described in more detail elsewhere herein. Preferably, the determination of the insulin therapy is based solely on the internally derived data and the engaged bolus constraint. In some preferred embodiments, the evaluation and/or calculation of therapy are performed iteratively. In some embodiments, a bolus constraint can be engaged (e.g., selected, initiated, activated) by pressing a programmable button or key, actuating a switch, selecting from a menu (e.g., scroll, pop-up or tab) and the like. In some embodiments, the system includes two or more bolus constraints, such as constraints associated with different types of meals and/or with different events. For example, one or more bolus constraint buttons can be programmed by the user (e.g., the host or a caretaker of the host) for insulin therapies sufficient to cover an average breakfast, lunch or dinner, to cover a high carbohydrate or high fat meal, or as a corrective insulin dose and the like. In a further embodiment, the system is configured to request host validation of the calculated bolus insulin therapy (e.g., by selecting yes or no, OK).

In some embodiments, the system is configured to include an on/off controller module and/or a dynamic basal controller module. On/off and dynamic basal controller modules are discussed in detail elsewhere herein.

Automated Integration

Automated integration medicament delivery devices 16 in the preferred embodiments are any delivery devices wherein an operable connection between the integrated components provides for full control of the system without required user interaction. Transdermal and implantable pumps are examples of medicament delivery devices that can be used with the preferred embodiments of the integrated system 10 to provide automated control of the medicament delivery device 16 and continuous glucose sensor 12. Some examples of medicament pumps that can be used with the preferred embodiments include, U.S. Pat. No. 6,471,689, PCT International Publication No. WO81/01794, and European Patent No. EP-1281351-B, each of which is incorporated herein by reference in its entirety.

Figure 8A:
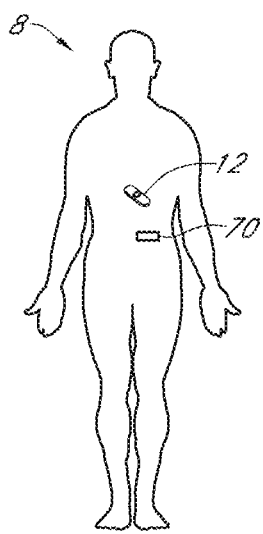
FIGS. 8A to 8C are perspective views of an integrated system in one embodiment, wherein a sensor and delivery pump, which are implanted or transdermally inserted into the patient, are operably connected to an integrated receiver, and optionally include a single point glucose monitor.
Figure 8B:
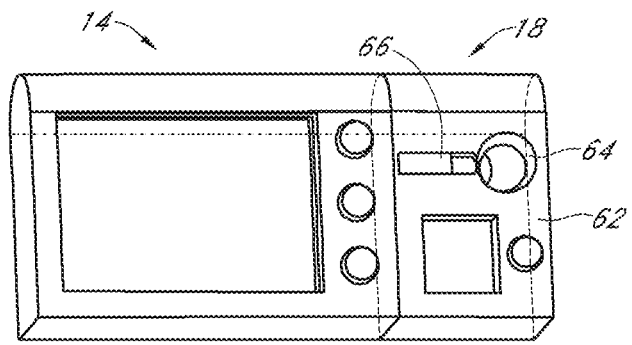
Figure 8C:
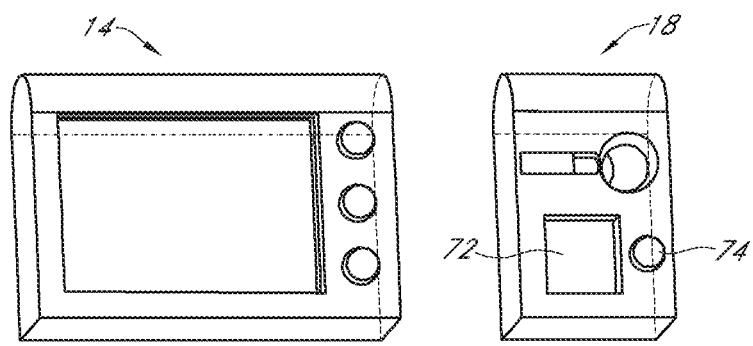

FIGS. 8A to 8C are perspective views of an integrated system in one embodiment, wherein a sensor and delivery pump, which are implanted or transdermally inserted into the host, are operably connected to an integrated receiver, and optionally include a single point glucose monitor. FIG. 8A is a perspective view of a host 8, in which is implanted or transdermally inserted a sensor 12 and a pump 70. FIGS. 8B and 8C are perspective views of the integrated receiver and optional single point glucose monitor in attached and unattached states. The pump 70 can be of any configuration known in the art, for example, such as cited above.

The receiver 14 receives, processes, and displays data associated with the continuous glucose monitor 12, data associated with the pump 70, and data manually entered by the host 8. In some embodiments, the receiver includes algorithms that use parameters provided by the continuous glucose sensor, such as glucose concentration, rate-of-change of the glucose concentration, and acceleration of the glucose concentration to determine the type, amount, and time of medicament administration. In fact, all of the functionality of the above-described manual and semi-automated integrated systems, including therapy recommendations, confirmation or validation of medicament delivery, adaptive programming for learning individual metabolic patterns, and prediction of glucose values, can be applied to the fully automated integrated system 10, such as described herein with reference to FIGS. 8A to 8C. However, the fully automated sensing and delivery system can run with or without user interaction. U.S. Patent Publication No. US-2003-0028089-A1 provides some systems and methods for providing control of insulin, which can be used with the preferred embodiments, and is incorporated herein by reference in its entirety.

In some embodiments of the automated integrated system 10, a fail-safe mode is provided, wherein the system is programmed with conditions whereby when anomalies or potentially clinically risky situations arise, for example when a reference glucose value (for example, from an SMBG) indicates a discrepancy from the continuous sensor that could cause risk to the host if incorrect therapy is administered. Another example of a situation that may benefit from a validation includes when a glucose values are showing a trend in a first direction that shows a possibility of "turn around," namely, the host may be able to reverse the trend with a particular behavior within a few minutes to an hour, for example. In such situations, the automated system can be programmed to revert to a semi-automated system requiring user validation or other user interaction to validate the therapy in view of the situation.

It is noted that in the illustrated embodiment, only one receiver 14 is shown, which houses the electronics for both the medicament delivery pump 70 and the continuous sensor 12. Although it is possible to house the electronics in two different receiver housings, providing one integrated housing 14 increases host convenience and minimizes confusion or errors. In some embodiments, the sensor receiver electronics and pump electronics are separate, but integrated. In some alternative embodiments, the sensor and pump share the same electronics.

Additionally, the integrated receiver for the sensor and pump, can be further integrated with any combination with the above-described integrated medicament delivery devices, including syringe, patch, inhaler, and pen, as is appreciated by one skilled in the art.

In some embodiments, the fully automated integrated system 10 includes an on/off controller module, as described elsewhere herein. Preferably, the on/off controller module is configured to intelligently and adaptively evaluate only internally derived data relative to a pre-programmed glucose boundary (e.g., about 70, 80, 90, 100, 110, 120, 130, 140, 150, or 160 mg/dl glucose) and to select between on and off instructions that actuate the system's integrated insulin delivery device. In one embodiment, integrated system 10 is configured to automatically (e.g., iteratively, continually or continuously) monitor and manage the host's glucose level in real-time, similarly to the glucose regulation by the pancreatic β-cells of a non-diabetic person. In generally, the glucose boundary is selected based on when insulin is, or is not, to be delivered to the host.

In some embodiments, the automated system includes an on/off controller and is configured for use with a flash insulin (e.g., an insulin having a substantially "instant on," rapid peak and short duration TAP, as described in the section entitled "Medicament Delivery Device"), such that the on/off controller can iteratively (e.g., automatically, periodically, or continually) evaluate the internally derived data, calculate and deliver flash insulin doses over a period of time (e.g., minutes, hours, days, etc.) and the effect of insulin dose stacking (e.g., to the host) is substantially negligible and/or can be algorithmically accounted for. On/off controller modules are described in greater detail in the section entitled "On/off Controller Module," and, for example, with reference to FIG. 15.

In some embodiments, the automated integrated system 10 includes a dynamic basal controller module configured to intelligently and adaptively evaluate solely internally derived data relative to a basal profile, and to calculate an insulin therapy within the basal profile, such that the host's glucose is substantially maintained within a target range over a period of hours, days or weeks, with the exception of expected increases in glucose associated with meals and the like. In general, the target range is a range of euglycemic glucose concentrations. Two exemplary target ranges are glucose concentrations from about 80 mg/dl to about 140 mg/dl and from about 100-mg-dl to about 160 mg/dl.

Figure 16:
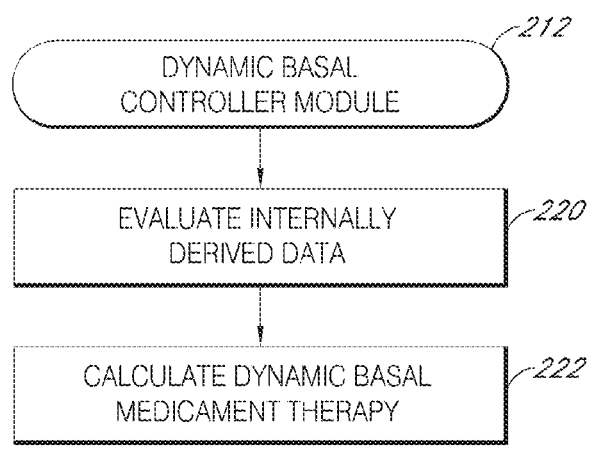
FIG. 16 is a flow chart that illustrates the process of calculating a medicament therapy based on internally derived data, using a dynamic basal controller module, in one embodiment.

Dynamic basal controller modules are described in greater detail in the section entitled "Dynamic Basal Controller Module," and, for example, with reference to FIG. 16.

In some embodiments, the fully automated integrated system is configured to continuously (e.g., intermittently, iteratively, periodically, or automatically) adaptively monitor and evaluate the host's metabolic profile and to determine (e.g., calculate) an insulin therapy. As is known to one skilled in the art, the host's metabolic profile can fluctuate over a period of days or weeks, depending upon the host's activity level and state of health, the types of foods the host is consuming, medications, and the like. Preferably, the controller module (e.g., on/off, basal and/or bolus controller modules) is configured to adaptively and intelligently adjust one or more system parameters (e.g., glucose boundary, basal profile, bolus constraint, insulin delivery rate, and the like) in response to internally derived data and the host's metabolic profile. While not wishing to be bound by theory, it is believed that configuring the fully automated integrated system to adaptively monitor and evaluate the user's metabolic profile promotes optimal insulin dosing, improves system accuracy and reduces the number of host hypoglycemic episodes, which ultimately promotes improved host health and safety.

Single Point Glucose Monitor

In the illustrated embodiments (FIGS. 5 to 8), the single point glucose monitor includes a meter for measuring glucose within a biological sample including a sensing region that has a sensing membrane impregnated with an enzyme, similar to the sensing membrane described with reference to U.S. Pat. Nos. 4,994,167 and 4,757,022, each which is incorporated herein in its entirety by reference. However, in alternative embodiments, the single point glucose monitor can use other measurement techniques such as conventional finger stick/test strip meters, optical devices, and the like. It is noted that the meter is optional in that a separate meter can be used and the glucose data downloaded or input by a user into the receiver. However the illustrated embodiments show an integrated system that exploits the advantages associated with integration of the single point glucose monitor with the receiver 14 and delivery device 16.

FIGS. 5 to 8 are perspective views of integrated receivers including a single point glucose monitor. It is noted that the integrated single point glucose monitor can be integral with, detachably connected to, and/or operably connected (wired or wireless) to the receiver 14 and medicament delivery device 16. The single point glucose monitor 18 integrates rapid and accurate measurement of the amount of glucose in a biological fluid and its associated processing with the calibration, validation, other processes associated with the continuous receiver 14, such as described in more detail with reference to U.S. Patent Publication No. US-2005-0154271-A1 which is incorporated herein by reference in its entirety.

In the illustrated embodiments, the single point glucose monitor 18, such as described in the above-cited U.S. Patent Publication No. US-2005-0154271-A1, includes a body 62 that houses a sensing region 64, which includes a sensing membrane located within a port. A shuttle mechanism 66 can be provided that preferably feeds a single-use disposable bioprotective film that can be placed over the sensing region 64 to provide protection from contamination. The sensing region includes electrodes, the top ends of which are in contact with an electrolyte phase (not shown), which is a free-flowing fluid phase disposed between the sensing membrane and the electrodes. The sensing region measures glucose in the biological sample in a manner such as described in more detail above, with reference the continuous glucose sensor, and as described in U.S. Pat. Nos. 4,994,167 and 4,757,022. The similarity of the measurement technologies used for the continuous glucose sensor and the single point glucose sensor provides an internal control that creates increased reliability by nature of consistency and decreased error potential that can otherwise be increased due to combining dissimilar measurement techniques. Additionally, the disclosed sensing membrane is known to provide longevity, repeatability, and cost effectiveness, for example as compared to single use strips, or the like. However, other single point glucose monitors can be used with the preferred embodiments.

In one alternative embodiment, the single point glucose monitor comprises an integrated lancing and measurement device such as described in U.S. Pat. No. 6,607,658. In another alternative embodiment, the single point glucose monitor comprises a near infrared device such as described in U.S. Pat. No. 5,068,536. In another alternative embodiment, the single point glucose monitor comprises a reflectance reading apparatus such as described in U.S. Pat. No. 5,426,032. In another alternative embodiment, the single point glucose monitor comprises a spectroscopic transflectance device such as described in U.S. Pat. No. 6,309,884. Each of the above patents and patent applications is incorporated in its entirety herein by reference.

In some embodiments, the single point glucose meter further comprises a user interface that includes a display 72 and a button 74; however, some embodiments utilize the display 48 and buttons 50 of the receiver 14 rather than providing a separate user interface for the monitor 18. In some embodiments the single point glucose monitor measured glucose concentration, prompts, and/or messages can be displayed on the user interface 48 or 72 to guide the user through the calibration and sample measurement procedures, or the like. In addition, prompts can be displayed to inform the user about necessary maintenance procedures, such as "Replace Sensor" or "Replace Battery." The button 74 preferably initiates the operation and calibration sequences. The button can be used to refresh, calibrate, or otherwise interface with the single point glucose monitor 18 as is appreciated by one skilled in the art.

Integrated Electronics

FIG. 9 is a block diagram that illustrates integrated system electronics in one embodiment. One embodiment is described wherein the processor module within the receiver performs much of the processing, however it is understood that all or some of the programming and processing described herein can be accomplished within the continuous glucose sensor, the receiver, the single point glucose monitor, and/or the delivery device, or any combination thereof. Similarly, displays, alarms, and other user interface functions can be incorporated into any of the individual components of the integrated delivery device.

A quartz crystal 76 is operably connected to an RF module 78 that together function to receive and synchronize data streams via an antenna 80 (for example, transmission 40 from the RF module 44 shown in FIG. 3). Once received, a processor module 82 processes the signals, such as described below. However, other methods of wired or wireless communication can be substituted for the RF communication described herein.

The processor module 82 is the central control unit that provides the processing for the receiver, such as storing data, analyzing continuous glucose sensor data stream, analyzing single point glucose values, accuracy checking, checking clinical acceptability, calibrating sensor data, downloading data, recommending therapy instructions, calculating medicament delivery amount, type and time, learning individual metabolic patterns, and controlling the user interface by providing prompts, messages, warnings and alarms, or the like. The processor module 82 can include all or part of the controller module, as described elsewhere herein, and with reference to FIGS. 13 to 17, for example. The processor module 82 can include hardware and software that performs the processing described herein, including for example, read only memory 84 (ROM), such as flash memory, provides permanent or semi-permanent storage of data, storing data such as sensor ID, receiver ID, and programming to process data streams (for example, programming for performing estimation and other algorithms described elsewhere herein), and random access memory 88 (RAM) stores the system's cache memory and is helpful in data processing. For example, the RAM 88 stores information from the continuous glucose sensor, delivery device, and/or single point glucose monitor for later recall by the user or a doctor; a user or doctor can transcribe the stored information at a later time to determine compliance with the medical regimen or evaluation of glucose response to medication administration (for example, this can be accomplished by downloading the information through the pc com port 90). In addition, the RAM 88 can also store updated program instructions and/or host specific information. FIGS. 10 and 11 describe more detail about programming that is preferably processed by the processor module 82. In some alternative embodiments, memory storage components comparable to ROM and RAM can be used instead of or in addition to the preferred hardware, such as SRAM, EEPROM, dynamic RAM, non-static RAM, rewritable ROMs, flash memory, or the like.

In some embodiments, the processor module 82 monitors the internally derived data (e.g., the continuous glucose sensor data stream) 40 to determine a preferable time for capturing glucose concentration values using the single point glucose monitor electronics 116 for calibration of the continuous sensor data stream. For example, when sensor glucose data (for example, observed from the data stream) changes too rapidly, a single point glucose monitor reading may not be sufficiently reliable for calibration during unstable glucose changes in the host; in contrast, when sensor glucose data are relatively stable (for example, relatively low rate of change), a single point glucose monitor reading can be taken for a reliable calibration. In some additional embodiments, the processor module can prompt the user via the user interface to obtain a single point glucose value for calibration at predetermined intervals. In some additional embodiments, the user interface can prompt the user to obtain a single point glucose monitor value for calibration based upon certain events, such as meals, exercise, large excursions in glucose levels, faulty or interrupted data readings, or the like. In some embodiments, certain acceptability parameters can be set for reference values received from the single point glucose monitor. For example, in one embodiment, the receiver only accepts reference glucose data between about 40 and about 400 mg/dL.

In some embodiments, the processor module 82 monitors the internally derived data, such as but not limited to the continuous glucose sensor data stream, to determine a preferable time for medicament delivery, including type, amount, and time. In some embodiments, the processor module is programmed to detect impending clinical risk and can request data input, a reference glucose value from the single point glucose monitor, or the like, in order to confirm a therapy recommendation. In some embodiments, the processor module is programmed to process internally derived data and medicament therapies to adaptive adjust to an individual's metabolic patterns. In some embodiments, the processor module is programmed to project glucose trends based on data from the integrated system (for example, medicament delivery information, user input, or the like). In some embodiments, the processor module is programmed to calibrate the continuous glucose sensor based on the integrated single point glucose monitor. Numerous other programming can be incorporated into the processor module, as is appreciated by one skilled in the art, as is described in cited patents and patent applications here, and as is described with reference to flowcharts of FIGS. 10 to 12.

It is noted that one advantage of integrated system of the preferred embodiments can be seen in the time stamp of the sensor glucose data, medicament delivery data, and reference glucose data. Namely, typical implementations of the continuous glucose sensor 12, wherein the medicament delivery 16 and/or single point glucose monitor 18 is not integral with the receiver 14, the reference glucose data or medicament delivery data can be obtained at a time that is different from the time that the data is input into the receiver 14. Thus, the user may not accurately input the "time stamp" of the delivery or, for example, the time or obtaining reference glucose value or administering the medicament, at the time of reference data input into the receiver. Therefore, the accuracy of the calibration of the continuous sensor, prediction of glucose values, therapy recommendations, and other processing is subject to human error (for example, due to inconsistencies in entering the actual time of the single point glucose test). In contrast, the preferred embodiments of the integrated system advantageously do no suffer from this potential inaccuracy when the time stamp is automatically and accurately obtained at the time of the event. Additionally, the processes of obtaining reference data and administering the medicament can be simplified and made convenient using the integrated receiver because of fewer loose parts (for example, cable, test strips, etc.) and less required manual data entry.

A battery 92 is operably connected to the processor module 82 and provides power for the receiver. In one embodiment, the battery is a standard AAA alkaline battery, however any appropriately sized and powered battery can be used. In some embodiments, a plurality of batteries can be used to power the system. In some embodiments, a charge port (not shown) is provided permit recharging of rechargeable batteries. A quartz crystal 94 is operably connected to the processor module 168 and maintains system time for the computer system as a whole.

A PC communication (com) port 90 can be provided to enable communication with systems, for example, a serial communications port, allows for communicating with another computer system (for example, PC, PDA, server, and the like). In one exemplary embodiment, the receiver is able to download historical data to a physician's PC for retrospective analysis by the physician. The PC communication port 90 can also be used to interface with other medical devices, for example pacemakers, implanted analyte sensor patches, infusion devices, telemetry devices, and the like.

A user interface 96 comprises a keyboard 98, speaker 100, vibrator 102, backlight 104, liquid crystal display (LCD) 106, one or more buttons 108, and/or a scroll wheel (not shown). The components that comprise the user interface 96 provide controls to interact with the user. The keyboard 98 can allow, for example, input of user information about himself/herself, such as mealtime, exercise, insulin administration, and reference glucose values. The speaker 100 can provide, for example, audible signals or alerts for conditions such as present and/or predicted hyper- and hypoglycemic conditions. The vibrator 102 can provide, for example, tactile signals or alerts for reasons such as described with reference to the speaker, above. The backlight 104 can be provided, for example, to aid the user in reading the LCD in low light conditions. The LCD 106 can be provided, for example, to provide the user with visual data output. In some embodiments, the LCD is a touch-activated screen. The buttons 108 can provide for toggle, menu selection, option selection, mode selection, and reset, for example. In some alternative embodiments, a microphone can be provided to allow for voice-activated control.

The user interface 96, which is operably connected to the processor module 82, serves to provide data input and output for both the continuous glucose sensor, delivery mechanism, and/or for the single point glucose monitor. Data output includes a numeric estimated analyte value, an indication of directional trend of analyte concentration, a graphical representation of the measured analyte data over a period of time, alarms/alerts, therapy recommendations, actual therapy administered, event markers, and the like. In some embodiments, the integrated electronics are configured to display a representation of a target glucose value or target glucose range on the user interface. Some additional data representations are disclosed in U.S. Patent Publication No. US-2005-0203360-A1, which is incorporated herein by reference in its entirety.

In some embodiments, prompts or messages can be displayed on the user interface to guide the user through the initial calibration and sample measurement procedures for the single point glucose monitor. Additionally, prompts can be displayed to inform the user about necessary maintenance procedures, such as "Replace Sensing Membrane" or "Replace Battery." Even more, the glucose concentration value measured from the single point glucose monitor can be individually displayed.

In some embodiments, prompts or messages can be displayed on the user interface to convey information to the user, such as malfunction, outlier values, missed data transmissions, or the like, for the continuous glucose sensor. Additionally, prompts can be displayed to guide the user through calibration of the continuous glucose sensor. Even more, calibrated sensor glucose data can be displayed, which is described in more detail with reference to U.S. Patent Publication No. US-2005-0027463-A1 and U.S. Patent Publication No. US-2005-0203360-A1, each of which is incorporated herein by reference in its entirety.

In some embodiments, prompts or messages about the medicament delivery device can be displayed on the user interface to inform or confirm to the user type, amount, and time of medicament delivery. In some embodiments, the user interface provides historical data and analytes pattern information about the medicament delivery, and the host's metabolic response to that delivery, which may be useful to a host or doctor in determining the level of effect of various medicaments.

Electronics 110 associated with the delivery device 16 (namely, the semi-automated and automated delivery devices) are operably connected to the processor module 82 and include a processor module 112 for processing data associated with the delivery device 16 and include at least a wired or wireless connection (for example, RF module) 114 for transmission of data between the processor module 82 of the receiver 14 and the processor module 112 of the delivery device 16. Other electronics associated with any of the delivery devices cited herein, or other known delivery devices, may be implemented with the delivery device electronics 110 described herein, as is appreciated by one skilled in the art.

In some embodiments, the processor module 112 comprises programming for processing the delivery information in combination with the internally derived data (e.g., continuous sensor information). In some embodiments, the processor module 112 includes all or part of the controller module, as described elsewhere herein. In some alternative embodiments, the processor module 82 comprises programming for processing the delivery information in combination with the internally derived data. In some embodiments, both processor modules 82 and 112 mutually process information related to each component.

In some embodiments, the medicament delivery device 16 further includes a user interface (not shown), which may include a display and/or buttons, for example. U.S. Pat. Nos. 6,192,891, 5,536,249, and 6,471,689 describe some examples of incorporation of a user interface into a medicament delivery device, as is appreciated by one skilled in the art.

Electronics 116 associated with the single point glucose monitor 18 are operably connected to the processor module 120 and include a potentiostat 118 in one embodiment that measures a current flow produced at the working electrode when a biological sample is placed on the sensing membrane, such as described above. The current is then converted into an analog signal by a current to voltage converter, which can be inverted, level-shifted, and sent to an A/D converter. The processor module can set the analog gain via a control port (not shown). The A/D converter is preferably activated at one-second intervals. The processor module evaluates the converter output with any number of pattern recognition algorithms known to those skilled in the art until a glucose peak is identified. A timer is then preferably activated for about 30 seconds at the end of which time the difference between the first and last electrode current values is calculated. This difference is then divided by the value stored in the memory during instrument calibration and is then multiplied by the calibration glucose concentration. The glucose value in milligram per deciliter, millimoles per liter, or the like, is then stored in the processor module, displayed on the user interface, used to calibrate of the glucose sensor data stream, downloaded, etc.

Programming and Processing

FIG. 10 is a flow chart that illustrates the process 130 of validating therapy instructions prior to medicament delivery in one embodiment. In some embodiments, the therapy recommendations include a suggestion on the user interface of time, amount, and type of medicament to delivery. In some embodiments, therapy instructions include calculating a time, amount, and/or type of medicament delivery to administer, and optionally transmitting those instructions to the delivery device. In some embodiments, therapy instructions include that portion of a closed loop system wherein the determination and delivery of medicament is accomplished, as is appreciated by one skilled in the art.

Although computing and processing of data is increasingly complex and reliable, there are circumstances by which the therapy recommendations necessitate human intervention. Some examples include when a user is about to alter his/her metabolic state, for example due to behavior such as exercise, meal, pending manual medicament delivery, or the like. In such examples, the therapy recommendations determined by the programming may not have considered present or upcoming behavior, which may change the recommended therapy. Numerous such circumstances can be contrived; suffice it to say that a validation may be advantageous in order to ensure that therapy recommendations are appropriately administered.

At block 132, a sensor data receiving module, also referred to as the sensor data module, receives sensor data (e.g., a data stream), including one or more time-spaced sensor data points, from a sensor via the receiver, which may be in wired or wireless communication with the sensor. The sensor data point(s) may be raw or smoothed, such as described in U.S. Patent Publication No. US-2005-0043598-A1 which is incorporated herein by reference in its entirety.

At block 134, a medicament calculation module, which is a part of a processor module, calculates a recommended medicament therapy based on the received sensor data. A variety of algorithms may be used to calculate a recommended therapy as is appreciated by one skilled in the art.

At block 136, a validation module, which is a part of the processor module, optionally validates the recommended therapy. The validation may include a request from the user, or from another component of the integrated system 10, for additional data to ensure safe and accurate medicament recommendation or delivery. In some embodiments, the validation requests and/or considers additional input, such as time of day, meals, sleep, calories, exercise, sickness, or the like. In some embodiments, the validation module is configured to request this information from the user. In some embodiments, the validation module is responsive to a user inputting such information.

In some embodiments, when the integrated system 10 is in fully automated mode, the validation module is triggered when a potential risk is evaluated. For example, when a clinically risky discrepancy is evaluated, when the acceleration of the glucose value is changing or is low (indicative of a significant change in glucose trend), when it is near a normal meal, exercise or sleep time, when a medicament delivery is expected based on an individual's dosing patterns, and/or a variety of other such situations, wherein outside influences (meal time, exercise, regular medicament delivery, or the like) may deem consideration in the therapy instructions. These conditions for triggering the validation module may be pre-programmed and/or may be learned over time, for example, as the processor module monitors and patterns an individual's behavior patterns.

In some embodiments, when the integrated system 10 is in semi-automated mode, the system may be programmed to request additional information from the user regarding outside influences unknown to the integrated system prior to validation. For example, exercise, food or medicament intake, rest, or the like may input into the receiver for incorporation into a parameter of the programming (algorithms) that processing the therapy recommendations.

At block 138, the receiver confirms and sends (for example, displays, transmits and/or delivers) the therapy recommendations. In manual integrations, the receiver may simply confirm and display the recommended therapy, for example. In semi-automated integrations, the receiver may confirm, transmit, and optionally delivery instructions to the delivery device regarding the recommended therapy, for example. In automated integrations the receiver may confirm and ensure the delivery of the recommended therapy, for example. It is noted that these examples are not meant to be limiting and there are a variety of methods by which the receiver may confirm, display, transmit, and/or deliver the recommended therapy within the scope of the preferred embodiments.

FIG. 11 is a flow chart 140 that illustrates the process of providing adaptive metabolic control using an integrated system in one embodiment. In this embodiment, the integrated system is programmed to learn the patterns of the individual's metabolisms, including metabolic response to medicament delivery.

At block 142, a medicament data receiving module, which may be programmed within the receiver 14 and/or medicament delivery device 16, receives medicament delivery data, including time, amount, and/or type. In some embodiments, the user is prompted to input medicament delivery information into the user interface. In some embodiments, the medicament delivery device 16 sends the medicament delivery data to the medicament data-receiving module.

At block 144, a sensor data receiving module, also referred to as the sensor data module, receives sensor data (e.g., a data stream), including one or more time-spaced sensor data points, from a sensor via the receiver, which may be in wired or wireless communication with the sensor.

At block 146, the processor module, which may be programmed into the receiver 14 and/or the delivery device 16 is programmed to monitor the sensor data from the sensor data module 142 and medicament delivery from the medicament delivery module 144 to determine an individual's metabolic profile, including their response to various times, amounts, and/or types of medicaments. The processor module uses any pattern recognition-type algorithm as is appreciated by one skilled in the art to quantify the individual's metabolic profile.

At block 148, a medicament calculation module, which is a part of a processor module, calculates the recommended medicament based on the sensor glucose data, medicament delivery data, and/or individual's metabolic profile. In some embodiments, the recommended therapy is validated such as described with reference to FIG. 10 above. In some embodiments, the recommended therapy is manually, semi-automatically, or automatically delivered to the host.

At block 150, the process of monitoring and evaluation a host's metabolic profile is repeated with new medicament delivery data, wherein the processor monitors the sensor data with the associated medicament delivery data to determine the individual's metabolic response in order to adaptively adjust, if necessary, to newly determined metabolic profile or patterns. This process may be continuous throughout the life of the integrated system, may be initiated based on conditions met by the continuous glucose sensor, may be triggered by a host or doctor, or may be provided during a start-up or learning phase.

While not wishing to be bound by theory, it is believed that by adaptively adjusting the medicament delivery based on an individual's metabolic profile, including response to medicaments, improved long-term host care and overall health can be achieved.

Figure 12:
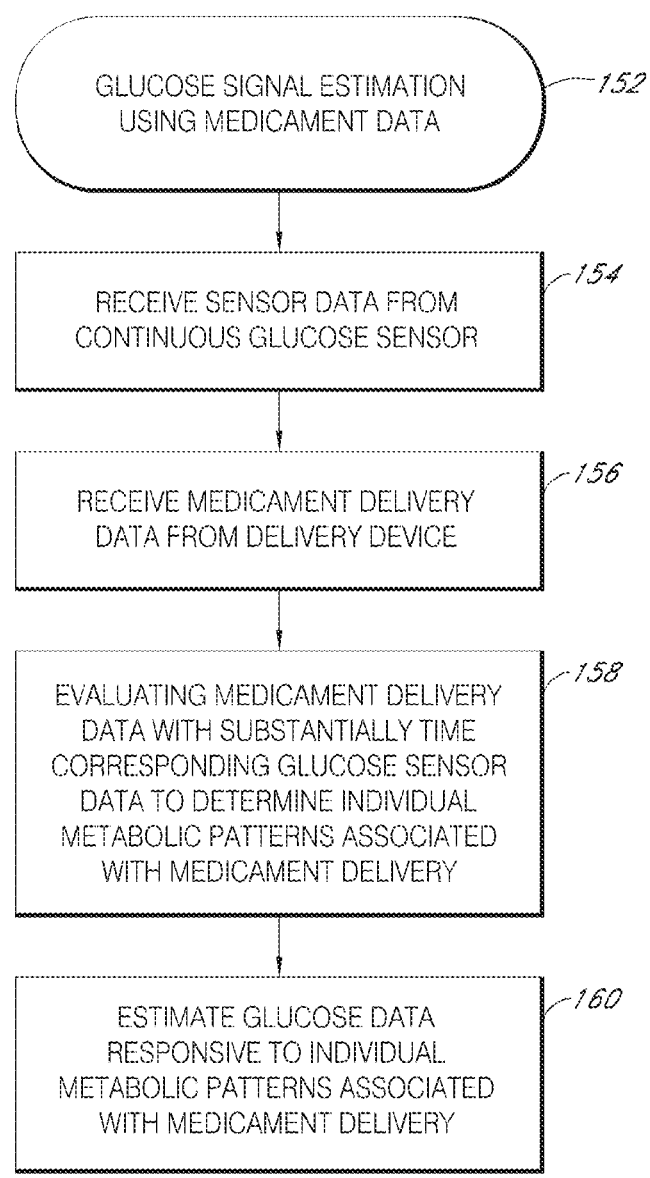
FIG. 12 is a flow chart that illustrates the process of glucose signal estimation using the integrated sensor and medicament delivery device in one embodiment.

FIG. 12 is a flow chart 152 that illustrates the process of glucose signal estimation using the integrated sensor and medicament delivery device in one embodiment. It is noted that glucose estimation and/or prediction are described in U.S. Patent Publication No. US-2005-0027463-A1 and U.S. Patent Publication No. US-2005-0203360-A1, each of which has been incorporated herein by reference in its entirety. However, the preferred embodiments described herein, further incorporated additional data of medicament delivery in estimating or predicting glucose trends.

At block 154, a sensor data receiving module, also referred to as the sensor data module, receives sensor data (e.g., a data stream), including one or more time-spaced sensor data points, from a sensor via the receiver, which may be in wired or wireless communication with the sensor.

At block 156, the medicament data receiving module, which may be programmed within the receiver 14 and/or medicament delivery device 16, receives medicament delivery data, including time, amount, and/or type.

At block 158, the processor module evaluates medicament delivery data with substantially time corresponding glucose sensor data to determine individual metabolic patterns associated with medicament delivery. "Substantially time corresponding data" refers to that time period during which the medicament is delivered and its period of release in the host.

At block 160, the processor module estimates glucose values responsive to individual metabolic patterns associated with the medicament delivery. Namely, the individual metabolic patterns associated with the medicament delivery are incorporated into the algorithms that estimate present and future glucose values, which are believed to increase accuracy of long-term glucose estimation.

Figure 13:
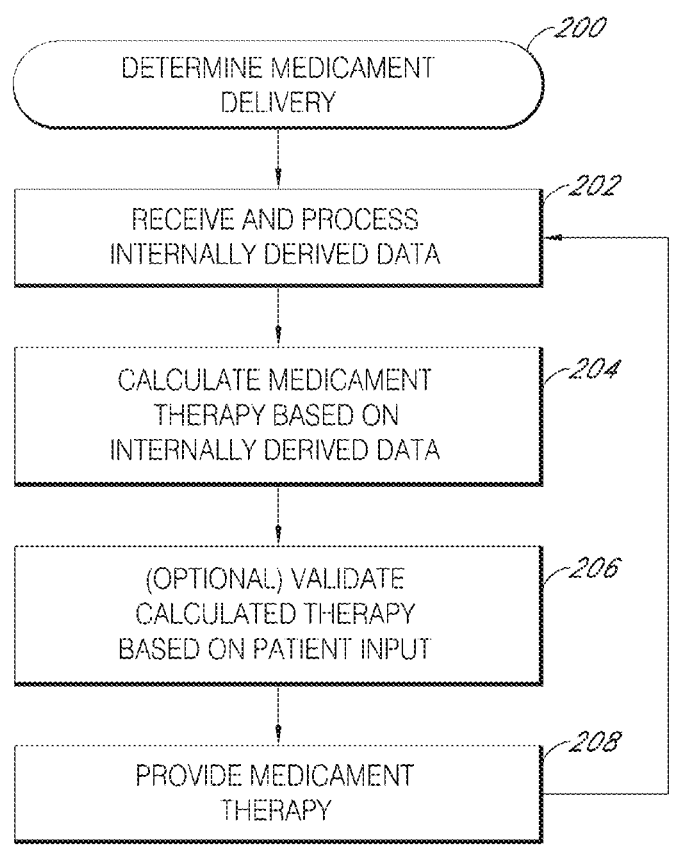
FIG. 13 is a flow chart that illustrates the process of determining medicament delivery in one embodiment.

FIG. 13 is a flow chart 200 that illustrates the process of determining medicament delivery using an integrated system 10, in one embodiment. In preferred embodiments, medicament (e.g., insulin or another drug) delivery is calculated to maintain the host substantially at and/or within a target range. In the case of insulin therapy, the target range is generally a range of preferred glucose concentrations within which the host is to maintain (at least to try) his blood sugar, as is discussed below. For example, in some circumstances, the target range is a range of euglycemic glucose concentrations. As is understood by those skilled in the art, glycemic ranges can vary, depending upon the therapy goals and the morbidity/mortality associated with a given glucose level (e.g., concentration). For example, according to the American Diabetes Association, a preferred target range is a euglycemic range that provides tight glucose control and substantially reduces diabetic morbidity and mortality, namely a fasting glucose of from 90 mg/dl to 130 mg/dl. Alternative target ranges can be used, such as from about 70, 80, 90, 100, 110 or 120 mg/dl to about 110, 120, 130, 140, 150 or 160 mg/dl or more. In some circumstances, the target range can be very wide (e.g., from about 80 mg/dl to about 160 mg/dl) or very narrow (e.g., 90 mg/dl to 120 mg/dl) or even a single glucose concentration. In some embodiments, the host and/or his health care professional select a target range. In some embodiments, the target range is programmable (e.g., pre-programmable, re-programmable), such as by the host, a caretaker of the host or the manufacturer. In some embodiments, the integrated system includes two or more target ranges. In some embodiments, the controller module is configured to adaptively/intelligently program (e.g., re-program) the target range, such as after evaluation of the internally derived data and the host's metabolic response to insulin therapy.

At block 202, the processor module is configured to receive and process internally derived data. Internally derived data can include but it not limited to continuous glucose sensor data, continuous glucose processed sensor data, auxiliary sensor data, processed auxiliary sensor data, delivery device data and processed delivery device data, including glucose concentration, glucose concentration range, change in glucose concentration, glucose concentration rate of change, acceleration of the glucose concentration rate of change, host insulin sensitivity, change in host insulin sensitivity, host metabolic response to insulin therapy, amount of insulin delivered, time of insulin delivery, insulin on board, time, acceleration, host activity level, pressure, a pH, a temperature, an oxygen level, the level of an analyte other than glucose, a proximity and orientation. In some embodiments, internally derived data can include data derived from algorithmic processing of continuous analyte sensor data and/or auxiliary sensor data and/or medicament delivery device data. In some embodiments, the system is configured to further received external data (e.g., meal occurrence/content, exercise, units of insulin delivered, time of insulin delivery, etc.) such as for historical purposes (e.g., as a diary or log).

At block 204, the system is configured to calculate (e.g., determine) a medicament therapy (e.g., insulin therapy) based solely on internally derived data and any constraint (e.g., range, boundary, profile and the like). In general, calculation of the medicament therapy is conducted by the system's controller module (e.g., on/off, dynamic basal and/or dynamic bolus controller module), as described elsewhere herein. In some embodiments, evaluation and calculation is iterative. In some embodiments, the calculated insulin therapy includes an instruction for delivery of the insulin therapy to the host.

At block 206, the system is optionally configured to validate the calculated therapy based on patient (e.g., host) input. For example, in some embodiments, the host must accept the calculated medicament therapy before the system can proceed to providing (e.g., delivering) the medicament therapy at block 208, and the system can return to block 202. If the host accepts calculated the medicament therapy (e.g., the dose is validated), the medicament therapy will be provided/delivered. Similarly, if the host does not accept the medicament therapy, no medicament will be given. In some embodiments, the system is configured such that the host can command the system to provide a manually calculated dose (e.g., calculated by the host). In some embodiments, the system is further configured to allow the system to adaptively and intelligently determine an appropriate and/or optimal delivery schedule for the commanded manually calculated dose.

At block 208, the system is configured to deliver the calculated insulin therapy, as described elsewhere herein. In some embodiments, the insulin delivery device is configured to deliver the calculated insulin therapy automatically upon receipt of an instruction from the controller module. After delivering the insulin therapy, the system is configured to return to block 202.

Figure 14:
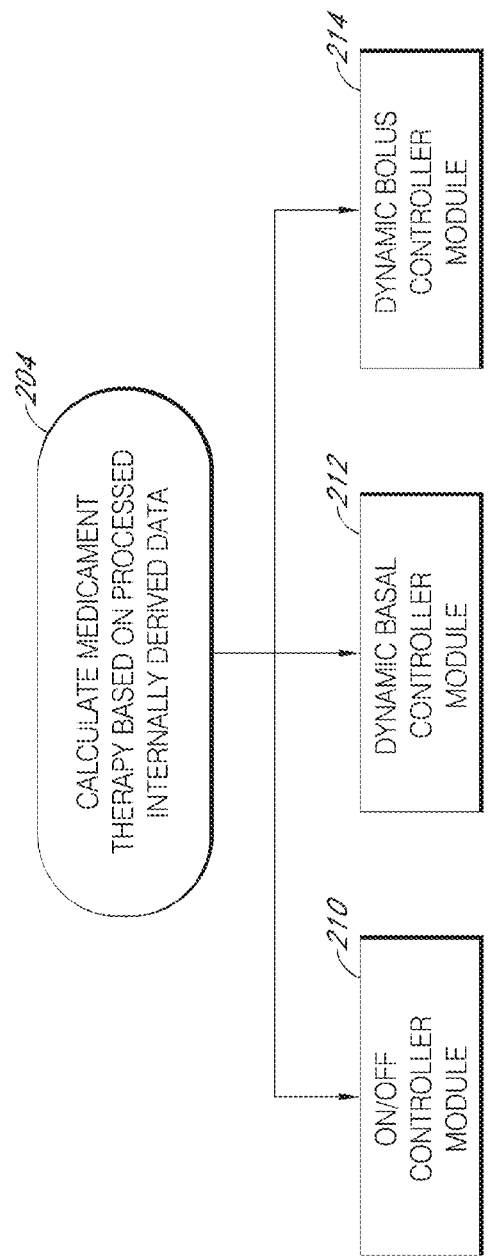
FIG. 14 is a flow chart that illustrates the process of calculating a medicament therapy based on internally derived data in one embodiment.

FIG. 14 is a flow chart 204 that illustrates calculation of a medicament therapy based on the internally derived data, in one embodiment. Generally, the system 10 is configured to use at least one controller module (all or in part) to calculate the insulin therapy, such as but not limited to an on/off controller module 210, a dynamic basal controller module 212 and a dynamic bolus controller module 214. In some embodiments, the system is configured with only one controller module. In other embodiments, the system is configured with two or all three of the controller modules. In one embodiment, the system includes two or more controller modules configured to work in concert (e.g., in conjunction, together, in combination). In some embodiments, the controller module is configured to provide all or some of the processing for block 204 of FIG. 13. The controller module can be incorporated into any portion of the integrated system, such as but not limited to the receiver, the medicament delivery device, a component separate from the receiver and the delivery device, or a combination thereof (e.g., integrated electronics, such as a processor module). In some embodiments, a controller module is included in processor module 82 and/or in processor module 112.

On/Off Controller Module

Figure 15:
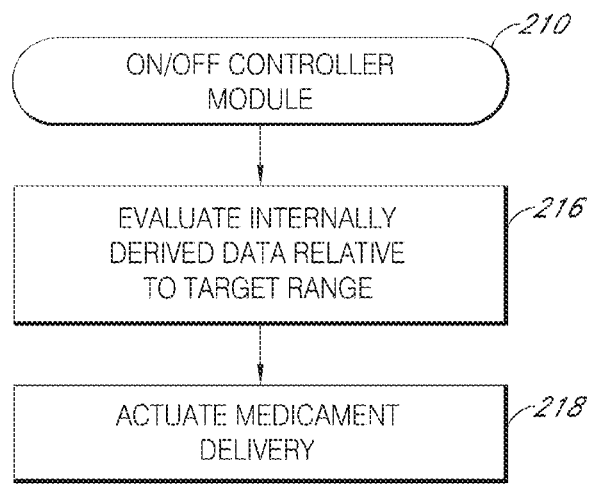
FIG. 15 is a flow chart that illustrates the process of calculating a medicament therapy based on internally derived data, using an on/off controller module, in one embodiment.

FIG. 15 is a flow chart that illustrates an on/off controller module 210, in one embodiment.

At block 216, the on/off controller module is configured to intelligently, adaptively and iteratively evaluate the internally derived data (e.g., raw and/or processed glucose sensor data) relative to a target range and/or a glucose boundary. In some embodiments, a glucose boundary is a host glucose concentration at which the system is configured to deliver insulin. In some embodiments, the target range and the glucose boundary are associated with each other. For example, the glucose boundary can be the upper limit of the target range. In some embodiments, the host does not validate either data or a calculated medicament therapy. In preferred embodiments, the system includes a continuous analyte sensor, and can include one or more auxiliary sensors, such as described elsewhere herein. In some embodiments, the glucose boundary can be programmable, such as by the host, a caretaker of the host and/or the manufacturer. In some embodiments, the glucose boundary is programmable by an intelligent/adaptive controller module.

At block 218, the on/off controller module is configured to actuate medicament delivery, such as by selecting between on and off instructions. The point at which the selection is made can be referred to as a setpoint. In some embodiments, the set point is the glucose boundary. In one exemplary embodiment, the system includes programming to select between the on and off instructions. When evaluation of the internally derived data indicates that the host's glucose is (or has) surpassing (or surpassed) a glucose boundary, the controller module selects the on instruction, which directs actuation of the insulin delivery device (e.g., turns on delivery). Conversely, when the host's glucose falls below a glucose boundary (as determined by evaluation of the internally derived data), the off instruction is selected and insulin delivery is terminated (e.g., turned off). In preferred embodiments, the insulin will be delivered at a programmable rate, which can be programmed by the host, a caretaker of the host, or the manufacturer, for example. In some embodiments, the on/off controller can include more than one setpoint, such as but not limited to a first set point to select the on instruction and a second setpoint to select the off instruction.

In some embodiments, the on/off controller module is configured to adjust the insulin delivery rate in response to evaluation of internally derived data and the host's metabolic response to insulin delivery (e.g., metabolic state). For example, the insulin can be delivered at relatively faster or slower rates, depending upon the evaluation of the internal data. In some circumstances, when the on instruction is selected, the medicament can be delivered substantially continuously and/or intermittently, such as but not limited to at a single rate (e.g., about 0.05 U, 0.1 U, 0.2 U, 0.3 U, 0.4 U, 0.5 U, 0.6 U, 0.7 U, 0.8 U or 0.9 U per hour or more).

In one exemplary embodiment, the integrated system 10 includes an on/off controller module configured to intelligently and adaptively evaluate the internally derived data relative to a programmed glucose boundary and then select between the on and off instructions. For example, if the glucose boundary is 140 mg/dl, then the controller module evaluates the internally derived data against the 140 mg/dl glucose boundary (block 216). If the host's glucose is above the 140 mg/dl glucose boundary, then the controller module selects the on instruction, which leads to actuation of insulin delivery at box 218. If the host's glucose is above the 140 mg/dl glucose boundary and insulin is currently being delivered (e.g., the on instruction was selected at an earlier time), then the controller module does nothing (e.g., insulin continues to be delivered). If the host's glucose is 140 mg/dl or less, the off instruction is selected (or the on instruction is de-selected/terminated), whereby insulin delivery is ceased. In some embodiments, the insulin is delivered (e.g., infused) substantially continuously, such as at a given rate (e.g., U/min), or substantially intermittently, such as small volumes every few minutes (e.g., 0.5-U every 6-minutes). In preferred embodiments, the system is configured, such that data evaluation and/or insulin delivery are iterative (e.g., cyclic, periodic, continuous, automatic, and the like). Because they system is configured to function intelligently and adaptively, in some embodiments, the system can modify (e.g., adjust, either with or without host validation) the glucose boundary and/or the insulin infusion rate, such that maintenance of the host within the target range is optimized.

In another exemplary embodiments, the system 10 includes an on/off controller module configured for use in combination with flash insulin. The flash insulin therapy can be delivered automatically, periodically, intermittently and/or substantially continually, in response to the on/off controller, such that the host is maintained substantially at and/or within the target range. For example, in some embodiments, the system is configured to intermittently deliver small doses of flash insulin when (while) the host's glucose is above the glucose boundary. The rate of flash insulin delivery is programmed such that when the host's glucose is rising and surpasses the glucose boundary, the on instruction is selected and a small amount of flash insulin is delivered. After delivery, the controller module can be configured to wait a brief period (e.g., a few minutes), and then evaluate the internally derived data relative the glucose boundary. If the internally derived data indicates that the host's glucose is still above the glucose boundary, then another small dose of flash insulin can be delivered. Alternatively, the system can be configured to wait until the delivered insulin has had a predetermined effect (e.g., time sufficient for the activity of about 50, 60, 70, 80, 90 or 95% of the delivered insulin to peak, or for the activity of about 50, 60, 70, 80, 90 or 95% of the delivered insulin to terminate), prior to returning to block 202 (FIG. 13). As is appreciated by one skilled in the art, the system can be configured to proceed through several cycles of these steps (e.g., iteratively evaluate and provide insulin doses using the on/off controller module), until the host's glucose level falls to/below the glucose boundary. When the host's glucose level falls to/below the glucose boundary, the on/off controller is configured to select the off instruction, which results in termination of insulin delivery. While not wishing to be bound by theory, it is believed that use of flash insulin in combination with an on/off controller module advantageously substantially prevents stacking of insulin doses and substantially avoids hypoglycemic episodes. Accordingly, improved host health and safety are promoted while diabetic complications are avoided or delayed during the host's lifetime.

In some embodiments, the integrated system is configured arranged for use with other insulins (e.g., regular (e.g., wild type), fast-acting or rapid-acting human insulin analogs, etc.), such that the on/off controller evaluates/tracks "insulin on-board" (e.g., the total amount of active insulin currently in the host's body).

Dynamic Basal Controller Module

As is understood by one skilled in the art, insulin needs vary between individuals and through out the day, both during and between meals. To take care of between meal glucose fluctuations, diabetic hosts generally employ a basal schedule (e.g., basal profile) for continuous delivery of low levels of insulin, such that, between meals, the host's glucose is relatively steady (e.g., remains within a target (e.g., euglycemic) range). Accordingly, in preferred embodiments, the integrated system 10 includes a dynamic basal controller module configured to iteratively evaluate internally derived data relative to a programmable basal profile and iteratively calculate a dynamic basal insulin therapy within the basal profile.

FIG. 16 is a flow chart that illustrates a dynamic basal controller module 212, in one embodiment. In preferred embodiments, the dynamic basal controller module can be part of the electronics module and is configured to evaluate internally derived data relative to a basal profile 220 and to intelligently and adaptively calculate a dynamic basal medicament therapy 222, based on that evaluation. In preferred embodiments, the insulin therapy is determined solely on internally derived data and the basal profile.

A basal profile generally includes a schedule of time blocks, each block being associated with an insulin delivery rate. In general, a diabetic host can determine his basal profile by experimentation. For example, the basal insulin delivery rate for a particular time period can be determined by fasting while periodically evaluating the glucose level. Neither food nor bolus insulin can be taken for 4-hours prior to or during the evaluation period. If the blood sugar level changes dramatically during evaluation, then the basal rate can be adjusted to increase or decrease insulin delivery to keep the blood sugar level approximately steady. For instance, to determine the host's morning basal requirement, he must skip breakfast. On waking, he would test his glucose level periodically until lunch. Changes in blood glucose level are compensated with adjustments in the morning basal rate. The process is repeated over several days, varying the fasting period, until a 24-hour basal profile (which keeps fasting blood sugar levels relatively steady) has been built up. As used herein, a basal profile includes a schedule of one or more time blocks, wherein each time block is associated with a maximum insulin delivery rate. As is described herein, in some embodiments, the dynamic basal controller module is constrained by the basal profile. Accordingly, in some embodiments, the controller module is configured to evaluate internally derived data (e.g., including re-evaluate internally derived data as it is received) and to iteratively calculate an insulin delivery rate (e.g., insulin therapy) up to the maximum rate of a current time block. Accordingly, the insulin therapy can include a delivery rate less than the maximum insulin delivery rate associated with the current time block. In some embodiments, the basal profile includes a 24-hour schedule. In some embodiments, the schedule can be shorter or longer than 24-hours. In some embodiments, the schedule is repeatable and/or cyclic (e.g., iterative). In some embodiments, the host, a caretaker of the host, and/or the manufacturer can program a basal profile. In some circumstances, an intelligent/adaptive controller module can be configured to program the basal profile.

At block 220, in preferred embodiments, the dynamic basal controller module is configured to evaluate solely internally derived data (e.g., from an operably connect continuous glucose sensor, from an auxiliary sensor and/or an insulin delivery device) relative to a programmed basal profile. Internally derived data includes but is not limited to glucose concentration, change in concentration, rate of change of concentration, acceleration (or deceleration) of the change, direction of the change, predicted analyte concentration for a future time, estimated analyte concentration, possible variations of analyte data (e.g., based on maximum possible error), trend information and the like. For example, in some circumstances, a low rate of change (in glucose concentration/level) is from about ±0 mg/dl/min to about 1 mg/dl/min, a moderate rate of change is from about 1 mg/dl/min to about 2 mg/dl/min, and a high rate of change is from about 3 mg/dl/min to about 6 mg/dl/min. In some embodiments, the calculation can include evaluation of the host's metabolic response to insulin therapy, which can depend upon a variety of factors, such as but not limited to the type of insulin delivered, the mode and/or location of delivery, and the like.

In some embodiments, internally derived data can include data received from one or more auxiliary sensors, such as but not limited to sensors for glucose, an analyte other than glucose, pH, temperature, pressure, host movement, host body position, proximity, and the like. For example, an accelerometer can provide data regarding the host's activity level (e.g., sedentary versus exercising versus sleeping), which can affect the host's insulin requirement. In one exemplary embodiment, the dynamic basal controller module is configured to evaluate accelerometer data in conjunction with internally derived data, depending upon if the accelerometer data is within or without a programmed range (e.g., whether or not the host is very active). For example, the system can be configured such that if the accelerometer data is above a setpoint (e.g., indicates that the host is very active or exercising), then the accelerometer data is considered by the controller module; if the accelerometer data is below the set point, the accelerometer is not considered. In one exemplary embodiment, the system is configured such that the basal controller module intelligently monitors the host's activity level (e.g., over a period of days and/or weeks) and adaptively adjusts the basal profile to maintain the host substantially within the target range during both active and inactive periods of the day. For example, in some embodiments, the controller module is configured to intelligently determine when the host is generally very active (e.g., exercising), less active (e.g., working at the computer) or sedentary (e.g., sleeping). Some hosts will tend to be more active than others. Advantageously, because the controller module responds to changes in the host's metabolic state, each host can have a basal profile optimized to his personal needs.

At block 222, in some embodiments, the dynamic basal controller module is configured to calculate (e.g., determine) a dynamic basal medicament therapy (also referred to as the "insulin therapy") based solely on the internally derived data and the basal profile (e.g., the evaluation thereof), wherein the calculated insulin therapy falls within the basal profile. The insulin therapy calculated by the dynamic basal controller module is a rate of insulin delivery less than or equal to the insulin delivery rate associated with the basal profile (e.g., at the current block of time). Preferably, the delivery rate is sufficient to bring the host's glucose concentration substantially within a pre-programmed target range (e.g., a euglycemic range). Over time, the insulin therapy can include a plurality of delivery rates at different time blocks calculated to maintain the host within the target range. In some embodiments, the maximum insulin therapy (e.g., delivery rate) is from about 0.01 U/hour or less to about 6.0 U/hour or more. For example, in some embodiments, the maximum insulin therapy is from about 0.01 U/hr to about 0.2 U/hr. In some embodiments, the maximum insulin therapy is from about 0.21 U/hr to about 0.3 U/hr. In some embodiments, the maximum insulin therapy is from about 0.31 U/hr to about 0.4 U/hr. In some embodiments, the maximum insulin therapy is from about 0.41 U/hr to about 0.5 U/hr. In some embodiments, the maximum insulin therapy is from about 0.51 U/hr to about 1.0 U/hr. In some embodiments, the maximum insulin therapy is about 1.5 U/hr, 2.0 U/hr, 2.5 U/hr, 3.0 U/hr, 3.5 U/hr, 4.0 U/hr, 4.5 U/hr, 5.0 U/hr, or 5.5 U/hr. In preferred embodiments, instructions for delivery of the calculated insulin therapy are sent to the insulin delivery device, which then automatically delivers the instructed insulin therapy. In some embodiments, dynamic basal controller module can include one or more instructions for calculation and/or delivery of the basal insulin therapy. The calculated insulin delivery rate can be an instruction provided to an insulin delivery device to delivery the insulin therapy, such as to automatically deliver the therapy.

In preferred embodiments, the system 10 is configured to iteratively (e.g., cyclic, periodic, and the like) evaluate the internally derived data (e.g., including past and newly/more recently received internally derived data) and to iteratively calculate an insulin delivery rate. Because the system is configured to function intelligently and adaptively, in some embodiments, the system can respond to changes in the host's metabolic state by modifying (e.g., adjusting, programming, re-programming, either with or without host validation) the basal profile, such that maintenance of the host within the selected target range is optimized. In some embodiments, the controller module includes programming to adjust the basal profile in response to internally derived data and the host's metabolic response. In some embodiments, the insulin therapy substantially maintains the host's glucose concentration within the target range without driving the host into a hyper- or hypoglycemic range. In some embodiments, the dynamic basal controller module includes one or more instructions configured to process the internally derived data and iteratively provide the therapy instructions. In a further embodiment, these instructions include instructions for evaluating the internally derived data and calculating the insulin therapy based solely on the internally derived data.

In one exemplary embodiment, the integrated system includes a dynamic basal controller module configured to iteratively (continually, automatically, periodically, or intermittently) evaluate the internally derived data relative to a programmable basal profile and calculate an insulin therapy that falls within the basal profile. For example, if the current time block of the basal profile specifies 2U of insulin per hour, then the controller module can calculate an insulin therapy up to that amount. Preferably, the calculated insulin therapy is optimal for maintaining the host within the selected (e.g., preferred, engaged, programmed) target range. As the system receives additional internal data, it is configured to adjust the insulin delivery rate in an intelligent and adaptive manner. For example, if the evaluation of currently received internal data indicates that for optimal control (e.g., of blood sugar) the insulin delivery rate should be increased from 0.5 U/hr to 1 U/hr, then the controller module can both send instructions to the integrated insulin delivery device to do so and reprogram the basal profile with the new delivery rate for that time block. In another example, if the evaluation might indicates that the delivery rate should be reduced to maintain optimal control, and then the controller module can calculate a new insulin therapy and instruct the delivery device accordingly. Internally derived data can include trend information, such as but not limited to changes in the host's insulin needs (e.g., response to delivered insulin, insulin sensitivity, or metabolic profile) over time. Accordingly, in preferred embodiments, the dynamic basal controller module is configured to evaluate this trend information and make intelligent adjustments to (e.g., re-program) the insulin therapy and/or the basal profile, such that between meal glucose control can be optimized (e.g., continually). In some embodiments, the system is configured to request validation of such a change (e.g., re-programming) in insulin therapy and/or the basal profile.

In some embodiments, the dynamic basal controller module can be configured to evaluate the internally derived data 220 with respect to one or more target ranges (which can overlap) to intelligently and adaptively direct calculation of the dynamic basal medicament therapy. For example, in one exemplary embodiment, as a first step, the dynamic basal controller module evaluates the internally derived data with respect to glycemic ranges (e.g., hypoglycemic, euglycemic, hyperglycemic or very hyperglycemic). If, for example, the host is euglycemic, a first calculation can be made; if the host is hyperglycemic a second calculation can be made; and if the host is hypoglycemic a third calculation can be made. In some embodiments, the controller evaluates the rate and/or direction of glucose concentration change and/or acceleration of the change (e.g., if glucose concentration has changed, if it is going up or down, if it is changing slowly or rapidly, etc.). For example, if the glucose level is very hyperglycemic and increasing rapidly, a first dynamic basal insulin dose (e.g., dose #1) can be calculated. If the glucose level is very hyperglycemic and decreasing slowly, a second dynamic basal insulin dose (e.g., dose #2), which might be smaller than dose #1, can be calculated. If the glucose level is slightly hyperglycemic and increasing slowly, a third dynamic basal insulin dose (dose #3) can be calculated. Dose #3 may be smaller than both dose #1 and dose #2. If, on the other hand, the glucose level is in the euglycemic range and decreasing slowly, insulin delivery can be terminated (e.g., until the glucose level was again above the euglycemic range). In another example, if the glucose level is in euglycemic range and decreasing rapidly, or in the hypoglycemic range, the controller can be configured to alert the host, such as by an alarm, for example so that he can eat some sugar to raise his glucose level.

In some embodiments, the dynamic basal controller module is configured for use in conjunction with a flash-acting insulin, as described elsewhere herein. In one exemplary embodiment, the onset of activity of the flash insulin is less than about 5-minutes as determined by plasma insulin concentration according to the methods of Frohnauer et al). In some embodiments, the flash insulin's activity peaks within about 10 to 30-minutes. In some embodiments, the flash insulin's duration of activity is about 30-minutes or less and up to about 1-hour. In some embodiments, the flash insulin's activity peaks within about 5-minutes of delivery and terminates within about 10-20 minutes.

In some embodiments, the dynamic basal controller module is configured for use in conjunction with a regular, rapid-acting or fast-acting insulin (including analogs), as described elsewhere herein. In a further embodiment, the dynamic basal controller module is configured to track the amount of insulin "on board" (e.g., the total amount of active insulin currently within the host and the insulin activity associated with that amount), and to evaluate the insulin on board when calculating a dynamic basal therapy.

Dynamic Bolus Controller Module

Conventionally, when a host is going to eat a meal, he calculates a bolus insulin dose that should be sufficient to cover the glucose increase anticipated due to consumption of the meal. He then gives himself the calculated bolus dose and eats the meal. Without careful measurement of carbohydrate and fat content of the meal and the host's insulin sensitivity, the calculated bolus dose can only estimate the amount of insulin to be taken for that meal. Thus, in general, the calculated bolus dose will not be the optimal dose to cover the actual glucose increase that occurs when the meal is eaten. The host's sugar may increase more than he thought it would, in which case the calculated bolus dose could be too small, which could lead to hyperglycemia. Alternatively, the host's sugar might not rise as high as he thought it would, in which case the calculated bolus dose may be too large, and could lead to hypoglycemia. Accordingly, in preferred embodiments, the integrated system 10 includes a dynamic bolus controller module configured to iteratively evaluate internally derived data relative to a programmable bolus constraint and iteratively calculate a dynamic bolus insulin therapy, upon host activation of the programmable bolus constraint.

Figure 17:
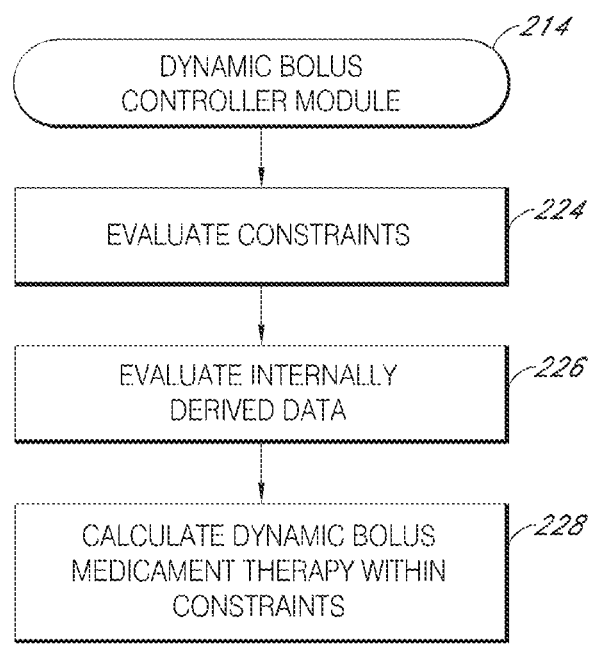
FIG. 17 is a flow chart that illustrates the process of calculating a medicament therapy based on internally derived data, using a dynamic bolus module, in one embodiment.

FIG. 17 is a flow chart illustrating a dynamic bolus controller module 214, in one embodiment. In preferred embodiments, the dynamic bolus controller module is included in the electronics module and is configured to evaluate an engageable constraint 224 as well as internally derived data 226. In some embodiments, the dynamic bolus controller module is configured to intelligently provide a dynamic bolus medicament therapy (e.g., insulin therapy) within a pre-set (e.g., programmable) constraint 228, such as in response to the host engaging the bolus constraint. Preferably, the dynamic bolus controller module is configured to iteratively calculate an insulin therapy based solely on evaluation of internally derived data (e.g., re-evaluation of internally derived data as it is received) and the bolus constraint. In some embodiments, the dynamic bolus controller module 214 allows host validation of the dynamic bolus medicament therapy (e.g., FIG. 13, box 206), which is believed to promote increased user confidence, increased host compliance and improved health status. Advantageously, the dynamic bolus controller module 214 can be configured to use a variety of insulins, including but not limited to regular or rapid/quick-acting insulins (e.g., slower onset and peak of activity, longer duration of activity) and flash insulins, described elsewhere herein.

In preferred embodiments, an engageable bolus constraint is associated with a programmable dynamic bolus insulin therapy. In preferred embodiments, the dynamic bolus insulin therapy is the maximum total insulin that can be delivered to the host over a specified period of time, in response to the host engaging (e.g., selecting) the bolus constraint associated with the insulin therapy. In some embodiments, the insulin therapy comprises one or more portions of the maximum total insulin dose, as described below. In some embodiments, the bolus constraint can be programmed (e.g., pre-programmed and/or pre-set), programmable and/or re-programmable. In some embodiments, the host and/or a caretaker of the host can program the bolus constraint. In some embodiments, the bolus constraint can be programmed by the manufacturer or the dynamic bolus controller module.

At block 224, the dynamic bolus controller module is configured to evaluate a bolus constraint (e.g., engageable/selectable, and programmable, re-programmable and/or pre-set limit), such as one that has been engaged by the host. In general, a bolus constraint is associated with an insulin therapy that has been calculated and/or estimated to be sufficient to cover an average expected rise in blood sugar, such as an increase in glucose that occurs (on average) when a host eats a given meal, such as but not limited to breakfast, lunch, dinner and the like. For example, on most days, the host may eat very similar breakfasts (e.g., an average (e.g., usual) breakfast), which can cause very similar glucose increases (e.g., an average increase in glucose). Accordingly, a "breakfast" bolus constraint can be calculated to cover the average rise in glucose associated with an average breakfast. In some embodiments, a bolus constraint can be associated with a host activity (e.g., to cover the glucose rise associated with host performance of about 30-minutes of vigorous exercise) or condition (e.g., a corrective bolus for when the insulin delivered is insufficient to cover an actual rise in glucose). In preferred embodiments, the system includes one or more selectable bolus constraints. The constraints can be selected by any means known in the art, such as by pushing a pre-programmed push-button or scrolling through a menu of selectable constraints with a slider or a scroll wheel.

In some embodiments, the controller module is configured (e.g., includes programming) to intelligently evaluate the internally derived data and the host's metabolic response to insulin therapy, and to adjust the bolus constraint based on that evaluation. Advantageously, a calculated insulin therapy is based on internally derived data, an engaged bolus constraint and the host's metabolic response to insulin therapy, which enables the system to optimize the insulin therapy to the host, who's metabolic response varies over time, depending upon a variety of factors, such as but not limited to changes in the host's activity level, dietary changes, medications (e.g., insulin-sensitizing agents, new insulin type), and the like. Depending upon the circumstances, the controller module can re-program a bolus constraint by adjusting the rate of insulin delivery, the amount of insulin that can be delivered and/or the time period over which the insulin can be delivered.

At block 226, in preferred embodiments, the dynamic bolus controller module is configured to evaluate the internally derived data. The internally derived data is evaluated in the context of (e.g., relative to) a selected bolus constraint and in response to selection (activation, engagement) of the bolus constraint. Returning to the example of the "Breakfast" bolus constraint, in general, the host will engage the breakfast bolus constraint (e.g., by pressing a pre-programmed button that is labeled "Breakfast") at the beginning of a breakfast meal. In general, as the host consumes his breakfast, his glucose will begin to change (e.g., rise), which the integrated system's continuous glucose sensor detects (e.g., measures, senses). Internally derived data will be generated as the system's continuous glucose sensor monitors the changes in the host's glucose level. The dynamic bolus controller module evaluates the sensor data (e.g., internally derived data) against (e.g., in the context of, relative to) the engaged breakfast constraint.

At block 228, the dynamic bolus controller module calculates a dynamic bolus medicament (e.g., insulin) therapy within the selected bolus constraint. Preferably, the dynamic bolus controller module adaptively determines a substantially optimal insulin therapy, such as for example, delivery of all or a portion (e.g., in one large dose or a plurality of smaller doses) of the maximum total insulin dose (associated with the engaged constraint) over the specified time period. For example, if the breakfast constraint is associated with a maximum of 10 U of insulin to be delivered over 30-minutes, then, when the host engages the breakfast constraint, the controller module evaluates the internally derived data and determines an insulin therapy (including instructions sent to the insulin delivery device, which automatically delivers the instructed insulin therapy). For example, in some circumstances, the calculated insulin therapy can include delivery of the entire total dose (e.g., 10 U) within the specified 30-minutes (or a shorter length of time). In other circumstances, the calculated insulin therapy can include dividing the total insulin therapy into two or more partial (e.g., smaller) doses, some or all of which can be delivered over the 30-minute period. Delivery of a partial dose depends upon the controller module's evaluation of internally derived data. For example, as the 30-minutes progress, the controller module continually (e.g., continuously, iteratively, intermittently, automatically) receives and iteratively re-evaluates internally derived data (e.g., as it becomes available) and determines, based thereon, if additional partial doses are needed to handle the rise (e.g., the actual rise) in glucose (e.g., up until the maximum dose has been delivered). In preferred embodiments, the system is configured to slow and/or stop insulin delivery in circumstances wherein the host is entering a severely hypoglycemic range (e.g., programmable, such as less than about 70 mg/dl).

In one exemplary embodiment, the dynamic bolus controller module is configured to calculate a percentage (e.g., portion, fraction) of the engaged bolus constraint (e.g., total insulin therapy) associated with a meal. For example, if the engaged bolus constraint is programmed for a total insulin dose (e.g., $D_0$) of 10 U in 1-hour, the controller module can calculate a first dose, such as about 7 U of insulin (e.g., dose $D_1$ at time $T_1$), based on the controller module's evaluation of the internally derived data relative to the engaged constraint. Instructions are sent to the integrated insulin delivery device and the partial dose is automatically delivered to the host. After an appropriate waiting period (e.g., depending upon the insulin's TAP), the controller module evaluates internally derived data (e.g., at time $T_2$, data more recent than data used to initially calculate $D_1$) and determines an additional insulin dose (e.g., dose $D_2$) required to bring the host's glucose concentration into a target range (at time $T_2$). For example, in some circumstances, an additional insulin dose may be necessary to bring the host's glucose concentration into the target range. In some other circumstances, no additional doses may be required (e.g., $D_2=0$). Suppose that, in this example, additional insulin is required, then the controller module can calculate and instruct delivery of up to 2 more units of insulin (e.g., $D_0-D_1-D_2=2$ U insulin remaining). In preferred embodiments, the insulin therapy delivered to the host is smallest total insulin dose necessary to maintain the host substantially within the target range (e.g., an euglycemic range).

In some embodiments, the system is configured for user validation of the dynamic bolus therapy, such as before delivery of the insulin (e.g., FIG. 13, box 206). In one exemplary embodiment, the system is configured to alert the host (e.g., that a dynamic bolus therapy has been calculated) and request host validation (e.g., that the host accepts the dynamic bolus therapy, such as a maximum amount of insulin to be delivered over a given period of time). Upon host validation, the calculated therapy is delivered.

In one exemplary embodiment, semi-automated integrated system 10 is configured such that the host can select a bolus constraint associated with a meal, such as by pressing one of a plurality of labeled, pre-programmed buttons or making a selection from a menu. For example, in this embodiment, each button is labeled with an icon of a food (e.g., cereal bowl, sandwich, slice of pizza, ice cream cone) and is associated with an insulin therapy calculated to be sufficient to cover that food (e.g., a meal) on average. For example, the sandwich bolus constraint is associated with an insulin dose that is generally sufficient to cover the glucose rise associated with host consumption of an average sandwich (e.g., a maximum total of up to 10 U of insulin to be delivered over 1-hour). When the host presses the sandwich button, the dynamic bolus controller module evaluates internally derived data and intelligently and adaptively determines a substantially optimal way (e.g., schedule of one or more insulin doses) to deliver a bolus insulin therapy (e.g., constrained by the sandwich constraint), preferably such that the host will not substantially enter a dangerous hypoglycemic state (e.g., glucose less than about 70 mg/dl) when the therapy is delivered. In preferred embodiments, the bolus controller module is configured to substantially continuously (e.g., constantly, automatically, iteratively, periodically, and/or intermittently) receive and evaluate internal data and to iteratively (e.g., automatically, periodically, and/or intermittently) determine an insulin therapy. For example, in some embodiments, the bolus controller module is configured to calculate a bolus therapy (e.g., based on solely the internally derived data) every about 5, 10, 15, 20, 30, 40 or 50-minutes. In some embodiments, the bolus controller module calculates a bolus therapy about every hour or longer. The calculated insulin therapy is then delivered (e.g., administered, such as automatically) to the host. In some embodiments, the insulin therapy associated with the engaged bolus constraint can be divided into portions (e.g., a total therapy of 10 U to be delivered in 1-hour is divided into two 5 U portions, five 2 U portions, or a 5 U portion, two 2 U portions and one 1 U portion) that can be delivered over time period associated with the engaged bolus constraint. In general, if portions of the total bolus therapy are delivered, the controller module is configured to wait a period of time for the delivered insulin to become active and to lower the host's blood sugar a pre-determined amount. The length of wait varies, depending upon the insulin's TAP and mode of delivery (e.g., injected subcutaneously by a pump versus by a syringe, inhaled, and the like) or the location of delivery, the type of meal being consumed, the host's insulin sensitivity and metabolic state, and the like. After the wait time, the controller module again evaluates the internally derived data and determines if additional insulin is required. For example, if the host's glucose is still increasing, another partial dose can be delivered. This cycle can be repeated until either the total bolus therapy has been delivered the delivery time has expired. In some embodiments, the system is further configured to request host validation of the therapy, such as by selection of either a YES or NO button, and the like, as is appreciated by one skilled in the art.

In some embodiments, the system is configured such that the host can manually enter a bolus insulin dose and the dynamic bolus controller module can evaluate the internally derived data and determine an insulin therapy within the entered bolus dose. For example, suppose the host wants to eat something for which there is no pre-programmed bolus constraint, such as a candy bar. In this circumstance, the host can calculate a bolus dose to cover the glucose increase that will probably occur when he eats that candy bar. He can enter the bolus dose he calculated and then have the system monitor his glucose and deliver the entered bolus dose as necessary (e.g., based upon evaluation of the internally derived data; to maintain and/or return the host within/to a target range). Preferably, the calculated therapy is substantially optimal for handling the glucose rise that will likely occur upon consumption of the meal for which the host calculated the bolus dose.

In some circumstances, a selected constraint may be insufficient to handle a meal that the host has consumed. For example, a meal can have more carbohydrates than the average meal the engaged constraint was pre-programmed to handle. Accordingly, is the controller module can be configured to alert the host to a need for additional insulin. As is understood by one in the art, a number of alerts and/or alarms can be built into the system, such as but not limited to safety alarms. The system can be configured to allow the selection of an additional meal constraint or a corrective bolus constraint and/or to allow the host to enter a manually calculated and enter a corrective bolus dose.

In preferred embodiments, the dynamic bolus controller module is configured to evaluate trend information (e.g., derived from the internally derived data; the host's metabolic response to delivered insulin) and to adapt accordingly, such as by adjusting (e.g., re-programming) the time and/or amount of an insulin therapy associated with a bolus constraint. As is understood by one skilled in the art, trend information can fluctuate over time, depending upon the host's health, activity level, medications consumed, and the like. In one exemplary embodiment, the controller module is configured to evaluate the host's insulin sensitivity over time, and to re-program a bolus constraint such that a substantially optimal insulin therapy can be delivered to the host upon engagement of the bolus constraint. For example, suppose the host is relatively insulin resistant and has a correction factor of 10:1 (e.g., 1 U of insulin will lower glucose by 10 mg/dl). Accordingly, 10 U of insulin would be required to lower the glucose level by 100 mg/dl. Suppose the host becomes more insulin sensitive, such as by increasing exercise, which would change his insulin needs. The controller module monitors these metabolic changes and adjusts calculation of the insulin therapy accordingly, such by modifying the correction factor (e.g., increase to 20:1) during insulin therapy calculation, for example. In preferred embodiments, intelligent and dynamic tracking of trends and calculation of bolus insulin therapies enables the dynamic bolus controller module to substantially minimize the risk of driving the host into a potentially dangerous state, such as but not limited to a severely hypoglycemic state (e.g., glucose concentration less than about 60 mg/dl).

In one exemplary embodiment, the controller module continually receives information (e.g., internally derived data) related to the host's glucose level and iteratively evaluates the data relative to a target glycemic range (e.g., a euglycemic range pre-set by the host, a caretaker of the host, or by the manufacturer, such as 80-120 mg/dl or 100-140 mg/dl). When the host selects a bolus constraint (e.g., 15 U to be delivered over the next hour, selected at the start of a meal), the controller module evaluates the internally derived data relative to the engaged constraint and calculates an insulin therapy that both 1) is sufficient to lower the host's glucose level to and/or within the target range and 2) is within the therapy associated with the engaged bolus constraint (e.g., will not exceed 15 U to be delivered over the next hour). If the calculated dose is less than or equal to the dose associated with the engaged constraint, the system delivers the calculated dose (e.g., a portion of the bolus dose). Generally, it will take some time for the insulin to have its effect (e.g., related to the insulin's TAP). In this embodiment, the controller module is configured to wait the appropriate period of time and then evaluate the host's response to the delivered insulin dose. In some circumstances, the host's response to the delivered insulin therapy may be insufficient (e.g., his glucose was not lowered to and/or maintained within the target range), so, the controller module will calculate and deliver an additional insulin dose (e.g., another portion of the dynamic bolus dose), based upon evaluation of the internally derived data. This iterative process continues until the time defined by the engaged bolus constraint expires (e.g., the 1-hour has passed). In some circumstances, the host's response to the initial insulin dose may be sufficient to maintain the host's blood glucose within the target range and additional insulin doses will not be calculated/delivered. While not wishing to be bound by theory, it is believed that the dynamic bolus controller module enables the use of less insulin while at the same time reducing the number of host hypoglycemic events than is possible using model-based systems or manual bolus calculation.

In one exemplary embodiment, the controller module of the system 10 is configured to continuously (e.g., continually, iteratively, intermittently, automatically, periodically) collect and/or evaluate internally derived data, including trend data, such as but not limited to the host's insulin sensitivity and metabolic profile. The controller module can be an on/off, dynamic basal and/or dynamic bolus controller module, and is configured to adaptively adjust to a newly determined metabolic profile when calculating an insulin therapy. In some embodiments, the system is configured to adjust the target range, the set point, the basal profile and/or the bolus constraint, so as to improve the accuracy of host glucose control. In some embodiments, the system (e.g., the electronics module) includes one controller module. In other embodiments, the system includes two controller modules, which are configured to work in concert with each other. For example, the system can include an on/off controller module and either the dynamic basal or dynamic bolus controller modules. In another example, the system can include the dynamic basal and dynamic bolus controller modules. In yet another embodiment, the system includes all three controller modules, which are configured to work in concert with each other.

In some embodiments, the system is configured such that the user can enter an insulin dose to be delivered. In some further embodiments, the system can be configured such that the controller module evaluates the internally derived data and calculates an appropriate and/or optimal delivery schedule for the entered dose. In some further embodiments, the system can be configured to deliver the entered dose substantially immediately.

Intelligent and Adaptive Data Evaluation and Therapy Calculation

A host's insulin requirements can fluctuate over time, due to changes in a variety of factors, such as but not limited to changes in the host's health, weight and/or exercise routine, changes in the type of insulin used and medications, dietary changes, and the like. Additionally, the condition of some components of the integrated system 10 can vary, either over time or from lot to lot. For example, many glucose sensors have some error in their function. This error can vary through out the sensor's lifetime and/or from manufacturing lot to manufacturing lot. Similarly, insulin formulations can vary between manufacturing lots, such as due to small variations in dilution or activity. In yet another example, the insulin deliver device can have some amount of error in measurement of insulin being delivered and/or remaining. Accordingly, in some embodiments, the system is configured to intelligently and adaptively adjust to changing circumstances (e.g., account for error in different system components when determining an insulin therapy), such that the host can be continuously provided with substantially optimum glucose control.

In some circumstances, one or more of the system 10 components have some amount of error. For example, in some circumstances, glucose data from a continuous glucose sensor may include some sensor error, such as about 1%, 2%, 5%, 10%, 15%, 20% or more error. In another example, in some circumstances, an insulin infusion device can have some error in measurement of the amount of insulin delivered (e.g., number of units, rate, volume, and the like) such as about 1%, 2%, 5%, 10%, 15%, 20% or more error. In yet another example, there can be small errors made when the insulin is formulated, such that it can have a slightly different activity or concentration than as labeled. Such system error can make it more difficult to control and host's glucose concentration, unless the system is configured to handle this error.

Accordingly, in some embodiments, the system 10 is configured such that the controller module (e.g., on/off, dynamic basal or dynamic bolus controller module) considers system error (e.g., sensor error, insulin activity/delivery errors) when calculating an insulin therapy (e.g., an insulin delivery rate, an insulin dose, selecting between the on and off instructions). In one exemplary embodiment, if an average sensor error is initially ±20%, then the controller module is configured to adjust the target glucose range by a similar amount up or down. Accordingly, if the original target range is 100-150 mg/dl, then the target range can be increased by 20% to about 120-180-gm/dl. This can prevent inadvertently driving the host too low (e.g., wherein the host's blood sugar is too close to a dangerous hypoglycemic level), such as by overshooting the target range (e.g., 100- to 150 mg/dl reduced by 20% would be 80- to 130 mg/dl). In another exemplary embodiment, the controller module is configured to track and/or evaluate system error (e.g., over time) and adjust one or more system parameters (e.g., target range, glucose boundary, bolus constraint, basal profile, rate if insulin delivery, time of insulin delivery and the like) such that the host is maintained substantially within the target range a substantial portion of the time the system 10 is in use (e.g., 50, 60, 70, 80, 90, or 99% of the time). For example, if sensor error increases to 30% on day-3 of use, the controller module is configured to adjust the target range a corresponding amount (e.g., increase the target range by 30%).

In some embodiments, the system 10 is includes two or all three controller modules which are configured to work in concert (e.g., switch therebetween), such that the host is maintained substantially within the target range a substantial portion of the time (e.g., 50%, 60%, 70%, 80%, 90%, 95% or more of the time) that the system is in use by the host. For example, in some embodiments, the system includes an on/off controller module and either a dynamic bolus controller module or a dynamic basal controller module. In some embodiments, the system includes both the dynamic basal and dynamic bolus controller modules, but not an on/off controller module. In some embodiments, the system includes the on/off controller module as well as both the dynamic basal and dynamic bolus controller modules.

In one exemplary embodiment, the system includes on/off and basal controller modules, and is configured such that determination of insulin therapy occurs in at least two steps. In a first step, the on/off controller module evaluates the internally derived data relative to a glucose boundary, and selects between the on and off instructions. If the on instruction is selected, the dynamic basal controller module evaluated the internally derived data relative to a programmed basal profile and calculated/determines an insulin therapy within the current time block of the basal profile. If the off instruction is selected, then insulin delivery is terminated. In a further exemplary embodiment, the system also includes a dynamic bolus controller module. In general, the on/off and basal controller modules can be configured to function automatically (e.g., perform their functions automatically and in concert with each other) until the user engages a programmable bolus constraint. When the user engages the bolus constraint, the bolus controller module calculates an insulin therapy within the engaged constraint. The system can be further configured to return to operation by the on/off and basal controller modules, until such time that the user again engages a bolus constraint. While not wishing to be bound by theory, it is believed that an intelligent, adaptive integrated system, which can switch between controller modules, can substantially improve consistency and accuracy of glucose control, which enables tight control by the host, and thereby improving the host's health and delaying diabetic complications.

In an exemplary embodiment of a fully automated integrated system 10, the system includes on/off, dynamic basal and dynamic bolus controller modules, is configured for use in conjunction with a flash insulin, and is configured to adaptively and intelligently switch (e.g., automatically, as described herein) between controller modules, depending upon evaluation of the internally derived data, system parameters (e.g., glucose boundary, target range, basal profile, bolus constraints, and the like) and system constraints, such that the host is maintained substantially at within a programmed target range at least 50% of the time the system is in use. In preferred embodiments, the host is maintained within the target range at least 60, 70, 80, 90, or 99% of the time the system is in use. More preferably, the system is further configured to maintain the host within the programmed target range regardless of the host's activity level, metabolic state and/or meal consumption. In such a system, a substantial portion of the host's day, he may experience only moderate increases/decreases in glucose. During these portions of his day, the on/off controller can select either the on or off instructions (e.g., to turn insulin delivery on and off), and when the on instruction is selected, the basal controller module can calculate delivery of basal levels of insulin. A portion of the host's day, an unexpected rapid rise in glucose concentration (e.g., the internally derived data) may occur, which may indicate that a meal is being or has been consumed. Generally, the host would require a bolus insulin therapy to handle the increased glucose that can result from meal consumption. Accordingly, the system can be configured such that the on/off controller can select the on instruction (e.g., turns on insulin delivery) and then the dynamic bolus controller module can calculate an appropriate bolus insulin therapy (e.g., within pre-programmed bolus constraints, non-host engageable). Similarly, as the glucose concentration is brought into the target range, the system can intelligently recognize a decreased requirement for insulin, and can switch from the dynamic bolus controller module, back to the dynamic basal controller module, which can calculate a basal insulin therapy (e.g., for the host's current needs). If the glucose is brought within the target range, the on/off controller can select the off instruction to terminate insulin delivery.

Examples

In one exemplary implementation of the preferred embodiments, the continuous glucose sensor (and its receiver) comprises programming to track a host during hypoglycemic or near-hypoglycemic conditions. In this implementation, the processor (e.g., controller module) includes programming that sends instructions to administer a hypoglycemic treating medicament, such as glucagon, via an implantable pump or the like, when the glucose level and rate of change surpass a predetermined threshold (for example, 80 mg/dL and 2 mg/dL/min). In this situation, the sensor waits a predetermined amount of time (for example, 40 minutes), while monitoring the glucose level, rate of change of glucose, and/or acceleration/deceleration of glucose in the host, wherein if the rate of change and/or acceleration shows a changing trend away from hypoglycemia (for example, decreased deceleration of glucose levels to non-hypoglycemia, then the host need not be alarmed. In this way, the automated glucagon delivery device can proactively preempt hypoglycemic conditions without alerting or awaking the host.

In one exemplary implementation of the preferred embodiments, a continuous glucose sensor is integrated with a continuous medicament delivery device (for example, an insulin pump) and a bolus medicament delivery device (for example, and insulin pen) and a controller module. In this embodiment, the integration exploits the benefits of automated and semi-automated device, for example, providing an automated integration with an infusion pump, while provide semi-automated integration with an insulin pen as necessary.

In one exemplary implementation of the preferred embodiments, a medicament delivery device is provided that includes reservoirs of both fast acting insulin and slow acting insulin. The medicament delivery device is integrated with a controller module as described elsewhere herein, however in this implementation, the controller module determines an amount of fast acting insulin and an amount of slow acting insulin, wherein the medicament delivery device is configured to deliver the two insulins separately and/or in combination, such that the host is maintained substantially at and/or within the target range. In this way, the receiver and medicament delivery device can work together in a feedback loop to iteratively optimize amounts of slow and fast acting insulin for a variety of situations (for example, based on glucose level, rate of change, acceleration, and behavioral factors such as diet, exercise, time of day, etc.) adapted to the individual host's metabolic profile.

In one exemplary implementation of the preferred embodiments, an integrated hypo- and hyper-glycemic treating system is provided. In this implementation, a manual-, semi-automated, or automated integration of an insulin delivery device is combined with a manual-, semi-automated, or automated integration of a glucose or glucagon delivery device. These devices are integrated with the receiver for the continuous glucose sensor and a controller module in any manner described elsewhere herein. While not wishing to be bound by theory, it is believed that the combination of a continuous glucose sensor, integrated insulin device, and integrated glucose or glucagon device provides a simplified, comprehensive, user friendly, convenient, long-term and continuous method of monitoring, treating, and optimizing comprehensive care for diabetes.

In one exemplary implementation of the preferred embodiments, an integrated hypo- and hyper-glycemic treating system is provided, including a continuous glucose sensor, an insulin infusion device and a dynamic controller module, wherein the system is configured to adaptively and intelligently evaluate the host's metabolic state (e.g., historical profile) and adjust the insulin therapy accordingly, in response to an unexpected increase in glucose above a programmed target range. In some circumstances, the boundaries between low, target and high glucose levels, between slow and fast rates of change, and between small and large insulin dose adjustments can be substantially sharp. Accordingly, in this embodiment, the dynamic controller module is configured to evaluate weighted sums (e.g., derived by processing the data collected from the continuous glucose sensor, use of a Kalman filter) to provide a suggested dynamic insulin therapy that is substantially adjusted for the host's current glucose profile (e.g., concentration, rate of change, acceleration, etc.). One skilled in the art understands that, generally, the weighting of a control action depends upon the degree to which its input condition is true. Thus, at the present time ($T_1$), the condition that best describes the glucose level and rate of change (e.g., at $T_1$) will have the largest influence on the control action (e.g., the amount of insulin to be calculated). For exemplary purposes, suppose the following conditions are defined: a very high glucose concentration is greater than 140 mg/dl; a moderately high glucose concentration is from 110 mg/dl to 140 mg/dl; a slow rise in glucose concentration is from 0.5 mg/dl/min to 1.0 mg/dl/min; and a stable glucose concentration is from −0.5-mg/dl/min to 0.5 mg/dl/min. Thus, if the measured glucose concentration is 140 mg/dl and it is rising at a rate of 0.5=mg/dl/min, then the host's current glucose profile falls on the boundary between very high and a little high glucose concentrations, as well as between rising slowly and stable rates. Accordingly, if a large insulin dose increase is defined as from 1-U/h to 2-U/h; a moderate dose increase as from 0.5-U/h to 1-U/h; and small dose increase as from 0.1-U/h to 0.5-U/h; then an optimal increase in insulin dose (e.g., to maintain the host in the target range) may be about 1.2-U/h, for example. Similarly, if the host is relatively insulin insensitive (e.g., resistant), a larger dose can be calculated; and if the host is relatively insulin sensitive, then a smaller dose can be calculated. Thus, the dynamic controller module is configured to adapt (e.g., adjust, modify, re-program) insulin therapy (e.g., dosing) to a given host and his current metabolic conditions. For example, the dynamic controller module can be configured to monitor (e.g., learn) the host's insulin sensitivity by comparing substantially more recent (prior minutes to hours) changes in glucose and insulin dose, and adjust the current dose boundaries accordingly. In a further example, the system can consider system error (e.g., sensor error, drug delivery error and the like) as a weighted sum, when determining the dynamic insulin therapy. For example, if the sensor error is very high and the rate of change is rising slowly, then the insulin therapy can be adjusted by a large increase; if the sensor error is very high and the rate of change is stable, then the insulin therapy can be adjusted by a medium increase; if the sensor error is a little high and the rate of change is stable, then the insulin therapy can be adjusted by a small increase. Advantageously, because any definition of boundaries between low, target and high glucose levels, between slow and fast rates of change, and between small and large insulin therapy adjustments is artificially sharp, the weighted sum provides a graded dose adjustment. Because the dynamic controller module is configured adaptively learn and track trends, the dose boundaries can be intelligently adjusted accordingly. While not wishing to be bound by theory, it is believed that due to its non-model-based nature, smooth transitions between ranges and adaptive learning, the dynamic controller module substantially increases accuracy for each host, which leads to a higher level of safety and improved host health.

In one exemplary implementation of the preferred embodiments, an integrated hypo- and hyper-glycemic treating system is provided, including a continuous glucose sensor, an insulin infusion device and a controller module (on/off, dynamic basal, dynamic bolus) configured to monitor and evaluate system error (e.g., errors in sensor readings and/or evaluation of the internally derived data) and to titrate the insulin therapy, such that the host substantially does not overshoot the euglycemic range (e.g., enter the hypoglycemic range) during delivery of the calculated dose. For example, if the sensor readings include a ±30% error, the target range is set an equivalent percent (e.g., ±30%) above the target range. For example, in some circumstances, if the preferred target range is 80-100 mg/dl, the target can be increased by 30%, to 110-140 mg/dl glucose. In other circumstances, the internally derived data can indicate that the target range should be lowered. Accordingly, the target range can be adjusted up or down, depending upon the error of the system, such that the host substantially does not enter a hypoglycemic (e.g., unsafe) glucose range.

In one exemplary implementation of the preferred embodiments, an integrated hypo- and hyper-glycemic treating system is provided, including a continuous glucose sensor, an insulin infusion device and a controller module configured to provide and/or evaluate trending information. Trend information can include changes in glucose concentration (increasing or decreasing), the rate of change, and the acceleration. Generally, consideration of trend information in insulin therapy calculation can direct relative increases and/or decreases in the calculated therapy and its delivery. For example, in a first exemplary circumstance, the host's glucose concentration is 200 mg/dl and slowly increasing; 5 U of insulin might be insufficient to bring his glucose down to the target level (e.g., 100 mg/dl). In a second exemplary circumstance, in contrast, if the host's glucose concentration is 200 mg/dl and rapidly decreasing, that same insulin dose (e.g., 5 U) might be too large and cause him to overshoot the target range (e.g., become hypoglycemic). In still another example, if the host's glucose concentration is 200 mg/dl and increasing rapidly, a larger insulin dose (e.g., 6, 7, 8, 9 or 10 U or more) may be required to bring his glucose substantially to the target range, relative to the dose required in the first exemplary circumstance. Accordingly, the controller module is configured to evaluate the trend information when calculating a medicament therapy.

In one exemplary implementation of the preferred embodiments, an integrated hypo- and hyper-glycemic treating system is provided, including a continuous glucose sensor, an insulin infusion device and a controller module, wherein the target range is a euglycemic glucose range (e.g., about 90 mg/dl to 140 mg/dl), a dynamic insulin therapy is an amount of a given insulin required to lower a hyperglycemic host's glucose concentration substantially to within about 90 mg/dl to 140 mg/dl glucose (e.g., at the time of calculation), substantially without reducing the host's glucose to a hypoglycemic range. Suppose the target range is 100-140 mg/dl, the host's current glucose concentration is 120 mg/dl and he has just consumed a meal (e.g., including an amount of carbohydrate). Generally, in response to the meal, the host's glucose will begin to rise. Preferably, the integrated system monitor's the host's glucose substantially continuously. If the host's glucose exceeds 140 mg/dl (e.g., at $T_1$), then the dynamic controller module will calculate a dynamic insulin dose (e.g., $D_1$) sufficient (at time $T_1$) to lower the host's glucose to at least 140 mg/dl. After delivery of $D_1$, the system will continue to monitor the host's glucose. Generally, a period of time sufficient for the insulin to act (e.g., depending upon the insulin's TAP) is allowed to pass. If, at a later time (e.g., $T_2$), the host's glucose exceeds 140 mg/dl, the dynamic controller module can calculate another dynamic insulin dose (e.g., $D_2$), sufficient (at time $T_2$) to lower the host's glucose to at least 140 mg/dl. If, at $T_2$, the host's glucose is within the target range, then no additional dynamic insulin doses will be calculated and/or delivered. This process can be repeated (e.g., iteratively), such that the host's glucose is maintained substantially within the target range (e.g., 100-140 mg/dl in this example). In preferred embodiments, the system is configured to stop insulin delivery and/or sound an alarm, if the host's glucose falls below the target range and/or within a dangerous range (e.g., hypoglycemic, such as less than 70 mg/dl).

In one exemplary implementation of the preferred embodiments, an integrated hypo- and hyper-glycemic treating system is provided, including a continuous glucose sensor, an insulin infusion device and a controller module, the dynamic controller module is configured to calculate an insulin therapy that, in a worst-case scenario, is not sufficient (e.g., insufficient) to drive the host into a severely hypoglycemic state (e.g., less than about 65 mg/dl). For exemplary purposes, let's suppose that the host's target glucose is 110 mg/dl, and his glucose level is currently increasing at ≥1 mg/dl/min and is projected to rise (based on the internally derived data) to 170 mg/dl. The dynamic controller module can be programmed such that at a programmed threshold level (e.g., 140 mg/dl), it calculates an insulin therapy that will be sufficient to lower the host's glucose concentration from the expected 170 mg/dl down to the target range (110 mg/dl; lowered by ~60 mg/dl). Suppose that the host's glucose actually does not rise above 140 mg/dl. In this circumstance, the 60-point correction will lower glucose to about 80 mg/dl, which is still about 20-30 mg/dl above what would be a dangerously hypoglycemic glucose concentration. On the other hand, in a best-case scenario, the dynamic controller module can anticipate and correct/prevent an expected rise in glucose concentration, such that the host is substantially maintained within a target blood glucose range, such as a euglycemic range. If the host's glucose concentration continues to rise after delivery of the insulin therapy (e.g., to 200 mg/dl), the dynamic controller module can calculate an additional insulin therapy sufficient to lower the host's glucose concentration the additional amount (e.g., 30-points). In some embodiments, the dynamic controller module is configured to divide the insulin therapy into two or more portions to be delivered over a given period of time. For example, if the insulin therapy is divided into two portions, the first portion can be delivered, and the host's response monitored. If, after the monitoring period has passed, the host's glucose concentration is still above the target, the second portion (all or a part thereof) can be delivered. If, on the other hand, the host's glucose concentration has been lowered to within a threshold (e.g., 110-140 mg/dl) or to the target range (e.g., 110 mg/dl), the second portion can be not delivered.

Methods and devices that are suitable for use in conjunction with aspects of the preferred embodiments are disclosed in U.S. Pat. Nos. 4,994,167; 4,757,022; 6,001,067; 6,741,877; 6,702,857; 6,558,321; 6,931,327; 6,862,465; 7,074,307; 7,081,195; 7,108,778; and 7,110,803.

Methods and devices that are suitable for use in conjunction with aspects of the preferred embodiments are disclosed in U.S. Patent Publication No. US-2005-0176136-A1; U.S. Patent Publication No. US-2005-0251083-A1; U.S. Patent Publication No. US-2005-0143635-A1; U.S. Patent Publication No. US-2005-0181012-A1; U.S. Patent Publication No. US-2005-0177036-A1; U.S. Patent Publication No. US-2005-0124873-A1; U.S. Patent Publication No. US-2005-0115832-A1; U.S. Patent Publication No. US-2005-0245799-A1; U.S. Patent Publication No. US-2005-0245795-A1; U.S. Patent Publication No. US-2005-0242479-A1; U.S. Patent Publication No. US-2005-0182451-A1; U.S. Patent Publication No. US-2005-0056552-A1; U.S. Patent Publication No. US-2005-0192557-A1; U.S. Patent Publication No. US-2005-0154271-A1; U.S. Patent Publication No. US-2004-0199059-A1; U.S. Patent Publication No. US-2005-0054909-A1; U.S. Patent Publication No. US-2005-0112169-A1; U.S. Patent Publication No. US-2005-0051427-A1; U.S. Patent Publication No. US-2003-0032874-A1; U.S. Patent Publication No. US-2005-0103625-A1; U.S. Patent Publication No. US-2005-0203360-A1; U.S. Patent Publication No. US-2005-0090607-A1; U.S. Patent Publication No. US-2005-0187720-A1; U.S. Patent Publication No. US-2005-0161346-A1; U.S. Patent Publication No. US-2006-0015020-A1; U.S. Patent Publication No. US-2005-0043598-A1; U.S. Patent Publication No. US-2003-0217966-A1; U.S. Patent Publication No. US-2005-0033132-A1; U.S. Patent Publication No. US-2005-0031689-A1; U.S. Patent Publication No. US-2004-0186362-A1; U.S. Patent Publication No. US-2005-0027463-A1; U.S. Patent Publication No. US-2005-0027181-A1; U.S. Patent Publication No. US-2005-0027180-A1; U.S. Patent Publication No. US-2006-0020187-A1; U.S. Patent Publication No. US-2006-0036142-A1; U.S. Patent Publication No. US-2006-0020192-A1; U.S. Patent Publication No. US-2006-0036143-A1; U.S. Patent Publication No. US-2006-0036140-A1; U.S. Patent Publication No. US-2006-0019327-A1; U.S. Patent Publication No. US-2006-0020186-A1; U.S. Patent Publication No. US-2006-0020189-A1; U.S. Patent Publication No. US-2006-0036139-A1; U.S. Patent Publication No. US-2006-0020191-A1; U.S. Patent Publication No. US-2006-0020188-A1; U.S. Patent Publication No. US-2006-0036141-A1; U.S. Patent Publication No. US-2006-0020190-A1; U.S. Patent Publication No. US-2006-0036145-A1; U.S. Patent Publication No. US-2006-0036144-A1; U.S. Patent Publication No. US-2006-0016700-A1; U.S. Patent Publication No. US-2006-0142651-A1; U.S. Patent Publication No. US-2006-0086624-A1; U.S. Patent Publication No. US-2006-0068208-A1; U.S. Patent Publication No. US-2006-0040402-A1; U.S. Patent Publication No. US-2006-0036142-A1; U.S. Patent Publication No. US-2006-0036141-A1; U.S. Patent Publication No. US-2006-0036143-A1; U.S. Patent Publication No. US-2006-0036140-A1; U.S. Patent Publication No. US-2006-0036139-A1; U.S. Patent Publication No. US-2006-0142651-A1; U.S. Patent Publication No. US-2006-0036145-A1; U.S. Patent Publication No. US-2006-0036144-A1; U.S. Patent Publication No. US-2006-0200022-A1; U.S. Patent Publication No. US-2006-0198864-A1; U.S. Patent Publication No. US-2006-0200019-A1; U.S. Patent Publication No. US-2006-0189856-A1; U.S. Patent Publication No. US-2006-0200020-A1; U.S. Patent Publication No. US-2006-0200970-A1; U.S. Patent Publication No. US-2006-0183984-A1; U.S. Patent Publication No. US-2006-0183985-A1; U.S. Patent Publication No. US-2006-0195029-A1; U.S. Patent Publication No. US-2006-0229512-A1; U.S. Patent Publication No. US-2006-0222566-A1; U.S. Patent Publication No. US-2007-0032706-A1; U.S. Patent Publication No. US-2007-0016381-A1; U.S. Patent Publication No. US-2007-0027370-A1; U.S. Patent Publication No.

US-2007-0027384-A1; U.S. Patent Publication No. US-2007-0032717-A1; and U.S. Patent Publication No. US-2007-0032718 A1.

Methods and devices that are suitable for use in conjunction with aspects of the preferred embodiments are disclosed in U.S. application Ser. No. 09/447,227 filed Nov. 22, 1999 and entitled "DEVICE AND METHOD FOR DETERMINING ANALYTE LEVELS"; U.S. application Ser. No. 11/515,342 filed Sep. 1, 2006 and entitled "SYSTEMS AND METHODS FOR PROCESSING ANALYTE SENSOR DATA"; U.S. application Ser. No. 11/654,135 filed Jan. 17, 2007 and entitled "POROUS MEMBRANES FOR USE WITH IMPLANTABLE DEVICES"; U.S. application Ser. No. 11/675,063 filed Feb. 14, 2007 and entitled "ANALYTE SENSOR"; U.S. application Ser. No. 11/543,734 filed Oct. 4, 2006 and entitled "DUAL ELECTRODE SYSTEM FOR A CONTINUOUS ANALYTE SENSOR"; U.S. application Ser. No. 11/654,140 filed Jan. 17, 2007 and entitled "MEMBRANES FOR AN ANALYTE SENSOR"; U.S. application Ser. No. 11/654,327 filed Jan. 17, 2007 and entitled "MEMBRANES FOR AN ANALYTE SENSOR"; U.S. application Ser. No. 11/543,396 filed Oct. 4, 2006 and entitled "ANALYTE SENSOR"; U.S. application Ser. No. 11/543,490 filed Oct. 4, 2006 and entitled "ANALYTE SENSOR"; U.S. application Ser. No. 11/543,404 filed Oct. 4, 2006 and entitled "ANALYTE SENSOR"; U.S. application Ser. No. 11/681,145 filed Mar. 1, 2007 and entitled "ANALYTE SENSOR"; and U.S. application Ser. No. 11/690,752 filed Mar. 23, 2007 and entitled "TRANSCUTANEOUS ANALYTE SENSOR".

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A method for determining insulin therapy for a patient, the method comprising:
   receiving, by a user interface of a receiver device that comprises the user interface, a display, and one or more processor modules, input from a user, wherein the input from the user sets a selectable glucose target;
   generating, by the one or more processor modules of the receiver device, glucose trend information, wherein the glucose trend information is based at least in part on sensor glucose data from a data stream comprising time-spaced sensor data points measured in a bodily fluid of the patient by a continuous glucose sensor;
   generating a predicted glucose concentration, wherein the predicted glucose concentration comprises a prediction of a future glucose concentration, wherein the prediction is generated based at least in part on an algorithm;
   generating, by the one or more processor modules of the receiver device, patient data,
   wherein the patient data comprises one or more of:
      an insulin sensitivity of the patient,
      a change in insulin sensitivity of the patient,
      a metabolic response of the patient to insulin therapy,
      an amount of insulin delivered to the patient,
      a time of insulin delivery to the patient, and/or
      an insulin on board of the patient;
   generating, by the one or more processor modules of the receiver device, a series of insulin therapy instructions by evaluating at least the glucose trend information, the patient data, and the selectable glucose target; and
   transmitting the series of insulin therapy instructions for use by an insulin delivery device,
   wherein a glucose concentration measured in a bodily fluid of the patient by the continuous glucose sensor following administration of insulin in accordance with the series of insulin therapy instructions is at or within the selectable glucose target.

2. The method of claim 1, wherein the selectable glucose target is a single glucose concentration.

3. The method of claim 1, wherein the selectable glucose target is a range of glucose concentrations.

4. The method of claim 1, wherein the selectable glucose target is selected from a predefined list of selectable glucose target options.

5. The method of claim 1, wherein calculating an insulin therapy instruction is based solely on evaluating the glucose trend information, the patient data, and the selectable glucose target.

6. The method of claim 1, wherein the selectable glucose target is set for a first specified time period.

7. The method of claim 6, wherein a second selectable glucose target is set for a second specified time period that is different from the first specified time period.

8. The method of claim 7, wherein subsequent glucose concentrations measured in a bodily fluid of the patient by the continuous glucose sensor following administration of insulin in accordance with the series of insulin therapy instructions is at or within the selectable glucose target 70% or more of time that the method is in use for the patient.

9. The method of claim 1, wherein subsequent glucose concentrations measured in a bodily fluid of the patient by the continuous glucose sensor following administration of insulin in accordance with the series of insulin therapy instructions is at or within the selectable glucose target 50% or more of time that the method is in use for the patient.

10. The method of claim 1, wherein the selectable glucose target is adaptively re-programmed based on evaluation of the patient data and/or an external input.

11. The method of claim 10, wherein the patient data comprises data associated with a metabolic response of the patient to insulin therapy.

12. The method of claim 10, wherein the external input is associated with an activity level of the patient.

13. The method of claim 1, wherein the selectable glucose target is displayed by the display of the receiver device.

14. The method of claim 1, wherein information associated with at least one insulin therapy instruction from the series of insulin therapy instructions is displayed by the display of the receiver device.

15. The method of claim 1, wherein the receiver device is integrally formed with the insulin delivery device.

16. The method of claim 1, wherein the insulin delivery device is an infusion pump and the series of insulin therapy instructions is transmitted by radio frequency wireless communication.

17. The method of claim 16, wherein at least one insulin therapy instruction in the series of insulin therapy instructions terminates insulin delivery when glucose trend information indicates a glucose level of the patient is in a euglycemic range and decreasing.

18. The method of claim 1, wherein the user is the patient.

\* \* \* \* \*